(12) United States Patent
More et al.

(10) Patent No.: US 12,006,294 B2
(45) Date of Patent: Jun. 11, 2024

(54) THERAPEUTIC COMPOUNDS

(71) Applicant: REGENTS OF THE UNIVERSITY OF MINNESOTA, Minneapolis, MN (US)

(72) Inventors: Swati S. More, Minneapolis, MN (US); Robert Vince, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 16/429,507

(22) Filed: Jun. 3, 2019

(65) Prior Publication Data

US 2019/0330157 A1 Oct. 31, 2019

Related U.S. Application Data

(63) Continuation of application No. 15/872,776, filed on Jan. 16, 2018, now abandoned.
(Continued)

(51) Int. Cl.
| | |
|---|---|
| C07D 233/64 | (2006.01) |
| A61K 31/167 | (2006.01) |
| A61P 5/48 | (2006.01) |
| A61P 25/16 | (2006.01) |
| A61P 35/00 | (2006.01) |

(Continued)

(52) U.S. Cl.
CPC ............ C07D 233/44 (2013.01); A61P 5/48 (2018.01); A61P 25/16 (2018.01); A61P 35/00 (2018.01); C07C 279/06 (2013.01); C07C 279/08 (2013.01); C07C 279/18 (2013.01); C07C 279/22 (2013.01); C07C 281/14 (2013.01); C07C 281/16 (2013.01); C07C 281/18 (2013.01); C07C 335/04 (2013.01); C07C 335/12 (2013.01); C07C 335/40 (2013.01); C07D 213/61 (2013.01); C07D 231/38 (2013.01); C07D 233/50 (2013.01); C07D 233/52 (2013.01); C07D 233/64 (2013.01); C07D 239/06 (2013.01);
(Continued)

(58) Field of Classification Search
CPC ... C07C 279/08; C07C 279/22; C07C 279/18; C07C 279/06; C07C 335/04; C07C 335/40; C07C 335/12; C07C 281/14; C07C 281/16; C07C 281/18; C07D 213/61; C07D 239/18; C07D 239/22; C07D 239/47; C07D 239/06; C07D 233/52; C07D 233/50; C07D 233/64; C07D 233/44; C07D 231/38; A61P 25/16; A61P 35/00; A61P 5/48; A61K 31/167
See application file for complete search history.

(56) References Cited

U.S. PATENT DOCUMENTS

| | | | |
|---|---|---|---|
| 3,592,852 A | 7/1971 | Houlihan et al. | |
| 3,975,533 A | 8/1976 | Kodama | |
| (Continued) | | | |

FOREIGN PATENT DOCUMENTS

| | | |
|---|---|---|
| DE | 2015321 A1 | 10/1970 |
| WO | 2002081430 A1 | 10/2002 |
| (Continued) | | |

OTHER PUBLICATIONS

Kaneto et al., 1983, caplus an 1983:27720.*
(Continued)

*Primary Examiner* — Sun Jae Yoo
(74) *Attorney, Agent, or Firm* — QUARLES & BRADY LLP

(57) ABSTRACT

The invention provides methods for producing analgesia in an animal comprising administering to the animal a compound of the formula Ia', Ib', Ic', and Id':

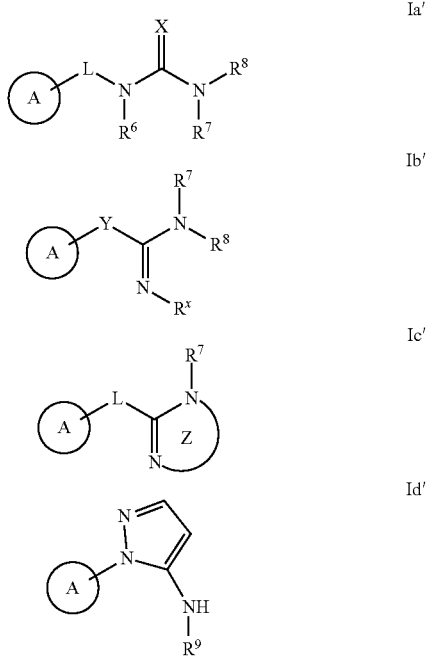

and pharmaceutically acceptable salts thereof, wherein the variables A, $R^6$, $R^7$, $R^8$, $R^9$, $R^x$, L, X, Y, and Z have the meaning as described herein.

12 Claims, 27 Drawing Sheets

Related U.S. Application Data

(60) Provisional application No. 62/446,087, filed on Jan. 13, 2017.

(51) Int. Cl.

| | | |
|---|---|---|
| *C07C 279/06* | (2006.01) | |
| *C07C 279/08* | (2006.01) | |
| *C07C 279/18* | (2006.01) | |
| *C07C 279/22* | (2006.01) | |
| *C07C 281/14* | (2006.01) | |
| *C07C 281/16* | (2006.01) | |
| *C07C 281/18* | (2006.01) | |
| *C07C 335/04* | (2006.01) | |
| *C07C 335/12* | (2006.01) | |
| *C07C 335/40* | (2006.01) | |
| *C07D 213/61* | (2006.01) | |
| *C07D 231/38* | (2006.01) | |
| *C07D 233/44* | (2006.01) | |
| *C07D 233/50* | (2006.01) | |
| *C07D 233/52* | (2006.01) | |
| *C07D 239/06* | (2006.01) | |
| *C07D 239/18* | (2006.01) | |
| *C07D 239/22* | (2006.01) | |
| *C07D 239/47* | (2006.01) | |

(52) U.S. Cl.
CPC ......... *C07D 239/18* (2013.01); *C07D 239/22* (2013.01); *C07D 239/47* (2013.01); *A61K 31/167* (2013.01)

(56) References Cited

U.S. PATENT DOCUMENTS

| | | | |
|---|---|---|---|
| 4,060,640 | A | 11/1977 | Kodama |
| 4,938,949 | A | 7/1990 | Borch et al. |
| 7,074,834 | B2 * | 7/2006 | Tobin .................. A61K 31/165 514/634 |
| 8,148,429 | B2 | 4/2012 | Lundstedt et al. |
| 2004/0068017 | A1 | 4/2004 | Pfeffer et al. |
| 2004/0106682 | A1 | 6/2004 | Unstedt |
| 2005/0136444 | A1 | 6/2005 | Scully |
| 2011/0251428 | A1 | 10/2011 | Blondel |
| 2016/0046589 | A1 | 2/2016 | Guedat |
| 2018/0111896 | A1 | 4/2018 | Bertolotti |
| 2018/0125801 | A1 | 5/2018 | Bertolotti |
| 2018/0303100 | A1 | 10/2018 | Hart-Cooper |

FOREIGN PATENT DOCUMENTS

| | | | |
|---|---|---|---|
| WO | 2003006426 | A1 | 1/2003 |
| WO | 2008041133 | A2 | 4/2008 |
| WO | 2008126088 | A2 | 10/2008 |
| WO | 2011023795 | A1 | 3/2011 |
| WO | 2014108520 | A1 | 7/2014 |
| WO | 2016001389 | A1 | 1/2016 |
| WO | 2016001390 | A1 | 1/2016 |
| WO | 2016123242 | A1 | 8/2016 |

OTHER PUBLICATIONS

Aira et al., 2014, caplus an 2014:1941939.*
Malin et al., Neuroscience Letters, 2015, 584, 141-145.*
Sakamoto-et-al., 1982, caplus an 1982:115870.*
Aguzzi, et al., "The immunobiology of prion diseases", Nat Rev Immunol 13, 888-902 (2013).
Braak, et al., "Staging of brain pathology related to sporadic Parkinson's disease", Neurobiol Aging 24(2), 197-211 (2003).
Colla, et al., "Accumulation of Toxic-Synuclein Oligomer within Endoplasmic Reticulum Occurs in a-Synucleinopathy in Vivo", Journal of Neuroscience 32(10), 3301-3305 (2012).
Colla, et al., "Endoplasmic Reticulum Stress Is important for the Manifestations of a-Synucleinopathy In Vivo", J Neurosci 32(10), 3306-3320 (2012).
Cooper, et al., "a-Synuclein Blocks ER-Golgi Traffic and Rab1 Rescues Neuron Loss in Parkinson's Models", Science 313(5785), 324-328 (2006).
Das, et al., "Preventing proteostasis diseases by selective inhibition of a phosphatase regulatory subunit", science 348 (6231), 239-242 (2015).
Del Tredici, et al., "Where Does Parkinson Disease Pathology Begin in the Brain?", J Neuropathol Exp Neurol 61 (5), 413-426 (2002).
Foufelle, et al., "Role of endoplasmic reticulum stress in drug-induced toxicity", Pharma Res Per 4(1), e00211, 28 pages (2016).
Gaubert, et al., "Discovery of Selective Nonpeptidergic Neuropeptide FF2 Receptor Agonists" , J Med chem 52(21) , 6511-6514 (2009).
Hertz, et al., "Targeting the unfolded protein response in disease", Nat Rev Drug Discov 12, 703-719 (2013).
Kim, et al., "Cell death and endoplasmic reticulum stress: disease relevance and therapeutic opportunities", Nat Rev Drug Discov 7(12), 1013-1030 (2008).
Lin, et al., "Endoplasmic Reticulum Stress in Disease Pathogenesis", Annu Rev Pathol 3, 399-425 (2008).
Phillipp, et al., "Physiological significance of a2-adrenergic receptor subtype diversity: one receptor is not enough", Am J Physiol regulatory Integrative comp Physiol 283, R287-R295 (2002).
Piztele, et al. J. Med. Chem. 1988 31, 138-144 (Year: 1988).
Ron, et al., "Signal integration in the endoplasmic reticulum unfolded protein response", Nat Rev Mol Cell Biol 8(7), 519-529 (2007).
Smith, et al., "Endoplasmic reticulum stress and mitochondrial cell death pathways mediate A53T mutant alpha-synuclein-induced toxicity" , Hum Mol Genet 14(24), 3801-3811 (2005).
Tanaka, et al., "Crystal Structure of Guanabenz Acetate", Analytical Sciences 24, x5-x6 (2008).
Tsaytler, et al., "Selective inhibition of a regulatory subunit of protein phosphatase 1 restores proteostasis", Science 332(6025) , 91-94 (2011).
Du et al., Oxidative Stress During Acetaminophen Hepatotoxicity: Sources, Pathophysiological Role and Therapeutic Potential, Redox Biology, 2016, 10:148-156.
Duvernay et al., A Conserved Motif for the Transport of G Protein-Coupled Receptors from the Endoplasmic Reticulum to the Cell Surface, Journal of Biological Chemistry, 2004, 279(29):30741-30750.
Fullwood et al., Targeting Phosphorylation of Eukaryotic Initiation Factor-2α to Treat Human Disease, Progress in Molecular Biology and Translational Science, 2012, 106:75-106.
Hur et al., IRE1α Activation Protects Mice Against Acetaminophen-Induced Hepatotoxicity, Journal of Experimental Medicine, 2012, 209(2):307-318.
Hinson et al., Mechanisms of Acetaminophen-Induced Liver Necrosis, Handbook of Experimental Pharmacology, 2010, (196):369-405.
Jaeschke et al., Oxidant Stress, Mitochondria, and Cell Death Mechanisms in Drug-Induced Liver Injury: Lessons Learned from Acetaminophen Hepatotoxicity, Drug Metabolism Reviews, 2012, 44(1): 88-106.
Kon et al., Mitochondrial Permeability Transition in Acetaminophen-Induced Necrosis and Apoptosis of Cultured Mouse Hepatocytes, Hepatology, 2004, 40(5): 1170-1179.
Lee, Acetaminophen and the U.S. Acute Liver Failure Study Group: Lowering the Risks of Hepatic Failure, Hepatology, 2004, 40(1):6-9.
Lee, Acetaminophen Toxicity: Changing Perceptions on a Social/Medical Issue, Hepatology, 2007, 46(4):966-970.
Li et al., Darwinian Evolution of Prions in Cell Culture, Science, 2010, 327(5967): 869-872.
Lin et al., Oligodendrocyte-Specific Activation of PERK Signaling Protects Mice Against Experimental Autoimmune Encephalomyelitis, Journal of Neuroscience, 2013, 33(14): 5980-5991.
Lin et al., PERK Activation Preserves the Viability and Function of Remyelinating Oligodendrocytes in Immune-Mediated Demyelinating Diseases, The American Journal of Pathology, 2014, 184(2):507-519.

(56) References Cited

OTHER PUBLICATIONS

Mahal et al., Prion Strain Discrimination in Cell Culture: The Cell Panel Assay, Proceedings of the National Academy of Sciences, 2007, 104(52):20908-20913.

Mazaleuskaya et al., PharmGKB Summary: Pathways of Acetaminophen Metabolism at the Therapeutic Versus Toxic Doses, Pharmacogenet Genomics, 2015, 25(8): 416-426.

More et al., Hepatoprotective Effect of ψ-Glutathione in a Murine Model of Acetaminophen-Induced Liver Toxicity, Chemical Research in Toxicology, 2017, 30(3):777-784.

Neuber et al., Guanabenz Interferes with ER Stress and Exerts Protective Effects in Cardiac Myocytes, PloS One, 2014, 9(6): e98893, pp. 1-9.

Nguyen et al., Structure-Activity Relationship Study Around Guanabenz Identifies Two Derivatives Retaining Antiprion Activity but Having Lost α2-Adrenergic Receptor Agonistic Activity, ACS Chemical Neuroscience, 2014, 5 (10): 1075-1082.

Ogilvie et al., Acetaminophen Overdose in Children, Canadian Medical Association Journal, 2012, 184 (13): 1492-1496.

Park et al., Paracetamol (Acetaminophen) Poisoning, BJM Clinical Evidence, 2015, 10(2101): 1-15.

Patil et al., Phase III Non-inferiority Study Evaluating Efficacy and Safety of Low Dose Gemcitabine Compared to Standard Dose Gemcitabine with Platinum in Advanced Squamous Lung Cancer, EClinicalMedicine, 2019, 9:19-25.

Stone et al., Morphine and Clonidine Combination Therapy Improves Therapeutic Window in Mice: Synergy in Antinociceptive but Not in Sedative or Cardiovascular Effects, PLOS One, 2014, 9(10): e109903, pp. 1-11.

Vieira et al., Guanabenz Treatment Accelerates Disease in a Mutant SOD1 Mouse Model of ALS, PloS One, 2015, 10(8): e0135570, pp. 1-15.

Walter et al., The Unfolded Protein Response: From Stress Pathway to Homeostatic Regulation, Science, 2011, 334(6059): 1081-1086.

Wu et al., Distinct Pathways for the Trafficking of Angiotensin II and Adrenergic Receptors from the Endoplasmic Reticulum to the Cell Surface: Rab1-Independent Transport of a G Protein-Coupled Receptor, Journal of Biological Chemistry, 2003, 278(47):47062-47069.

Yamamoto et al., Transcriptional Induction of Mammalian ER Quality Control Proteins is Mediated by Single or Combined Action of ATF6alpha and XBP1, Developmental Cell, 2007, 13(3):365-376.

Yan et al., Mechanisms of Acetaminophen-Induced Liver Injury and its Implications for Therapeutic Interventions, Redox Biology, 2018, 17:274-283.

Ye et al., Genetic and Pharmacological Inhibition of XBP1 Protects Against APAP Hepatotoxicity Through the Activation of Autophagy, Cell Death & Disease, 2022, 13(2): 143, pp. 1-13.

Yoshino et al., Administration of Small-Molecule Guanabenz Acetate Attenuates Fatty Liver and Hyperglycemia Associated with Obesity, Scientific Reports, 2020, 10(1): 13671, pp. 1-10.

Zaher et al., Protection Against Acetaminophen Toxicity in CYP1A2 and CYP2E1 Double-Null Mice, Toxicology and Applied Pharmacology, 1998, 152(1): 193-199.

\* cited by examiner

Figure 3C

Table. Effect of Combination Therapy on Drug Potency

| Assay | Route | Time (min) | Morphine $ED_{50}(\pm SEM)$ | Guanabenz $ED_{50}(\pm SEM)$ | Observed Combination $ED_{50}(\pm SEM)$ | Theoretical Combination ED50($\pm$SEM) | γ | Interaction | P-value |
|---|---|---|---|---|---|---|---|---|---|
| Tail Flick | s.c. | 15 | 35.09 ± 177.5 | 117.9 ± 3269 | 8.031 ± 20.43 | 39.75 ± 199.6 | 0.202673 | Additive | 0.5218 |
| | | 30 | 8.458 ± 6.795 | 0.6925 ± 0.5393 | 1.629 ± 1.533 | 2.948 ± 1.768 | 0.552557 | Additive | 0.0515 |
| | | 45 | 5.784 ± 7.704 | 0.4949 ± 0.2241 | 1.597 ± 1.529 | 2.08 ± 1.06 | 0.767908 | Additive | 0.3066 |
| | | 60 | 49.67 ± 127.7 | 0.4495 ± 0.1869 | 1.4 ± 1.118 | 2.58 ± 1.066 | 0.542584 | Synergistic | 0.0166 |

THERAPEUTIC COMPOUNDS

CROSS-REFERENCE TO RELATED APPLICATIONS

This application is a continuation of U.S. patent application Ser. No. 15/872,776, filed on Jan. 16, 2018, which claims priority to U.S. Provisional Patent Application No. 62/446,087, filed Jan. 13, 2017, all of which are incorporated herein by reference.

STATEMENT REGARDING FEDERALLY SPONSORED RESEARCH

This invention was made with government support under NS086074 awarded by the National Institutes of Health. The government has certain rights in the invention.

BACKGROUND

Parkinson's Disease (PD) is a common, late onset, progressive neurodegenerative disease characterized by the selective loss of various neuronal populations, including the dopaminergic (DAergic) neurons of substantia nigra, pars compacta (SNpc), and the presence of fibrillar, cytoplasmic inclusions called Lewy bodies (LBs) and Lewy neurites (LNs). While degeneration of the SNpc DAergic neurons is responsible for much of the motoric abnormalities, neurodegeneration in PD extends well beyond the SNpc DAergic neurons (Del Tredici K, et al., (2002) *J Neuropathol Exp Neurol* 61(5):413-426; and Braak H, et al. (2003) *Neurobiol Aging* 24(2): 197-211). The extranigral symptoms of PD are often more debilitating for patients. While the causes of disease is unknown in most cases of PD, the current view is that abnormalities in a neuronal protein called α-synuclein (αS) is responsible for the progressive nature of PD as well as extranigral degeneration. Given this view, compounds that can ameliorate αS abnormalities and/or associated neurodegeneration would qualify as disease modifying therapies for sporadic PD cases. Unfortunately, there are no therapies that can alter the progressive nature of PD.

The endoplasmic reticulum stress/unfolded protein response (ERS/UPR) is an integrated cellular response to the accumulation of misfolded proteins, particularly resulting from ER dysfunction, in attempts to protect cells from accumulation of toxic misfolded proteins (Ron D & Walter P (2007) *Nat Rev Mol Cell Biol* 8(7):519-529; and Kim I, et al. (2008) *Nat Rev Drug Discov* 7(12): 1013-1030). However, chronic unabated ERS leads to the activation cell death cascade. Potential involvement of chronic ERS in αS-dependent neurodegeneration was first demonstrated in a PC12 cell model of αS toxicity (Smith W W, et al. (2005) *Hum Mol Genet* 14(24):3801-3811). A recent series of reports suggest that increased αS expression can cause ER stress in yeast and other cells by interrupting Rab-dependent ER to Golgi membrane trafficking (Cooper A A, et al. (2006) *Science* 313(5785):324-328). It is shown that progressive ERS and activation of ER associated cell death pathway occurs with the accumulation of αS oligomers in the ER (Colla E, et al. (2012) *J Neurosci* 32(10):3306-3320; and Colla E, et al. (2012) *J Neurosci* 32(10):3301-3305). Moreover, the pathologic relevance of ERS in disease by showing that pharmacological attenuation of ERS can delay disease onset (Colla E, et al. (2012) *J Neurosci* 32(10):3306-3320).

Chronic ERS is important pathologic factor in α-synucleinopathy. The toxic nature of the ER associated αS oligomers are also supported by the fact that the accumulation of αS in the ER is associated with the onset of α-synucleinopathy and activation of ER-stress response/unfolded-protein response (UPR) as indicated by increase in ER chaperones in neurons exhibiting αS pathology onset (Colla E, et al. (2012) *J Neurosci* 32(10):3306-3320). It is suggested that ERS is a valid target for development of disease modifying therapy for PD. However, while endoplasmic reticulum stress/unfolded protein response (ERS/UPR) has been implicated in the disease mechanism for many neurodegenerative diseases, there has not been a clinical compound that has targeted this pathway.

Currently, there is a need for new methods to treat PD and other neurodegenerative diseases.

In addition, there are three α2-adrenergic receptor subtypes, $\alpha_{2A}$, $\alpha_{2B}$ and $\alpha_{2C}$. All there subtypes are involved in the control of pain perception in mice. The antihypertensive (sedative) effect in mice is solely mediated by the $\alpha_{2A}$-receptor subtype. Compounds that show selective affinities towards 2B and/or 2C would remain of the analgesic activity without the undesirable antihypertensive or other side effects. These compounds would not possess the dependency issues as most of the analgesics in the market do. There is currently also a need for new compounds with selective $\alpha_{2A}$-receptor subtype selectivity. In addition, there is need for new methods to produce analgesia.

SUMMARY

The invention provides a method for treating neurodegenerative disorders in an animal comprising administering to the animal an effective amount of compound of formula Ia', Ib' Ic', or Id':

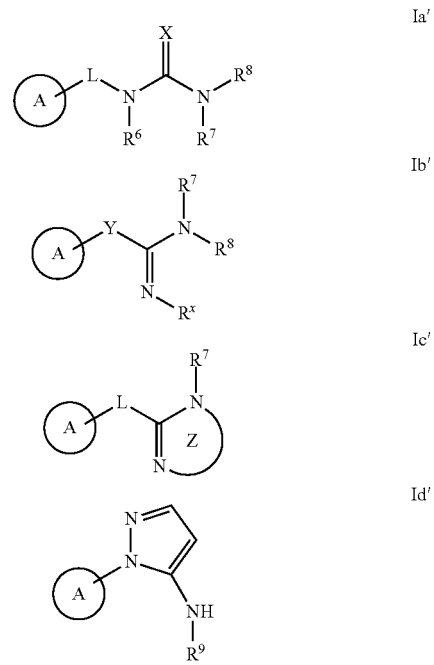

or a pharmaceutically acceptable salt thereof;
i) wherein the compound of formula Ia':
ring A is phenyl, napthyl, thienyl, or 6-membered heteroaryl, which phenyl, napthyl, thienyl, or 6-membered heteroaryl is optionally substituted with one or more groups independently selected from the group consisting of $C_{1-4}$ alkyl, $C_{1-4}$ haloalkyl, $C_{3-8}$ cycloalkyl, —F, —Cl, —Br, —I, —OR$^a$, —SR$^a$, —N(R$^a$)$_2$, —NO$_2$ and —CN;

L is selected from the group consisting of:
—CH$_2$CH$_2$—, —CH$_2$NH—, —CH$_2$C(=O)—, —CH(OH)CH$_2$—,

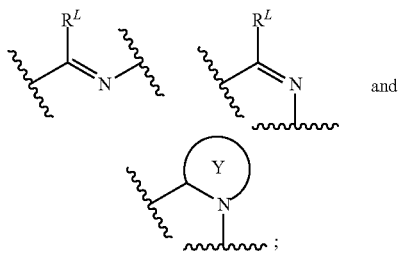

and

R$^L$ is hydrogen, $C_{1-4}$ alkyl, $C_{1-4}$ haloalkyl or $C_{3-8}$ cycloalkyl;

ring Y is heteroaryl that is optionally substituted with one or more groups selected from —F, —Cl, —Br, —I, —OR$^y$, —SR$^y$, —N(R$^y$)$_2$, —NO$_2$ or —CN;

R$^6$ is hydrogen, or $C_{1-6}$ alkyl that is optionally substituted with one or more groups selected from —F, —Cl, —Br, —I, —OR$^f$, —SR$^f$, —N(R$^f$)$_2$, oxo, —NO$_2$ or —CN; or R$^6$ and R$^8$ taken together with the atoms to which they are attached form a heterocycle that is optionally substituted with one or more groups selected from —F, —Cl, —Br, —I, —OR$^i$, —SR$^i$, —N(R$^i$)$_2$, —NO$_2$ or —CN;

R$^7$ is hydrogen, or $C_{1-6}$ alkyl that is optionally substituted with one or more groups selected from —F, —Cl, —Br, —I, —OR$^g$, —SR$^g$, —N(R$^g$)$_2$, oxo, —NO$_2$ or —CN;

R$^8$ is hydrogen, or $C_{1-6}$ alkyl that is optionally substituted with one or more groups selected from —F, —Cl, —Br, —I, —OR$^h$, —SR$^h$, —N(R$^h$)$_2$, oxo, —NO$_2$ or —CN; or R$^6$ and R$^8$ taken together with the atoms to which they are attached form a heterocycle that is optionally substituted with one or more groups selected from —F, —Cl, —Br, —I, —OR$^i$, —SR$^i$, —N(R$^i$)$_2$, —NO$_2$ or —CN;

X is =O, =S or =N—R$^x$; wherein R$^x$ is hydrogen, or $C_{1-6}$ alkyl that is optionally substituted with one or more groups selected from —F, —Cl, —Br, —I, —OR$^i$, —SR$^i$, —N(R$^i$)$_2$, —NO$_2$ or —CN; or R$^x$ and R$^8$ taken together with the nitrogen atoms to which they are attached form a heteroaryl or an unsaturated heterocycle; wherein the heteroaryl and heterocycle are optionally substituted with one or more groups selected from —F, —Cl, —Br, —I, —OR$^i$, —SR$^i$, —N(R$^i$)$_2$, —NO$_2$ or —CN;

each R$^a$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^a$ groups taken together with the nitrogen to which they are attached form pyrrolidinyl, piperidinyl, piperazinyl or morpholinyl;

each R$^b$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^b$ groups taken together with the nitrogen to which they are attached form pyrrolidinyl, piperidinyl, piperazinyl or morpholinyl;

each R$^c$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^c$ groups taken together with the nitrogen to which they are attached form pyrrolidinyl, piperidinyl, piperazinyl or morpholinyl;

each R$^d$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^d$ groups taken together with the nitrogen to which they are attached form pyrrolidinyl, piperidinyl, piperazinyl or morpholinyl;

each R$^e$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^e$ groups taken together with the nitrogen to which they are attached form pyrrolidinyl, piperidinyl, piperazinyl or morpholinyl;

each R$^f$ is independently hydrogen, $C_{1-4}$ alkyl or $C_{1-4}$ haloalkyl; or two R$^f$ groups taken together with the nitrogen to which they are attached form pyrrolidinyl, piperidinyl, piperazinyl or morpholinyl;

each R$^g$ is independently hydrogen, $C_{1-4}$ alkyl or $C_{1-4}$ haloalkyl; or two R$^g$ groups taken together with the nitrogen to which they are attached form pyrrolidinyl, piperidinyl, piperazinyl or morpholinyl;

each R$^h$ is independently hydrogen, $C_{1-4}$ alkyl or $C_{1-4}$ haloalkyl; or two R$^h$ groups taken together with the nitrogen to which they are attached form pyrrolidinyl, piperidinyl, piperazinyl or morpholinyl;

each R$^i$ is independently hydrogen, $C_{1-4}$ alkyl or $C_{1-4}$ haloalkyl; or two R$^i$ groups taken together with the nitrogen to which they are attached form pyrrolidinyl, piperidinyl, piperazinyl or morpholinyl; and each R$^y$ is independently hydrogen, $C_{1-4}$ alkyl or $C_{1-4}$ haloalkyl; or two R$^y$ groups taken together with the nitrogen to which they are attached form pyrrolidinyl, piperidinyl, piperazinyl or morpholinyl;

ii) wherein the compound of formula Ib':

ring A is phenyl, napthyl, thienyl, or 6-membered heteroaryl, which phenyl, napthyl, thienyl, or 6-membered heteroaryl is optionally substituted with one or more groups independently selected from the group consisting of $C_{1-4}$ alkyl, $C_{1-4}$ haloalkyl, $C_{3-8}$ cycloalkyl, —F, —Cl, —Br, —I, —OR$^a$, —SR$^a$, —N(R$^a$)$_2$, —NO$_2$ and —CN;

Y is S or —NR$^6$—;

R$^6$ is hydrogen, or $C_{1-6}$ alkyl that is optionally substituted with one or more groups selected from —F, —Cl, —Br, —I, —OR$^f$, —SR$^f$, —N(R$^a$)$_2$, oxo, —NO$_2$ or —CN;

R$^7$ is hydrogen, or $C_{1-6}$ alkyl that is optionally substituted with one or more groups selected from —F, —Cl, —Br, —I, —OR$^g$, —SR$^g$, —N(R$^g$)$_2$, oxo, —NO$_2$ or —CN;

R$^8$ is hydrogen, phenyl, or $C_{1-6}$ alkyl that is optionally substituted with one or more groups selected from —F, —Cl, —Br, —I, —OR$^h$, —SR$^h$, —N(R$^h$)$_2$, oxo, —NO$_2$ or —CN;

R$^x$ is hydrogen, or $C_{1-6}$ alkyl that is optionally substituted with one or more groups selected from —F, —Cl, —Br, —I, —OR$^i$, —SR$^i$, —N(R$^i$)$_2$, —NO$_2$ or —CN; or R$^x$ and R$^8$ taken together with the nitrogen atoms to which they are attached form a heteroaryl or an unsaturated heterocycle; wherein the heteroaryl and heterocycle are optionally substituted with one or more groups selected from —F, —Cl, —Br, —I, —OR$^i$, —SR$^i$, —N(R$^i$)$_2$, —NO$_2$ or —CN;

each R$^a$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^a$ groups taken together with the nitrogen to which they are attached form pyrrolidinyl, piperidinyl, piperazinyl or morpholinyl;

each $R^b$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^b$ groups taken together with the nitrogen to which they are attached form pyrrolidinyl, piperidinyl, piperazinyl or morpholinyl;

each $R^c$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^c$ groups taken together with the nitrogen to which they are attached form pyrrolidinyl, piperidinyl, piperazinyl or morpholinyl;

each $R^d$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^d$ groups taken together with the nitrogen to which they are attached form pyrrolidinyl, piperidinyl, piperazinyl or morpholinyl;

each $R^e$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^e$ groups taken together with the nitrogen to which they are attached form pyrrolidinyl, piperidinyl, piperazinyl or morpholinyl;

each $R^f$ is independently hydrogen, $C_{1-4}$ alkyl or $C_{1-4}$ haloalkyl; or two $R^f$ groups taken together with the nitrogen to which they are attached form pyrrolidinyl, piperidinyl, piperazinyl or morpholinyl;

each $R^g$ is independently hydrogen, $C_{1-4}$ alkyl or $C_{1-4}$ haloalkyl; or two $R^g$ groups taken together with the nitrogen to which they are attached form pyrrolidinyl, piperidinyl, piperazinyl or morpholinyl;

each $R^h$ is independently hydrogen, $C_{1-4}$ alkyl or $C_{1-4}$ haloalkyl; or two $R^h$ groups taken together with the nitrogen to which they are attached form pyrrolidinyl, piperidinyl, piperazinyl or morpholinyl; and each $R^i$ is independently hydrogen, $C_{1-4}$ alkyl or $C_{1-4}$ haloalkyl; or two $R^i$ groups taken together with the nitrogen to which they are attached form pyrrolidinyl, piperidinyl, piperazinyl or morpholinyl;

iii) wherein the compound of formula Ic':
ring A is phenyl, napthyl, thienyl, or 6-membered heteroaryl, which phenyl, napthyl, thienyl, or 6-membered heteroaryl is optionally substituted with one or more groups independently selected from the group consisting of $C_{1-4}$ alkyl, $C_{1-4}$ haloalkyl, $C_{3-8}$ cycloalkyl, —F, —Cl, —Br, —I, —$OR^a$, —$SR^a$, —$N(R^a)_2$, —$NO_2$ and —CN;

L is —CH=N—, or $C_{1-4}$ alkylene that is optionally substituted with one or more groups selected from halo, hydroxy or $C_{3-8}$ cycloalkyl;

$R^7$ is hydrogen, or $C_{1-6}$ alkyl that is optionally substituted with one or more groups selected from —F, —Cl, —Br, —I, —$OR^g$, —$SR^g$, —$N(R^g)_2$, oxo, —$NO_2$ or —CN;

ring Z is heteroaryl or unsaturated heterocycle; wherein the heteroaryl and heterocycle are optionally substituted with one or more groups selected from oxo (=O), $C_{1-4}$ alkyl, —F, —Cl, —Br, —I, —$OR^i$, —$SR^i$, —$N(R^i)_2$, —$NO_2$ or —CN;

each $R^a$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^a$ groups taken together with the nitrogen to which they are attached form pyrrolidinyl, piperidinyl, piperazinyl or morpholinyl;

each $R^e$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^e$ groups taken together with the nitrogen to which they are attached form pyrrolidinyl, piperidinyl, piperazinyl or morpholinyl;

each $R^g$ is independently hydrogen, $C_{1-4}$ alkyl or $C_{1-4}$ haloalkyl; or two $R^g$ groups taken together with the nitrogen to which they are attached form pyrrolidinyl, piperidinyl, piperazinyl or morpholinyl; and each $R^i$ is independently hydrogen, $C_{1-4}$ alkyl or $C_{1-4}$ haloalkyl; or two $R^i$ groups taken together with the nitrogen to which they are attached form pyrrolidinyl, piperidinyl, piperazinyl or morpholinyl;

iv) wherein the compound of formula Id':
ring A is phenyl, napthyl, thienyl, or 6-membered heteroaryl, which phenyl, napthyl, thienyl, or 6-membered heteroaryl is optionally substituted with one or more groups independently selected from the group consisting of $C_{1-4}$ alkyl, $C_{1-4}$ haloalkyl, $C_{3-8}$ cycloalkyl, —F, —Cl, —Br, —I, —$OR^a$, —$SR^a$, —$N(R^a)_2$, —$NO_2$ and —CN; and $R^9$ is hydrogen or —C(=NH)—$NH_2$.

The invention also provides a compound of formula Ia', Ib' Ic', or Id', or a pharmaceutically acceptable salt thereof; provided that the compound is not:

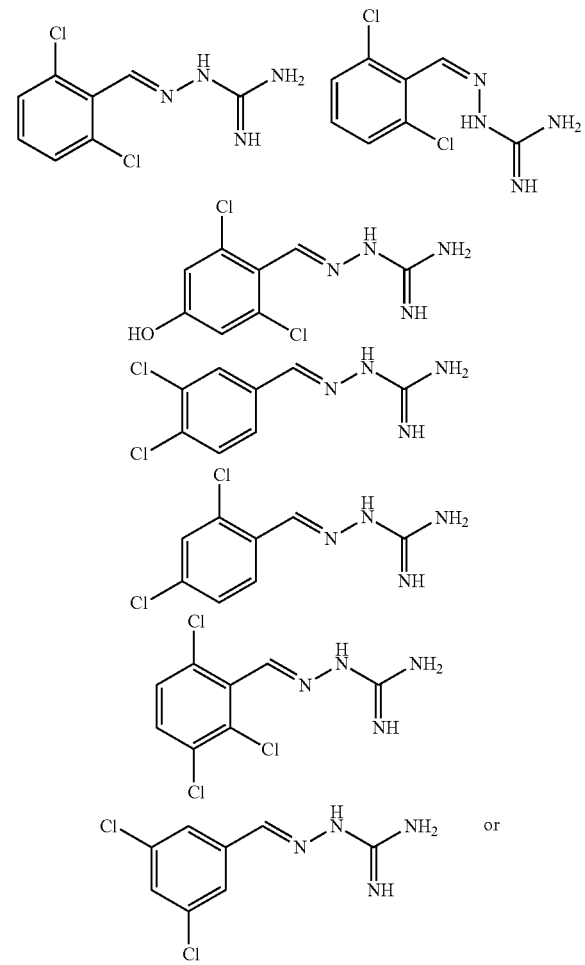

-continued

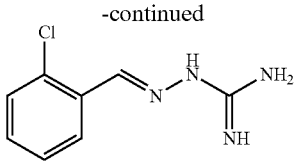

The invention also provides a pharmaceutical composition comprising a compound of formula Ia', Ib' Ic', or Id', or a pharmaceutically acceptable salt thereof, and a pharmaceutically acceptable carrier.

The invention also provides a method for producing analgesia in an animal comprising administering to the animal a compound of formula Ia', Ib' Ic', or Id' or a pharmaceutically acceptable salt thereof.

The invention also provides a pharmaceutical composition comprising: 1) a drug that is associated with unwanted endoplasmic reticulum stress, 2) a compound of formula Ia', Ib' Ic', or Id', or a pharmaceutically acceptable salt thereof, and 3) a pharmaceutically acceptable carrier;
provided the compound of formula Ia', Ib' Ic', or Id' is not

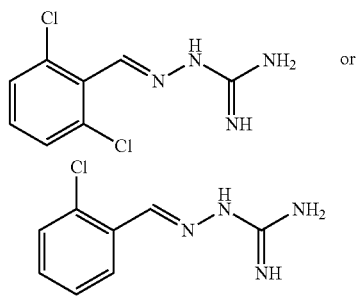

or a pharmaceutically acceptable salt thereof.

The invention also provides a method for reducing endoplasmic reticulum stress in an animal comprising administering to the animal a compound of formula Ia', Ib' Ic', or Id', or a pharmaceutically acceptable salt thereof;
provided the compound of formula Ia', Ib' Ic', or Id' is not

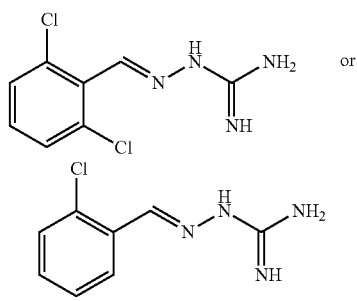

or a pharmaceutically acceptable salt thereof.

The invention also provides a method for reducing drug-induced toxicity in an animal comprising administering to the animal a compound of formula Ia', Ib' Ic', or Id', or a pharmaceutically acceptable salt thereof.

The invention also provides a method for treating a disease selected from the group consisting of diabetes, viral infection, and cancer in an animal comprising administering to the animal a compound of formula Ia', Ib' Ic', or Id', or a pharmaceutically acceptable salt thereof;
provided the compound of formula Ia', Ib' Ic', or Id' is not

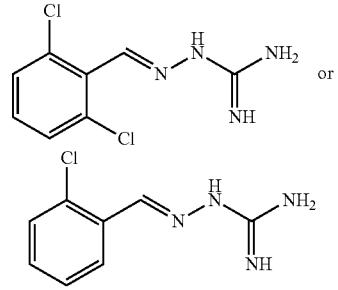

or a pharmaceutically acceptable salt thereof.

The invention also provides a compound of formula Ia', Ib', Ic', or Id' or a pharmaceutically acceptable salt thereof.

The invention also provides a pharmaceutical composition comprising a compound of formula Ia', Ib', Ic', or Id' or a pharmaceutically acceptable salt thereof, and a pharmaceutically acceptable carrier.

The invention also provides processes and intermediates disclosed herein that are useful for preparing a compound of formula Ia', Ib', Ic', or Id' or a salt thereof.

BRIEF DESCRIPTION OF THE FIGURES

FIG. 3B shows data on the combination of BC1-45-1 with morphine and FIG. 3C shows the analysis of the analgesic interaction between guanabenz and morphine.

DETAILED DESCRIPTION

Figure 1A:
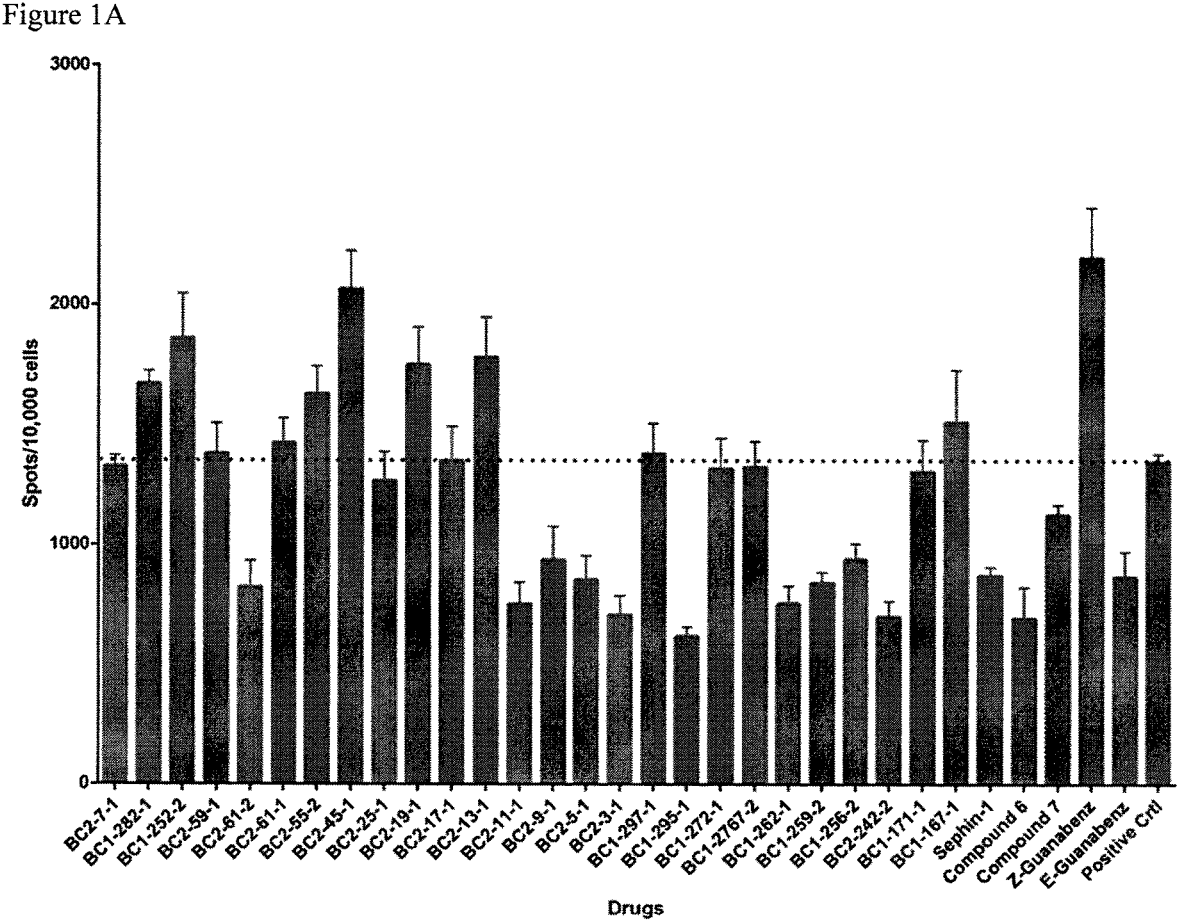
FIGS. 1A and 1B show the anti-prion activities produced by representative compounds. The bottom line in FIG. 1B indicates that the reduction in spots is due to actual anti-prion activity and not just a lack of cells.

The term "alkyl", by itself or as part of another substituent, means, unless otherwise stated, a straight or branched chain hydrocarbon radical, having the number of carbon atoms designated (i.e., $C_{1-6}$ means one to six carbons). Non limiting examples of "alkyl" include methyl, ethyl, propyl, isopropyl, butyl, iso-butyl, sec-butyl, pentyl, 3-pentyl and hexyl.

The term "alkylene" by itself or as part of another substituent means a divalent radical derived from an alkane (including straight and branched alkanes), as exemplified by —CH$_2$—, —CH(CH$_3$)—, —CH$_2$CH$_2$CH$_2$CH$_2$— and —CH(CH$_3$)CH$_2$CH$_2$—.

The term "halo" mean —F, —Cl, —Br or —I.

The term "haloalkyl" means an alkyl that is optionally substituted with one or more (e.g., 1, 2, 3, 4, or 5) halo. Non limiting examples of "haloalkyl" include iodomethyl, bromomethyl, chloromethyl, fluoromethyl, trifluoromethyl, 2-chloroethyl, 2-fluoroethyl, 2,2,2-trifluoroethyl 2,2-difluoroethyl and pentafluoroethyl.

The term "aryl" as used herein refers to a single all carbon aromatic ring or a multiple condensed all carbon ring system wherein at least one of the rings is aromatic. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1, 2, 3, 4-tetrahydronaphthyl, anthracenyl, and the like.

The term "heteroaryl" as used herein refers to a 3-6 membered single aromatic ring that has at least one (e.g., 1, 2, 3 or 4) atom other than carbon in the ring, wherein the atom is selected from the group consisting of oxygen, nitrogen and sulfur; "heteroaryl" also includes 7-20 membered multiple condensed ring systems that have at least one such aromatic ring, which multiple condensed ring systems are further described below. The rings of the multiple condensed ring system can be connected to each other via fused, spiro and bridged bonds when allowed by valency requirements. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole. One preferred embodiment of "6-membered heteroaryl" is pyridine, 1,4-diazine, 1,3-diazine, 1,2-diazine, 1,2,3-triazine, 1,2,4-triazine or 1,3,5-triazine.

The term "heterocycle" refers to a saturated or partially unsaturated ring system radical having the overall having from 3-20 ring atoms that contain from one to ten heteroatoms selected from N, O, and S. Unless otherwise stated, a "heterocycle" ring can be a monocyclic, a bicyclic, spirocyclic or a polycyclic ring system. Non limiting examples of "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and the like. A "heterocycle" group can be attached to the remainder of the molecule through one or more ring carbons or heteroatoms.

The term "unsaturated heterocycle" means a single or bicyclic 3-10 membered ring system that has one or two double bonds and has at least one (e.g., 1, 2, 3 or 4) atom other than carbon in the ring, wherein the atom is selected from the group consisting of oxygen, nitrogen and sulfur. One preferred embodiment of "unsaturated heterocycle" is 2-imidazoline.

The term "cycloalkyl" refers to hydrocarbon ringsystem having 3 to 8 overall number of ring atoms and for a 3-5 membered cycloalkyl being fully saturated or having no more than one double bond between ring vertices and for a 6 membered cycloalkyl or larger being fully saturated or having no more than two double bonds between ring vertices. One preferred embodiment of "cycloalkyl" is cyclopropyl.

The terms "treat" and "treatment" refer to both therapeutic treatment and/or prophylactic treatment or preventative measures, wherein the object is to prevent or slow down (lessen) an undesired physiological change or disorder, such as, for example, Parkinson's disease. For purposes of this invention, beneficial or desired clinical results include, but are not limited to, alleviation of symptoms, diminishment of extent of disease or disorder, stabilized (i.e., not worsening)

state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

"α2-adrenergic receptor" is a G protein-coupled receptor. There are three α2-adrenergic receptor subtypes, $α_{2A}$, $α_{2B}$ and $α_{2C}$. All there subtypes are involved in the control of pain perception in mice. The antihypertensive (sedative) effect in mice is solely mediated by the $α_{2A}$-receptor subtype. Compounds that show selective affinities towards 2B and/or 2C would remain of the analgesic activity without the undesirable antihypertensive or other side effects.

Endoplasmic Reticulum Stress

The compounds of the invention are also useful to reduce endoplasmic reticulum stress. Accordingly, the compounds are useful to treat diseases and conditions that are associated with undesirable endoplasmic reticulum stress. Such conditions include drug-induced toxicity, heavy metal-induced (e.g. cadmium, lead, copper, arsenic and mercury) toxicity, carbon monoxide poisoning, and cyanide poisoning. For a discussion of endoplasmic reticulum stress and drug-induced toxicity, please see F. Foufelle and B. Fromerty, *Pharmacology Research & Perspectives,* 2016, 4, 1-28, which is incorporated herein in its entirety. Other diseases and conditions that are associated with undesirable endoplasmic reticulum stress include diabetes, viral infection (e.g., HIV, HSV, HBV) and cancer (see F. Foufelle and B. Fromerty, *Pharmacology Research & Perspectives,* 2016, 4, 1-28; and J. Lin et al., *Annu Rev Pathol.,* 2008, 3, 399-425, which are both incorporated herein in their entirety)

In one embodiment the invention provides a method for reducing endoplasmic reticulum stress in an animal comprising administering to the animal an effective amount of compound of formula Ia', Ib' Ic', or Id', or a pharmaceutically acceptable salt thereof.

In one embodiment the invention provides a method for reducing drug-induced toxicity in an animal comprising administering to the animal an effective amount of compound of formula Ia', Ib' Ic', or Id', or a pharmaceutically acceptable salt thereof. In one embodiment, the drug is acetaminophen, amiodarone, arsenic trioxide, bleomycin, bortezomib, cisplatin, clozapine, olanzapine, cyclosporine, diclofenac, efavirenz, erlotinib, furosemide, indomethacin, taxol, protease inhibitors (e.g. indinavir and ritonavir), sertraline, and thaosigargin. In one embodiment the invention provides a method for reducing drug-induced toxicity in an animal comprising administering to the animal an effective amount of compound of formula Ia', Ib' Ic', or Id', or a pharmaceutically acceptable salt thereof in combination with the drug. In one embodiment the invention provides a composition comprising: 1) a drug that is associated with unwanted endoplasmic reticulum stress, 2) a compound of formula Ia', Ib' Ic', or Id', or a pharmaceutically acceptable salt thereof, and 3) a pharmaceutically acceptable carrier.

In one embodiment the invention provides a method for reducing heavy metal-induced toxicity in an animal comprising administering to the animal an effective amount of compound of formula Ia', Ib' Ic', or Id', or a pharmaceutically acceptable salt thereof.

In one embodiment the invention provides a method for treating carbon monoxide poisoning in an animal comprising administering to the animal an effective amount of compound of formula Ia', Ib' Ic', or Id', or a pharmaceutically acceptable salt thereof.

In one embodiment the invention provides a method for treating cyanide poisoning in an animal comprising administering to the animal an effective amount of compound of formula Ia', Ib' Ic', or Id', or a pharmaceutically acceptable salt thereof.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

In one embodiment, the neurodegenerative disorder is Parkinson's disease (PD), Alzheimer's disease (AD), amyotrophic lateral sclerosis (ALS), Prion disease, Huntington's disease (HD) or multiple sclerosis (MS).

In one embodiment, the neurodegenerative disorder is Parkinson's disease (PD), Alzheimer's disease (AD), amyotrophic lateral sclerosis (ALS), Prion disease, or multiple sclerosis (MS).

In one embodiment, the neurodegenerative disorder is Parkinson's disease.

In one embodiment, the neurodegenerative disorder is Prion disease.

In one embodiment, the neurodegenerative disorder is multiple sclerosis.

The invention also provides a method for producing analgesia in an animal (e.g., a mammal, such as a human) comprising administering to the animal an effective amount of compound of formula Ia, Ib or Ic, or a pharmaceutically acceptable salt thereof.

The invention provides a compound of formula Ia, Ib or Ic or a pharmaceutically acceptable salt thereof for use in producing analgesia in an animal.

The invention provides the use of a compound of formula Ia, Ib or Ic or a pharmaceutically acceptable salt thereof for the manufacture of a medicament for producing analgesia in an animal.

In one embodiment, the animal is morphine dependent and/or morphine tolerant.

In one embodiment, the method for producing analgesia further comprises administering morphine to the animal.

In one embodiment, the analgesia is produced for synergy in antinociception with reduced sedation or cardiovascular effects.

In one embodiment, the animal is administered with an effective amount of compound of formula Ia, or a pharmaceutically acceptable salt thereof.

In one embodiment, the animal is administered with an effective amount of compound of formula Ib, or a pharmaceutically acceptable salt thereof.

In one embodiment, the animal is administered with an effective amount of compound of formula Ic, or a pharmaceutically acceptable salt thereof.

In one embodiment, the compound administered in the method for treating Parkinson's disease is a compound of formula Ia:

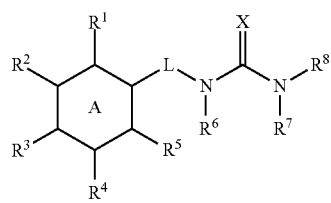

Ia or a pharmaceutically acceptable salt thereof, wherein:
ring A is phenyl;
at least one of $R^1$, $R^2$, $R^3$, $R^4$, and $R^5$ is Cl or Br;
and the group

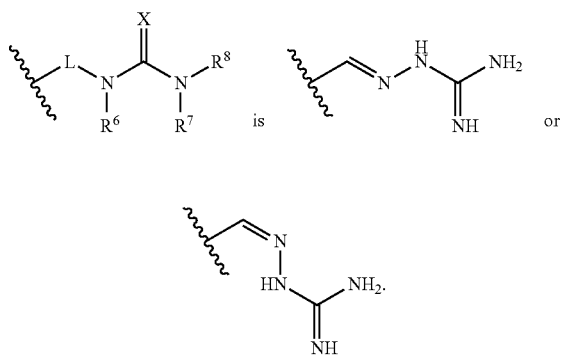

In one embodiment, the compound administered in the method for treating Parkinson's disease is selected from the group consisting of:

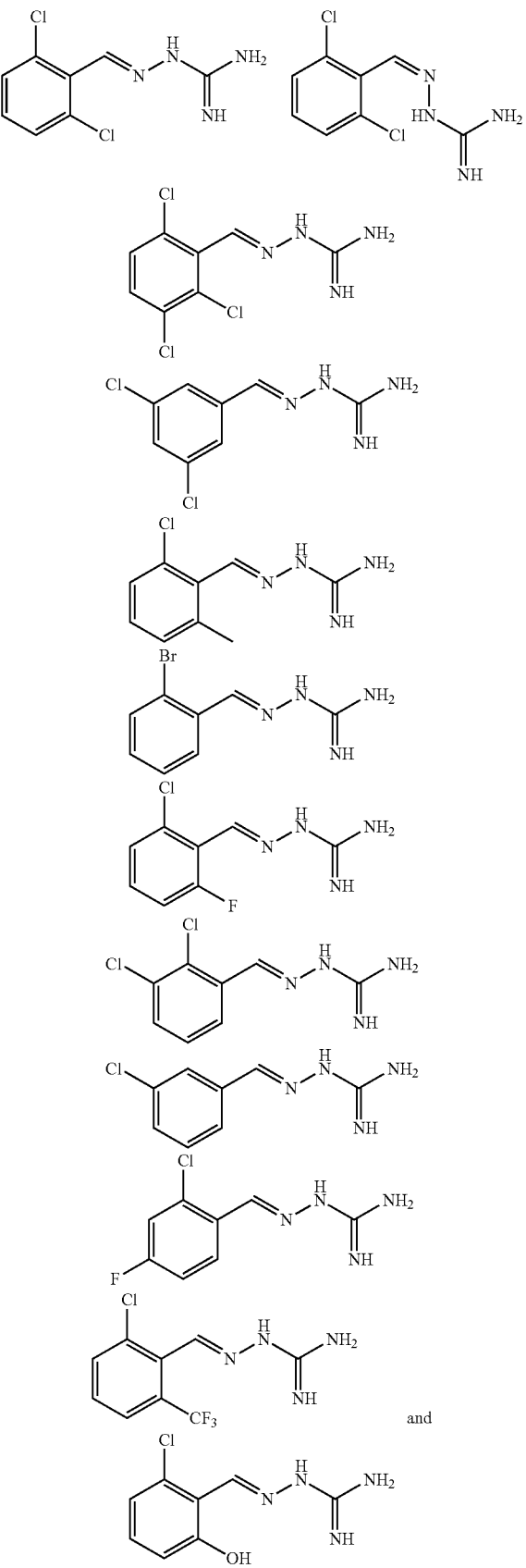

and pharmaceutically acceptable salts thereof.

In one embodiment, the compound administered in the method for treating Prion disease is a compound of formula Ia or Ib:

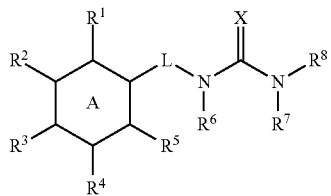

Ia

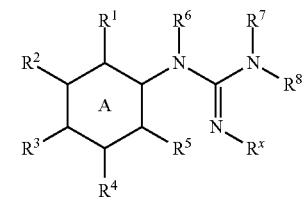

Ib or a pharmaceutically acceptable salt thereof;
i) wherein the compound of formula Ia:
ring A is phenyl;
the group

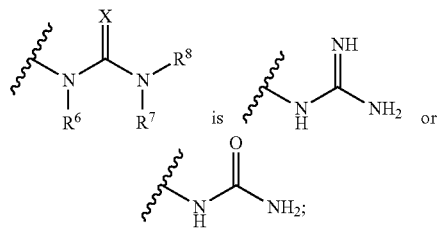

ii) wherein the compound of formula Ib:
ring A is phenyl;
the group

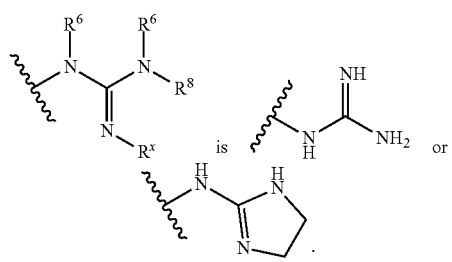

In one embodiment, the compound administered in the method for treating Prion disease is selected from the group consisting of:

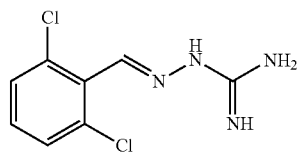
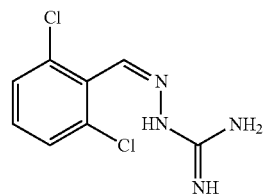

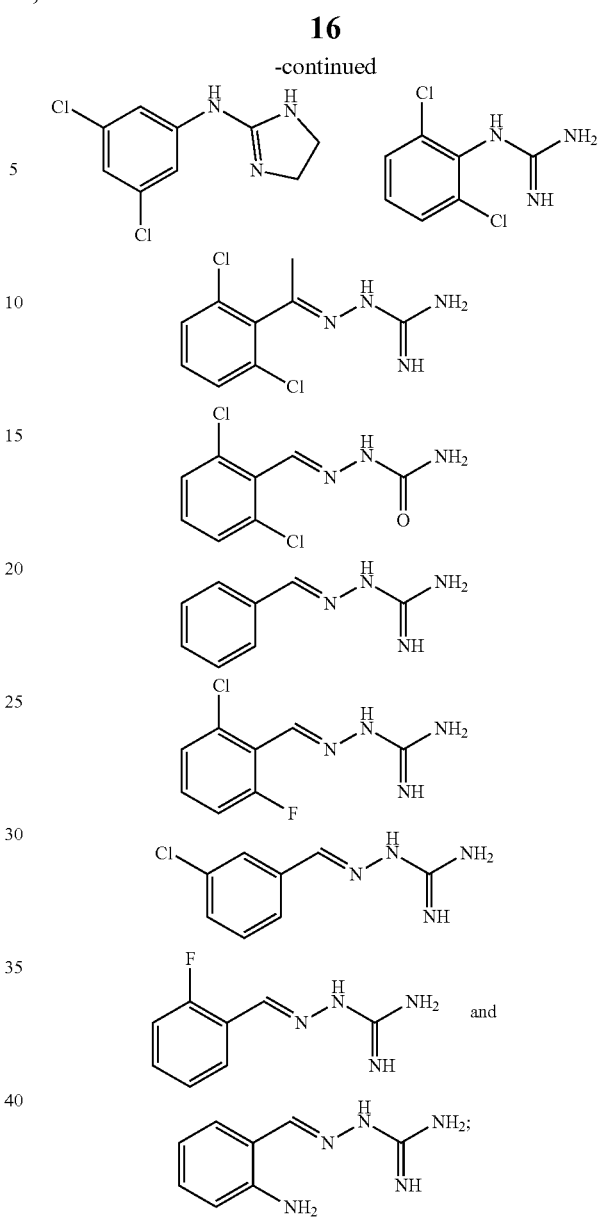

and pharmaceutically acceptable salts thereof.

In one embodiment, the compound administered in the method for treating multiple sclerosis is a compound of formula Ia:

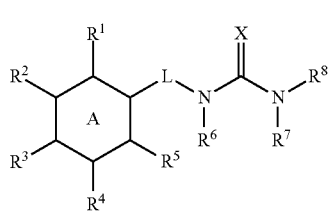

Ia or a pharmaceutically acceptable salt thereof, wherein:
ring A is phenyl;
at least one of $R^1$, $R^2$, $R^3$, $R^4$, and $R^5$ is Cl or Br; and the group

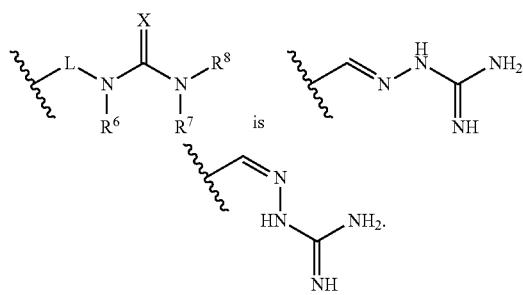

In one embodiment, the compound administered in the method for treating multiple sclerosis is

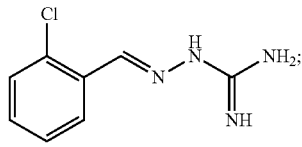 [SMILES: N=C(N)N/N=C/c1ccccc1Cl]

or a pharmaceutically acceptable salt.

In one embodiment, the compound administered in the method for producing analgesia is a compound of formula Ia:

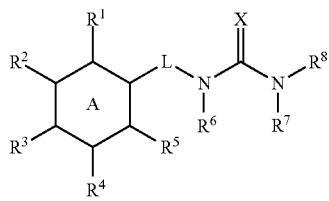

Ia or a pharmaceutically acceptable salt thereof, wherein:
ring A is phenyl;
$R^1$ is not hydrogen;
$R^5$ is not hydrogen;
and the group

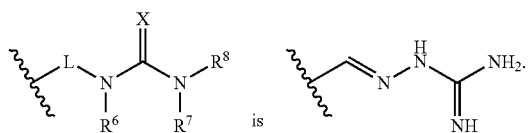

In one embodiment, the compound administered in the method for producing analgesia is selected from the group consisting of:

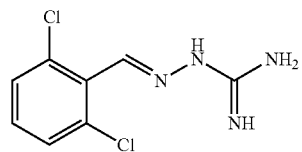

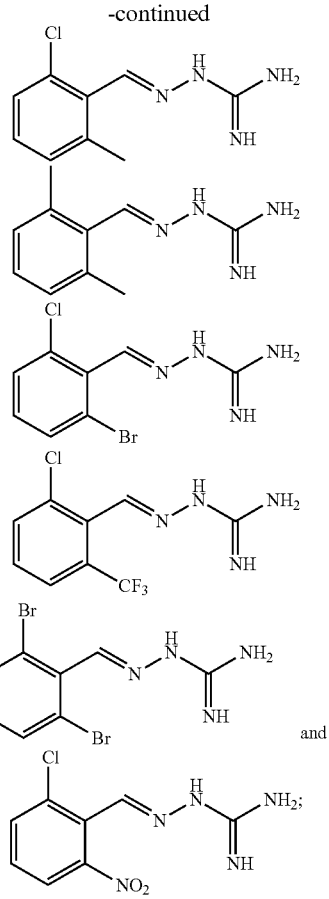

and pharmaceutically acceptable salts thereof.

The invention provides a method for modulating (e.g., increasing or decreasing) the activity of α2-adrenergic receptor in vivo or in vitro comprising contacting the receptor with an effective amount of compound of formula Ia, Ib or Ic, or a pharmaceutically acceptable salt thereof.

In one embodiment, the α2-adrenergic receptor is $\alpha_{2B}$-adrenergic receptor and or $\alpha_{2C}$-adrenergic receptor.

In one embodiment, the invention also provides novel compounds of formula Ia, Ib or Ic, which are compounds of the invention.

In one embodiment, the compound is a compound of formula Ia, Ib or Ic, or a pharmaceutically acceptable salt thereof, provided that the compound is not:

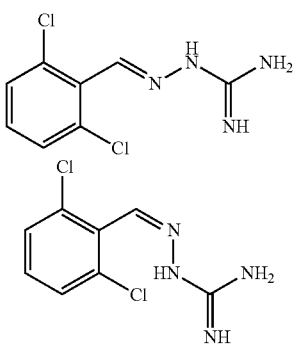

-continued
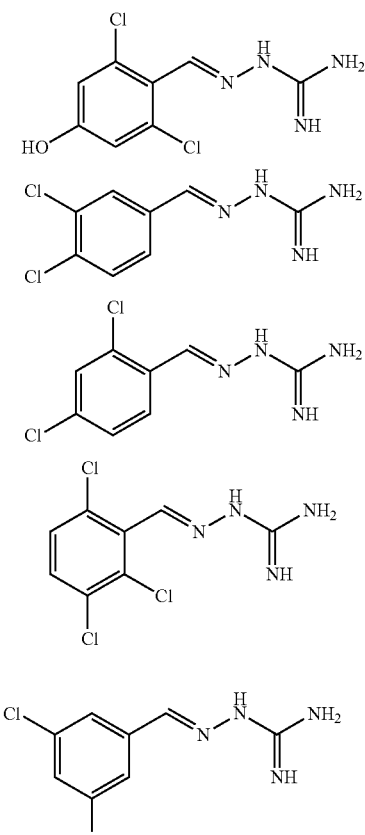
In one embodiment, the compound is a compound of formula Ia:
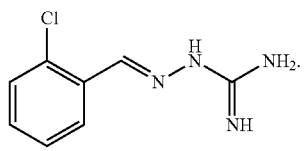
or a pharmaceutically acceptable salt thereof;
provided that that the compound is not:
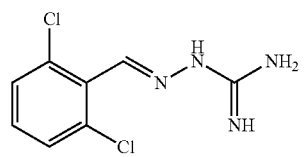
-continued
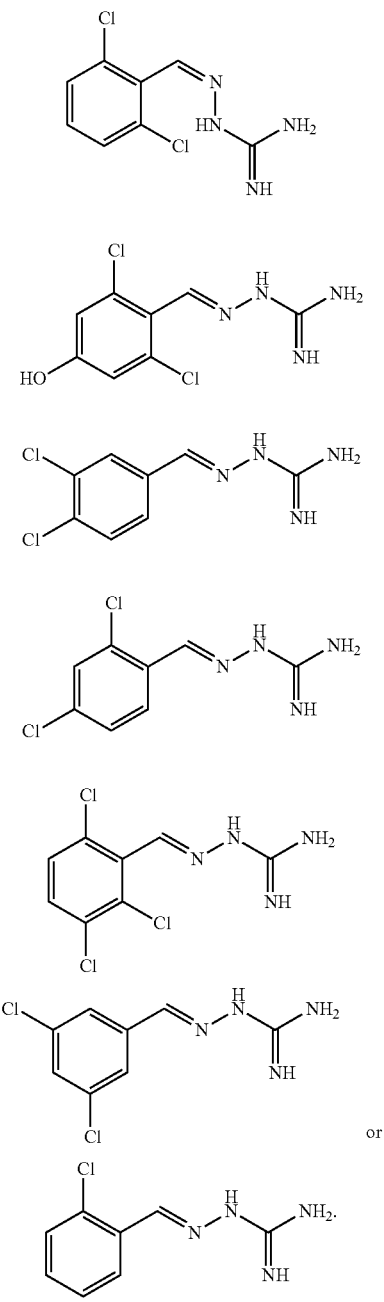
In one embodiment, the compound is a compound of formula Ib:
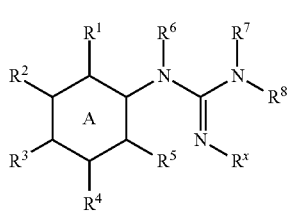
or a pharmaceutically acceptable salt thereof.

In one embodiment, the compound is a compound of formula Ic:

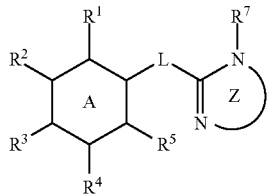

Ic or a pharmaceutically acceptable salt thereof.

In one embodiment, the compound is a compound of formula Ia:

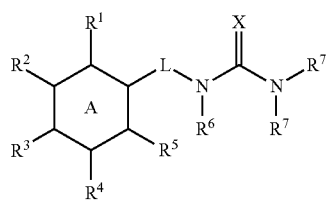

Ia or a pharmaceutically acceptable salt thereof, wherein X is O or S.

In one embodiment, the compound is a compound of formula Id:

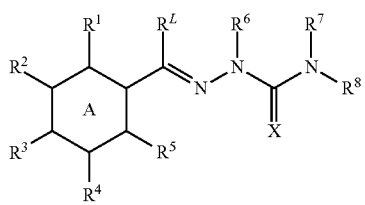

Id or a pharmaceutically acceptable salt thereof, wherein:

ring A is phenyl or 6-membered heteroaryl;

$R^1$ is absent, hydrogen, $C_{1-4}$ alkyl, $C_{1-4}$ haloalkyl, $C_{3-8}$ cycloalkyl, —F, —Cl, —Br, —I, —OR$^a$, —SR$^a$, —N(R$^a$)$_2$, —NO$_2$ or —CN;

$R^2$ is absent, hydrogen, $C_{1-4}$ alkyl, $C_{1-4}$ haloalkyl, $C_{3-8}$ cycloalkyl, —F, —Cl, —Br, —I, —OR$^b$, —SR$^b$, —N(R$^b$)$_2$, —NO$_2$ or —CN;

$R^3$ is absent, hydrogen, $C_{1-4}$ alkyl, $C_{1-4}$ haloalkyl, $C_{3-8}$ cycloalkyl, —F, —Cl, —Br, —I, —OR$^c$, —SR$^c$, —N(R$^c$)$_2$, —NO$_2$ or —CN;

$R^4$ is absent, hydrogen, $C_{1-4}$ alkyl, $C_{1-4}$ haloalkyl, $C_{3-8}$ cycloalkyl, —F, —Cl, —Br, —I, —OR$^d$, —SR$^d$, —N(R$^d$)$_2$, —NO$_2$ or —CN;

$R^5$ is absent, hydrogen, $C_{1-4}$ alkyl, $C_{1-4}$ haloalkyl, $C_{3-8}$ cycloalkyl, —F, —Cl, —Br, —I, —OR$^e$, —SR$^e$, —N(R$^e$)$_2$, —NO$_2$ or —CN;

$R^L$ is $C_{1-4}$ alkyl, $C_{1-4}$ haloalkyl or $C_{3-8}$s cycloalkyl;

$R^6$ is hydrogen, or $C_{1-6}$ alkyl that is optionally substituted with one or more groups selected from —F, —Cl, —Br, —I, —OR$^f$, —SR$^f$, —N(R$^f$)$_2$, oxo, —NO$_2$ or —CN;

$R^7$ is hydrogen, or $C_{1-6}$ alkyl that is optionally substituted with one or more groups selected from —F, —Cl, —Br, —I, —OR$^g$, —SR$^g$, —N(R$^g$)$_2$, oxo, —NO$_2$ or —CN;

$R^8$ is hydrogen, or $C_{1-6}$ alkyl that is optionally substituted with one or more groups selected from —F, —Cl, —Br, —I, —OR$^h$, —SR$^h$, —N(R$^h$)$_2$, oxo, —NO$_2$ or —CN;

X is =O, =S or =N—R$^x$; wherein R$^x$ is hydrogen, or $C_{1-6}$ alkyl that is optionally substituted with one or more groups selected from —F, —Cl, —Br, —I, —OR$^i$, —SR$^i$, —N(R$^i$)$_2$, —NO$_2$ or —CN; or R$^x$ and $R^8$ taken together with the nitrogen atoms to which they are attached form a heteroaryl or an unsaturated heterocycle; wherein the heteroaryl and heterocycle are optionally substituted with one or more groups selected from —F, —Cl, —Br, —I, —OR$^i$, —SR$^i$, —N(R$^i$)$_2$, —NO$_2$ or —CN;

each R$^a$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^a$ groups taken together with the nitrogen to which they are attached form pyrrolidinyl, piperidinyl, piperazinyl or morpholinyl;

each R$^b$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^b$ groups taken together with the nitrogen to which they are attached form pyrrolidinyl, piperidinyl, piperazinyl or morpholinyl;

each R$^c$ is independently hydrogen, C1-4 alkyl or C1-4 haloalkyl, wherein the C1-4 alkyl and $C_{1-4}$ haloalkyl are optionally substituted with aryl or heteroaryl; or two R$^c$ groups taken together with the nitrogen to which they are attached form pyrrolidinyl, piperidinyl, piperazinyl or morpholinyl;

each R$^d$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^d$ groups taken together with the nitrogen to which they are attached form pyrrolidinyl, piperidinyl, piperazinyl or morpholinyl;

each R$^e$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^e$ groups taken together with the nitrogen to which they are attached form pyrrolidinyl, piperidinyl, piperazinyl or morpholinyl;

each R$^f$ is independently hydrogen, $C_{1-4}$ alkyl or $C_{1-4}$ haloalkyl; or two R$^f$ groups taken together with the nitrogen to which they are attached form pyrrolidinyl, piperidinyl, piperazinyl or morpholinyl;

each R$^g$ is independently hydrogen, $C_{1-4}$ alkyl or $C_{1-4}$ haloalkyl; or two R$^g$ groups taken together with the nitrogen to which they are attached form pyrrolidinyl, piperidinyl, piperazinyl or morpholinyl;

each R$^h$ is independently hydrogen, $C_{1-4}$ alkyl or $C_{1-4}$ haloalkyl; or two R$^h$ groups taken together with the nitrogen to which they are attached form pyrrolidinyl, piperidinyl, piperazinyl or morpholinyl; and each R$^i$ is independently hydrogen, $C_{1-4}$ alkyl or $C_{1-4}$ haloalkyl; or two R$^i$ groups taken together with the nitrogen to which they are attached form pyrrolidinyl, piperidinyl, piperazinyl or morpholinyl.

In one embodiment, the compound is a compound of formula Ie:

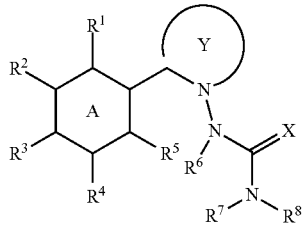

Ie or a pharmaceutically acceptable salt thereof, wherein:
ring A is phenyl or 6-membered heteroaryl;
R¹ is absent, hydrogen, $C_{1-4}$ alkyl, $C_{1-4}$ haloalkyl, $C_{3-8}$ cycloalkyl, —F, —Cl, —Br, —I, —OR$^a$, —SR$^a$, —N(R$^a$)$_2$, —NO$_2$ or —CN;
R² is absent, hydrogen, $C_{1-4}$ alkyl, $C_{1-4}$ haloalkyl, $C_{3-8}$ cycloalkyl, —F, —Cl, —Br, —I, —OR$^b$, —SR$^b$, —N(R$^b$)$_2$, —NO$_2$ or —CN;
R³ is absent, hydrogen, $C_{1-4}$ alkyl, $C_{1-4}$ haloalkyl, $C_{3-8}$ cycloalkyl, —F, —Cl, —Br, —I, —OR$^c$, —SR$^c$, —N(R$^c$)$_2$, —NO$_2$ or —CN;
R⁴ is absent, hydrogen, $C_{1-4}$ alkyl, $C_{1-4}$ haloalkyl, $C_{3-8}$ cycloalkyl, —F, —Cl, —Br, —I, —OR$^d$, —SR$^d$, —N(R$^d$)$_2$, —NO$_2$ or —CN;
R⁵ is absent, hydrogen, $C_{1-4}$ alkyl, $C_{1-4}$ haloalkyl, $C_{3-8}$ cycloalkyl, —F, —Cl, —Br, —I, —OR$^e$, —SR$^e$, —N(R$^e$)$_2$, —NO$_2$ or —CN;
ring Y is heteroaryl that is optionally substituted with one or more groups selected from —F, —Cl, —Br, —I, —OR$^y$, —SR$^y$, —N(R$^y$)$_2$, —NO$_2$ or —CN;
R⁶ is hydrogen, or $C_{1-6}$ alkyl that is optionally substituted with one or more groups selected from —F, —Cl, —Br, —I, —OR$^f$, —SR$^f$, —N(R$^f$)$_2$, oxo, —NO$_2$ or —CN;
R⁷ is hydrogen, or $C_{1-6}$ alkyl that is optionally substituted with one or more groups selected from —F, —Cl, —Br, —I, —OR$^g$, —SR$^g$, —N(R$^g$)$_2$, oxo, —NO$_2$ or —CN;
R⁸ is hydrogen, or $C_{1-6}$ alkyl that is optionally substituted with one or more groups selected from —F, —Cl, —Br, —I, —OR$^h$, —SR$^h$, —N(R$^h$)$_2$, oxo, —NO$_2$ or —CN;
X is =O, =S or =N—R$^x$; wherein R$^x$ is hydrogen, or $C_{1-6}$ alkyl that is optionally substituted with one or more groups selected from —F, —Cl, —Br, —I, —OR$^i$, —SR$^i$, —N(R$^i$)$_2$, —NO$_2$ or —CN; or R$^x$ and R⁸ taken together with the nitrogen atoms to which they are attached form a heteroaryl or an unsaturated heterocycle; wherein the heteroaryl and heterocycle are optionally substituted with one or more groups selected from —F, —Cl, —Br, —I, —OR$^i$, —SR$^i$, —N(R$^i$)$_2$, —NO$_2$ or —CN;
each R$^a$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^a$ groups taken together with the nitrogen to which they are attached form pyrrolidinyl, piperidinyl, piperazinyl or morpholinyl;
each R$^b$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^b$ groups taken together with the nitrogen to which they are attached form pyrrolidinyl, piperidinyl, piperazinyl or morpholinyl;
each R$^c$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^c$ groups taken together with the nitrogen to which they are attached form pyrrolidinyl, piperidinyl, piperazinyl or morpholinyl;
each R$^d$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^d$ groups taken together with the nitrogen to which they are attached form pyrrolidinyl, piperidinyl, piperazinyl or morpholinyl;
each R$^e$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^e$ groups taken together with the nitrogen to which they are attached form pyrrolidinyl, piperidinyl, piperazinyl or morpholinyl;
each R$^f$ is independently hydrogen, $C_{1-4}$ alkyl or $C_{1-4}$ haloalkyl; or two R$^f$ groups taken together with the nitrogen to which they are attached form pyrrolidinyl, piperidinyl, piperazinyl or morpholinyl;
each R$^g$ is independently hydrogen, $C_{1-4}$ alkyl or $C_{1-4}$ haloalkyl; or two R$^g$ groups taken together with the nitrogen to which they are attached form pyrrolidinyl, piperidinyl, piperazinyl or morpholinyl;
each R$^h$ is independently hydrogen, $C_{1-4}$ alkyl or $C_{1-4}$ haloalkyl; or two R$^h$ groups taken together with the nitrogen to which they are attached form pyrrolidinyl, piperidinyl, piperazinyl or morpholinyl;
each R$^i$ is independently hydrogen, $C_{1-4}$ alkyl or $C_{1-4}$ haloalkyl; or two R$^i$ groups taken together with the nitrogen to which they are attached form pyrrolidinyl, piperidinyl, piperazinyl or morpholinyl; and
each R$^y$ is independently hydrogen, $C_{1-4}$ alkyl or $C_{1-4}$ haloalkyl; or two R$^y$ groups taken together with the nitrogen to which they are attached form pyrrolidinyl, piperidinyl, piperazinyl or morpholinyl.

In one embodiment, the compound is a compound of formula Ig:

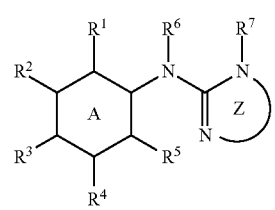

Ig or a pharmaceutically acceptable salt thereof, wherein:
ring A is phenyl or 6-membered heteroaryl;
R¹ is absent, hydrogen, $C_{1-4}$ alkyl, $C_{1-4}$ haloalkyl, $C_{3-8}$ cycloalkyl, —F, —Cl, —Br, —I, —OR$^a$, —SR$^a$, —N(R$^a$)$_2$, —NO$_2$ or —CN;
R² is absent, hydrogen, $C_{1-4}$ alkyl, $C_{1-4}$ haloalkyl, $C_{3-8}$ cycloalkyl, —F, —Cl, —Br, —I, —OR$^b$, —SR$^b$, —N(R$^b$)$_2$, —NO$_2$ or —CN;
R³ is absent, hydrogen, $C_{1-4}$ alkyl, $C_{1-4}$ haloalkyl, $C_{3-8}$ cycloalkyl, —F, —Cl, —Br, —I, —OR$^c$, —SR$^c$, —N(R$^c$)$_2$, —NO$_2$ or —CN;
R⁴ is absent, hydrogen, $C_{1-4}$ alkyl, $C_{1-4}$ haloalkyl, $C_{3-8}$ cycloalkyl, —F, —Cl, —Br, —I, —OR$^d$, —SR$^d$, —N(R$^d$)$_2$, —NO$_2$ or —CN;
R⁵ is absent, hydrogen, $C_{1-4}$ alkyl, $C_{1-4}$ haloalkyl, $C_{3-8}$ cycloalkyl, —F, —Cl, —Br, —I, —OR$^e$, —SR$^e$, —N(R$^e$)$_2$, —NO$_2$ or —CN;

$R^6$ is hydrogen, or $C_{1-6}$ alkyl that is optionally substituted with one or more groups selected from —F, —Cl, —Br, —I, —OR$^f$, —SR$^f$, —N(R$^f$)$_2$, oxo, —NO$_2$ or —CN; L is $C_{1-4}$ alkylene that is optionally substituted with one or more groups selected from halo, hydroxy or $C_3$-$8$s cycloalkyl;

$R^7$ is hydrogen, or $C_{1-6}$ alkyl that is optionally substituted with one or more groups selected from —F, —Cl, —Br, —I, —OR$^g$, —SR$^g$, —N(R$^g$)$_2$, oxo, —NO$_2$ or —CN;

ring Z is heteroaryl or unsaturated heterocycle; wherein the heteroaryl and heterocycle are optionally substituted with one or more groups selected from —F, —Cl, —Br, —I, —OR$^i$, —SR$^i$, —N(R$^i$)$_2$, —NO$_2$ or —CN;

each $R^a$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^a$ groups taken together with the nitrogen to which they are attached form pyrrolidinyl, piperidinyl, piperazinyl or morpholinyl;

each $R^b$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^b$ groups taken together with the nitrogen to which they are attached form pyrrolidinyl, piperidinyl, piperazinyl or morpholinyl;

each $R^c$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^c$ groups taken together with the nitrogen to which they are attached form pyrrolidinyl, piperidinyl, piperazinyl or morpholinyl;

each $R^d$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^d$ groups taken together with the nitrogen to which they are attached form pyrrolidinyl, piperidinyl, piperazinyl or morpholinyl;

each $R^e$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^e$ groups taken together with the nitrogen to which they are attached form pyrrolidinyl, piperidinyl, piperazinyl or morpholinyl;

each $R^f$ is independently hydrogen, $C_{1-4}$ alkyl or $C_{1-4}$ haloalkyl; or two $R^f$ groups taken together with the nitrogen to which they are attached form pyrrolidinyl, piperidinyl, piperazinyl or morpholinyl;

each $R^g$ is independently hydrogen, $C_{1-4}$ alkyl or $C_{1-4}$ haloalkyl; or two $R^g$ groups taken together with the nitrogen to which they are attached form pyrrolidinyl, piperidinyl, piperazinyl or morpholinyl; and each $R^i$ is independently hydrogen, $C_{1-4}$ alkyl or $C_{1-4}$ haloalkyl; or two $R^i$ groups taken together with the nitrogen to which they are attached form pyrrolidinyl, piperidinyl, piperazinyl or morpholinyl.

In one embodiment, ring A is phenyl.

In one embodiment, $R^1$ is hydrogen, —F, —Cl, —Br, —I or $C_{1-4}$ alkyl.

In one embodiment, $R^1$ is hydrogen, —F, —Cl, —Br, —I or -Me.

In one embodiment, $R^2$ is hydrogen or —Cl.

In one embodiment, $R^3$ is hydrogen, —F, —Cl, or —OR$^e$; $R^e$ is hydrogen, or $C_{1-4}$ alkyl that is optionally substituted with aryl or heteroaryl.

In one embodiment, $R^3$ is hydrogen, —F, —Cl, —OH, —OCH$_3$, or —OCH$_2$Ph.

In one embodiment, $R^4$ is hydrogen, or —Cl.

In one embodiment, $R^5$ is hydrogen, $C_{1-4}$ alkyl, $C_{1-4}$ haloalkyl, —F, —Cl, —Br, —I, —OR$^e$, —N(R$^e$)$_2$ or —NO$_2$.

In one embodiment, $R^5$ is hydrogen, -Me, —CF$_3$, —F, —Cl, —Br, —I, —OH, —NH$_2$ or —NO$_2$.

In one embodiment, at least one of $R^1$, $R^2$, $R^3$, $R^4$ and $R^5$ is not hydrogen.

In one embodiment, at least two of $R^1$, $R^2$, $R^3$, $R^4$ and $R^5$ are hydrogen.

In one embodiment, the group

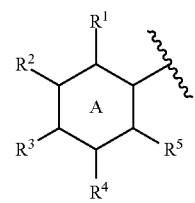

is selected from the group consisting of:

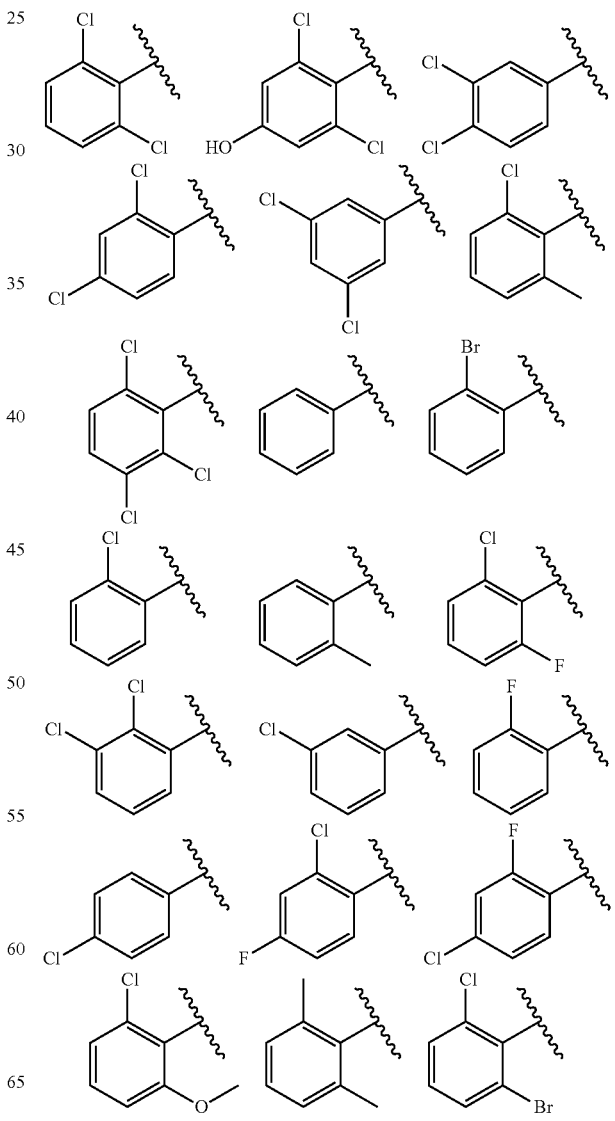

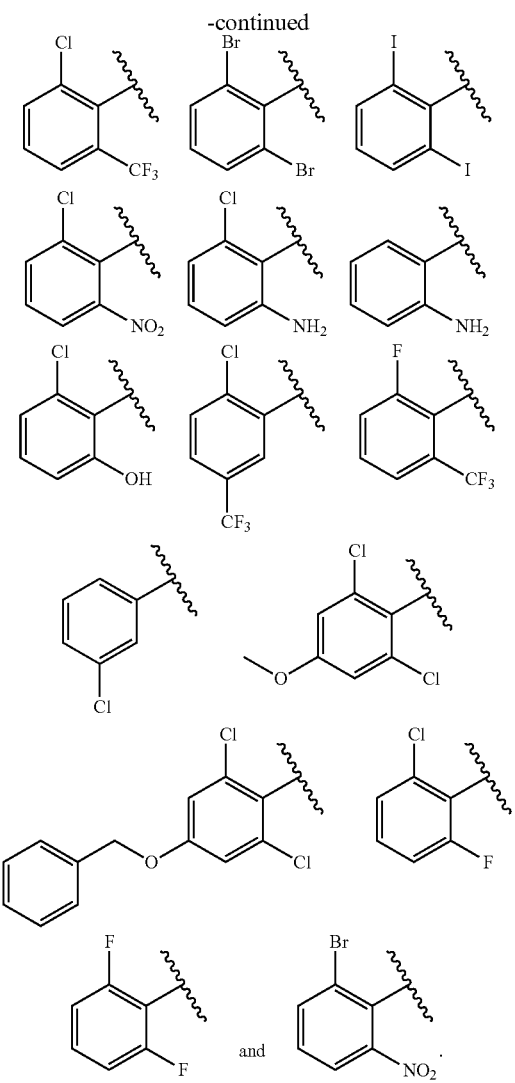

In one embodiment, L is

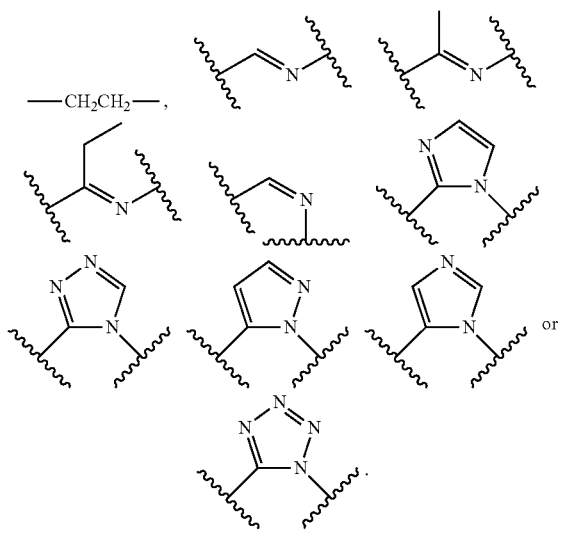

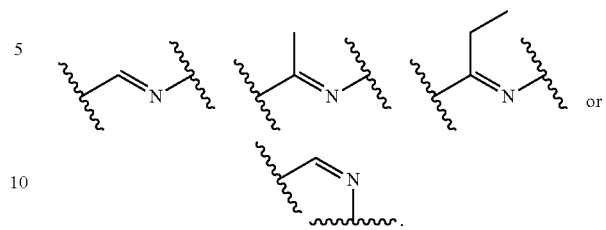

In one embodiment, ring Y is

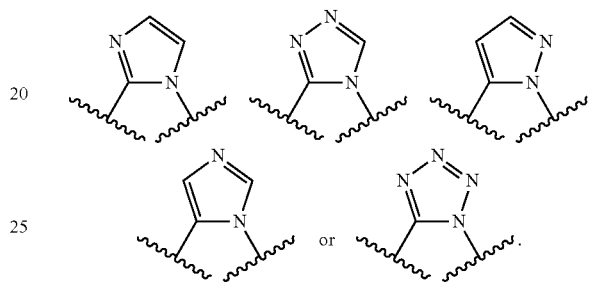

In one embodiment, $R^6$ is hydrogen or —CH$_3$.
In one embodiment, $R^8$ is hydrogen or —CH$_3$.
In one embodiment, $R^8$ is hydrogen or —CH3.
In one embodiment, X is =N—$R^x$; and $R^x$ is hydrogen, or $C_{1-6}$ alkyl that is optionally substituted with one or more groups selected from —F, —Cl, —Br, —I, —OR$^i$, —SR$^i$, —N(R$^i$)$_2$, —NO$_2$ or —CN.
In one embodiment, $R^x$ is hydrogen or —CH$_3$.
In one embodiment, $R^x$ and $R^8$ taken together with the nitrogen atoms to which they are attached form an unsaturated heterocycle.
In one embodiment, $R^7$ is hydrogen; $R^x$ and $R^8$ taken together with the carbon and nitrogen to which they are attached form

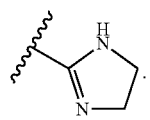

In one embodiment, wherein X is =O or =S.
In one embodiment, $R^6$, $R^7$, $R^8$ and $R^x$ are hydrogen.
In one embodiment, wherein $R^6$ and $R^7$ are hydrogen; $R^x$ and $R^8$ taken together with the nitrogen atoms to which they are attached form

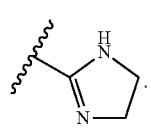

In one embodiment, L is —CH$_2$—, or —CH(CH$_3$)—.

In one embodiment, R⁷ is hydrogen; ring Z is

In one embodiment, the compound is selected from the group consisting of:

31
-continued
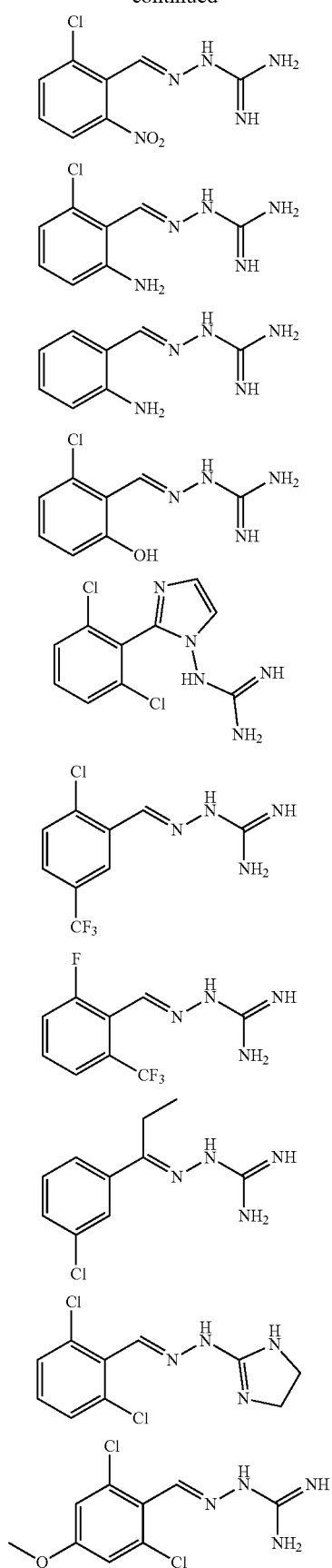
32
-continued
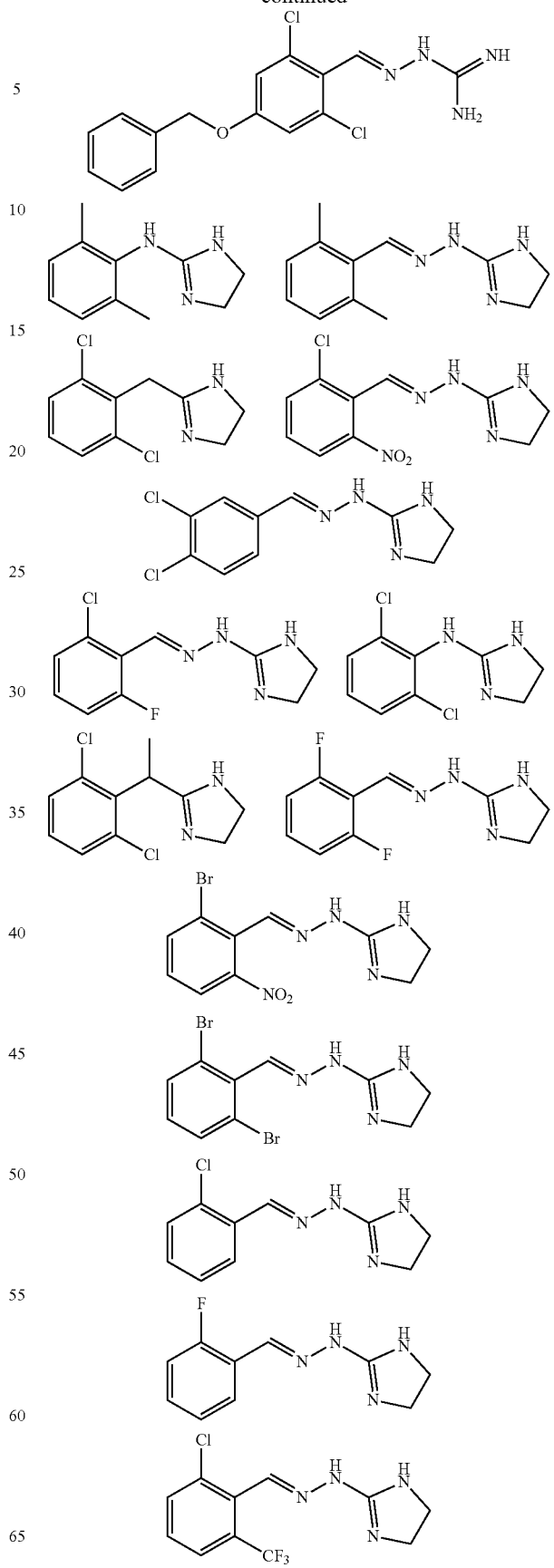

-continued

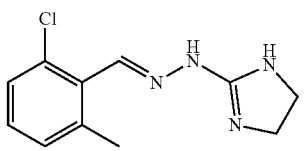 and

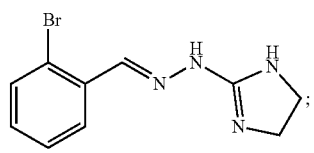

and pharmaceutically acceptable salts thereof.

In one embodiment, the compound is selected from the group consisting of:

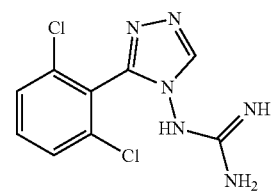 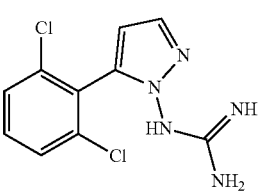

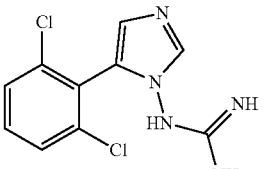 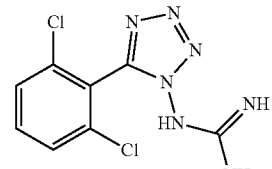

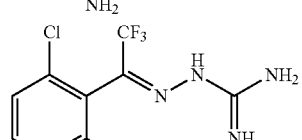

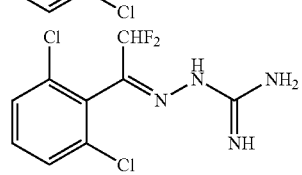

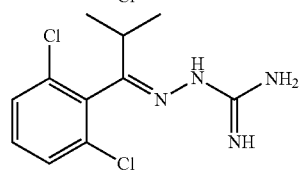

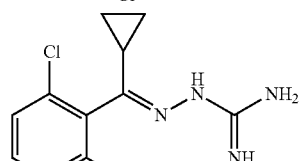

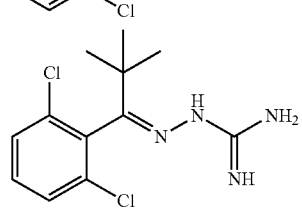

-continued

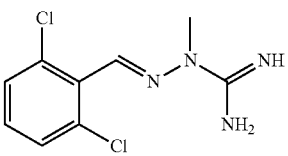

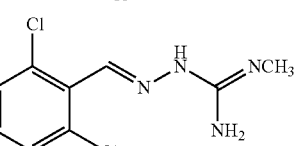

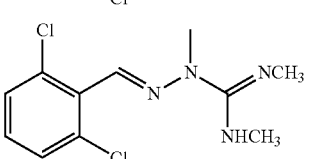

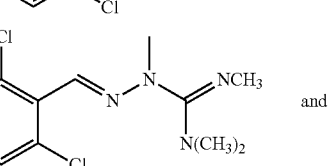 and

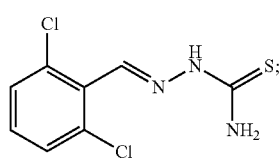 [SMILES: NC(=S)N/N=C/c1c(Cl)cccc1Cl]

and pharmaceutically acceptable salts thereof.

In one embodiment, the compound is a compound of formula Ia', which is a compound of formula Ij:

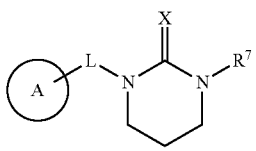

Ij or a pharmaceutically acceptable salt thereof.

In one embodiment, the compound is a compound of formula Ia', which is a compound of formula Ik:

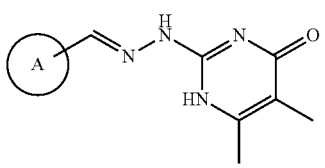

Ik or a pharmaceutically acceptable salt thereof.

In one embodiment, the invention provides a method for treating A neurodegenerative disorder in an animal (e.g., a mammal, such as a human) comprising administering to the animal an effective amount of compound of formula Ia, Ib or Ic:

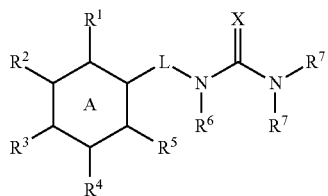

Ia

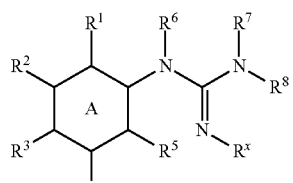

Ib

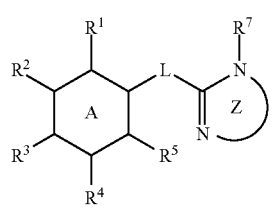

Ic or a pharmaceutically acceptable salt thereof;
i) wherein the compound of formula Ia:
ring A is phenyl or 6-membered heteroaryl;
$R^1$ is absent, hydrogen, $C_{1-4}$ alkyl, $C_{1-4}$ haloalkyl, $C_{3-8}$ cycloalkyl, —F, —Cl, —Br, —I, —OR$^a$, —SR$^a$, —N(R$^a$)$_2$, —NO$_2$ or —CN;
$R^2$ is absent, hydrogen, $C_{1-4}$ alkyl, $C_{1-4}$ haloalkyl, $C_{3-8}$ cycloalkyl, —F, —Cl, —Br, —I, —OR$^b$, —SR$^b$, —N(R$^b$)$_2$, —NO$_2$ or —CN;
$R^3$ is absent, hydrogen, $C_{1-4}$ alkyl, $C_{1-4}$ haloalkyl, $C_{3-8}$ cycloalkyl, —F, —Cl, —Br, —I, —OR$^c$, —SR$^c$, —N(R$^c$)$_2$, —NO$_2$ or —CN;
$R^4$ is absent, hydrogen, $C_{1-4}$ alkyl, $C_{1-4}$ haloalkyl, $C_{3-8}$ cycloalkyl, —F, —Cl, —Br, —I, —OR$^d$, —SR$^d$, —N(R$^d$)$_2$, —NO$_2$ or —CN;
$R^5$ is absent, hydrogen, $C_{1-4}$ alkyl, $C_{1-4}$ haloalkyl, $C_{3-8}$ cycloalkyl, —F, —Cl, —Br, —I, —OR$^e$, —SR$^e$, —N(R$^e$)$_2$, —NO$_2$ or —CN;
L is selected from the group consisting of:
—CH$_2$CH$_2$—

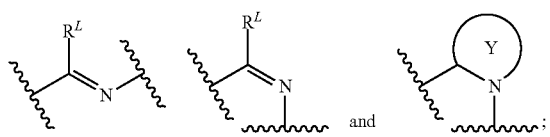

$R^L$ is hydrogen, $C_{1-4}$ alkyl, $C_{1-4}$ haloalkyl or $C_{3-8}$ cycloalkyl;
ring Y is heteroaryl that is optionally substituted with one or more groups selected from —F, —Cl, —Br, —I, —OR$^y$, —SR$^y$, —N(R$^y$)$_2$, —NO$_2$ or —CN;
$R^6$ is hydrogen, or $C_{1-6}$ alkyl that is optionally substituted with one or more groups selected from —F, —Cl, —Br, —I, —OR$^f$, —SR$^f$, —N(R$^f$)$_2$, oxo, —NO$_2$ or —CN;
$R^7$ is hydrogen, or $C_{1-6}$ alkyl that is optionally substituted with one or more groups selected from —F, —Cl, —Br, —I, —OR$^g$, —SR$^g$, —N(R$^g$)$_2$, oxo, —NO$_2$ or —CN;

$R^8$ is hydrogen, or $C_{1-6}$ alkyl that is optionally substituted with one or more groups selected from —F, —Cl, —Br, —I, —OR$^h$, —SR$^h$, —N(R$^h$)$_2$, oxo, —NO$_2$ or —CN;

X is =O, =S or =N—R$^x$; wherein R$^x$ is hydrogen, or $C_{1-6}$ alkyl that is optionally substituted with one or more groups selected from —F, —Cl, —Br, —I, —OR$^i$, —SR$^i$, —N(R$^i$)$_2$, —NO$_2$ or —CN; or R$^x$ and R$^8$ taken together with the nitrogen atoms to which they are attached form a heteroaryl or an unsaturated heterocycle; wherein the heteroaryl and heterocycle are optionally substituted with one or more groups selected from —F, —Cl, —Br, —I, —OR$^i$, —SR$^i$, —N(R$^i$)$_2$, —NO$_2$ or —CN;

each R$^a$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^a$ groups taken together with the nitrogen to which they are attached form pyrrolidinyl, piperidinyl, piperazinyl or morpholinyl;

each R$^b$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^b$ groups taken together with the nitrogen to which they are attached form pyrrolidinyl, piperidinyl, piperazinyl or morpholinyl;

each R$^c$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^c$ groups taken together with the nitrogen to which they are attached form pyrrolidinyl, piperidinyl, piperazinyl or morpholinyl;

each R$^d$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^d$ groups taken together with the nitrogen to which they are attached form pyrrolidinyl, piperidinyl, piperazinyl or morpholinyl;

each R$^e$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^e$ groups taken together with the nitrogen to which they are attached form pyrrolidinyl, piperidinyl, piperazinyl or morpholinyl;

each R$^f$ is independently hydrogen, $C_{1-4}$ alkyl or $C_{1-4}$ haloalkyl; or two R$^f$ groups taken together with the nitrogen to which they are attached form pyrrolidinyl, piperidinyl, piperazinyl or morpholinyl;

each R$^g$ is independently hydrogen, $C_{1-4}$ alkyl or $C_{1-4}$ haloalkyl; or two R$^g$ groups taken together with the nitrogen to which they are attached form pyrrolidinyl, piperidinyl, piperazinyl or morpholinyl;

each R$^h$ is independently hydrogen, $C_{1-4}$ alkyl or $C_{1-4}$ haloalkyl; or two R$^h$ groups taken together with the nitrogen to which they are attached form pyrrolidinyl, piperidinyl, piperazinyl or morpholinyl;

each R$^i$ is independently hydrogen, $C_{1-4}$ alkyl or $C_{1-4}$ haloalkyl; or two R$^i$ groups taken together with the nitrogen to which they are attached form pyrrolidinyl, piperidinyl, piperazinyl or morpholinyl; and each Ry is independently hydrogen, C1-4 alkyl or C1-4 haloalkyl; or two Ry groups taken together with the nitrogen to which they are attached form pyrrolidinyl, piperidinyl, piperazinyl or morpholinyl;

ii) wherein the compound of formula Ib:
ring A is phenyl or 6-membered heteroaryl;
$R^1$ is absent, hydrogen, $C_{1-4}$ alkyl, $C_{1-4}$ haloalkyl, $C_{3-8}$ cycloalkyl, —F, —Cl, —Br, —I, —OR$^a$, —SR$^a$, —N(R$^a$)$_2$, —NO$_2$ or —CN;
$R^2$ is absent, hydrogen, $C_{1-4}$ alkyl, $C_{1-4}$ haloalkyl, $C_{3-8}$ cycloalkyl, —F, —Cl, —Br, —I, —OR$^b$, —SR$^b$, —N(R$^b$)$_2$, —NO$_2$ or —CN;
$R^3$ is absent, hydrogen, $C_{1-4}$ alkyl, $C_{1-4}$ haloalkyl, $C_{3-8}$ cycloalkyl, —F, —Cl, —Br, —I, —OR$^c$, —SR$^c$, —N(R$^c$)$_2$, —NO$_2$ or —CN;
$R^4$ is absent, hydrogen, $C_{1-4}$ alkyl, $C_{1-4}$ haloalkyl, $C_{3-8}$ cycloalkyl, —F, —Cl, —Br, —I, —OR$^d$, —SR$^d$, —N(R$^d$)$_2$, —NO$_2$ or —CN;
$R^5$ is absent, hydrogen, $C_{1-4}$ alkyl, $C_{1-4}$ haloalkyl, $C_{3-8}$ cycloalkyl, —F, —Cl, —Br, —I, —OR$^e$, —SR$^e$, —N(R$^e$)$_2$, —NO$_2$ or —CN;
$R^6$ is hydrogen, or $C_{1-6}$ alkyl that is optionally substituted with one or more groups selected from —F, —Cl, —Br, —I, —OR$^f$, —SR$^f$, —N(R$^a$)$_2$, oxo, —NO$_2$ or —CN;
$R^7$ is hydrogen, or $C_{1-6}$ alkyl that is optionally substituted with one or more groups selected from —F, —Cl, —Br, —I, —OR$^g$, —SR$^g$, —N(R$^g$)$_2$, oxo, —NO$_2$ or —CN;
$R^8$ is hydrogen, or $C_{1-6}$ alkyl that is optionally substituted with one or more groups selected from —F, —Cl, —Br, —I, —OR$^h$, —SR$^h$, —N(R$^h$)$_2$, oxo, —NO$_2$ or —CN;
$R^x$ is hydrogen, or $C_{1-6}$ alkyl that is optionally substituted with one or more groups selected from —F, —Cl, —Br, —I, —OR$^i$, —SR$^i$, —N(R$^i$)$_2$, —NO$_2$ or —CN; or $R^x$ and $R^8$ taken together with the nitrogen atoms to which they are attached form a heteroaryl or an unsaturated heterocycle; wherein the heteroaryl and heterocycle are optionally substituted with one or more groups selected from —F, —Cl, —Br, —I, —OR$^i$, —SR$^i$, —N(R$^i$)$_2$, —NO$_2$ or —CN;
each $R^a$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^a$ groups taken together with the nitrogen to which they are attached form pyrrolidinyl, piperidinyl, piperazinyl or morpholinyl;
each $R^b$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^b$ groups taken together with the nitrogen to which they are attached form pyrrolidinyl, piperidinyl, piperazinyl or morpholinyl;
each $R^c$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^c$ groups taken together with the nitrogen to which they are attached form pyrrolidinyl, piperidinyl, piperazinyl or morpholinyl;
each $R^d$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^d$ groups taken together with the nitrogen to which they are attached form pyrrolidinyl, piperidinyl, piperazinyl or morpholinyl;
each $R^e$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^e$ groups taken together with the nitrogen to which they are attached form pyrrolidinyl, piperidinyl, piperazinyl or morpholinyl;
each $R^f$ is independently hydrogen, $C_{1-4}$ alkyl or $C_{1-4}$ haloalkyl; or two $R^f$ groups taken together with the nitrogen to which they are attached form pyrrolidinyl, piperidinyl, piperazinyl or morpholinyl;
each $R^g$ is independently hydrogen, $C_{1-4}$ alkyl or $C_{1-4}$ haloalkyl; or two $R^g$ groups taken together with the nitrogen to which they are attached form pyrrolidinyl, piperidinyl, piperazinyl or morpholinyl;
each $R^h$ is independently hydrogen, $C_{1-4}$ alkyl or $C_{1-4}$ haloalkyl; or two $R^h$ groups taken together with the nitrogen to which they are attached form pyrrolidinyl, piperidinyl, piperazinyl or morpholinyl; and
each $R^i$ is independently hydrogen, $C_{1-4}$ alkyl or $C_{1-4}$ haloalkyl; or two $R^i$ groups taken together with the nitrogen to which they are attached form pyrrolidinyl, piperidinyl, piperazinyl or morpholinyl;
iii) wherein the compound of formula Ic:
ring A is phenyl or 6-membered heteroaryl;
$R^1$ is absent, hydrogen, $C_{1-4}$ alkyl, $C_{1-4}$ haloalkyl, $C_{3-8}$ cycloalkyl, —F, —Cl, —Br, —I, —OR$^a$, —SR$^a$, —N(R$^a$)$_2$, —NO$_2$ or —CN;
$R^2$ is absent, hydrogen, $C_{1-4}$ alkyl, $C_{1-4}$ haloalkyl, $C_{3-8}$ cycloalkyl, —F, —Cl, —Br, —I, —OR$^b$, —SR$^b$, —N(R$^b$)$_2$, —NO$_2$ or —CN;
$R^3$ is absent, hydrogen, $C_{1-4}$ alkyl, $C_{1-4}$ haloalkyl, $C_{3-8}$ cycloalkyl, —F, —Cl, —Br, —I, —OR$^c$, —SR$^c$, —N(R$^c$)$_2$, —NO$_2$ or —CN;
$R^4$ is absent, hydrogen, $C_{1-4}$ alkyl, $C_{1-4}$ haloalkyl, $C_{3-8}$ cycloalkyl, —F, —Cl, —Br, —I, —OR$^d$, —SR$^d$, —N(R$^d$)$_2$, —NO$_2$ or —CN;
$R^5$ is absent, hydrogen, $C_{1-4}$ alkyl, $C_{1-4}$ haloalkyl, $C_{3-8}$ cycloalkyl, —F, —Cl, —Br, —I, —OR$^e$, —SR$^e$, —N(R$^e$)$_2$, —NO$_2$ or —CN;
L is $C_{1-4}$ alkylene that is optionally substituted with one or more groups selected from halo, hydroxy or $C_{3-8}$ cycloalkyl;
$R^7$ is hydrogen, or $C_{1-6}$ alkyl that is optionally substituted with one or more groups selected from —F, —Cl, —Br, —I, —OR$^g$, —SR$^g$, —N(R$^g$)$_2$, oxo, —NO$_2$ or —CN;
ring Z is heteroaryl or unsaturated heterocycle; wherein the heteroaryl and heterocycle are optionally substituted with one or more groups selected from —F, —Cl, —Br, —I, —OR$^i$, —SR$^i$, —N(R$^i$)$_2$, —NO$_2$ or —CN;
each $R^a$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^a$ groups taken together with the nitrogen to which they are attached form pyrrolidinyl, piperidinyl, piperazinyl or morpholinyl;
each $R^b$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^b$ groups taken together with the nitrogen to which they are attached form pyrrolidinyl, piperidinyl, piperazinyl or morpholinyl;
each $R^c$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^c$ groups taken together with the nitrogen to which they are attached form pyrrolidinyl, piperidinyl, piperazinyl or morpholinyl;
each $R^d$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^d$ groups taken together with the nitrogen to which they are attached form pyrrolidinyl, piperidinyl, piperazinyl or morpholinyl;
each $R^e$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^e$ groups taken together with the nitrogen to which they are attached form pyrrolidinyl, piperidinyl, piperazinyl or morpholinyl;

each $R^g$ is independently hydrogen, $C_{1-4}$ alkyl or $C_{1-4}$ haloalkyl; or two $R^g$ groups taken together with the nitrogen to which they are attached form pyrrolidinyl, piperidinyl, piperazinyl or morpholinyl; and each $R^i$ is independently hydrogen, $C_{1-4}$ alkyl or $C_{1-4}$ haloalkyl; or two $R^i$ groups taken together with the nitrogen to which they are attached form pyrrolidinyl, piperidinyl, piperazinyl or morpholinyl.

In one embodiment, the compound of formula Ia', Ib', Ic', or Id' is a compound of formula Ia, Ib, or Ic.

In one embodiment, the invention provides a novel compound shown in the following table, or a free base or a salt thereof. The invention also provides a method for treating a neurodegenerative disorder in an animal comprising administering to the animal an effective amount of compound shown in the following table, or a free base or a pharmaceutically acceptable salt thereof. The invention also provides a method for producing analgesia in an animal comprising administering to the animal a compound shown in the following table, or a free base or a pharmaceutically acceptable salt thereof.

The invention also provides a method for reducing endoplasmic reticulum stress in an animal comprising administering to the animal a compound shown in the following table, or a free base or a pharmaceutically acceptable salt thereof.

The invention also provides a method for reducing drug-induced toxicity in an animal comprising administering to the animal a compound shown in the following table, or a free base or a pharmaceutically acceptable salt thereof.

The invention also provides a method for reducing drug-induced toxicity in an animal comprising administering to the animal a compound shown in the following table, or a free base or a pharmaceutically acceptable salt thereof in combination with the drug.

The invention provides a composition comprising: 1) a drug that is associated with unwanted endoplasmic reticulum stress, 2) a compound shown in the following table, or a free base or a pharmaceutically acceptable salt thereof, and 3) a pharmaceutically acceptable carrier.

The invention also provides a method for reducing heavy metal-induced toxicity in an animal comprising administering to the animal a compound shown in the following table, or a free base or a pharmaceutically acceptable salt thereof in combination with the drug.

The invention also provides a method for treating carbon monoxide poisoning in an animal comprising administering to the animal a compound shown in the following table, or a free base or a pharmaceutically acceptable salt thereof.

The invention also provides a method for treating cyanide poisoning in an animal comprising administering to the animal a compound shown in the following table, or a free base or a pharmaceutically acceptable salt thereof.

| NUMBER | EXAMPLE | MW | STRUCTURE |
|---|---|---|---|
| BC1-45-1 E-GA | 1 | 291.13 | [structure] $CH_3COOH$ |
| BC1-55-1 Z-GA | 55 | 291.13 | [structure] $CH_3COOH$ |
| BC1-167-1 Metabolite | 2 | 307.13 | [structure] $CH_3COOH$ |
| BC1-171-1 | 56 | 307.13 | [structure] $CH_3COOH$ |
| BC1-189-1 | 3 | 291.13 | [structure] $CH_3COOH$ |

-continued
| NUMBER | EXAMPLE | MW | STRUCTURE |
|---|---|---|---|
| BC1-236-1 | 4 | 291.13 | 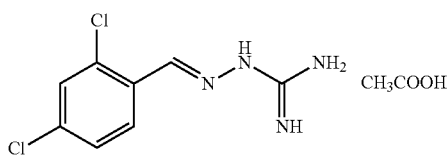 CH₃COOH |
| BC1-242-2 | 27 | 230.09 | 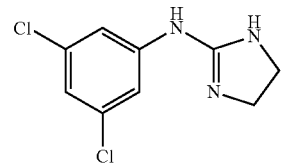 [SMILES: Clc1cc(Cl)cc(NC2=NCCN2)c1] |
| BC1-252-2 | 29 | 232.11 | 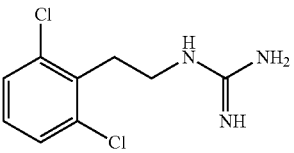 [SMILES: N=C(N)NCCc1c(Cl)cccc1Cl] |
| BC1-256-2 | 28 | 204.06 | 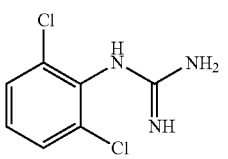 |
| BC1-259-2 | 30 | 245.11 | 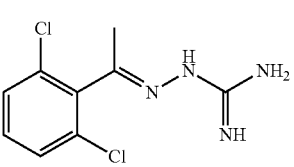 |
| BC1-262-1 | 26 | 268.53 | 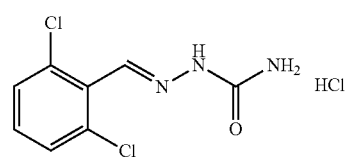 [SMILES: NC(=O)N/N=C/c1c(Cl)cccc1Cl ; Cl] HCl |
| BC1-272-1 | 5 | 270.72 | 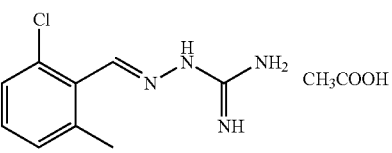 CH₃COOH |
| BC1-282-1 | 6 | 325.58 | 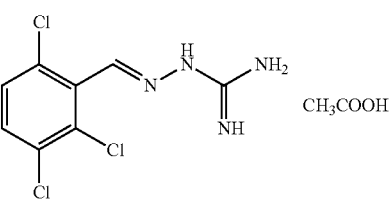 CH₃COOH |
| BC1-283-1 | 7 | 291.13 | 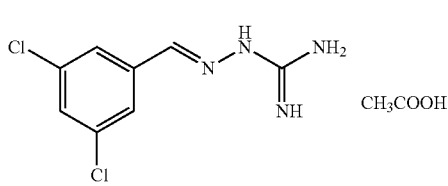 CH₃COOH |

-continued
| NUMBER | EXAMPLE | MW | STRUCTURE |
|---|---|---|---|
| BC1-295-1 | 8 | 222.24 | 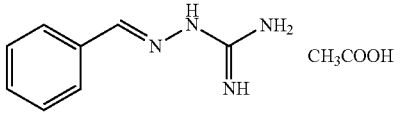 CH₃COOH |
| BC1-297-1 | 9 | 301.14 | 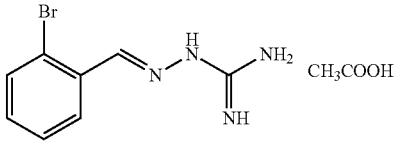 CH₃COOH |
| BC1-299-1 | 10 | 256.69 | 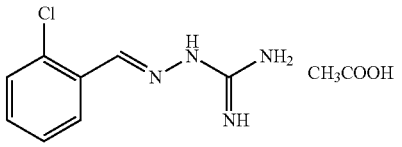 CH₃COOH |
| BC2-3-1 | 11 | 236.27 | 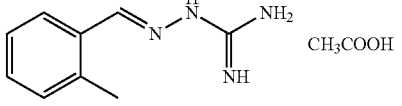 CH₃COOH |
| BC2-5-1 | 12 | 274.68 | 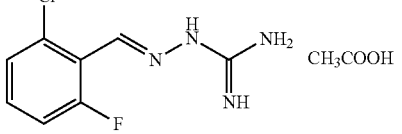 CH₃COOH |
| BC2-7-1 | 13 | 291.13 | 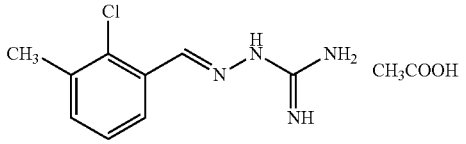 CH₃COOH |
| BC2-9-1 | 14 | 256.69 | 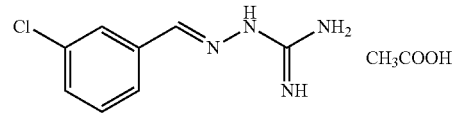 CH₃COOH |
| BC2-11-1 | 15 | 240.23 | 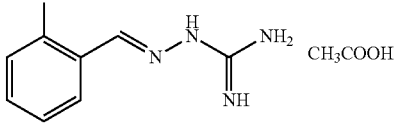 CH₃COOH |
| BC2-13-1 | 16 | 256.69 | 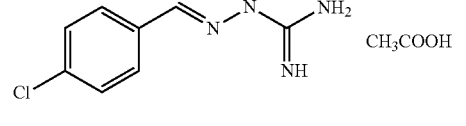 CH₃COOH |
| BC2-17-1 | 17 | 274.68 | 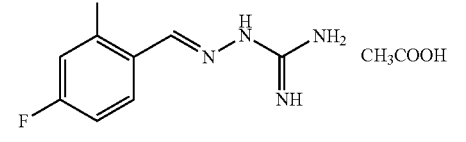 CH₃COOH |

| NUMBER | EXAMPLE | MW | STRUCTURE |
|---|---|---|---|
| BC2-19-1 | 18 | 274.68 | 4-chloro-2-fluorobenzaldehyde aminoguanidine · CH₃COOH |
| BC2-25-1 | 19 | 286.71 | 2-chloro-6-methoxybenzaldehyde aminoguanidine · CH₃COOH |
| BC2-27-1 | 20 | 250.30 | 2,6-dimethylbenzaldehyde aminoguanidine · CH₃COOH |
| BC2-35-1 | 21 | 335.58 | 2-bromo-6-chlorobenzaldehyde aminoguanidine · CH₃COOH |
| BC2-45-1 | 22 | 324.69 | 2-chloro-6-(trifluoromethyl)benzaldehyde aminoguanidine · CH₃COOH |
| BC2-47-1 | 23 | 380.04 | 2,6-dibromobenzaldehyde aminoguanidine · CH₃COOH |
| BC2-55-2 | 31 | 413.98 | 2,6-diiodobenzaldehyde aminoguanidine |
| BC2-57-2 | 24 | 301.69 | 2-chloro-6-nitrobenzaldehyde aminoguanidine · CH₃COOH |
| BC2-61-1 | 32 | 211.65 | 2-amino-6-chlorobenzaldehyde aminoguanidine |
| BC2-61-2 | 32 | 177.21 | 2-aminobenzaldehyde aminoguanidine |

-continued

| NUMBER | EXAMPLE | MW | STRUCTURE |
|---|---|---|---|
| BC2-59-2 | 25 | 272.69 | 2-chloro-6-hydroxybenzaldehyde aminoguanidine · CH₃COOH |
| BC1-267-2 | 57 | 270.12 | 2-(2,6-dichlorophenyl)-1H-imidazol-1-yl aminoguanidine |
| JM1-111-2 | 112 | 212.25 | naphthalen-2-yl aminoguanidine |
| JM1-113-2 | 113 | 231.67 | 2-chloro-6-fluorobenzaldehyde thiosemicarbazone |
| JM1-115-2 | 114 | 248.12 | 2,6-dichlorobenzaldehyde thiosemicarbazone |
| JM1-121-2 | 115 | 207.29 | 2,6-dimethylbenzaldehyde thiosemicarbazone |
| JM1-125-2 | 116 | 258.68 | 2-chloro-6-nitrobenzaldehyde thiosemicarbazone |
| JM1-127-2 | 117 | 337.03 | 2,6-dibromobenzaldehyde thiosemicarbazone |
| JM1-129-2 | 118 | 229.30 | naphthalen-2-yl thiosemicarbazone |
| JM1-135-2 | 119 | 197.23 | 2-fluorobenzaldehyde thiosemicarbazone |

-continued

| NUMBER | EXAMPLE | MW | STRUCTURE |
|---|---|---|---|
| JM1-141-2 | 120 | 231.08 | 2,6-dichlorobenzaldehyde aminoguanidine · CF₃COOH |
| JM1-143-2 | 121 | 319.98 | 2,6-dibromobenzaldehyde aminoguanidine · CF₃COOH |
| JM1-175-2 | 122 | 286.08 | 2-bromo-6-nitrobenzaldehyde aminoguanidine · CH₃COOH |
| JM1-177-2 | 123 | 250.14 | 2,6-dichlorobenzyl isothiourea |
| JM1-179-2 | 124 | 225.18 | 2-fluoro-6-nitrobenzaldehyde aminoguanidine · CH₃COOH |
| JM1-185-2 | 125 | 274.68 | 2-chloro-5-fluorobenzaldehyde aminoguanidine · CH₃COOH |
| JM1-191-2 | 126 | 258.22 | 2,6-difluorobenzaldehyde aminoguanidine · CH₃COOH |
| JM1-195-2 | 127 | 254.26 | 2-fluoro-6-methylbenzaldehyde aminoguanidine · CH₃COOH |
| JM1-217-2 | 128 | 228.07 | 1-(2,6-dichlorophenyl)-5-aminopyrazole |

| NUMBER | EXAMPLE | MW | STRUCTURE |
|---|---|---|---|
| JM1-221-2 | 33 | 324.68 | 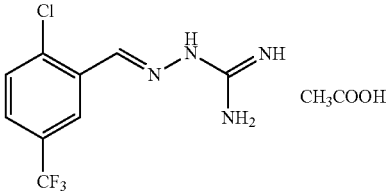 CH₃COOH |
| JM1-223-2 | 34 | 308.23 | 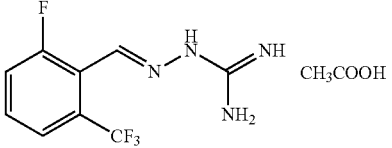 CH₃COOH |
| JM1-257-2 | 35 | 224.69 | 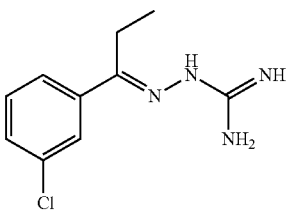 |
| JM1-285-2 | 130 | 270.11 | 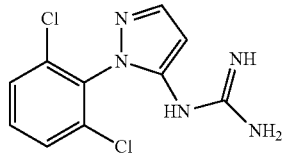 [SMILES: N=C(N)Nc1ccnn1-c1c(Cl)cccc1Cl] |
| JM2-59-2 | 36 | 225.72 | 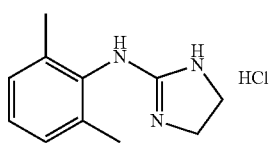 HCl |
| JM2-63-2 | 37 | 261.10 | 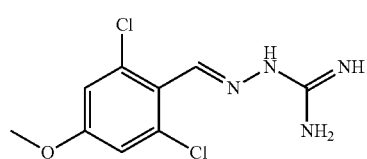 |
| JM2-67-2 | 38 | 337.20 | 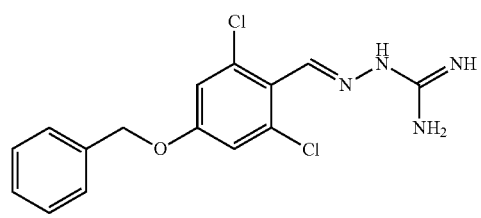 [SMILES: N=C(N)N/N=C/c1c(Cl)cc(OCc2ccccc2)cc1Cl] |
| JM2-83-2 | 39 | 293.57 | 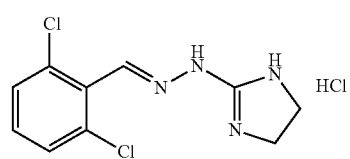 [SMILES: Clc1cccc(Cl)c1/C=N/NC1=NCCN1 ; Cl] HCl |

-continued
| NUMBER | EXAMPLE | MW | STRUCTURE |
|---|---|---|---|
| JM2-85-2 | 40 | 252.74 | 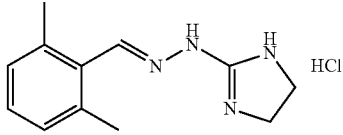 [SMILES: Cc1cccc(C)c1/C=N/NC1=NCCN1 ; Cl] |
| JM2-87-2 | 41 | 229.10 | 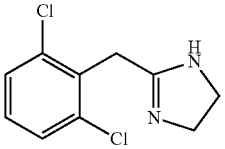 [SMILES: Clc1cccc(Cl)c1CC1=NCCN1] |
| JM2-89-2 | 42 | 304.13 | 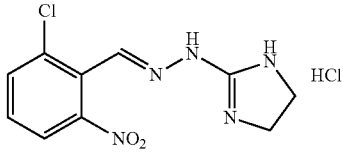 [SMILES: O=[N+]([O-])c1cccc(Cl)c1/C=N/NC1=NCCN1 ; Cl] |
| JM2-91-2 | 43 | 293.57 | 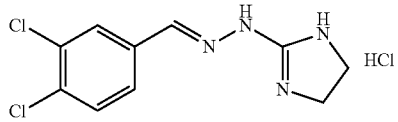 [SMILES: Clc1ccc(/C=N/NC2=NCCN2)cc1Cl ; Cl] |
| JM2-95-2 | 44 | 277.12 | 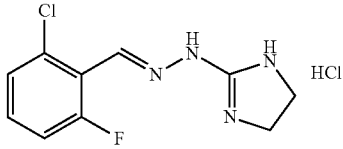 |
| JM2-97-2 | 45 | 266.55 | 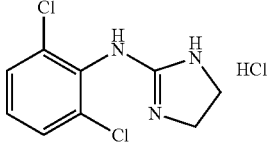 |
| JM2-101-2 | 46 | 243.13 | 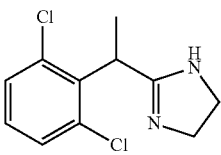 |
| JM2-103-2 | 47 | 260.67 | 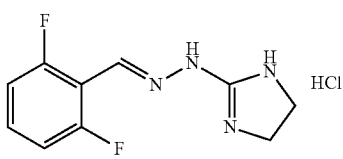 [SMILES: Fc1cccc(F)c1/C=N/NC1=NCCN1 ; Cl] |
| JM2-109-2 | 48 | 348.58 | 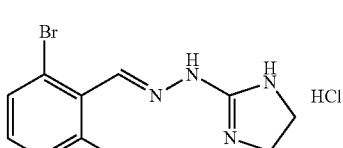 |
| JM2-111-2 | 49 | 382.48 | 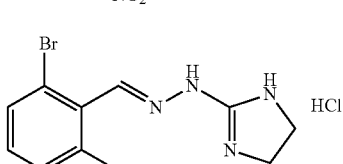 |

-continued
| NUMBER | EXAMPLE | MW | STRUCTURE |
|---|---|---|---|
| JM2-113-2 | 50 | 259.13 | 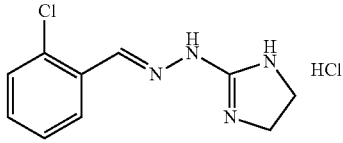 [SMILES: Clc1ccccc1/C=N/NC1=NCCN1 ; Cl] |
| JM2-115-2 | 51 | 242.68 | 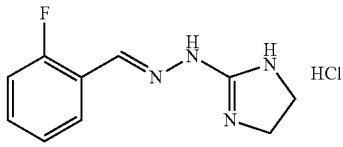 [SMILES: Fc1ccccc1/C=N/NC1=NCCN1 ; Cl] |
| JM2-131-2 | 52 | 327.13 | 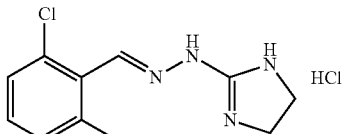 |
| JM2-133-2 | 53 | 273.16 | 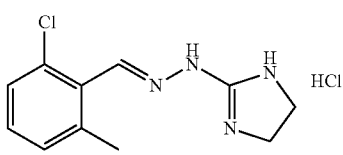 [SMILES: Cc1cccc(Cl)c1/C=N/NC1=NCCN1 ; Cl] |
| JM2-171-2 | 58 | 373.01 | 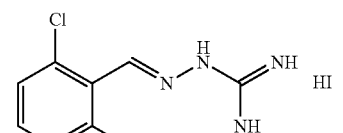 |
| JM2-175-2 | 131 | 435.09 | 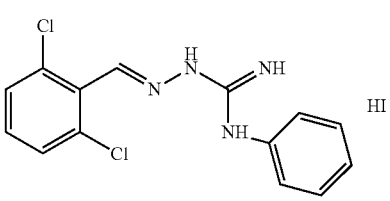 |
| JM2-185-2 | 132 | 233.09 | 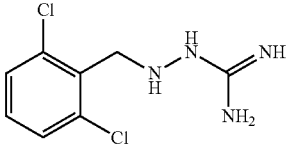 |
| JM2-191-2 | 54 | 303.58 | 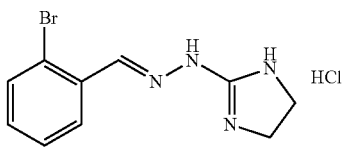 [SMILES: Brc1ccccc1/C=N/NC1=NCCN1 ; Cl] |
| JM2-195-2 | 133 | 397.25 | 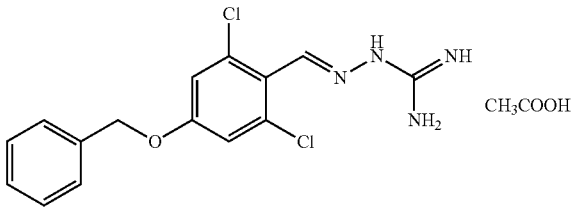 |

-continued

| NUMBER | EXAMPLE | MW | STRUCTURE |
|---|---|---|---|
| JM2-233-2 | 129 | 280.32 | 2,6-diethylbenzaldehyde aminoguanidine · $H_2CO_3$ |
| JM2-255-2 | 60 | 307.60 | 2,6-dichlorobenzaldehyde (1,4,5,6-tetrahydropyrimidin-2-yl)hydrazone · HCl |
| JM2-257-2 | 61 | 266.77 | 2,6-dimethylbenzaldehyde (1,4,5,6-tetrahydropyrimidin-2-yl)hydrazone · HCl |
| JM2-263-2 | 62 | 318.15 | 2-chloro-6-nitrobenzaldehyde (1,4,5,6-tetrahydropyrimidin-2-yl)hydrazone · HCl |
| JM2-265-2 | 63 | 287.18 | 2-chloro-6-methylbenzaldehyde (1,4,5,6-tetrahydropyrimidin-2-yl)hydrazone · HCl |
| JM2-271-2 | 64 | 243.13 | 2-(2,6-dichlorobenzyl)-1,4,5,6-tetrahydropyrimidine |
| JM2-275-2 | 65 | 292.01 | 2-(2-chloro-6-nitrophenyl)-N-carbamimidoylacetamide · HCl |
| JM2-279-2 | 66 | 168.21 | thiophene-2-carbaldehyde aminoguanidine |
| JM2-287-2 | 67 | 282.54 | 2-(2,6-dichlorophenyl)-N-carbamimidoylacetamide · HCl |
| JM2-289-2 | 59 | 387.04 | 2,6-dichlorobenzaldehyde (N,N-dimethylguanidino)hydrazone · HI |

-continued
| NUMBER | EXAMPLE | MW | STRUCTURE |
|---|---|---|---|
| JM3-11-2 | 68 | 291.13 | 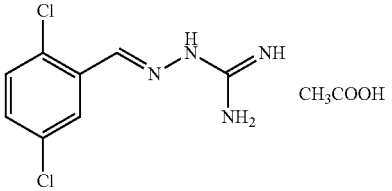 CH₃COOH |
| JM3-13-2 | 69 | 267.24 | 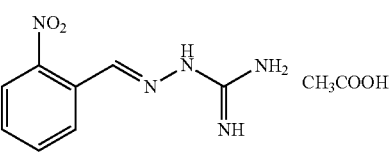 CH₃COOH |
| JM3-17-2 | 70 | 238.24 | 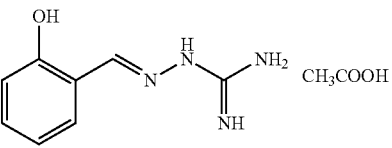 CH₃COOH |
| JM3-27-2 | 71 | 248.10 | 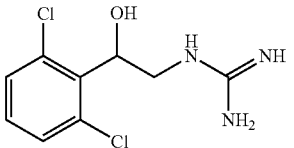 [SMILES: N=C(N)NCC(O)c1c(Cl)cccc1Cl] |
| JM3-29-2 | 72 | 292.12 | 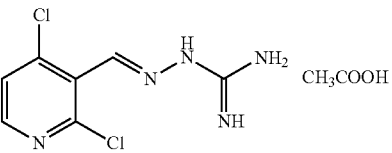 CH₃COOH |
| JM3-57-2 | 73 | 335.58 | 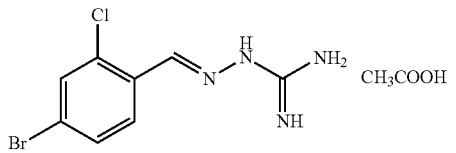 CH₃COOH |
| JM3-63-2 | 74 | 332.78 | 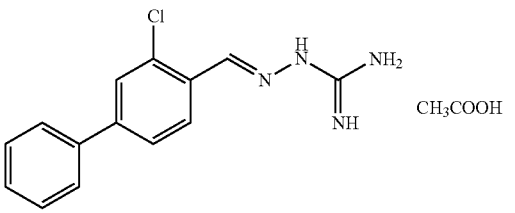 CH₃COOH |
| JM3-67-2 | 75 | 307.17 | 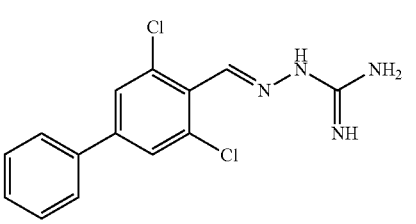 [SMILES: N=C(N)N/N=C/c1c(Cl)cc(-c2ccccc2)cc1Cl] |
| JM3-81-2 | 76 | 287.74 | 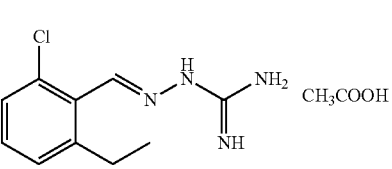 CH₃COOH |

-continued
| NUMBER | EXAMPLE | MW | STRUCTURE | |
|---|---|---|---|---|
| JM3-89-2 | 77 | 298.77 | 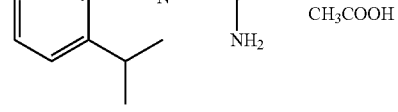 | a |
| JM3-99-2 | 78 | 306.41 | 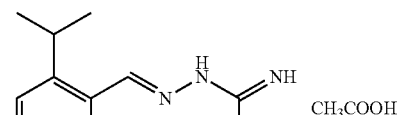 | |
| JM3-131-2 | 79 | 227.08 | 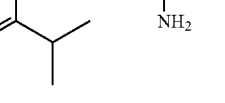 | |
| JM3-141-2 | 80 | 358.24 | 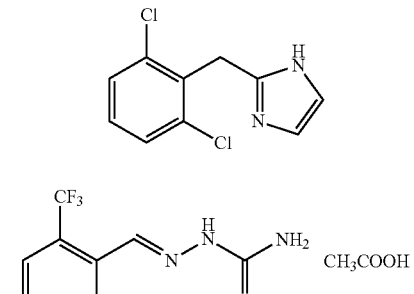 | |
| JM3-149-2 | 81 | 293.57 | 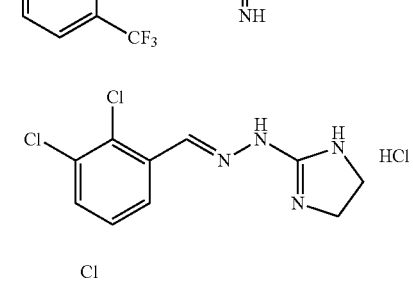 | |
| JM3-151-2 | 82 | 328.02 | 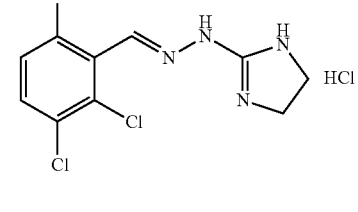 | |
| JM3-153-2 | 83 | 307.60 | 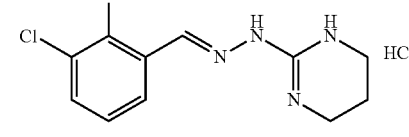 | |
| JM3-155-2 | 84 | 342.04 | 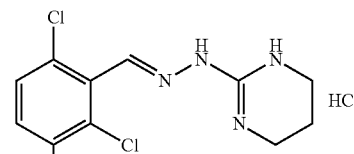 | |

-continued

| NUMBER | EXAMPLE | MW | STRUCTURE |
|---|---|---|---|
| JM3-161-2 | 85 | 415.10 | 2,6-dichlorobenzaldehyde N-butylguanylhydrazone · HI |
| JM3-179-2 | 86 | 229.10 | 2-(2,3-dichlorobenzyl)-4,5-dihydro-1H-imidazole |
| JM3-181-2 | 87 | 243.13 | 2-(2,3-dichlorobenzyl)-1,4,5,6-tetrahydropyrimidine |
| JM3-183-2 | 88 | 348.14 | 2-iodobenzaldehyde guanylhydrazone · CH$_3$COOH |
| JM3-191-2 | 89 | 311.16 | 2,6-dichlorobenzaldehyde (5,6-dimethyl-4-oxo-1,4-dihydropyrimidin-2-yl)hydrazone |
| JM3-195-2 | 90 | 311.16 | 2,3-dichlorobenzaldehyde (5,6-dimethyl-4-oxo-1,4-dihydropyrimidin-2-yl)hydrazone |
| JM3-197-2 | 91 | 297.13 | 2,6-dichlorobenzaldehyde (6-methyl-4-oxo-1,4-dihydropyrimidin-2-yl)hydrazone |
| JM3-199-2 | 92 | 297.13 | 2,3-dichlorobenzaldehyde (6-methyl-4-oxo-1,4-dihydropyrimidin-2-yl)hydrazone |

-continued
| NUMBER | EXAMPLE | MW | STRUCTURE |
|---|---|---|---|
| JM3-201-2 | 93 | 331.58 | 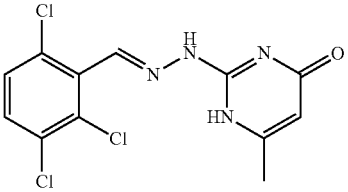 |
| JM2-203-2 | 94 | 280.68 | 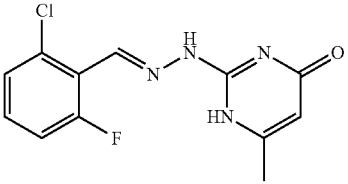 [SMILES: Cc1cc(=O)nc(N/N=C/c2c(F)cccc2Cl)[nH]1] |
| JM3-205-2 | 95 | 345.60 | 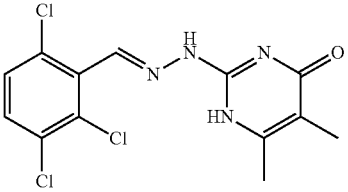 [SMILES: Cc1[nH]c(N/N=C/c2c(Cl)ccc(Cl)c2Cl)nc(=O)c1C] |
| JM3-207-2 | 96 | 294.71 | 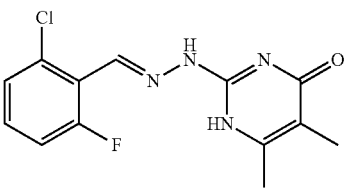 |
| JM3-209-2 | 97 | 311.16 | 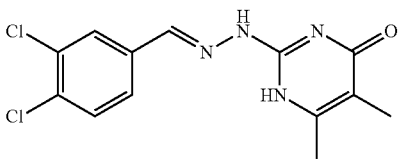 [SMILES: Cc1[nH]c(N/N=C/c2ccc(Cl)c(Cl)c2)nc(=O)c1C] |
| JM3-211-2 | 98 | 297.14 | 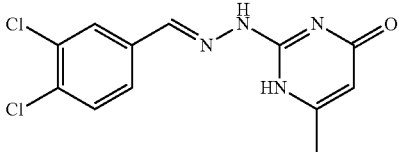 [SMILES: Cc1cc(=O)nc(N/N=C/c2ccc(Cl)c(Cl)c2)[nH]1] |
| JM3-213-2 | 99 | 276.72 | 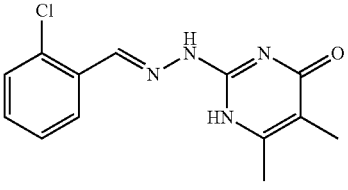 [SMILES: Cc1[nH]c(N/N=C/c2ccccc2Cl)nc(=O)c1C] |
| JM3-215-2 | 100 | 262.69 | 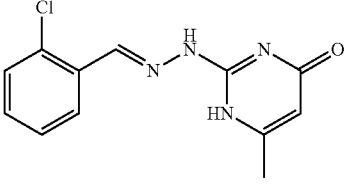 [SMILES: Cc1cc(=O)nc(N/N=C/c2ccccc2Cl)[nH]1] |

-continued
| NUMBER | EXAMPLE | MW | STRUCTURE |
|---|---|---|---|
| JM3-219-2 | 101 | 278.53 | 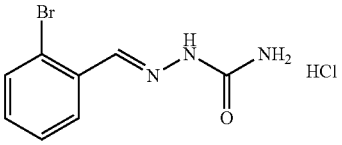 [SMILES: NC(=O)N/N=C/c1ccccc1Br ; Cl] |
| JM3-221-2 | 102 | 217.62 | 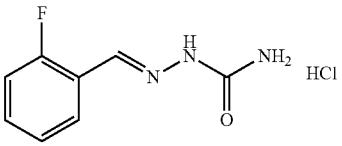 |
| JM3-223-2 | 103 | 234.08 | 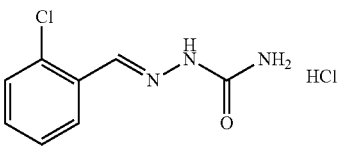 |
| JM3-225-2 | 104 | 325.53 | 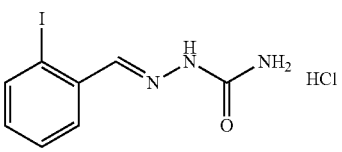 [SMILES: NC(=O)N/N=C/c1ccccc1I ; Cl] |
| JM3-227-2 | 105 | 233.09 | 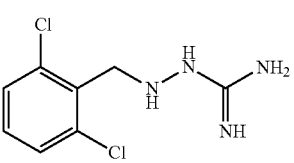 |
| JM3-239-2 | 106 | 305.15 | 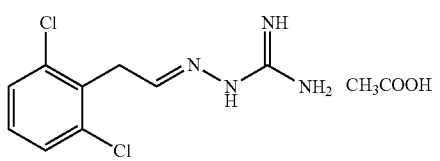 |
| JM3-255-2 | 107 | 352.05 | 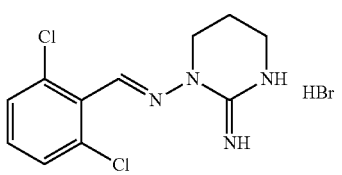 [SMILES: N=C1NCCCN1/N=C/c1c(Cl)cccc1Cl ; Br] |
| JM3-257-2 | 108 | | 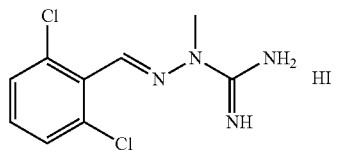 |
| JM2-233-2 | 109 | | 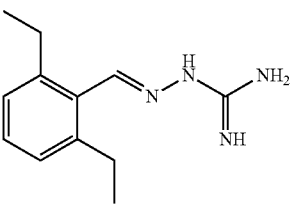 [SMILES: CCc1cccc(CC)c1/C=N/NC(=N)N] |

| NUMBER | EXAMPLE | MW | STRUCTURE |
|---|---|---|---|
| JM2-169-2 | 110 | | ![structure] 2,6-dichlorobenzaldehyde derivative with =N-NH-C(=NH)-S-CH$_3$, HI salt |

Processes and intermediates useful for preparing compounds of formula Ia', Ib', Ic', or Id' are provided as further embodiments of the invention and are illustrated by the following procedures in which the meanings of the generic radicals are as given above unless otherwise qualified.

Compounds of formula Ia', Ib', Ic', or Id' may be prepared by the process illustrated in Schemes a and b.

a)

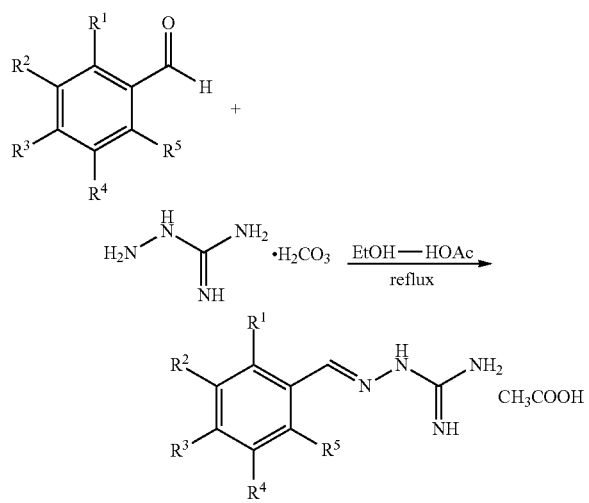

b)

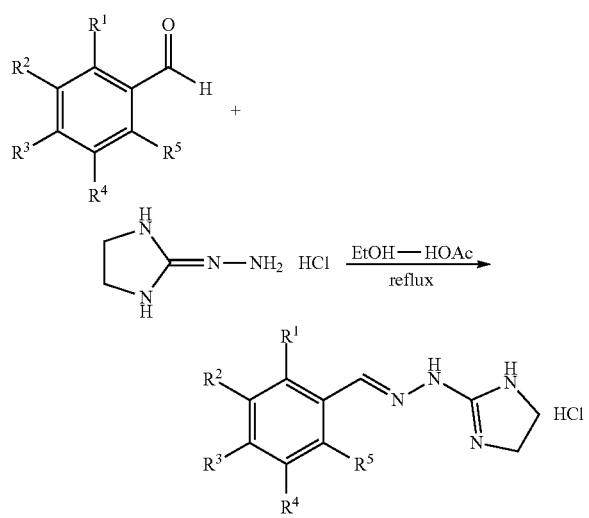

Schemes a and b. General synthetic routes to representative compounds of formula I.

(1a) The aldehyde (1 equivalent), aminoguanidine bicarbonate (1 equivalent) and AcOH (2 equivalents) in EtOH was refluxed for 12 hours. After cooling at room temperature, the final compound was recovered as a precipitate after filtration. If it did not precipitate, a crude reaction mixture was evaporated under vacuum and triturated with dry Et$_2$O before filtration. The precipitate was recrystallized from Ethanol to give the desired compound. The yields were around 70%-90%.

(1b) The aldehyde (1 equivalent), 2-hydrazonoimidazolidine hydrochloride (1 equivalent) and AcOH (few drops) in EtOH was refluxed for 12 hours. After cooling at room temperature, the final compound was recovered as a precipitate after filtration. If it did not precipitate, a crude reaction mixture was evaporated under vacuum and triturated with dry Et$_2$O before filtration. The precipitate was recrystallized from Ethanol to give the desired compound. The yields are all around 70%-90%.

In cases where compounds are sufficiently basic or acidic, a salt of a compound of formula Ia, Ib or Ic can be useful as an intermediate for isolating or purifying a compound of formula I. Additionally, administration of a compound of formula Ia, Ib or Ic as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula Ia, Ib or Ic can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula Ia, Ib or Ic can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples. The compounds identified in Preparative Examples 1-25 are intermediate compounds that can be used to prepare compounds of formula Ia', Ib', Ic', or Id'.

All commercial reagents and solvents were used as provided. Flash chromatography was performed with Ultra Pure silica gel or with RediSep Rf silica gel columns on a Teledyne ISCO CombiFlash Rf system using the solvents as indicated. Nuclear magnetic resonance spectra were recorded on a Varian 600 MHz with Me$_4$Si or signals from residual solvent as the internal standard for $^1$H and $^{13}$C. Chemical shifts are reported in ppm, and signals are described as s (singlet), d (doublet), t (triplet), q (quartet), m (multiplet), brs (broad singlet), and dd (double doublet). Values given for coupling constants are first order. High resolution and low resolution mass spectra were recorded on

PREPARATIVE EXAMPLES

Preparative Example 1 (E)-N-butyl-1-(2,6-difluorophenyl)methanimine (JM2-209-2)

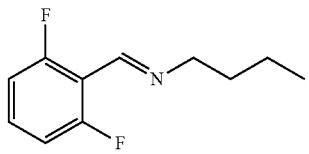

To a solution of 2,6-difluorobenzaldehyde (500 mg, 3.52 mmol) in toluene (5 mL) was added p-TsOH (13.3 mg, 2 mol %) and n-butyl amine (257 mg, 3.52 mmol). The reaction mixture was stirred at room temp for 30 h. The resulting solution was diluted with toluene (10 mL), washed with 5% NaHCO$_3$ solution, water followed by brine. The organic layer was dried over Na$_2$SO$_4$ and evaporated to get the final compound as yellow oil (80%). $^1$H NMR (dmso-d$_6$, 600 MHz) δ 8.41 (s, 1H), 7.51-7.44 (m, 1H), 7.12 (t, 2H, J=8.8 Hz), 3.56 (t, 2H, J=7.0 Hz), 1.58-1.53 (m, 2H), 1.33-1.25 (m, 2H), 0.87 (t, 3H, J=7.0 Hz). $^{13}$C NMR (150 MHz, dmso-d$_6$) δ 162.13, 160.44, 151.20, 132.52, 113.75, 112.71, 112.68, 112.58, 112.54, 62.27, 32.78, 20.22, 14.08. ESI-MS (M+H)$^+$ 198.12.

Preparative Example 2
1-(2,6-dichlorophenyl)propan-1-ol (JM2-213-2)

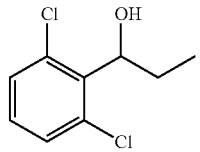

2,6-dichlorobenzaldehyde (1.0 g, 5.7 mmol) was dissolved in tetrahydrofuran (10 mL). The solution was cooled to −10° C., added ethyl magnesium chloride solution (3.6 mL, 7.2 mmol) dropwise under argon. The reaction mixture was allowed to room temp, stirred for overnight and quenched with sat. NH$_4$Cl solution at 0° C. The compound was extracted with ether and washed with brine, dried over Na$_2$SO$_4$, and concentrated in vacuo. The crude was purified by silica gel chromatography using 0-20% ethyl acetate in hexanes. Colorless oil (43%).

$^1$H NMR (cdcl$_3$, 600 MHz) δ 7.26 (d, 2H, J=8.2 Hz), 7.11 (t, 1H, J=8.2 Hz), 5.32 (t, 1H, J=8.2 Hz), 2.11-2.02 (m, 2H), 1.99-1.90 (m, 1H), 0.97 (t, 3H, J=7.6 Hz). $^{13}$C NMR (150 MHz, cdcl$_3$) δ 137.83, 134.24, 129.31, 128.70, 73.56, 28.66, 10.50. ESI-MS (M−H)$^-$ 203.01.

Preparative Example 3 (E)-N-butyl-1-(2,6-diethylphenyl)methanimine (JM2-215-2)

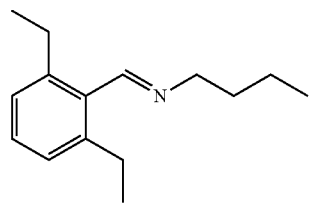 [SMILES: CCCC/N=C/c1c(CC)cccc1CC]

(E)-N-butyl-1-(2,6-difluorophenyl)methanimine (300 mg, 1.52 mmol) was dissolved in tetrahydrofuran (8 mL). The solution was cooled to −10° C., added ethyl magnesium chloride solution (1.7 mL, 3.4 mmol) dropwise under argon. The reaction mixture was allowed to room temp, stirred for overnight and quenched with sat. NaHCO$_3$ solution. The compound was extracted with ethyl acetate and washed with brine, dried over Na$_2$SO$_4$, and concentrated in vacuo to get final compound as colorless oil (91%). $^1$H NMR (dmso-d$_6$, 600 MHz) δ 8.60 (s, 1H), 7.18 (t, 1H, J=7.6 Hz), 7.03 (d, 2H, J=7.6 Hz), 3.56 (t, 2H, J=6.5 Hz), 2.66 (q, 4H, J=7.6 Hz), 7.61 (d, 2H, J=8.2 Hz), 1.61-1.54 (m, 2H), 1.39-1.31 (m, 2H), 1.06 (t, 6H, J=7.6 Hz), 0.89 (t, 3H, J=7.6 Hz). $^{13}$C NMR (150 MHz, dmso-d$_6$) δ 160.43, 143.19, 133.89, 129.20, 127.09, 61.73, 33.13, 26.38, 20.40, 16.22, 14.15. ESI-MS (M+H)$^+$ 218.19.

Preparative Example 4
1-(2,6-dichlorophenyl)propan-1-one (JM2-223-2)

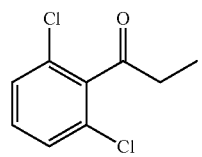

To a stirred solution of 1-(2,6-dichlorophenyl)propan-1-ol (200 mg, 0.98 mmol) in dichloromethane (5 mL) was added Dess-Martin periodinane (582 mg, 1.37 mmol) and stirring was continued for 3 h. The reaction mixture was filtered on celite pad and washed with dichloromethane. The filtrate was washed with sat. NaHCO$_3$, brine, dried over Na$_2$SO$_4$ and concentrated in vacuo. The crude was purified on silica gel chromatography using EtOAc and hexane to obtain final compound as colorless oil (81%). $^1$H NMR (dmso-d$_6$, 600 MHz) δ 7.30 (d, 1H, J=7.0 Hz), 7.25 (t, 2H, J=7.0 Hz), 2.85 (q, 2H, J=7.0 Hz), 1.22 (t, 6H, J=7.0 Hz). $^{13}$C NMR (150 MHz, dmso-d$_6$) δ 203.05, 140.01, 130.34, 130.31, 128.01, 37.02, 7.25. ESI-MS (M)$^+$ 201.99.

Preparative Example 5 2,6-dimethylbenzaldehyde (JM2-227-2)

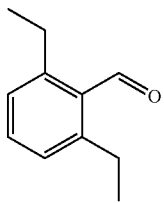

A solution of (E)-N-butyl-1-(2,6-diethylphenyl)methanimine (200 mg, 0.92 mmol) in H$_2$SO$_4$/H$_2$O (2:8) was refluxed for 2 h. The reaction mixture was cooled to room temp, extracted with ethyl acetate washed with water followed by 5% NaHCO$_3$ solution, brine, dried over Na$_2$SO$_4$ and concentrated in vacuo. The crude was purified on silica gel chromatography using EtOAc and hexane to obtain final compound as colorless oil (80%). $^1$H NMR (dmso-d$_6$, 600 MHz) δ 10.49 (s, 1H), 7.41 (t, 1H, J=7.6 Hz), 7.15 (d, 2H, J=7.6 Hz), 2.88 (q, 4H, J=7.0 Hz), 1.12 (t, 6H, J=7.6 Hz). $^{13}$C NMR (150 MHz, dmso-d$_6$) δ 194.82, 146.94, 133.61, 131.99, 128.61, 26.24, 17.06. ESI-MS (M+H)$^+$ 163.11.

Preparative Example 6 Ethyl 2-(2-chloro-6-nitrophenyl)-2-cyanoacetate (JM2-231)

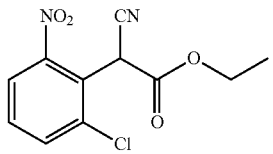 [SMILES: CCOC(=O)C(C#N)c1c(Cl)cccc1[N+](=O)[O-]]

To a suspension of NaH (409 mg, 17.0 mmol, 60% dispersion in oil) in DMSO (8 mL) at 0° C. was added ethyl cyanoacetate (1.96 g, 17.0 mmol) slowly, and the mixture was stirred at room temp for 30 min before 1-chloro-2-fluoro-3-nitrobenzene (1.5 g, 8.54 mmol) in DMSO (8 mL) was added. The resulting solution was stirred at 90° C. for overnight and quenched by adding 2 N HCl (10 mL). After extraction with the EtOAc the combined organics were washed with NaHCO$_3$, brine, dried over Na$_2$SO$_4$, and concentrated in vacuo to leave brown oil. The crude material was used for next step without further purification. ESI-MS (M−H)$^−$ 267.02.

Preparative Example 7 2-(2-chloro-6-nitrophenyl)acetonitrile (JM2-237-2)

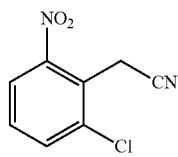

A solution of ethyl 2-(2-chloro-6-nitrophenyl)-2-cyanoacetate (2.1 g, 8.16 mmol) in DMSO/H$_2$O (9:1) mixture was stirred at 120° C. for 16 h before being quenched with water. The aqueous solution was extracted using EtOAc (2×30 mL). The combined organics were washed with water and brine, dried over Na$_2$SO$_4$, and concentrated in vacuo. The crude was purified on silica gel chromatography using EtOAc and hexane to obtain final compound as yellow solid (80%, over 2 steps). $^1$H NMR (dmso-d$_6$, 600 MHz) δ 8.06 (d, 1H, J=8.2 Hz), 7.97 (d, 1H, J=8.2 Hz), 7.68 (t, 1H, J=8.2 Hz), 4.19 (s, 2H). $^{13}$C NMR (150 MHz, dmso-d$_6$) δ 150.71, 136.11, 135.27, 131.31, 124.73, 124.34, 116.95, 19.35. ESI-MS (M−H)$^−$ 194.99.

Preparative Example 8 Methyl 2-(2-chloro-6-nitrophenyl)acetate (JM2-241-2)

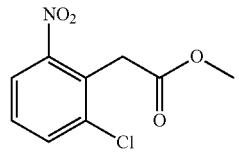

A solution of 2-(2-chloro-6-nitrophenyl)acetonitrile (300 mg, 1.52 mmol) in 45% sulfuric acid in water and methanol (5 mL) was refluxed for overnight. The reaction mixture was evaporated and extracted with EtOAc and washed with sat. NaHCO$_3$ solution followed by brine. The organic layer was dried over Na$_2$SO$_4$ and evaporated. The crude was purified on silica gel chromatography using EtOAc and hexane to obtain final compound as colorless oil (50%). $^1$H NMR (dmso-d$_6$, 600 MHz) δ 8.03 (d, 1H, J=8.2 Hz), 7.91 (d, 1H, J=8.2 Hz), 7.60 (t, 1H, J=8.2 Hz), 4.08 (s, 2H), 3.64 (s, 3H). $^{13}$C NMR (150 MHz, dmso-d$_6$) δ 169.60, 150.93, 136.59, 134.75, 130.15, 127.85, 124.35, 65.64, 35.49. ESI-MS (MH)$^+$ 229.01.

Preparative Example 9 2-(methylthio)-1,4,5,6-tetrahydropyrimidine hydroiodide (JM2-243-2)

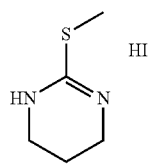

A solution of tetrahydropyrimidine-2(1H)-thione (1.5 g, 12.9 mmol) and methyl iodide (2.2 g, 15.48 mmol) in 15 mL of methanol was refluxed for 6 h. The solvent was evaporated, washed with ether to yield final product as light yellow solid (98%). $^1$H NMR (dmso-d$_6$, 600 MHz) δ 9.51 (br s, 2H), 3.36 (t, 4H, J=5.8 Hz), 2.57 (s, 3H), 1.90-1.85 (m, 2H). $^{13}$C NMR (150 MHz, dmso-d$_6$) δ 163.33, 40.48, 18.61, 13.72. ESI-MS (M+H)$^+$ 131.06.

Preparative Example 10
2-hydrazonohexahydropyrimidine hydrochloride
(JM2-251-2)

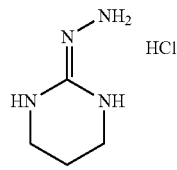

A solution of 2-(methylthio)-1,4,5,6-tetrahydropyrimidine hydroiodide (1.0 g, 3.87 mmol) was cooled to 0° C. in ethanol and 50-60% hydrazine hydrate (434 mg, 13.56 mmol) was added in one portion under argon. The resulting mixture was stirred for 1 h and then heated to reflux for 4 h. The solution was evaporated under vacuum followed by azeotropy with water (3×10 mL). The residue was acidified with 10 mL of 1 N HCl and the solvent was removed in vacuum to obtain product as yellow powder (96%). $^1$H NMR (D$_2$O, 600 MHz) δ 3.20 (t, 4H, J=5.8 Hz), 1.82-1.77 (m, 2H). $^{13}$C NMR (150 MHz, D$_2$O) δ 37.88, 19.50. ESI-MS (M+H)$^+$ 115.09.

Preparative Example 11 1-(2,6-dichlorophenyl)-2-nitroethan-1-ol (JM3-3-2)

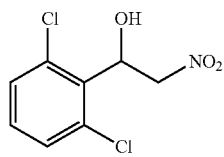 [SMILES: O=[N+]([O-])CC(O)c1c(Cl)cccc1Cl]

To a stirred solution of 2,6-dichlorobenzaldehyde (875 mg, 5.0 mmol) in methanol (4 mL) was added nitromethane (305 mg, 5.0 mmol) and stirred vigorously. To this solution was added 1 mL of 10.5 mol/L KOH solution was added dropwise in an ice bath and stirring was continued for 15 min at 0° C. followed by dropwise addition of Conc. HCl (3 mL). The reaction mixture was extracted with EtOAc (2×), washed with water, brine and dried over Na$_2$SO$_4$. The organics were evaporated and crude was purified on silica gel chromatography using EtOAc and hexane to obtain final compound as colorless oil (85%). $^1$H NMR (dmso-d$_6$, 600 MHz) δ 7.47 (d, 2H, J=7.6 Hz), 7.36 (t, 1H, J=8.2 Hz), 6.33 (d, 1H, J=4.7 Hz), 6.09-6.03 (m, 1H), 5.04 (dd, 1H, J=9.9 Hz), 4.92 (dd, 1H, J=12.9 Hz). $^{13}$C NMR (150 MHz, dmso-d$_6$) δ 134.85, 134.37, 131.13, 130.13, 78.58, 67.63. ESI-MS (M–H)$^-$ 233.97.

Preparative Example 12 (E)-1,3-dichloro-2-(2-nitrovinyl)benzene (JM3-15-2)

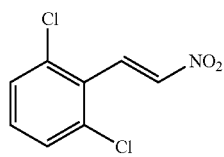 [SMILES: O=[N+]([O-])/C=C/c1c(Cl)cccc1Cl]

To a stirred solution of 1-(2,6-dichlorophenyl)-2-nitroethane-1-ol (900 mg, 3.82 mmol) and mesyl chloride (523 mg, 4.57 mmol) in tetrahydrofuran (10 mL) was added triethylamine (807 mg, 2.1 mmol) dropwise at 0° C. After 1.5 h, saturated ammonium chloride was added to the reaction mixture and aqueous phase was extracted with EtOAc. The extract was washed with 1N HCl, NaHCO$_3$ and brine, dried over Na$_2$SO$_4$, filtrated and concentrated in vacuo. The residual solid was purified by recrystallization from EtOAc and hexane to obtain final compound as light yellow powder (81%). $^1$H NMR (dmso-d$_6$, 600 MHz) δ 8.12 (d, 1H, J=14.1 Hz), 8.02 (d, 1H, J=14.1 Hz), 7.63 (d, 2H, J=8.2 Hz), 7.51 (t, 1H, J=8.2 Hz). $^{13}$C NMR (150 MHz, dmso-d$_6$) δ 144.02, 135.02, 132.90, 132.64, 129.71, 127.98. ESI-MS (M)$^+$ 216.95.

Preparative Example 13 2-amino-1-(2,6-dichlorophenyl)ethan-1-ol (JM3-23-2)

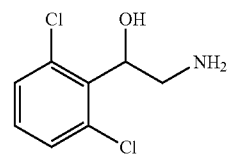

To a stirred solution of tin (II)chloride dehydrate (1.29 mg, 5.72 mmol) in ethanol (6 mL) and 0.8 mL of Conc. HCl was added 1-(2,6-dichlorophenyl)-2-nitroethan-1-ol (3 portion over 15 min) at 70° C. After the addition the solution was refluxed for 2.5 h. To this reaction mixture was added 6 mL of water then stirred at 10-15° C. for 20 min. The solution was basified with 2 N NaOH (pH ~12) followed by evaporation of ethanol in vacuo. The residue was dissolved in EtOAC washed with water, brine and dried over Na$_2$SO$_4$. The crude was recrystallized from EtOAc and hexane to obtain final compound as light yellow solid (72%). $^1$H NMR (dmso-d$_6$, 600 MHz) δ 7.37 (d, 2H, J=7.6 Hz), 7.23 (t, 1H, J=7.6 Hz), 5.44 (s, 1H), 5.18-5.13 (m, 1H), 3.04 (dd, 1H, J=9.9 Hz), 2.70 (dd, 1H, J=12.9 Hz), 1.52 (br s, 2H). $^{13}$C NMR (150 MHz, dmso-d$_6$) δ 138.16, 134.61, 129.85, 129.70, 73.00, 45.59. ESI-MS (M+H)$^+$ 206.01.

Preparative Example 14
3,5-dichloro-4-formylphenyl trifluoromethanesulfonate (JM3-61-2)

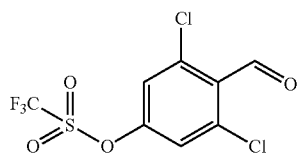 [SMILES: O=Cc1c(Cl)cc(OS(=O)(=O)C(F)(F)F)cc1Cl]

To a solution of 2,6-dichloro-4-hydroxybenzaldehyde (500 mg, 2.62 mmol) and pyridine (498 mg, 2.4 mmol) in dichloromethane at 0° C. was added dropwise trifluoromethanesulfonic anhydride (1.57 g, 5.24 mmol). The solution was allowed to warm to room temperature while stirring overnight. The reaction mixture was quenched by the addition of saturated sodium bicarbonate solution (10 mL). The resulting mixture was extracted with water (20 mL) and EtOAc (2×20 mL) followed by washing with brine, dried over Na₂SO₄, filtered and evaporated. The residue was purified by silica gel chromatography using 10% ethyl acetate in hexanes to yield yellow oil (42%). ¹H NMR (dmso-d₆, 600 MHz) δ 10.29 (s, 1H), 8.01 (s, 2H). ¹³C NMR (150 MHz, dmso-d₆) δ 189.07, 150.63, 136.78, 131.63, 123.98, 119.64, 109.99. ESI-MS (M+H)⁺ 321.07.

Preparative Example 15 (E)-4-((2-carbamimidoyl-hydrazono)methyl)-3,5-dichlorophenyl trifluoromethanesulfonate (JM3-65-1)

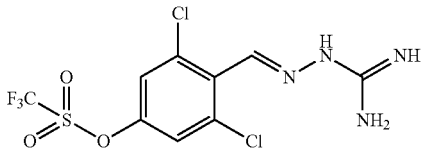 [SMILES: N=C(N)N/N=C/c1c(Cl)cc(OS(=O)(=O)C(F)(F)F)cc1Cl]

A solution of 3,5-dichloro-4-formylphenyl trifluoromethanesulfonate (300 mg, 0.93 mmol) and amino guanidine bicarbonate (127 mg, 0.93 mmol) in ethanol was refluxed for overnight. The reaction mixture was evaporated, followed by trituration with diethyl ether yielded crude compound. The crude material was used for next step without further purification.

Preparative Example 16 (E)-N-butyl-1-(2-chloro-6-fluorophenyl)methanimine (JM3-71-2)

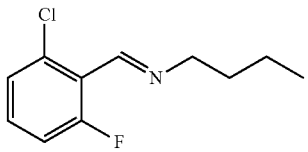

To a solution of 2-chloro-6-fluorobenzaldehyde (1.00 g, 6.30 mmol) in toluene (10 mL) was added p-TsOH (23.0 mg, 2 mol %) and n-butyl amine (506 mg, 6.93 mmol). The reaction mixture was stirred at room temp for 30 h. The resulting solution was diluted with toluene (10 mL), washed with 5% NaHCO₃ solution, water followed by brine. The organic layer was dried over Na₂SO₄ and evaporated to get the final compound as light yellow oil (80%). ¹H NMR (dmso-d₆, 400 MHz) δ 8.45 (s, 1H), 7.46 (q, 1H, J=8.2 Hz), 7.37 (d, 1H, J=8.2 Hz), 7.27 (t, 1H, J=9.3 Hz) 3.60 (t, 2H, J=7.0 Hz), 1.59 (quin, 2H, J=7.0 Hz), 1.32 (sex, 2H, J=7.6 Hz), 0.89 (t, 3H, J=7.0 Hz). ¹³C NMR (100 MHz, dmso-d₆) δ 161.79, 160.10, 154.14, 134.15, 132.19, 126.33, 123.19, 115.93, 61.88, 32.69, 20.15, 14.08. ESI-MS (M+H)⁺ 214.07.

Preparative Example 17 (E)-N-butyl-1-(2-chloro-6-ethylphenyl)methanimine (JM3-73-2)

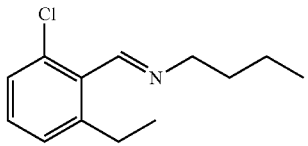

To a solution of (E)-N-butyl-1-(2-chloro-6-fluorophenyl)methanimine (500 mg, 2.33 mmol) in tetrahydrofuran (12 mL) at −10° C. was added ethyl magnesium chloride solution (1.28 mL, 2.57 mmol) dropwise under argon. The reaction mixture was allowed to room temp, stirred for overnight and quenched with sat. NaHCO₃ solution. The compound was extracted with ethyl acetate and washed with brine, dried over Na₂SO₄, and concentrated in vacuo to get final compound as light yellow oil (56%). ¹H NMR (dmso-d₆, 400 MHz) δ 8.56 (s, 1H), 7.32 (d, 2H, J=8.2 Hz), 7.24 (t, 1H, J=8.2 Hz), 3.60 (t, 2H, J=6.4 Hz), 2.79 (q, 2H, J=7.3 Hz), 1.60 (quin, 2H, J=7.0 Hz), 1.38 (sex, 2H, J=7.6 Hz), 1.09 (t, 3H, J=7.6 Hz), 0.91 (t, 3H, J=7.0 Hz). ¹³C NMR (100 MHz, dmso-d₆) δ 158.63, 145.89, 134.72, 133.08, 130.71, 128.95, 127.44, 61.58, 32.92, 26.29, 20.31, 16.19, 14.15. ESI-MS (M+H)⁺ 224.12.

Preparative Example 18
2-chloro-6-ethylbenzaldehyde (JM3-75-2)

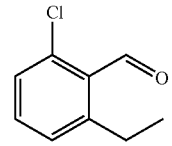

A solution of (E)-N-butyl-1-(2-chloro-6-ethylphenyl)methanimine (100 mg, 0.92 mmol) in H₂SO₄/water (2:8) was refluxed for 3 h. The reaction mixture was cooled to room temp, extracted with ethyl acetate washed with water followed by 5% NaHCO₃ solution, brine, dried over Na₂SO₄ and concentrated in vacuo. The crude was purified on silica gel chromatography using EtOAc and hexane to obtain final compound as light yellow oil (93%). ¹H NMR (dmso-d₆, 400 MHz) δ 10.48 (s, 1H), 7.54 (t, 1H, J=7.6 Hz), 7.45 (d, 1H, J=8.2 Hz), 7.34 (d, 1H, J=7.6 Hz) 2.86 (q, 2H, J=7.6 Hz), 1.12 (t, 3H, J=7.6 Hz). ¹³C NMR (100 MHz, dmso-d₆) δ 193.01, 148.10, 136.89, 134.72, 131.07, 130.00, 128.76, 26.29, 16.29. ESI-MS (M−H)⁻ 167.02.

Preparative Example 19 (E)-N-butyl-1-(2-chloro-6-isopropylphenyl)methanimine (JM3-83-2)

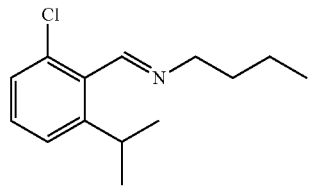 [SMILES: CCCC/N=C/c1c(Cl)cccc1C(C)C]

To a solution of (E)-N-butyl-1-(2-chloro-6-fluorophenyl)methanimine (350 mg, 1.64 mmol) in tetrahydrofuran (8 mL) at −10° C. was added isopropyl magnesium bromide solution (1.8 mL, 1.8 mmol) dropwise under argon. The reaction mixture was allowed to room temp, stirred for overnight and quenched with sat. NaHCO₃ solution. The compound was extracted with ethyl acetate and washed with brine, dried over Na₂SO₄, and concentrated in vacuo to get final compound as light yellow oil (51%). ¹H NMR (dmso-d₆, 400 MHz) δ 8.55 (s, 1H), 7.35 (t, 2H, J=8.2 Hz), 7.30 (t, 1H, J=8.2 Hz), 3.57 (t, 2H, J=7.0 Hz), 3.47 (sep, 1H, J=7.0

Hz), 1.60 (quin, 2H, J=7.0 Hz), 1.38 (sex, 2H, J=7.6 Hz), 1.13 (d, 6H, J=7.6 Hz), 0.91 (t, 3H, J=7.0 Hz). $^{13}$C NMR (100 MHz, dmso-d$_6$) δ 158.63, 145.89, 134.72, 133.08, 130.71, 128.95, 127.44, 61.58, 32.92, 26.29, 20.31, 16.19, 14.15. ESI-MS (M+H)$^+$ 238.13.

Preparative Example 20
2-chloro-6-isopropylbenzaldehyde (JM3-87-2)

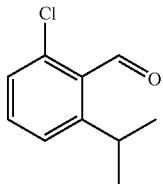

A solution of (E)-N-butyl-1-(2-chloro-6-isopropylphenyl)methanimine (120 mg, 0.50 mmol) in H$_2$SO$_4$/water (2:8) was refluxed for 2 h. The reaction mixture was cooled to room temp, extracted with ethyl acetate washed with water followed by 5% NaHCO$_3$ solution, brine, dried over Na$_2$SO$_4$ and concentrated in vacuo. The crude was purified on silica gel chromatography using EtOAc and hexane to obtain final compound as light yellow color oil (98%). $^1$H NMR (dmso-d$_6$, 400 MHz) δ 10.56 (s, 1H), 7.63 (t, 1H, J=7.8 Hz), 7.57 (d, 1H, J=7.8 Hz), 7.49 (d, 1H, J=7.8 Hz) 2.86 (sep, 1H, J=6.8 Hz), 125 (d, 6H, J=6.8 Hz). $^{13}$C NMR (100 MHz, dmso-d$_6$) δ 194.05, 152.04, 135.62, 134.42, 131.70, 128.34, 126.07, 28.56, 24.07. ESI-MS (M)$^+$ 182.04.

Preparative Example 21 (E)-N-butyl-1-(2,6-diisopropylphenyl)methanimine (JM3-95-2)

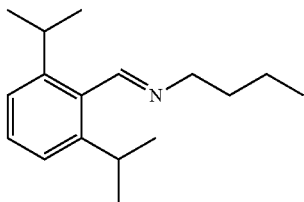 [SMILES: CCCC/N=C/c1c(C(C)C)cccc1C(C)C]

To a solution of (E)-N-butyl-1-(2,6-difluorophenyl)methanimine (500 mg, 2.50 mmol) in tetrahydrofuran (12 mL) at –10° C. was added ethyl magnesium chloride solution (5.0 mL, 5.0 mmol) dropwise under argon. The reaction mixture was allowed to room temp, stirred for overnight and quenched with sat. NaHCO$_3$ solution. The compound was extracted with ethyl acetate and washed with brine, dried over Na$_2$SO$_4$, and concentrated in vacuo to get final compound as light yellow color oil (60%). $^1$H NMR (dmso-d$_6$, 400 MHz) δ 8.75 (s, 1H), 7.35 (t, 1H, J=7.8 Hz), 7.23 (d, 2H, J=7.5 Hz), 3.67 (t, 2H, J=6.6 Hz), 3.23 (sep, 2H, J=7.3 Hz), 1.67 (quin, 2H, J=7.0 Hz), 1.46 (sex, 2H, J=7.3 Hz), 1.21 (d, 12H, J=6.8 Hz), 0.99 (t, 3H, J=7.5 Hz). $^{13}$C NMR (100 MHz, dmso-d$_6$) δ 161.24, 146.69, 134.33, 129.14, 122.88, 61.55, 33.08, 29.39, 23.99, 20.43, 14.21. ESI-MS (M+H)$^+$ 246.22.

Preparative Example 22
2,6-diisopropylbenzaldehyde (JM3-97-2)

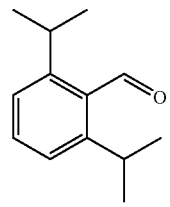

A solution of (E)-N-butyl-1-(2,6-diethylphenyl)methanimine (200 mg, 0.92 mmol) in H$_2$SO$_4$/water (2:8) was refluxed for 2 h. The reaction mixture was cooled to room temp, extracted with ethyl acetate washed with water followed by 5% NaHCO$_3$ solution, brine, dried over Na$_2$SO$_4$ and concentrated in vacuo. The crude was purified on silica gel chromatography using EtOAc and hexane to obtain final compound as light yellow oil (80%). $^1$H NMR (dmso-d$_6$, 400 MHz) δ 10.71 (s, 1H), 7.54 (t, 2H, J=7.8 Hz), 7.35 (d, 1H, J=7.8 Hz), 3.49 (sep, 2H, J=6.8 Hz), 1.25 (d, 12H, J=6.8 Hz). $^{13}$C NMR (100 MHz, dmso-d$_6$) δ 197.63, 149.07, 133.59, 132.65, 123.87, 28.67, 24.41. ESI-MS (M)$^+$ 190.13.

Preparative Example 23
(2,6-bis(trifluoromethyl)phenyl)methanol (JM3-1352-2)

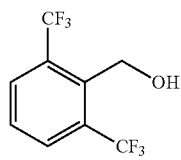 [SMILES: OCc1c(C(F)(F)F)cccc1C(F)(F)F]

To a solution of KO$^t$Bt (1.3 g, 11.62 mmol) in THF at –70° C. was added 2,6-bis(trifluoromethyl)benzene (2.0 g, 9.3 mmol) dropwise over a period of 30 min. To this solution was added n-BuLi (18.6 mmol, 2.5 M in hexanes) dropwise for 30 min, stirring continued at –70° C. for 60 min. To this mixture was added Paraformaldehyde (61.2 g, 37.2 mmol) and stirring continued at –70° C. for 30 min, then allowed to room temperature for 3 h. The reaction mixture was poured into conc. HCl (2 mL) and ice water (60 mL) and stirred for 1 h, extracted with hexanes (3×10 mL) and washed with brine, dried over Na$_2$SO$_4$, and concentrated in vacuo to get final compound as dark brown oil (40%). ESI-MS (M)$^+$ 244.03.

Preparative Example 24
2,6-bis(trifluoromethyl)benzaldehyde (JM3-139-2)

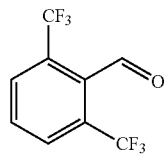

To a stirred solution of (2,6-bis(trifluoromethyl)phenyl)methanol (300 mg, 1.2 mmol) in dichloromethane (5 mL) was added Dess-Martin periodinane (782 mg, 1.84 mmol) and stirring was continued at room temp for 3 h. The reaction mixture was filtered on celite pad and washed with dichloromethane. The filtrate was washed with sat. NaHCO$_3$, brine, dried over Na$_2$SO$_4$ and concentrated in vacuum. The crude was purified on silica gel chromatography using EtOAc and hexane to obtain final compound as light yellow oil (33%). $^1$H NMR (dmso-d$_6$, 400 MHz) δ 10.66 (s, 1H), 8.23 (d, 2H, J=8.0 Hz), 8.01 (t, 1H, J=7.8 Hz). $^{13}$C NMR (100 MHz, dmso-d$_6$) δ 193.64, 132.99, 131.35, 128.45, 128.13, 124.88. ESI-MS (M)$^+$ 242.01.

Preparative Example 25
2-(2,6-dichlorophenyl)acetaldehyde (JM3-237-2)

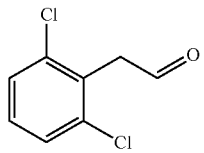 [SMILES: O=CCc1c(Cl)cccc1Cl]

To a stirred solution of (2,6-trichloro-phenyl)-acetonitrile (800 mg, 4.3 mmole) in 10 mL toluene at 0° C. was added DIBAL-H (3.34 mL of 25% w/w in hexane, 4.7 mmol) dropwise over a period of 30 min. The reaction mixture was allowed to room temp and stirred for overnight. The reaction was quenched by dropwise addition of 12 mL of 2 N HCl at 0° C. and was kept for 30 min at ambient temperature. Toluene layer was separated and aq. layer was extracted with ethyl acetate (3×20 mL). The combined organic layer was washed with brine and dried over sodium sulfate. The organic layer was concentrated under vacuum to yield final compound as light yellow solid (72%). $^1$H NMR (CDCl$_3$, 400 MHz) δ 9.74 (s, 1H), 7.36 (d, 2H, J=8.1 Hz), 7.20 (t, 1H, J=8.01 Hz), 4.11 (s, 2H). $^{13}$C NMR (100 MHz, CDCl$_3$) δ 196.59, 136.10, 133.68, 129.81, 129.29, 128.21, 45.84.

Preparative Example Salubrinal (JM3-177-2 & JM3-189-2)

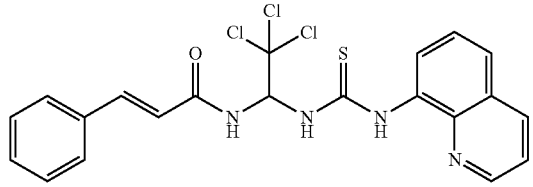 [SMILES: O=C(/C=C/c1ccccc1)NC(NC(=S)Nc1cccc2cccnc12)C(Cl)(Cl)Cl]

N-(2,2,2-trichloro-1-isothiocyanatoethyl)cinnamamide (400 mg, 1.2 mmol) was dissolved in 10 mL of tetrahydrofuran, added 8-amino quinoline (172.mg, 1.2 mmol). The reaction mixture was heated at 60° C. for overnight. The crude mixture was evaporated, extracted with water and ethyl acetate. The organic layer was washed with brine dried with Na$_2$SO$_4$. The solvent was evaporated and crude compound was purified on silica with 0-10% methanol in dichloromethane to yield final compound (52%). $^1$H NMR (dmso-d$_6$, 600 MHz) δ 11.02 (s, 1H), 9.54 (d, 1H, J=9.4 Hz), 9.01 (d, 1H, d, J=6.4 Hz), 8.94 (d, 1H, d, J=4.1 Hz), 8.41 (d, 1H, d, J=7.0 Hz), 7.71 (d, 1H, d, J=8.2 Hz), 7.76-7.53 (m, 6H), 7.44-7.37 (m, 3H), 6.8 (d, 1H, J=15.8 Hz). $^{13}$C NMR (100 MHz, dmso-d$_6$) δ 181.01, 164.84, 149.37, 141.40, 140.15, 137.20, 135.88, 135.13, 130.33, 129.48, 128.44, 128.21, 126.66, 123.30, 122.28, 121.49, 120.65, 101.88, 70.15. ESI-HRMS Calc m/z for C$_{21}$H$_{18}$Cl$_3$N$_4$OS 479.0261 (M+H)$^+$, found 479.0257. HPLC 96.05% purity $t_R$=14.17 min.

EXAMPLES

Using the appropriately substituted starting materials, compounds of formula Ia, Ib or Ic in Examples 1-25 and 33-35 were prepared following the procedure as described above in Scheme 1a.

Using the appropriately substituted starting material, compounds of formula Ia, Ib or Ic in Examples 39-40, 42-44 and 47-54 were prepared following the procedure as described above in Scheme 1b.

Example 1. (E)-2-(2,6-dichlorobenzylidene)hydrazinecarboximidamide acetate (BC1-45-1)

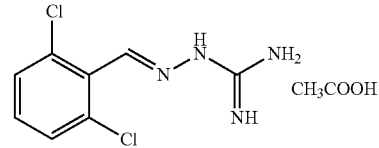

White powder. $^1$H NMR (DMSO-d$_6$, 600 MHz) δ 8.20 (s, 1H), 7.48 (d, 2H, J=6.0 Hz), 7.31 (t, 1H, J=6.0 Hz), 6.85 (brs, 4H), 1.82 (s, 3H). $^{13}$C NMR (151 MHz, dmso) δ 174.67, 159.82, 139.25, 134.04, 131.45, 130.29, 129.56, 22.97. ESI-HRMS Calc m/z (M+H)$^+$ Calc m/z 231.0199 Found 231.0212. HPLC 98.58% purity $t_R$=5.99 min.

Example 2. (E)-2-(2,6-dichloro-4-hydroxybenzylidene)hydrazinecarboximidamide acetate (BC1-167-1)

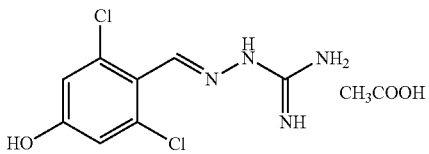

Light yellow powder. 1H NMR (600 MHz, cd3od) δ 8.31 (s, 1H), 6.84 (s, 2H), 1.92 (s, 3H). $^{13}$C NMR (151 MHz, cd$_3$od) δ 177.83, 160.34, 156.27, 143.19, 135.41, 119.44, 116.43, 53.13, 47.99, 47.85, 47.71, 47.56, 47.42, 47.28, 47.14, 21.89. ESI-HRMS Calc m/z (M+H)$^+$ Calc m/z 247.0148 Found 247.0149. HPLC 96.43% purity $t_R$=4.42 min.

Example 3. (E)-2-(3,4-dichlorobenzylidene)hydrazinecarboximidamide acetate (BC1-189-1)

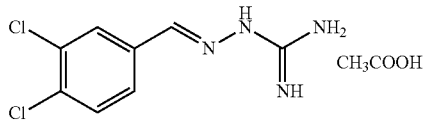

White powder. $^1$H NMR (600 MHz, dmso) δ 8.07 (s, 1H), 7.97 (s, 1H), 7.67 (d, J=8.3 Hz, 1H), 7.58 (d, J=8.1 Hz, 1H), 6.67 (brs, 4H), 1.84 (s, 3H). $^{13}$C NMR (151 MHz, dmso) δ 174.21, 160.16, 141.27, 137.50, 131.87, 130.98, 130.60, 127.97, 127.12, 40.37, 40.23, 40.09, 39.95, 39.81, 39.67, 39.53, 22.80. ESI-HRMS Calc m/z (M+H)$^+$ Calc m/z 231.0199 Found 231.0215. HPLC 95.58% purity $t_R$=5.45 min.

Example 4. (E)-2-(2,4-dichlorobenzylidene)hydrazinecarboximidamide acetate (BC1-236-1)

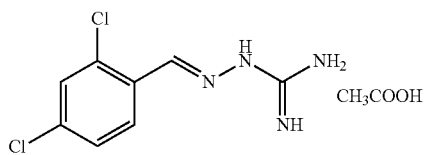

White powder. $^1$H NMR (600 MHz, cd$_3$od) δ 8.47 (s, 1H), 8.15 (d, J=8.5 Hz, 1H), 7.53 (s, 1H), 7.38 (d, J=8.2 Hz, 1H), 1.92 (s, 3H). 13C NMR (151 MHz, cd3od) δ 178.37, 157.02, 142.09, 136.15, 134.40, 130.16, 129.17, 128.16, 127.38, 22.22. ESI-HRMS Calc m/z (M+H)$^+$ Calc m/z 231.0199 Found 231.0214. HPLC 96.11% purity $t_R$=5.38 min.

Example 5. (E)-2-(2-chloro-6-methylbenzylidene)hydrazinecarboximidamide acetate (BC1-272-1)

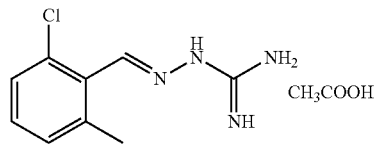

White powder. $^1$H NMR (600 MHz, cd$_3$od) δ 8.52 (s, 1H), 7.31 (d, J=7.8 Hz, 1H), 7.26 (t, J=7.7 Hz, 1H), 7.23 (d, J=7.2 Hz, 1H), 2.54 (s, 3H), 1.92 (s, 3H). $^{13}$C NMR (151 MHz, cd$_3$od) δ 175.79, 156.63, 145.70, 139.81, 134.65, 130.00, 129.77, 129.71, 127.09, 22.44, 20.74. ESI-HRMS Calc m/z (M+H)$^+$ Calc m/z 211.0745 Found 211.0755. HPLC 99.01% purity $t_R$=5.09 min.

Example 6. (E)-2-(2,3,6-trichlorobenzylidene)hydrazinecarboximidamide acetate (BC1-282-1)

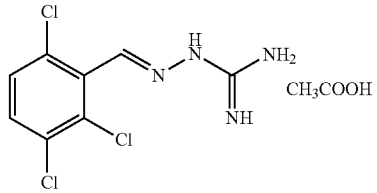

White powder. $^1$H NMR (600 MHz, cd3od) δ 8.30 (s, 1H), 7.55 (d, J=8.7 Hz, 1H), 7.45 (d, J=8.7 Hz, 1H), 1.94 (s, 3H). $^{13}$C NMR (151 MHz, cd3od) δ 179.07, 157.11, 141.76, 132.91, 132.83, 132.18, 132.04, 130.99, 129.30, 22.49. ESI-HRMS Calc m/z (M+H)$^+$ Calc m/z 231.0199 Found 231.0206. HPLC 96.36% purity $t_R$=5.32 min.

Example 7. (E)-2-(3,5-dichlorobenzylidene)hydrazinecarboximidamide acetate (BC1-283-1)

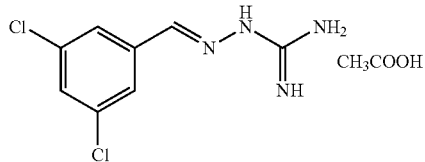

White powder. $^1$H NMR (600 MHz, cd3od) δ 8.13 (s, 1H), 7.88 (s, 2H), 7.57 (s, 1H), 2.03 (s, 3H). $^{13}$C NMR (151 MHz, cd3od) δ 178.46, 157.04, 144.09, 137.46, 135.21, 129.18, 125.28, 22.26. ESI-HRMS Calc m/z (M+H)$^+$ Calc m/z 264.9809 Found 264.9810. HPLC 97.25% purity $t_R$=5.53 min.

Example 8. (E)-2-benzylidenehydrazinecarboximidamide acetate (BC1-295-1)

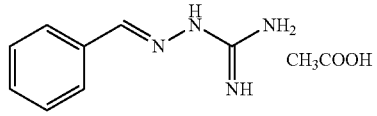

White powder. $^1$H NMR (600 MHz, cd$_3$od) δ 8.16 (s, 1H), 7.81 (s, 2H), 7.45 (s, 3H), 1.99 (s, 3H). $^{13}$C NMR (151 MHz, cd3od) δ 179.41, 156.29, 147.36, 133.65, 130.21, 128.39, 127.15, 22.78. ESI-HRMS Calc m/z (M+H)$^+$ Calc m/z 163.0978 Found 163.0991. HPLC 96.38% purity $t_R$=2.29 min.

Example 9. (E)-2-(2-bromobenzylidene)hydrazinecarboximidamide acetate (BC1-297-1)

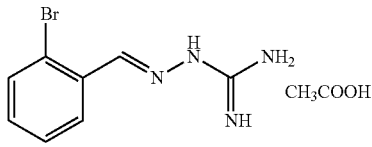

White powder. ¹H NMR (600 MHz, cd₃od) δ 8.62 (s, 1H), 8.25 (d, J=7.7 Hz, 1H), 7.74 (d, J=8.0 Hz, 1H), 7.51 (t, J=7.6 Hz, 1H), 7.43 (t, J=7.6 Hz, 1H), 2.05 (s, 3H). ¹³C NMR (151 MHz, cd₃od) δ 178.90, 156.55, 145.76, 132.89, 132.54, 131.49, 127.56, 127.50, 123.76, 48.00, 47.86, 47.72, 47.57, 47.43, 47.29, 47.15, 22.50. ESI-HRMS Calc m/z (M+H)⁺ Calc m/z 241.0083 Found 241.0087. HPLC 97.41% purity $t_R$=4.87 min.

Example 10. (E)-2-(2-chlorobenzylidene)hydrazinecarboximidamide acetate (BC1-299-1)

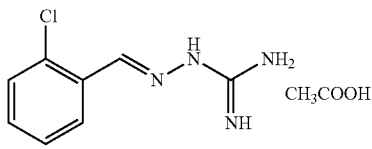

White powder. ¹H NMR (600 MHz, cd3od) δ 8.71 (s, 1H), 8.33 (d, J=7.8 Hz, 1H), 7.61 (d, J=8.0 Hz, 1H), 7.57 (t, J=7.6 Hz, 1H), 7.53 (t, J=7.5 Hz, 1H), 2.11 (s, 3H). ¹³C NMR (151 MHz, cd₃od) δ 178.99, 156.53, 143.35, 133.97, 131.28, 131.01, 129.54, 127.17, 126.94, 48.00, 47.86, 47.72, 47.57, 47.43, 47.29, 47.15, 22.52. ESI-HRMS Calc m/z (M+H)⁺ Calc m/z 197.0589 Found 197.0593. HPLC 95.48% purity $t_R$=4.76 min.

Example 11. (E)-2-(2-methylbenzylidene)hydrazinecarboximidamide acetate (BC2-3-1)

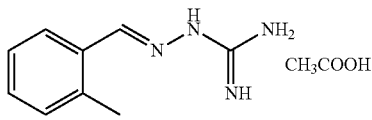

White powder. ¹H NMR (600 MHz, cd3od) δ 8.57 (s, 1H), 8.09 (d, J=7.2 Hz, 1H), 7.45 (t, J=6.8 Hz, 1H), 7.37 (t, J=7.6 Hz, 2H), 2.62 (s, 3H), 2.07 (s, 3H). ¹³C NMR (151 MHz, cd3od) δ 178.53, 156.08, 146.17, 137.34, 131.38, 130.50, 130.11, 126.27, 125.88, 22.30, 18.03. ESI-HRMS Calc m/z (M+H)⁺ Calc m/z 177.1135 Found 177.1147. HPLC 95.73% purity $t_R$=4.67 min.

Example 12. (E)-2-(2-chloro-6-fluorobenzylidene)hydrazinecarboximidamide acetate (BC2-5-1)

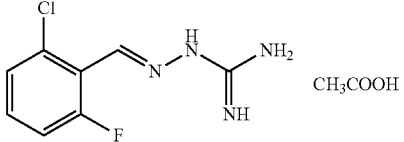

White powder. ¹H NMR (600 MHz, cd3od) δ 8.52 (s, 1H), 7.59-7.50 (m, 1H), 7.48 (d, J=7.9 Hz, 1H), 7.33 (t, J=9.2 Hz, 1H), 2.07 (s, 3H). ¹³C NMR (151 MHz, cd3od) δ 179.09, 161.87, 160.16, 156.60, 140.03, 134.51, 134.48, 131.37, 131.30, 125.80, 125.78, 120.09, 120.00, 114.96, 114.81, 22.51. ESI-HRMS Calc m/z (M+H)⁺ Calc m/z 215.0494 Found 215.0507. HPLC 95.39% purity $t_R$=4.56 min.

Example 13. (E)-2-(2,3-dichlorobenzylidene)hydrazinecarboximidamide acetate (BC2-7-1)

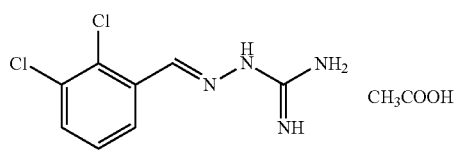

White powder. ¹H NMR (600 MHz, cd3od) δ 8.54 (s, 1H), 8.16-8.04 (m, 1H), 7.64-7.52 (m, 1H), 7.40-7.23 (m, 1H), 1.93 (s, 3H). ¹³C NMR (151 MHz, cd₃od) δ 178.84, 156.82, 142.89, 133.50, 133.07, 131.77, 131.44, 127.54, 125.55, 22.42. ESI-HRMS Calc m/z (M+H)⁺ Calc m/z 231.0199 Found 231.0195. HPLC 97.70% purity $t_R$=5.30 min.

Example 14. (E)-2-(3-chlorobenzylidene)hydrazinecarboximidamide acetate (BC2-9-1)

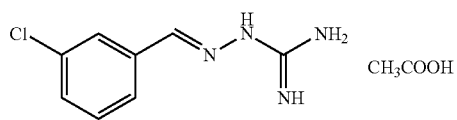

White powder. ¹H NMR (600 MHz, cd3od) δ 8.15 (s, 1H), 7.95 (s, 1H), 7.71 (s, 1H), 7.47 (s, 2H), 2.01 (s, 3H). ¹³C NMR (151 MHz, cd₃od) δ 179.30, 156.48, 145.64, 135.80, 134.52, 129.92, 129.89, 126.36, 125.82, 22.69. ESI-HRMS Calc m/z (M+H)⁺ Calc m/z 197.0589 Found 197.0602. HPLC 97.92% purity $t_R$=4.92 min.

Example 15. (E)-2-(2-fluorobenzylidene)hydrazinecarboximidamide acetate (BC2-11-1)

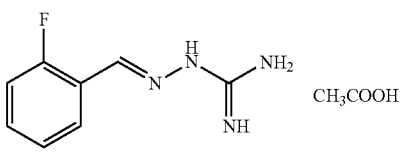

White powder. $^{1}$H NMR (600 MHz, cd3od) δ 8.35 (s, 1H), 8.08 (t, J=7.5 Hz, 1H), 7.44 (dd, J=13.8, 7.2 Hz, 1H), 7.22 (t, J=7.6 Hz, 1H), 7.15 (t, 1H), 1.93 (s, 3H). $^{13}$C NMR (151 MHz, cd$_3$od) δ 179.22, 162.25, 160.58, 156.46, 140.06, 140.03, 132.03, 131.97, 126.65, 126.64, 124.31, 124.29, 121.34, 121.27, 115.45, 115.31, 48.00, 47.86, 47.72, 47.58, 47.44, 47.29, 47.15, 22.61. ESI-HRMS Calc m/z (M+H)$^+$ Calc m/z 181.0884 Found 181.0898. HPLC 98.05% purity $t_R$=2.28 min.

Example 16. (E)-2-(4-chlorobenzylidene)hydrazinecarboximidamide acetate (BC2-13-1)

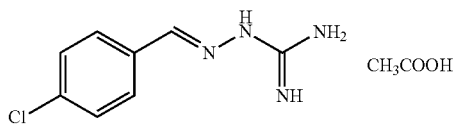

White powder. $^{1}$H NMR (600 MHz, cd$_3$od) δ 8.09 (s, 1H), 7.75 (d, J=8.3 Hz, 2H), 7.41 (d, J=8.3 Hz, 2H), 1.94 (s, 3H). $^{13}$C NMR (151 MHz, cd$_3$od) δ 179.34, 156.38, 145.89, 135.93, 132.49, 128.60, 128.51, 22.72. ESI-HRMS Calc m/z (M+H)$^+$ Calc m/z 197.0589 Found 197.0599. HPLC 96.79% purity $t_R$=4.96 min.

Example 17. (E)-2-(2-chloro-4-fluorobenzylidene)hydrazinecarboximidamide acetate (BC2-17-1)

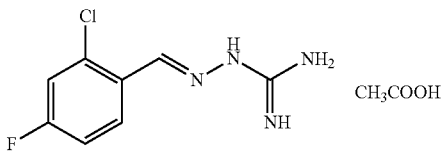

White powder. $^{1}$H NMR (600 MHz, cd$_3$od) δ 8.47 (s, 1H), 8.29-8.08 (m, 1H), 7.34-7.23 (m, 1H), 7.14 (s, 1H), 1.93 (s, 3H). $^{13}$C NMR (151 MHz, cd$_3$od) δ 179.15, 164.38, 162.70, 156.55, 142.19, 134.88, 134.81, 129.01, 128.95, 127.76, 127.74, 116.65, 116.47, 114.67, 114.53, 22.59. ESI-HRMS Calc m/z (M+H)$^+$ Calc m/z 215.0494 Found 215.0495. HPLC 95.95% purity $t_R$=4.95 min.

Example 18. (E)-2-(4-chloro-2-fluorobenzylidene)hydrazinecarboximidamide acetate (BC2-19-1)

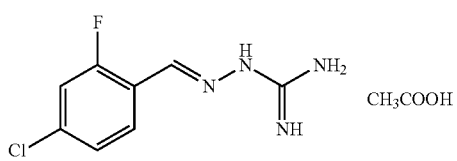

White powder. $^{1}$H NMR (600 MHz, cd3od) δ 8.52 (s, 1H), 8.33 (t, J=8.1 Hz, 1H), 7.58-7.41 (m, 2H), 2.17 (s, 3H). 13C NMR (151 MHz, cd$_3$od) δ 179.05, 161.85, 160.16, 156.66, 138.85, 138.82, 136.71, 136.64, 127.68, 127.66, 124.88, 124.86, 120.49, 120.42, 116.20, 116.04, 22.50. ESI-HRMS Calc m/z (M+H)$^+$ Calc m/z 215.0494 Found 215.0513. HPLC 95.29% purity $t_R$=5.06 min.

Example 19. (E)-2-(2-chloro-6-methoxybenzylidene)hydrazinecarboximidamide acetate (BC2-25-1)

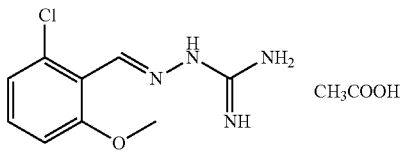

Pale yellow powder. $^{1}$H NMR (600 MHz, cd3od) δ 8.49 (s, 1H), 7.47 (t, J=8.3 Hz, 1H), 7.20 (d, J=12.0 Hz, 1H), 7.16 (d, J=6.0 Hz, 1H), 4.01 (s, 3H), 2.04 (s, 3H). $^{13}$C NMR (151 MHz, cd$_3$od) δ 178.39, 159.60, 156.36, 142.61, 133.60, 131.11, 122.35, 120.01, 109.76, 55.40, 22.26. ESI-HRMS Calc m/z (M+H)$^+$ Calc m/z 227.0694 Found 227.0699. HPLC 95.71% purity $t_R$=4.59 min.

Example 20. (E)-2-(2,6-dimethylbenzylidene)hydrazinecarboximidamide acetate (BC2-27-1)

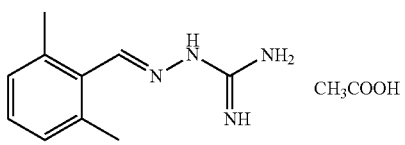

White powder. $^{1}$H NMR (600 MHz, cd$_3$od) δ 8.54 (s, 1H), 7.23 (t, J=7.1 Hz, 1H), 7.14 (d, J=7.3 Hz, 2H), 2.51 (s, 6H), 1.98 (s, 3H). $^{13}$C NMR (151 MHz, cd$_3$od) δ 179.14, 156.33, 147.66, 137.59, 130.45, 129.05, 128.31, 22.67, 19.86. ESI-HRMS Calc m/z (M+H)$^+$ Calc m/z 191.1291 Found 191.1297. HPLC 95.55% purity $t_R$=5.07 min.

Example 21. (E)-2-(2-bromo-6-chlorobenzylidene)hydrazinecarboximidamide acetate (BC2-35-1)

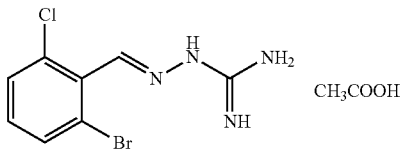

White powder. $^{1}$H NMR (600 MHz, cd3od) δ 8.29 (s, 1H), 7.61 (d, J=8.0 Hz, 1H), 7.47 (d, J=8.1 Hz, 1H), 7.25 (t, J=8.0 Hz, 1H), 1.95 (s, 3H). $^{13}$C NMR (151 MHz, cd$_3$od) δ 178.67, 156.49, 143.53, 134.57, 132.08, 131.11, 131.05, 129.38, 123.64, 22.45. ESI-HRMS Calc m/z (M+H)$^+$ Calc m/z 274.9694 Found 274.9697. HPLC 95.51% purity $t_R$=5.02 min.

Example 22. (E)-2-(2-chloro-6-(trifluoromethyl) benzylidene)hydrazinecarboximidamide acetate (BC2-45-1)

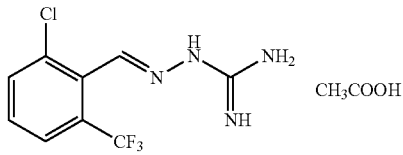

White powder. $^1$H NMR (600 MHz, cd$_3$od) δ 8.51 (s, 1H), 8.00-7.79 (m, 2H), 7.79-7.63 (m, 1H), 2.05 (s, 3H). $^{13}$C NMR (151 MHz, cd$_3$od) δ 178.70, 156.62, 141.74, 135.30, 133.47, 130.65, 130.54, 130.37, 130.16, 125.14, 125.10, 125.07, 125.03, 124.24, 122.43, 22.25. ESI-HRMS Calc m/z (M+H)$^+$ Calc m/z 265.0462 Found 265.0457. HPLC 97.55% purity t$_R$=5.11 min.

Example 23. (E)-2-(2,6-dibromobenzylidene)hydrazinecarboximidamide acetate (BC2-47-1)

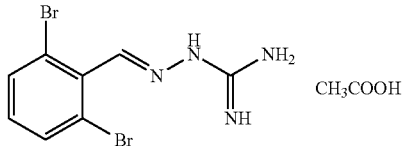

White powder. $^1$H NMR (600 MHz, cd$_3$od) δ 8.23 (s, 1H), 7.67 (d, J=7.9 Hz, 2H), 7.18 (t, J=7.8 Hz, 1H), 1.94 (s, 3H). $^{13}$C NMR (151 MHz, cd$_3$od) δ 178.80, 156.63, 145.29, 133.03, 132.53, 131.35, 123.43, 22.38. ESI-HRMS Calc m/z (M+H)$^+$ Calc m/z 318.9188 Found 318.9181. HPLC 95.86% purity t$_R$=5.11 min.

Example 24. (E)-2-(2-chloro-6-nitrobenzylidene) hydrazinecarboximidamide acetate (BC2-57-1)

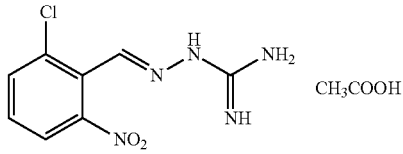

Yellow powder. $^1$H NMR (600 MHz, cd3od) δ 8.54 (s, 1H), 7.94-7.90 (m, 2H), 7.75-7.72 (m, 1H), 2.11 (s, 3H). $^{13}$C NMR (151 MHz, cd3od) δ 179.33, 157.20, 149.60, 139.44, 135.00, 133.24, 130.78, 125.51, 122.33, 22.68. ESI-HRMS Calc m/z (M+H)$^+$ Calc m/z 242.0439 Found 242.0450. HPLC 95.14% purity t$_R$=4.31 min.

Example 25. (E)-2-(2-chloro-6-hydroxybenzylidene) hydrazinecarboximidamide acetate (BC2-59-1)

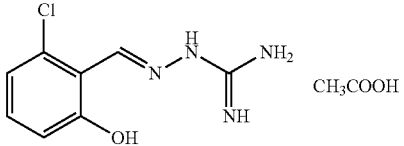

White powder. $^1$H NMR (600 MHz, cd$_3$od) δ 8.88 (s, 1H), 7.38 (t, J=8.0 Hz, 1H), 7.12 (d, J=7.6 Hz, 1H), 7.03 (d, J=8.2 Hz, 1H), 2.10 (s, 3H). $^{13}$C NMR (151 MHz, cd$_3$od) δ 177.68, 158.85, 156.91, 147.07, 134.26, 131.51, 120.47, 115.47, 115.40, 21.71. ESI-HRMS Calc m/z (M+H)$^+$ Calc m/z 213.0538 Found 213.0545. HPLC 96.07% purity t$_R$=4.45 min.

Example 26. (E)-2-(2,6-dichlorobenzylidene)hydrazinecarboxamide hydrochloride (BC1-262-1)

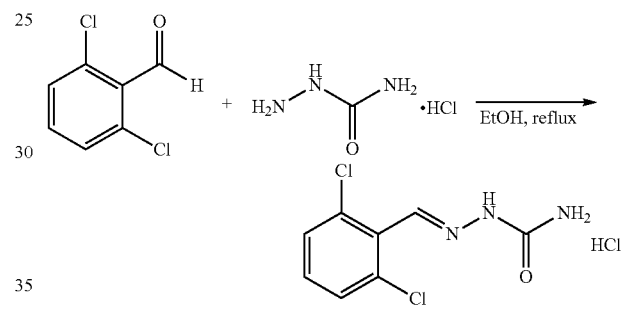

The 2,6-dichlorobenzaldehyde (5 mmol, 875 mg) and hydrazinecarboxamide hydrochloride (5 mmol, 558 mg) in EtOH (10 ml) were shaken at reflux for 12 hours. After cooling at room temperature, the final compound was recovered as a precipitate after filtration. The crude compound was recrystallized from water to give the title compound (1.04 g, 79%) as a white powder. $^1$H NMR (600 MHz, cd3od) δ 8.13 (s, 1H), 7.44 (d, J=8.1 Hz, 2H), 7.31 (t, J=8.1 Hz, 1H). $^{13}$C NMR (151 MHz, cd3od) δ 158.44, 136.36, 134.45, 130.14, 129.96, 128.81. ESI-HRMS Calc m/z (M+H)$^+$ Calc m/z 232.0039 Found 232.0049. HPLC 95.70% purity t$_R$=4.58 min.

Example 27. N-(3,5-dichlorophenyl)-4,5-dihydro-1H-imidazol-2-amine (BC1-242-2)

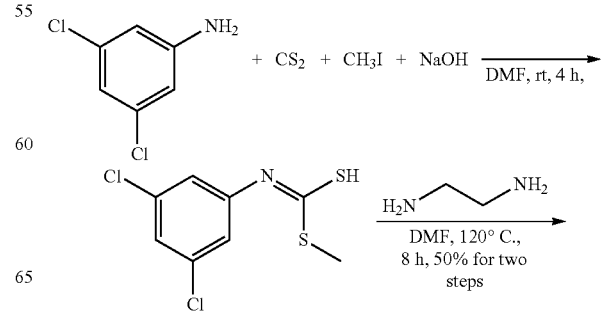

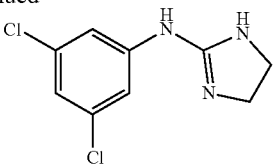

Step 1. methyl hydrogen (3,5-dichlorophenyl)carbonimidodithioate

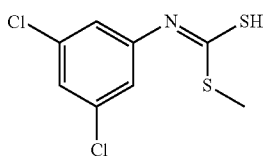

To a well stirred cold solution of 3,5-dichloroaniline (1.62 g, 10 mmol) in DMF (20 ml) were added aqueous NaOH (20M, 1 ml), CS₂ (0.75 ml, 12.5 mmol) and CH₃I (0.78 ml, 12.5 mmol) in sequence at intervals of 30 min and stirring was continued for 4 h. The reaction mixture was then separated between water and EA. The EA layer was washed with water two times, dried with Na₂SO₄, evaporated and the residue obtained was used in the next step without further purification.

Step 2. N-(3,5-dichlorophenyl)-4,5-dihydro-1H-imidazol-2-amine (BC1-242-2)

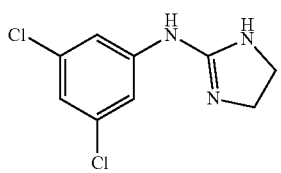 [SMILES: Clc1cc(Cl)cc(NC2=NCCN2)c1]

A solution of methyl hydrogen (3,5-dichlorophenyl)carbonimidodithioate (5 mmol, 1.26 g) in DMF (5 ml) was added to a solution of 1,2-diaminoethane (1.34 ml, 20 mmol) in DMF (5 ml) with stirring at rt. The reaction mixture was maintained at 120° C. for 8 h. Then the mixture was cooled and added to ice cold water. The resulting solid was purified by silica gel chromatography using EtOAc/hexanes, to obtain the title compound (50% for two steps) as a light yellow powder. ¹H NMR (600 MHz, cdcl₃) δ 6.92 (s, 1H), 6.85 (s, 2H), 5.59 (s, 2H), 3.52 (s, 4H). ¹³C NMR (151 MHz, cdcl₃) δ 158.77, 151.62, 135.02, 121.69, 121.52, 42.44. ESI-HRMS Calc m/z (M+H)⁺ Calc m/z 230.0246 Found 230.0251. HPLC 96.70% purity $t_R$=4.55 min.

Example 28. 1-(2,6-dichlorophenyl)guanidine (BC1-256-2)

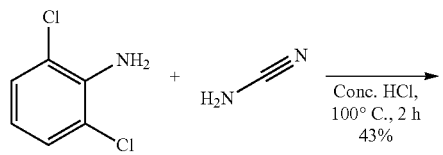

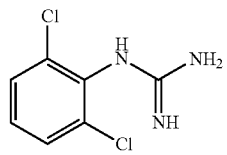

2,6-dichloroaniline (810 mg, 5 mmol), cyanamide (1.05 g, 25 mmol) and conc. HCl (5 ml) were heated together at 100° C. for 2 h. The mixture was cooled to 20° C. and made strongly basic with 7.5N NaOH solution, and the mixture was extracted with DCM three times. Organic layer was combined then dried over Na₂SO₄, evaporated and the residue obtained was purified by silica gel chromatography using DCM/MeOH, to obtain the title compound as a white powder (426 mg, 43% yield). ¹H NMR (600 MHz, cd3od) δ 7.31 (d, J=8.1 Hz, 2H), 6.95 (t, J=8.0 Hz, 1H). ¹³C NMR (151 MHz, cd₃od) δ 154.62, 142.75, 130.94, 128.03, 123.75. ESI-HRMS Calc m/z (M+H)⁺ Calc m/z 204.0090 Found 204.0096. HPLC 95.67% purity $t_R$=1.85 min.

Example 29. 1-(2,6-dichlorophenethyl)guanidine (BC1-252-2)

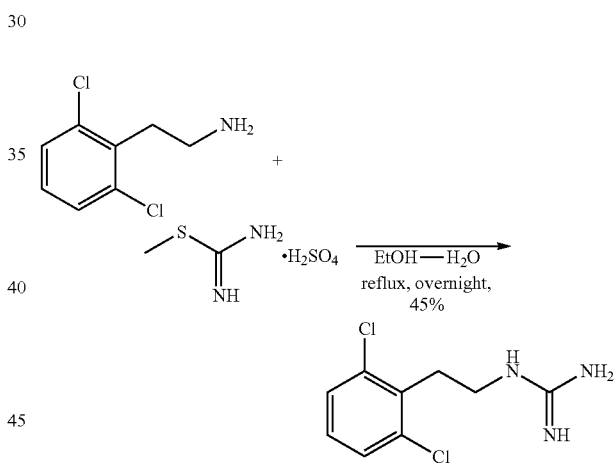

A mixture of 2,6-dichlorophenethylamine (0.57 g, 3 mmol), S-methylisothiouronium sulfate (0.56 g, 3 mmol), EtOH (4 ml) and water (2 ml) was refluxed until the evolution of MeSH ceased. The mixture was cooled to 20° C. and made strongly basic with 1N NaOH solution, and the mixture was extracted with DCM three times. Organic layer was combined then dried over Na₂SO₄, evaporated and the residue was recrystallized with water to give the title compound as a white powder (45%). ¹H NMR (600 MHz, cd₃od) δ 7.27 (d, J=7.9 Hz, 2H), 7.12 (t, J=7.9 Hz, 1H), 3.34 (t, J=6.8 Hz, 2H), 3.15 (t, J=6.7 Hz, 2H). ¹³C NMR (151 MHz, cd₃od) δ 157.49, 135.49, 133.81, 128.78, 128.23, 39.25, 30.10. ESI-HRMS Calc m/z (M+H)⁺ Calc m/z 232.0403 Found 232.0410. HPLC 95.70% purity $t_R$=4.58 min.

Example 30. (E)-2-(1-(2,6-dichlorophenyl)ethylidene)hydrazinecarboximidamide (BC1-259-2)

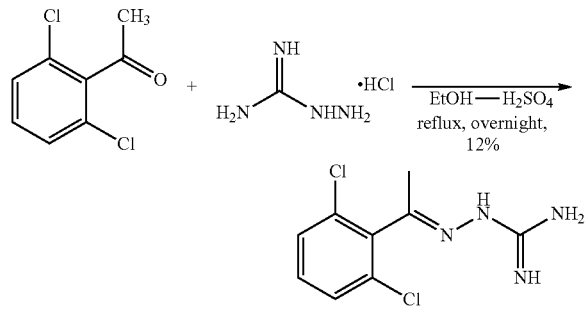

1-(2,6-dichlorophenyl)ethanone (373 mg, 1.97 mmol) and aminoguanidine hydrochloride (218 mg, 1.97 mmol) were refluxed in 10 ml EtOH with 78 ul of concentrated $H_2SO_4$ for 3 h. The reaction mixture was neutralized with 1N NaOH to PH=13. The solvent was evaporated and the residue was purified by silica gel chromatography using DCM/MeOH/$NH_3 \cdot H_2O$, to obtain the title compound as a white powder (12% yield). $^1H$ NMR (600 MHz, cd$_3$od) δ 7.39 (d, J=7.9 Hz, 2H), 7.30 (t, J=8.0 Hz, 1H), 2.18 (s, 3H). $^{13}C$ NMR (151 MHz, cd$_3$od) δ 159.47, 147.37, 137.15, 132.11, 129.84, 127.75, 21.20. ESI-HRMS Calc m/z (M+H)$^+$ Calc m/z 245.0355 Found 245.0359. HPLC 95.25% purity $t_R$=5.11 min.

Example 31. (E)-2-(2,6-diiodobenzylidene)hydrazinecarboximidamide (BC2-55-2)

Step 1. 2,6-diiodobenzaldehyde

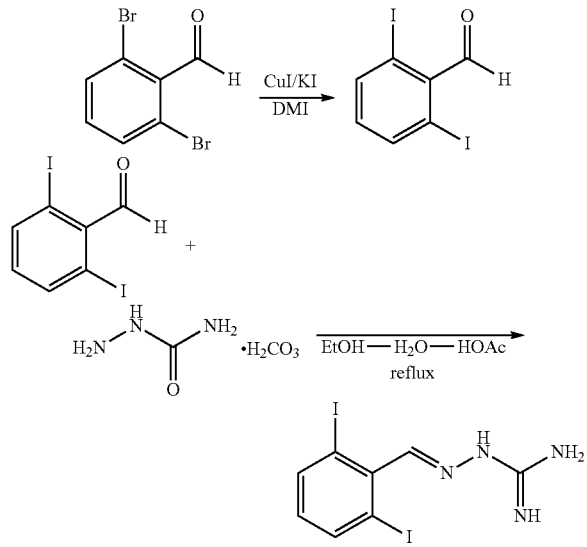

A mixture of 2,6-dibromobenzaldehyde (792 mg, 3 mmol), CuI (6.86 g, 36 mmol) and KI (19.92 g, 120 mmol) were refluxed in 20 ml 1,3-Dimethyl-2-imidazolidinone overnight. After cooled to rt, the reaction mixture was filtered and the filtrate was portioned between water and Et$_2$O. The aqueous layer was extracted with Et$_2$O three times and then the combined organic phase was washed with brine and dried over Na$_2$SO$_4$, evaporated and the residue was purified by silica gel chromatography using hexane/EA, to obtain the title compound as a yellow powder (355 mg, 35%). $^1H$ NMR (600 MHz, cdcl$_3$) δ 9.77 (s, 1H), 8.00 (d, J=7.8 Hz, 2H), 6.85 (t, J=7.8 Hz, 1H). $^{13}C$ NMR (151 MHz, cdcl$_3$) δ 195.58, 141.39, 135.28, 134.46, 97.38.

Step 2. (E)-2-(2,6-diiodobenzylidene)hydrazinecarboximidamide (BC2-55-2)

2,6-diiodobenzaldehyde (355 mg, 0.99 mmol) and aminoguanidine bicarbonate (135 mg, 0.99 mmol) in EtOH (2 ml)-H$_2$O (4 ml)-HOAc (0.1 ml) were shaken at reflux for 12 hours. After cooling at room temperature, the solvent was evaporated and the residue was purified by silica gel chromatography using DCM/MeOH/NH$_3 \cdot$H$_2$O, to obtain the title compound as a yellow powder (200 mg, 49%). $^1H$ NMR (600 MHz, cd$_3$od) δ 7.97-7.96 (m, 3H), 6.71-6.68 (m, 1H). $^{13}C$ NMR (151 MHz, cd$_3$od) δ 149.06, 144.67, 140.07, 139.52, 130.30, 96.29. ESI-HRMS Calc m/z (M+H)$^+$ Calc m/z 414.8911 Found 414.8919. HPLC 96.13% purity $t_R$=5.19 min.

Example 32. (E)-2-(2-amino-6-chlorobenzylidene)hydrazinecarboximidamide (BC2-61-1) and (E)-2-(2-aminobenzylidene)hydrazinecarboximidamide (bc2-61-2)

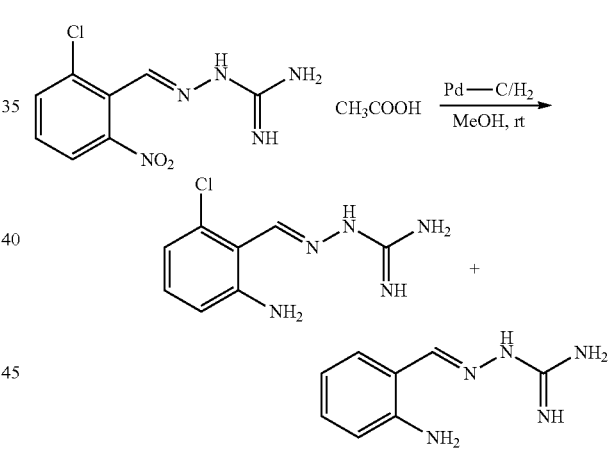

To a stirred solution of (E)-2-(2-chloro-6-nitrobenzylidene)hydrazinecarboximidamide acetate (650 mg, 2.16 mol) in MeOH (10 ml) was added Pd—C (33 mg), the resulting mixture was stirred under H$_2$ at rt overnight. After filtration, the filtrate was concentrated and the residue was purified by silica gel chromatography using DCM/MeOH/NH$_3 \cdot$H$_2$O, to obtain the (E)-2-(2-amino-6-chlorobenzylidene)hydrazinecarboximidamide as a white powder (150 mg, 33%) $^1H$ NMR (600 MHz, cd$_3$od) δ 8.78 (s, 1H), 6.94 (t, J=8.0 Hz, 1H), 6.67-6.63 (m, 2H), $^{13}C$ NMR (151 MHz, cd$_3$od) δ 159.82, 148.70, 147.29, 134.86, 129.14, 116.91, 116.88, 114.13, ESI-HRMS Calc m/z (M+H)$^+$ Calc m/z 212.0697 Found 212.0710 HPLC 98.75% purity $t_R$=4.54 min and (E)-2-(2-aminobenzylidene)hydrazinecarboximidamide as a white powder (120 mg, 32%) $^1H$ NMR (600 MHz, cd$_3$od) δ 8.26 (s, 1H), 7.19 (d, J=4.2 Hz, 1H), 7.10 (d, J=6.8 Hz, 1H), 6.81 (d, J=4.6 Hz, 1H), 6.72 (d, J=3.0 Hz, 1H), $^{13}C$ NMR (151 MHz, cd$_3$od) δ 159.47, 150.94, 146.63, 131.58, 128.85, 118.17, 116.40, 115.45, ESI-HRMS Calc m/z (M+H)⁺ Calc m/z 178.1087 Found 178.1100. HPLC 99.04% purity $t_R$=2.29 min.

Example 33. (E)-2-(2-chloro-5-(trifluoromethyl)benzylidene)hydrazine-1-carboximidamide acetate (JM1-221-2)

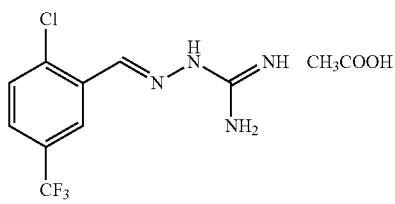

White powder. ¹H NMR (dmso-d₆, 600 MHz) δ 8.46 (s, 1H), 8.28 (s, 1H), 7.62 (d, 1H, J=8.2 Hz), 7.56 (d, 1H, J=8.2 Hz), 6.50 (br s, 2H), 6.14 (br s, 2H), 1.87 (s, 3H). ¹³C NMR (150 MHz, dmso-d₆) δ 174.12, 160.12, 138.40, 138.18, 136.01, 134.38, 131.20, 128.76, 128.54, 124.13, 123.90, 22.88. ESI-HRMS Calc m/z for $C_9H_9ClF_3N_4$ 265.0462 (M+H)⁺, found 265.0467. HPLC 99.8% purity $t_R$=6.37 min.

Example 34. (E)-2-(2-fluoro-6-(trifluoromethyl)benzylidene)hydrazine-1-carboximidamide acetate (JM1-223-2)

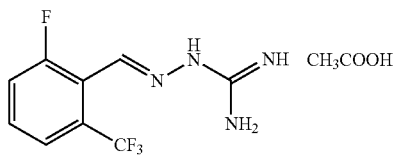

White powder. ¹H NMR (dmso-d₆, 600 MHz) δ 8.10 (s, 1H), 7.57 (d, 1H, J=7.6 Hz), 7.53 (t, 1H, J=8.8 Hz), 7.46 (q, 1H, J=7.0 Hz), 5.90 (br s, 4H), 1.87 (s, 3H). ¹³C NMR (150 MHz, dmso-d₆) δ 173.90, 161.51, 160.69, 129.84, 134.88, 129.99, 128.08, 124.96, 122.75, 121.08, 22.42. ESI-HRMS Calc m/z for $C_9H_9F_4N_4$ 249.0758 (M+H)⁺, found 249.0761. HPLC 99.8% purity $t_R$=5.54 min.

Example 35. (E)-2-(1-(3-chlorophenyl)propylidene)hydrazine-1-carboximidamide (JM1-257-2)

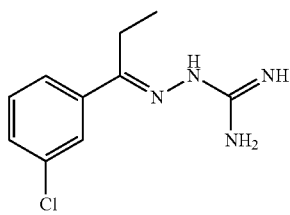

¹H NMR (cd₃od, 600 MHz) δ 7.96 (s, 1H), 7.77 (d, 1H, J=7.0 Hz), 7.42 (t, 1H, d, J=8.8 Hz), 2.81 (q, 2H, J=7.6 Hz), 1.18 (t, 3H, J=7.6 Hz). ¹³C NMR (150 MHz, cd3od) δ 156.03, 155.14, 137.98, 134.08, 130.72, 130.00, 126.83, 15.51, 10.94. ESI-HRMS Calc m/z for $C_{10}H_{14}ClN_4$ 225.0907 (M+H)⁺, found 25.0897. HPLC 99.68% purity $t_R$=6.24 min.

Example 36. N-(2,6-dimethylphenyl)-4,5-dihydro-1H-imidazol-2-amine (JM2-59-2)

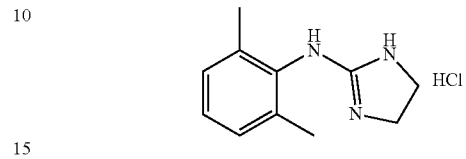

A mixture of sodium hydroxide (171.5 mg, 4.28 mmol) and ethylene diamine (184 mg, 3.06 mmol) were dissolved in 10 mL of ethanol and stirred at room temperature until obtained clear solution. To this solution was added drop wise 1,3-dimethyl-2-thionitrosobenzene (500 mg, 3.06 mmol) in 2 mL ethanol and refluxed for 20 h. The resulting solution was allowed to room temperature and acidified to pH ~2 by bubbling hydrogen chloride through it. The suspension was filtered, the residue well washed with ethanol and the filtrate evaporated to yield crude compound. The crude was purified on silica using methanol in dichloromethane to obtain final compound as white solid. Yield 500 mg (72%). ¹H NMR (cd₃od, 600 MHz) δ 7.22 (t, 1H, J=8.2 Hz), 7.45 (d, 2H, J=7.0 Hz), 3.79 (s, 4H), 2.22 (s, 6H). ¹³C NMR (150 MHz, cd₃od) δ 159.17, 136.71, 136.31, 128.77, 128.43, 39.25, 16.47. ESI-HRMS Calc m/z for $C_{11}H_{16}N_3$ 190.1339 (M+H)⁺, found 190.1342.

Example 37. (E)-2-(2,6-dichloro-4-methoxybenzylidene)hydrazine-1-carboximidamide (JM2-63-2)

Step 1. 2,6-dichloro-4-methoxybenzaldehyde

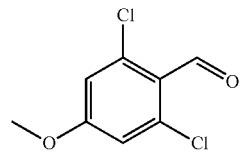

To a solution of 2,6-dichloro-4-hydroxybenzaldehyde (140 mg, 0.73 mmol) in 4 mL DMF added 203 mg (1.465 mmol) of $K_2CO_3$ and stirred at room temperature for 3 h. The reaction mixture was extracted with water and ethyl acetate. The organic layer was washed with brine (×3), dried on $Na_2SO_4$. The solvent was evaporated to obtain crude compound as dark red color. The crude was purified on silica with hexane/ethyl acetate to obtain white solid (130 mg, 87%). ¹H NMR (dmso-d₆, 600 MHz) δ 10.35 (s, 1H), 6.85 (s, 1H), 3.81 (s, 3H).

Step 2. (E)-2-(2,6-dichloro-4-methoxybenzylidene)hydrazine-1-carboximidamide (JM2-63-2)

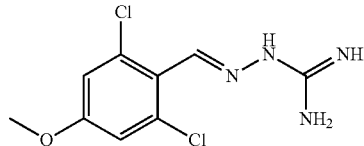 [SMILES: COc1cc(Cl)c(/C=N/NC(=N)N)c(Cl)c1]

To a solution of 2,6-dichloro-4-methoxybenzaldehyde (90 mg, 0.44 mmol) in 2 mL ethanol was added aminoguanidine bicarbonate (60.3 mg, 0.44 mmol) and refluxed for overnight. The solvent was evaporated after allowing to room temperature and recrystallized from ethanol. Brown crystals (80 mg, 69%). $^1$H NMR (dmso-d$_6$, 600 MHz) δ 8.10 (s, 1H), 7.06 (s, 2H), 5.71 (s, 2H), 5.60 (s, 2H), 3.28 (s, 3H). $^{13}$C NMR (150 MHz, dmso-d$_6$) δ 161.51, 158.63, 138.15, 134.40, 124.82, 115.56, 56.46. ESI-HRMS Calc m/z for $C_9H_{11}Cl_2N_4O$ 261.0304 (M+H)$^+$, found 261.0310. HPLC 99.72% purity $t_R$=6.10 min.

Example 38. (E)-2-(4-(benzyloxy)-2,6-dichlorobenzylidene)hydrazine-1-carboximidamide (JM2-67-2)

Step 1. 4-(benzyloxy)-2,6-dichlorobenzaldehyde

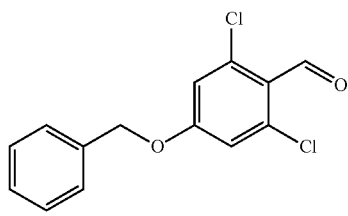 [SMILES: O=Cc1c(Cl)cc(OCc2ccccc2)cc1Cl]

To a solution of 2,6-dichloro-4-hydroxybenzaldehyde (200 mg, 1.04 mmol) in 8 mL DMF added 287 mg (2.08 mmol) of K$_2$CO$_3$ and stirred at room temperature for 1 h. The reaction mixture was extracted with water and ethyl acetate. The organic layer was washed with brine (×3), dried on Na$_2$SO$_4$. The solvent was evaporated to obtain crude compound as dark red color. The crude was purified on silica with hexane/ethyl acetate to obtain white solid (220 mg, 75%). $^1$H NMR (dmso-d$_6$, 600 MHz) δ 10.25 (s, 1H), 7.42 (d, 2H, J=7.6 Hz), 7.38 (t, 2H, d, J=7.0 Hz), 7.34 (d, 1H, J=7.6 Hz), 7.28 (s, 2H), 5.24 (s, 2H). $^{13}$C NMR (150 MHz, dmso-d$_6$) δ 168.01, 162.24, 138.03, 135.96, 128.99, 128.75, 128.44, 126.82, 122.89, 117.08, 70.08.

Step 2. (E)-2-(4-(benzyloxy)-2,6-dichlorobenzylidene)hydrazine-1-carboximidamide (JM2-67-2)

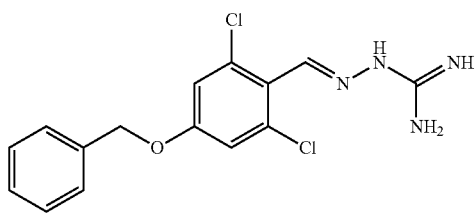 [SMILES: N=C(N)N/N=C/c1c(Cl)cc(OCc2ccccc2)cc1Cl]

To a solution of 4-(benzyloxy)-2,6-dichlorobenzaldehyde (150 mg, 0.53 mmol) in 4 mL ethanol was added aminoguanidine bicarbonate (72.6 mg, 0.53 mmol) and refluxed for overnight. The solvent was evaporated after allowing to room temperature and recrystallized from ethanol. Off-white needles: $^1$H NMR (dmso-d$_6$, 600 MHz) δ 8.09 (s, 1H), 7.41 (d, 2H, J=7.0 Hz), 7.37 (t, 2H, d, J=7.0 Hz), 7.31 (t, 1H, J=7.0 Hz), 7.15 (s, 2H), 5.71 (s, 2H), 5.61 (s, 2H), 5.15 (s, 2H). $^{13}$C NMR (150 MHz, dmso-d$_6$) δ 161.52, 157.64, 138.10, 136.58, 134.37, 128.93, 128.53, 128.26, 125.07, 116.40, 70.38. ESI-HRMS Calc m/z for $C_{15}H_{15}Cl_2N_4O$ 337.0617 (M+H)$^+$, found 337.0612. HPLC 99.64% purity $t_R$=8.02 min.

Example 39. (E)-2-(2-(2,6-dichlorobenzylidene)hydrazinyl)-4,5-dihydro-1H-imidazole hydrochloride (JM2-83-2)

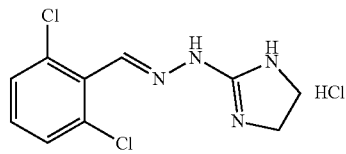

$^1$H NMR (dmso-d$_6$, 600 MHz) δ 12.60 (s, 1H), 8.59 (br s, 2H), 8.38 (s, 1H), 7.56 (d, 2H, J=8.2 Hz), 7.45 (t, 1H, J=8.2 Hz), 3.68 (s, 4H). $^{13}$C NMR (150 MHz, dmso-d$_6$) δ 158.10, 144.69, 134.47, 132.25, 129.47, 43.31. ESI-HRMS Calc m/z for $C_{10}H_{11}Cl_2N_4$ 257.0355 (M+H)$^+$, found 257.0349. HPLC 99.37% purity $t_R$=6.44 min.

Example 40. (E)-2-(2-(2,6-dimethylbenzylidene)hydrazinyl)-4,5-dihydro-1H-imidazole hydrochloride (JM2-85-2)

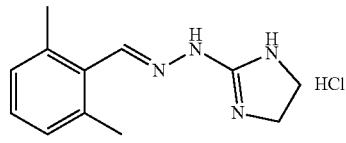 [SMILES: Cc1cccc(C)c1/C=N/NC1=NCCN1 ; Cl]

1H NMR (dmso-d$_6$, 600 MHz) δ 12.27 (s, 1H), 8.49 (s, 1H), 8.45 (br s, 2H), 7.18 (t, 1H, J=7.6 Hz), 7.08 (d, 2H, J=7.6 Hz), 3.68 (s, 4H), 2.37 (s, 6H). $^{13}$C NMR (150 MHz, dmso-d$_6$) δ 158.03, 149.34, 137.92, 130.66, 129.81, 128.26, 43.25, 21.25. ESI-HRMS Calc m/z for $C_{12}H_{17}N_4$ 217.1448 (M+H)$^+$, found 217.1440. HPLC 98.73% purity $t_R$=5.72 min.

Example 41. 2-(2,6-dichlorobenzyl)-4,5-dihydro-1H-imidazole (JM2-87-2)

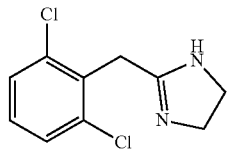 [SMILES: Clc1cccc(Cl)c1CC1=NCCN1]

The mixture of 2-(2,6-dichlorophenyl)acetonitrile (200 mg, 1.07 mmol), ethylene diamine (484 mg, 8.06 mmol) and Sulfur (17.5 mg, 0.54 mmol) heated at 200° C. for 20 min at microwave. After allowing to room temperature added cold water and extracted with ether to yield crude product. The crude was purified on silica column using methanol in dichloromethane as eluent. The final product was obtained as off-white solid (67%). $^1$H NMR (dmso-d$_6$, 600 MHz) δ 7.40 (d, 2H, J=8.2 Hz), 7.25 (t, 1H, J=8.2 Hz), 6.32 (br s, 2H), 3.66 (s, 2H), 3.31 (s, 4H). $^{13}$C NMR (150 MHz, dmso-d$_6$) δ 163.73, 135.68, 133.89, 129.37, 128.45, 31.31. ESI-HRMS Calc m/z for C$_{10}$H$_{11}$Cl$_2$N$_2$ 229.0294 (M+H)$^+$, found 229.0301. HPLC 96%.

Example 42. (E)-2-(2-(2-chloro-6-nitrobenzylidene)hydrazinyl)-4,5-dihydro-1H-imidazole hydrochloride (JM2-89-2)

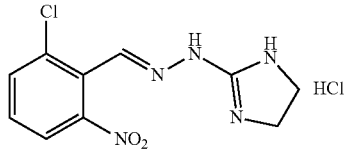 [SMILES: O=[N+]([O-])c1cccc(Cl)c1/C=N/NC1=NCCN1 ; Cl]

$^1$H NMR (dmso-d$_6$, 600 MHz) δ 12.81 (s, 1H), 8.59 (br s, 2H), 8.47 (s, 1H), 8.06 (d, 1H, J=7.0 Hz), 7.95 (d, 1H, J=7.6 Hz), 7.71 (t, 1H, J=8.2 Hz), 3.65 (s, 4H). $^{13}$C NMR (150 MHz, dmso-d$_6$) δ 158.10, 149.76, 143.82, 135.01, 132.32, 126.84, 124.02, 43.28. ESI-HRMS Calc m/z for C$_{10}$H$_{11}$ClN$_5$O$_2$ 268.0596(M+H)$^+$, found 268.0587. HPLC 98.25% purity $t_R$=6.77 min.

Example 43. (E)-2-(2-(3,4-dichlorobenzylidene)hydrazinyl)-4,5-dihydro-1H-imidazole hydrochloride (JM2-91-2)

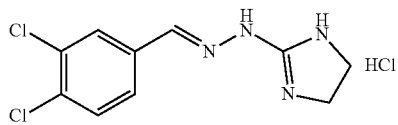 [SMILES: Clc1ccc(/C=N/NC2=NCCN2)cc1Cl ; Cl]

$^1$H NMR (dmso-d$_6$, 600 MHz) δ 12.43 (s, 1H), 8.18 (s, 1H), 8.12 (s, 1H), 7.76 (d, 1H, J=8.2 Hz), 7.71 (d, 1H, J=8.2 Hz), 3.72 (s, 4H). $^{13}$C NMR (150 MHz, dmso-d$_6$) δ 158.30, 145.85, 134.52, 133.26, 132.25, 131.42, 128.96, 128.34, 43.33. ESI-HRMS Calc m/z for C$_{10}$H$_{11}$Cl$_2$N$_4$ 257.0355 (M+H)$^+$, found 257.0343. HPLC 98.38% purity $t_R$=7.03 min.

Example 44. (E)-2-(2-(2-chloro-6-fluorobenzylidene)hydrazinyl)-4,5-dihydro-1H-imidazole hydrochloride (JM2-95-2)

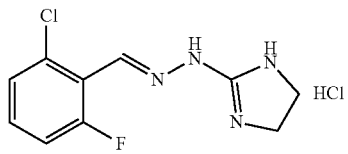

$^1$H NMR (dmso-d$_6$, 600 MHz) δ 12.62 (s, 1H), 8.91 (br s, 2H), 8.49 (s, 1H), 8.08 (d, 1H, J=9.4 Hz), 7.58 (t, 1H, J=7.0 Hz), 7.35 (t, 1H, J=7.6 Hz), 3.74 (s, 4H). $^{13}$C NMR (150 MHz, dmso-d$_6$) δ 162.22, 160.60, 158.14, 143.19, 133.00, 132.28, 129.04, 119.72, 114.02, 43.15. ESI-HRMS Calc m/z for C$_{10}$H$_{11}$ClFN$_4$ 241.0651 (M+H)$^+$, found 241.0662. HPLC 99.75% purity $t_R$=6.21 min.

Example 45. N-(2,6-dichlorophenyl)-4,5-dihydro-1H-imidazol-2-amine hydrochloride (JM2-97-2)

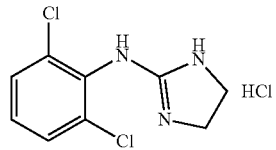 [SMILES: Clc1cccc(Cl)c1NC1=NCCN1 ; Cl]

A mixture of sodium hydroxide (171.5 mg, 4.28 mmol) and ethylene diamine (184 mg, 3.06 mmol) were dissolved in 10 mL of ethanol and stirred at room temperature until obtained clear solution. To this solution was added drop wise 1,3-dichloro-2-thionitrosobenzene (500 mg, 3.06 mmol) in 2 mL ethanol and refluxed for 20 h. The resulting solution was allowed to room temperature and acidified to pH ~2 by bubbling hydrogen chloride through it. The suspension was filtered, the residue well washed with ethanol and the filtrate evaporated to yield crude compound. The crude was purified on silica using methanol in dichloromethane to obtain final compound as white solid. Yield 470 mg (72%). $^1$H NMR (dmso-d$_6$, 600 MHz) δ 10.67 (s, 1H), 8.49 (br s, 2H), 7.61 (d, 2H, J=7.6 Hz), 7.45 (t, 1H, J=7.6 Hz), 3.29 (s, 4H). $^{13}$C NMR (150 MHz, dmso-d$_6$) δ 158.43, 134.49, 131.30, 129.64, 109.99, 43.15. ESI-HRMS Calc m/z for C$_9$H$_{10}$Cl$_2$N$_3$ 230.0246 (M+H)$^+$, found 230.0254. HPLC 99.54% purity $t_R$=3.72 min.

Example 46. 2-(1-(2,6-dichlorophenyl)ethyl)-4,5-dihydro-1H-imidazole (JM2-101-2)

Step 1. 2-(2,6-dichlorophenyl)propanenitrile

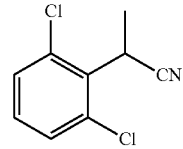

1,3-dichloro-2-(chloromethyl)benzene (500 mg, 2.7 mmol) was dissolved in THF (6 mL) under Argon. The mixture was cooled to −70° C. then added KO$^t$Bu (303 mg, 2.7 mg) followed by methyl iodide (381 mg, 2.7 mmol) under argon. The reaction was stirred at −70° C. for 1 h then was allowed to warm to room temperature and stirring continued for 12 h. The solution was concentrated in vacuo to remove THF and extracted with ethyl acetate and 1 M HCl followed by washing with sat. NaHCO$_3$ solution, brine, was dried over Na$_2$SO$_4$, and concentrated. The residue was purified by silica gel chromatography using 10% ethyl acetate in hexanes. The final product obtained as a yellow color oil. Yield 480 mg (89%). $^1$H NMR (cdcl$_3$, 600 MHz)

δ 7.34 (d, 2H, J=8.2 Hz), 7.20 (t, 1H, J=8.2 Hz), 4.82 (q, 1H, J=7.0 Hz), 1.68 (d, 3H, J=7.0 Hz). ESI-MS (M+H)⁺ 200.01.

Step 2. 2-(1-(2,6-dichlorophenyl)ethyl)-4,5-dihydro-1H-imidazole (JM2-101-2)

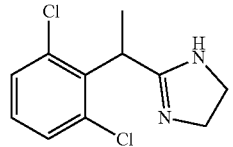

The mixture of 2-(2,6-dichlorophenyl)propanenitrile (200 mg, 1.0 mmol), ethylene diamine (450 mg, 7.5 mmol) and Sulfur (16 mg, 0.5 mmol) heated at 200° C. for 25 min in microwave. After allowing to room temperature added cold water and extracted with ether to yield crude product. The crude was purified on silica column using methanol in dichloromethane as eluent. The final product was obtained as off-white solid (42%). ¹H NMR (cdcl₃, 600 MHz) δ 7.34 (d, 2H, J=8.2 Hz), 7.20 (t, 1H, J=8.2 Hz), 4.82 (q, 1H, J=7.0 Hz), 3.41 (s, 4H), 1.68 (d, 3H, J=7.0 Hz). ¹³C NMR (150 MHz, dmso-d₆) δ 167.60, 138.22, 135.14, 129.51, 129.44, 36.70, 15.48. ESI-HRMS Calc m/z for $C_{11}H_{13}Cl_2N_2$ 243.0450 (M+H)⁺, found 243.0443.

Example 47. (E)-2-(2-(2,6-difluorobenzylidene)hydrazinyl)-4,5-dihydro-1H-imidazole hydrochloride (JM2-103-2)

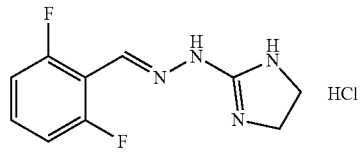 [SMILES: Fc1cccc(F)c1/C=N/NC1=NCCN1 ; Cl]

¹H NMR (dmso-d₆, 600 MHz) δ 12.47 (s, 1H), 8.54 (br s, 2H), 8.31 (s, 1H), 7.53 (t, 1H, J=7.0 Hz), 7.20 (t, 2H, J=8.2 Hz), 3.69 (s, 4H). ¹³C NMR (150 MHz, dmso-d₆) δ 161.51, 159.86, 157.89, 139.55, 133.17, 112.74, 110.91, 43.33. ESI-HRMS Calc m/z for $C_{10}H_{11}F_2N_4$ 225.0946 (M+H)⁺, found 225.0955. HPLC 99.57% purity $t_R$=4.66 min.

Example 48. (E)-2-(2-(2-bromo-6-nitrobenzylidene)hydrazinyl)-4,5-dihydro-1H-imidazole hydrochloride (JM2-109-2)

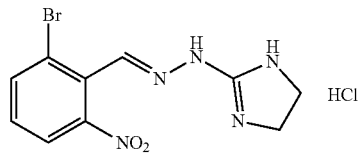

Yellow powder. ¹H NMR (dmso-d₆, 600 MHz) δ 12.77 (s, 1H), 8.61 (br s, 2H), 8.43 (s, 1H), 8.09 (t, 2H, J=7.6 Hz), 7.63 (t, 1H, J=7.6 Hz), 3.65 (s, 4H). ¹³C NMR (150 MHz, dmso-d₆) δ 158.03, 149.84, 145.46, 138.00, 132.58, 128.37, 124.55, 124.47, 43.28. ESI-HRMS Calc m/z for $C_{10}H_{11}BrN_5O_2$ 312.0091 (M+H)⁺, found 312.0082. HPLC 96.81% purity $t_R$=6.65 min.

Example 49. (E)-2-(2-(2,6-dibromobenzylidene)hydrazinyl)-4,5-dihydro-1H-imidazole hydrochloride (JM2-111-2)

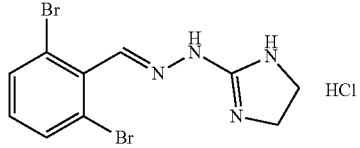 [SMILES: Brc1cccc(Br)c1/C=N/NC1=NCCN1 ; Cl]

Cream color powder. ¹H NMR (dmso-d₆, 600 MHz) δ 12.58 (s, 1H), 8.63 (br s, 2H), 8.25 (s, 1H), 7.75 (d, 2H, J=7.6 Hz), 7.29 (t, 1H, J=7.6 Hz), 3.68 (s, 4H). ¹³C NMR (150 MHz, dmso-d₆) δ 158.08, 147.92, 135.51, 132.94, 132.89, 123.81, 43.31. ESI-HRMS Calc m/z for $C_{10}H_{11}Br_2N_4$ 344.9345 (M+H)⁺, found 344.9357. HPLC 97.29% purity $t_R$=6.73 min.

Example 50. (E)-2-(2-(2-chlorobenzylidene)hydrazinyl)-4,5-dihydro-1H-imidazole hydrochloride (JM2-113-2)

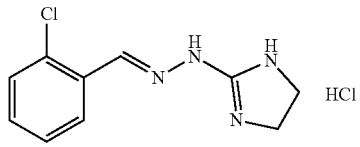 [SMILES: Fc1ccccc1/C=N/NC1=NCCN1 ; Cl]

Yellow color powder. ¹H NMR (dmso-d₆, 600 MHz) δ 12.51 (s, 1H), 8.79 (br s, 2H), 8.55 (s, 1H), 8.18 (d, 1H, J=7.6 Hz), 7.51 (d, 1H, J=7.6 Hz), 7.46 (t, 1H, J=7.0 Hz), 7.41 (t, 1H, J=7.6 Hz), 3.73 (s, 4H). ¹³C NMR (150 MHz, dmso-d₆) δ 158.13, 144.43, 133.81, 132.58, 130.91, 130.38, 127.93, 127.82, 43.32. ESI-HRMS Calc m/z for $C_{10}H_{12}ClN_4$ 223.0745 (M+H)⁺, found 223.0736. HPLC 98.73% purity $t_R$=5.52 min.

Example 51. (E)-2-(2-(2-fluorobenzylidene)hydrazinyl)-4,5-dihydro-1H-imidazole hydrochloride (JM2-115-2)

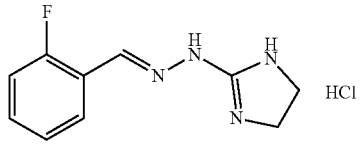

Purple color powder. ¹H NMR (dmso-d₆, 600 MHz) δ 12.23 (s, 1H), 8.75 (br s, 2H), 8.36 (s, 1H), 8.10 (t, 1H, J=7.0 Hz), 7.79 (q, 1H, J=6.4 Hz), 7.28 (t, 2H, J=8.2 Hz), 3.72 (s, 4H). ¹³C NMR (150 MHz, dmso-d₆) δ 158.17, 141.28, 133.23, 133.17, 127.19, 125.25, 116.55, 116.42, 43.24. ESI-HRMS Calc m/z for $C_{10}H_{12}FN_4$ 207.1041 (M+H)⁺, found 207.1030. HPLC 98.15% purity $t_R$=4.91 min.

Example 52. (E)-2-(2-(2-chloro-6-(trifluoromethyl)benzylidene)hydrazinyl)-4,5-dihydro-1H-imidazole hydrochloride (JM2-131-2)

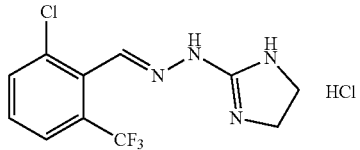 [SMILES: FC(F)(F)c1cccc(Cl)c1/C=N/NC1=NCCN1 ; Cl]

White solid. $^1$H NMR (dmso-d$_6$, 600 MHz) δ 12.80 (s, 1H), 8.73 (br s, 3H), 7.54 (d, 1H, J=8.2 Hz), 7.50 (t, 1H, J=7.6 Hz), 7.46 (d, 1H, J=7.6 Hz), 3.87 (s, 4H), 2.65 (s, 3H). $^{13}$C NMR (150 MHz, dmso-d$_6$) δ 158.04, 147.26, 140.30, 134.42, 131.21, 130.59, 129.79, 127.72, 43.27, 22.07. ESI-HRMS Calc m/z for C$_{11}$H$_{11}$ClF$_3$N$_4$ 291.0619 (M+H)$^+$, found 291.0608.

Example 53. (E)-2-(2-(2-fluoro-6-methylbenzylidene)hydrazinyl)-4,5-dihydro-1H-imidazole hydrochloride (JM2-133-2)

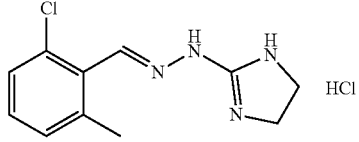 [SMILES: Cc1cccc(Cl)c1/C=N/NC1=NCCN1 ; Cl]

Yellow powder. $^1$H NMR (dmso-d$_6$, 600 MHz) δ 12.42 (s, 1H), 8.53 (br s, 2H), 8.51 (s, 1H), 7.37 (d, 1H, J=7.6 Hz), 7.33 (t, 1H, J=7.6 Hz), 7.27 (d, 1H, J=7.0 Hz), 3.70 (s, 4H). $^{13}$C NMR (150 MHz, dmso-d$_6$) δ 158.06, 147.22, 140.29, 134.41, 131.20, 130.58, 129.82, 127.72, 43.28, 22.07. ESI-HRMS Calc m/z for C$_{11}$H$_{14}$ClN$_4$ 279.0619 (M+H)$^+$, found 276.0629.

Example 54. (E)-2-(2-(2-bromobenzylidene)hydrazinyl)-4,5-dihydro-1H-imidazole hydrochloride (JM2-191-2)

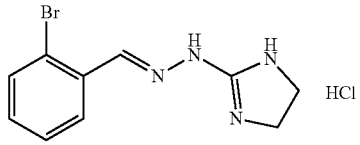

Yellow powder. $^1$H NMR (dmso-d$_6$, 600 MHz) δ 12.63 (s, 1H), 8.92 (br s, 2H), 8.61 (s, 1H), 8.27 (d, 1H, J=8.2 Hz), 7.79 (d, 1H, J=8.2 Hz), 7.56 (t, 1H, J=7.6 Hz), 7.48 (t, 1H, J=8.2 Hz), 3.83 (s, 4H). $^{13}$C NMR (150 MHz, dmso-d$_6$) δ 160.31, 148.98, 135.80, 134.99, 134.58, 130.59, 130.38, 126.38. ESI-HRMS Calc m/z for C$_{10}$H$_{12}$BrN$_4$ 267.0240 (M+H)$^+$, found 267.0252.

Example 55. (Z)-2-(2,6-dichlorobenzylidene)hydrazinecarboximidamide acetate (BC1-55-1)

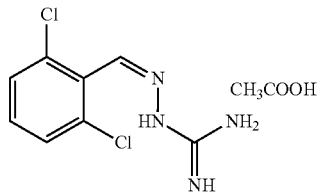

White powder. $^1$H NMR (600 MHz, CD3OD) δ 7.67 (s, 1H), 7.54 (d, 2H, J=6.0 Hz), 7.50 (t, 1H, J=6.0 Hz), 1.84 (s, 3H). $^{13}$C NMR (150 MHz, CD3OD) δ 178.8, 156.7, 140.2, 133.5, 132.2, 129.0, 128.4, 22.6. ESI-HRMS Calc m/z for C$_8$H$_9$Cl$_2$N$_4$ 231.0199 (M+H)$^+$, found 231.0198.

Example 56. (Z)-2-(2,6-dichloro-4-hydroxybenzylidene)hydrazinecarboximidamide acetate (BC1-167-1)

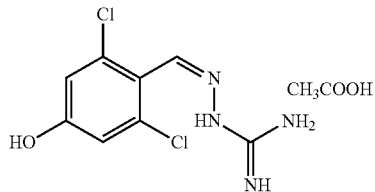

Light yellow solid. $^1$H NMR (600 MHz, cd$_3$od) δ 8.31 (s, 1H), 6.84 (s, 2H), 1.92 (s, 3H).

$^{13}$C NMR (151 MHz, cd$_3$od) δ 177.83, 160.34, 156.27, 143.19, 135.41, 119.44, 116.43, 53.13, 47.99, 47.85, 47.71, 47.56, 47.42, 47.28, 47.14, 21.89. ESI-HRMS Calc m/z for C$_8$H$_9$Cl$_2$N$_4$O 247.0148 (M+H)$^+$, found 247.0149.

Example 57. 1-(2-(2,6-dichlorophenyl)-1H-imidazol-1-yl)guanidine (BC1-267-2)

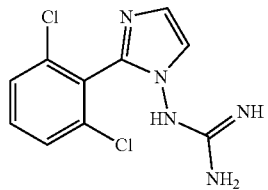 [SMILES: N=C(N)Nn1ccnc1-c1c(Cl)cccc1Cl]

$^1$H NMR (600 MHz, cd$_3$od) δ 7.49-7.43 (m, 3H), 7.20 (s, 1H), 7.17 (s, 1H). $^{13}$C NMR (151 MHz, cd$_3$od) δ 161.67, 140.40, 136.96, 131.34, 129.08, 127.59, 125.5, 120.01. ESI-HRMS Calc m/z for C$_{10}$H$_{10}$Cl$_2$N$_5$ 270.0313 (M+H)$^+$, found 270.0314.

Example 58. (E)-2-(2,6-dichlorobenzylidene)-N-methylhydrazine-1-carboximidamide hydroiodide (JM2-171-2)

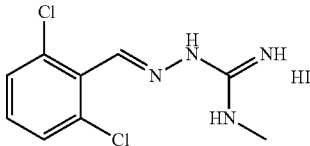

Yellow solid. $^1$H NMR (dmso-d$_6$, 600 MHz) δ 11.79 (s, 1H), 8.38 (s, 1H), 7.90 (br s, 1H), 7.84 (br s, 2H), 7.57 (d, 2H, J=8.2 Hz), 7.46 (t, 1H, J=8.2 Hz), 2.84 (d, 3H, J=4.1 Hz). $^{13}$C NMR (150 MHz, dmso-d$_6$) δ 155.51, 134.45, 133.47, 131.95, 130.51, 129.48, 28.62. ESI-MS (M+H)$^+$ 245.03.

Example 59. (E)-2-(2,6-dichlorobenzylidene)-N,N-dimethylhydrazine-1-carboximidamide hydroiodide (JM2-289-2)

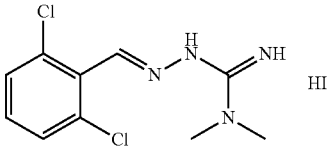

White solid. $^1$H NMR (dmso-d$_6$, 600 MHz) δ 11.55 (s, 1H), 8.53 (s, 1H), 7.63 (br s, 2H), 7.57 (d, 2H, J=7.6 Hz), 7.45 (t, 1H, J=8.2 Hz), 3.07 (s, 6H). $^{13}$C NMR (150 MHz, dmso-d$_6$) δ 156.69, 134.74, 134.16, 130.92, 130.61, 129.69, 40.52. ESI-MS (M+H)$^+$ 259.05. ESI-HRMS Calc m/z for C$_{10}$H$_{13}$Cl$_2$N$_4$ 259.0512 (M+H)$^+$, found 259.0519. HPLC 95.24% purity t$_R$=8.55 min.

Example 60. (E)-2-(2-(2,6-dichlorobenzylidene)hydrazinyl)-1,4,5,6-tetrahydropyrimidine hydrochloride (JM2-255-2)

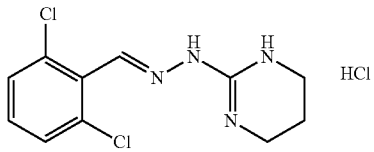 [SMILES: Clc1cccc(Cl)c1/C=N/NC1=NCCCN1 ; Cl]

White solid (40%). $^1$H NMR (dmso-d$_6$, 600 MHz) δ 12.57 (s, 1H), 8.38 (s, 1H), 8.33 (br s, 2H), 7.55 (d, 2H, J=8.2 Hz), 7.45 (t, 1H, J=8.2 Hz), 3.32 (m, 4H), 1.86 (t, 2H, J=5.2 Hz). $^{13}$C NMR (150 MHz, dmso-d$_6$) δ 151.46, 141.87, 134.48, 132.00, 130.56, 129.39, 38.55, 19.83. ESI-HRMS Calc m/z for C$_{11}$H$_{13}$Cl$_2$N$_4$ 271.0512 (M+H)$^+$, found 271.0524. HPLC 98.82% purity t$_R$=7.80 min.

Example 61. (E)-2-(2-(2,6-dichlorobenzylidene)hydrazinyl)-1,4,5,6-tetrahydropyrimidine hydrochloride (JM2-257-2)

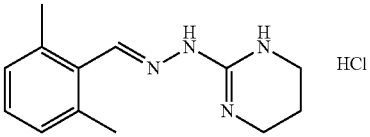 [SMILES: Cc1cccc(C)c1/C=N/NC1=NCCCN1 ; Cl]

White solid (45%). $^1$H NMR (dmso-d$_6$, 600 MHz) δ 11.99 (s, 1H), 8.47 (s, 1H), 8.20 (br s, 2H), 7.17 (t, 1H, J=7.6 Hz), 7.08 (d, 2H, J=7.6 Hz), 3.32 (m, 4H), 2.37 (s, 6H), 1.87 (t, 2H, J=4.1 Hz). $^{13}$C NMR (150 MHz, dmso-d$_6$) δ 151.48, 146.83, 137.68, 131.22, 129.51, 128.84, 38.55, 21.15, 20.02. ESI-HRMS Calc m/z for C$_{13}$H$_{19}$N$_4$ 231.1604 (M+H)$^+$, found 231.1609. HPLC 98.92% purity t$_R$=8.07 min.

Example 62. (E)-2-(2-(2-chloro-6-nitrobenzylidene)hydrazinyl)-1,4,5,6-tetrahydropyrimidine hydrochloride (JM2-263-2)

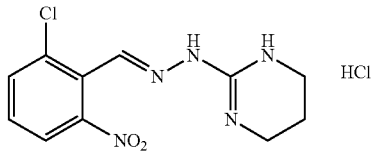 [SMILES: O=[N+]([O-])c1cccc(Cl)c1/C=N/NC1=NCCCN1 ; Cl]

Yellow solid (37%). $^1$H NMR (dmso-d$_6$, 600 MHz) δ 12.29 (s, 1H), 8.48 (s, 1H), 8.27 (br s, 2H), 7.36 (d, 1H, J=7.6 Hz), 7.32 (t, 1H, J=7.6 Hz), 7.27 (t, 1H, J=7.6 Hz), 3.33 (m, 4H), 1.87 (t, 2H, J=4.7 Hz). $^{13}$C NMR (150 MHz, dmso-d$_6$) δ 151.33, 149.87, 140.80, 134.87, 132.09, 127.15, 123.97, 38.46, 19.74. ESI-HRMS Calc m/z for C$_{11}$H$_{13}$ClN$_5$O$_2$ 282.0752 (M+H)$^+$, found 282.0746. HPLC 96.41% purity t$_R$=7.14 min.

Example 63. (E)-2-(2-(2-chloro-6-methylbenzylidene)hydrazinyl)-1,4,5,6-tetrahydropyrimidine hydrochloride (JM2-265-2)

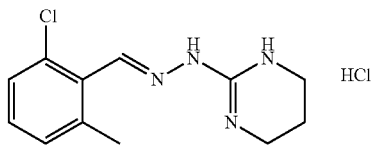 [SMILES: Cc1cccc(Cl)c1/C=N/NC1=NCCCN1 ; Cl]

Yellow solid (44%). $^1$H NMR (dmso-d$_6$, 600 MHz) δ 12.60 (s, 1H), 8.47 (s, 1H), 8.33 (br s, 2H), 8.06 (d, 1H, J=8.2 Hz), 7.96 (d, 1H, J=7.6 Hz), 7.71 (t, 1H, J=8.2 Hz), 3.29 (m, 4H), 2.48 (s, 3H), 1.84 (t, 2H, J=4.7 Hz). $^{13}$C NMR (150 MHz, dmso-d$_6$) δ 153.64, 146.77, 142.33, 136.39, 133.09, 132.62, 132.54, 129.80, 40.73, 24.09, 22.09. ESI-HRMS Calc m/z for C$_{12}$H$_{16}$ClN$_4$ 251.1058 (M+H)$^+$, found 251.1064. HPLC 98.55% purity t$_R$=7.82 min.

Example 64. 2-(2,6-dichlorobenzyl)-1,4,5,6-tetrahydropyrimidine (JM2-271-2)

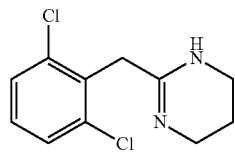

2-(2,6-dichlorophenyl)acetonitrile (100 mg, 0.54 mmol) and propane-1,3-diamine (298 mg, 4.0 mmol) was taken in a reaction vial and added sulfur (8.5 mg, 0.29 mmol). The reaction mixture was heated at 100° C. for overnight. After allowing to room temp added cold water and extracted with ether to yield crude product. The crude was purified on silica column using methanol in dichloromethane as eluent. The final product was obtained as dark brown solid (42%). $^1$H NMR (dmso-d$_6$, 600 MHz) δ 7.37 (d, 2H, J=8.2 Hz), 7.23 (t, 1H, J=8.2 Hz), 3.59 (s, 2H), 3.07 (t, 4H, J=5.2 Hz), 1.56-1.53 (m, 2H). $^{13}$C NMR (150 MHz, dmso-d$_6$) δ 153.38, 136.01, 134.31, 129.06, 128.32, 37.00, 20.89, 15.62. ESI-HRMS Calc m/z for C$_{11}$H$_{13}$Cl$_2$N$_2$ 243.0450 (M+H)$^+$, found 243.0456. HPLC 95.36% purity t$_R$=7.41 min.

Example 65. N-carbamimidoyl-2-(2-chloro-6-nitrophenyl)acetamide hydrochloride (JM2-275-2)

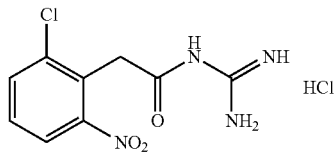 [SMILES: N=C(N)NC(=O)Cc1c(Cl)cccc1[N+](=O)[O-] ; Cl]

A solution of methyl 2-(2-chloro-6-nitrophenyl)acetate (80 mg, 0.35 mmol) in ethanol (3 mL) was added to a solution of guanidine hydrochloride (34 mg, 0.35 mmol) and sodium ethoxide (8.1 mg of sodium in 2 mL methanol). The resulting solution was stirred at room temp for 16 h. The reaction mixture was evaporated and extracted with chloroform/water. The organic layer was mixed with ethanolic solution to get product as hydrochloric salt. White Solid (35 mg, 34%). $^1$H NMR (dmso-d$_6$, 600 MHz) δ 12.74 (s, 1H), 8.00 (d, 1H, J=8.2 Hz), 7.89 (d, 1H, J=7.6 Hz), 7.58 (t, 1H, J=8.2 Hz), 3.99 (s, 2H). $^{13}$C NMR (150 MHz, dmso-d$_6$) δ 170.39, 151.03, 136.50, 134.66, 129.86, 128.51, 124.11, 35.80. ESI-HRMS Calc m/z for C$_9$H$_{10}$ClN$_4$O$_3$ 257.0436 (M+H)$^+$, found 257.0449. HPLC 97.60% purity t$_R$=19.16 min.

Example 66. (E)-2-(thiophen-2-ylmethylene)hydrazine-1-carboximidamide (JM2-279-2)

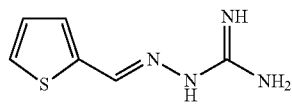 [SMILES: N=C(N)N/N=C/c1cccs1]

Yellow crystals (75%). $^1$H NMR (dmso-d$_6$, 600 MHz) δ 7.54 (s, 1H), 7.47 (d, 1H, J=4.7 Hz), 7.26 (d, 1H, J=3.52 Hz), 7.00 (t, 1H, J=3.52 Hz), 5.89 (br s, 2H), 5.51 (br s, 2H). $^{13}$C NMR (150 MHz, dmso-d$_6$) δ 160.41, 136.23, 135.51, 129.81, 128.58, 125.85. ESI-HRMS Calc m/z for C$_6$H$_9$N$_4$S 169.0542 (M+H)$^+$, found 169.0560. HPLC 98.56% purity t$_R$=7.96 min.

Example 67. N-carbamimidoyl-2-(2,6-dichlorophenyl)acetamide hydrochloride (JM2-287-2)

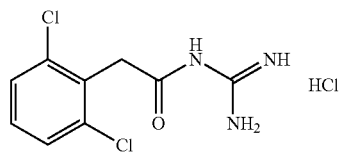 [SMILES: N=C(N)NC(=O)Cc1c(Cl)cccc1Cl ; Cl]

A solution of methyl 2-(2,6-dichlorophenyl)acetate (75 mg, 0.26 mmol) in ethanol (3 mL) was added to a solution of guanidine hydrochloride (25 mg, 0.26 mmol) and sodium ethoxide (6.0 mg of sodium in 2 mL methanol). The resulting solution was stirred at room temp for 30 h. The reaction mixture was evaporated and extracted with chloroform/water. The organic layer was mixed with ethanolic solution to get product as hydrochloric salt. White Solid (15 mg, 15%). $^1$H NMR (dmso-d$_6$, 600 MHz) δ 12.18 (s, 1H), 8.40 (br s, 2H), 8.18 (br s, 2H), 7.51 (d, 2H, J=8.2 Hz), 7.38 (t, 1H, J=7.6 Hz), 4.13 (s, 2H). $^{13}$C NMR (150 MHz, dmso-d$_6$) δ 170.91, 154.88, 135.92, 130.67, 130.58, 128.74, 39.34. ESI-HRMS Calc m/z for C$_9$H$_{10}$Cl$_2$N$_3$O 246.0195 (M+H)$^+$, found 246.0200. HPLC 96.56% purity t$_R$=19.17 min.

Example 68. (E)-2-(2,5-dichlorobenzylidene)hydrazine-1-carboximidamide acetate (JM3-11-2)

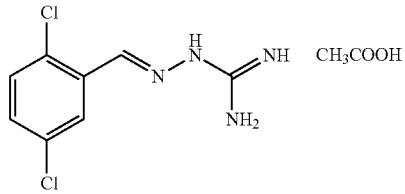

White solid. $^1$H NMR (dmso-d$_6$, 600 MHz) δ 8.29 (s, 1H), 8.25 (s, 1H), 7.43 (d, 1H, J=8.2 Hz), 7.34 (t, 1H, J=8.2 Hz), 7.06 (br s, 4H), 1.82 (s, 3H). $^{13}$C NMR (150 MHz, dmso-d$_6$) δ 174.86, 159.62, 138.38, 134.98, 132.68, 131.67, 130.87, 129.76, 126.57, 23.15. ESI-HRMS Calc m/z for C$_8$H$_9$Cl$_2$N$_4$ 231.0199 (M+H)$^+$, found 231.0202. HPLC 99.64% purity t$_R$=7.95 min.

Example 69. (E)-2-(2-nitrobenzylidene)hydrazine-1-carboximidamide acetate (JM3-13-2)

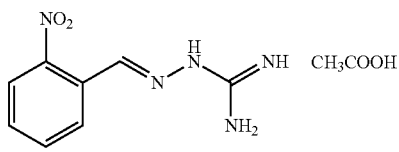

Light yellow powder. $^1$H NMR (dmso-d$_6$, 600 MHz) δ 8.30 (s, 1H), 8.29 (s, 1H), 7.92 (d, 1H, J=8.2 Hz), 7.66 (t, 1H, J=7.6 Hz), 7.50 (t, 1H, J=7.6 Hz), 6.90 (br s, 4H), 1.83 (s, 3H). $^{13}$C NMR (150 MHz, dmso-d$_6$) δ 174.57, 160.21, 147.99, 138.68, 133.28, 130.22, 129.31, 128.45, 124.67, 22.94. ESI-HRMS Calc m/z for C$_8$H$_{10}$N$_5$O$_2$ 208.0829 (M+H)$^+$, found 208.0839. HPLC 97.52% purity t$_R$=5.16 min.

Example 70. (E)-2-(2-hydroxybenzylidene)hydrazine-1-carboximidamide acetate (JM3-17-2)

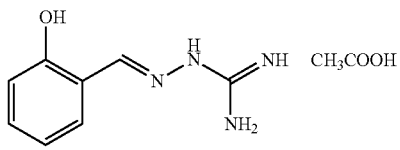

Light orange powder. $^1$H NMR (dmso-d$_6$, 600 MHz) δ 11.24 (br s, 1H), 8.22 (s, 1H), 7.43 (d, 1H, J=7.6 Hz), 7.16 (t, 1H, J=7.0 Hz), 6.84 (t, 2H, J=8.8 Hz), 6.04 (br s, 4H), 1.88 (s, 3H). $^{13}$C NMR (150 MHz, dmso-d$_6$) δ 175.39, 157.94, 157.08, 144.66, 30.73, 128.18, 120.67, 119.45, 116.32, 23.71. ESI-HRMS Calc m/z for C$_8$H$_{11}$N$_4$O 179.0927 (M+H)$^+$, found 179.0932. HPLC 98.13% purity t$_R$=4.84 min.

Example 71. 1-(2-(2,6-dichlorophenyl)-2-hydroxyethyl)guanidine (JM3-27-2)

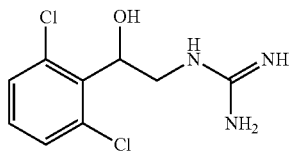 [SMILES: N=C(N)NCC(O)c1c(Cl)cccc1Cl]

A mixture of 2-amino-1-(2,6-dichlorophenyl)ethan-1-ol (50 mg, 0.24 mmol), S-methylisothiouronium sulfate (33 mg, 0.12 mmol), EtOH (2 ml) and water (1 ml) was refluxed until the evolution of MeSH ceased. The mixture was allowed to room temp and made strongly basic with 1N NaOH solution, and the mixture was extracted with dichloromethane (3×). Organic layer was combined then dried over Na$_2$SO$_4$, evaporated and the residue was recrystallized with ethanol/water to give the title compound as a white powder (50%). $^1$H NMR (dmso-d$_6$+3 drops of cd3od, 400 MHz) δ 7.45 (d, 2H, J=7.5 Hz), 7.34 (t, 1H, J=7.5 Hz), 5.42 (dd, 1H, J=4.4 Hz), 3.70 (dd, 1H, J=4.6 Hz), 3.38 (dd, 1H, J=4.6 Hz). $^{13}$C NMR (100 MHz, dmso-d$_6$) δ 158.07, 136.36, 134.77, 130.41, 129.96, 69.13, 44.90. ESI-HRMS Calc m/z for C$_9$H$_{12}$Cl$_2$N$_3$O 248.0352 (M+H)$^+$, found 248.0354. HPLC 96.25% purity t$_R$=1.99 min.

Example 72. (E)-2-((2,4-dichloropyridin-3-yl)methylene)hydrazine-1-carboximidamide acetate (JM3-29-2)

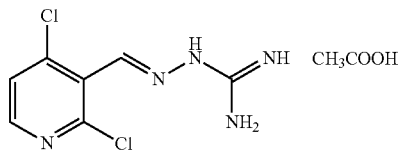

White powder. $^1$H NMR (dmso-d$_6$, 600 MHz) δ 8.20 (d, 1H, J=4.7 Hz), 8.14 (s, 1H), 7.59 (d, 1H, J=5.2 Hz), 5.96 (s, 4H), 1.89 (s, 3H). $^{13}$C NMR (150 MHz, dmso-d$_6$) δ 173.03, 161.69, 150.35, 147.80, 143.29, 136.34, 128.89, 125.75, 21.90. ESI-HRMS Calc m/z for C$_7$H$_8$Cl$_2$N$_5$ 232.0151 (M+H)$^+$, found 232.0157. HPLC 99.30% purity t$_R$=4.95 min.

Example 73. (E)-2-(4-bromo-2-chlorobenzylidene)hydrazine-1-carboximidamide acetate (JM3-57-2)

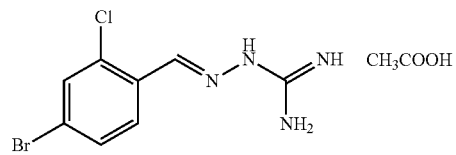

Off-white powder. $^1$H NMR (dmso-d$_6$, 600 MHz) δ 8.22 (s, 1H), 8.11 (d, 1H, J=8.2 Hz), 7.68 (s, 1H), 7.47 (d, 1H, J=8.2 Hz), 6.52 (br s, 4H), 1.85 (s, 3H). $^{13}$C NMR (150 MHz, dmso-d$_6$) δ 173.80, 160.73, 138.23, 133.19, 132.91, 132.09, 130.58, 128.74, 121.60, 22.48. ESI-HRMS Calc m/z for C$_{14}$H$_{14}$ClN$_4$ 273.0902 (M+H)$^+$, found 273.0899. HPLC 99.83% purity t$_R$=9.29 min.

Example 74. (E)-2-((3-chloro-[1,1'-biphenyl]-4-yl)methylene)hydrazine-1-carboximidamide acetate (JM3-63-2)

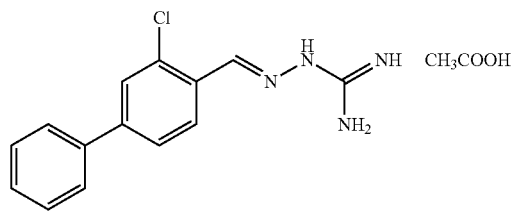

The mixture of compound (E)-2-(4-bromo-2-chlorobenzylidene)hydrazine-1-carboximidamide (90 mg, 0.33 mmol), phenyl boronic acid (52 mg, 0.42 mmol), Pd(PPh$_3$)$_4$ (19 mg, 0.06 mmol), and K$_2$CO$_3$ (112 mg, 0.82 mmol)) in dimethoxyethane/H$_2$O (4:1) was irradiated at 150° C. for 30 min under microwave conditions. The black residue formed was filtered through Celite and the solvent was concentrated in vacuo. The residue was purified by silica gel chromatography using methanol in dichloromethane as eluent to yield solid. The solid was dissolved in diethyl ether (5 mL) then added AcOH (1 equiv) to furnish final compound as off-white powder (68%). $^1$H NMR (dmso-d$_6$, 600 MHz) δ 8.38 (s, 1H), 8.27 (d, 1H, J=8.2 Hz), 7.73 (d, 3H, J=8.8 Hz), 7.63 (t, 1H, J=7.6 Hz), 7.47 (t, 2H, J=7.6 Hz), 7.39 (d, 1H, J=7.0 Hz), 6.71 (br s, 4H), 1.87 (s, 3H). $^{13}$C NMR (150 MHz, dmso-d$_6$) δ 173.29, 159.47, 142.03, 140.09, 138.56, 133.21, 132.08, 129.53, 128.70, 127.98, 127.81, 127.16, 125.83, 22.08. ESI-HRMS Calc m/z for C$_{14}$H$_{14}$ClN$_4$ 273.0902 (M+H)$^+$, found 273.0899. HPLC 96.54% purity t$_R$=11.51 min.

Example 75. (E)-2-((3,5-dichloro-[1,1'-biphenyl]-4-yl)methylene)hydrazine-1-carboximidamide (JM3-67-2)

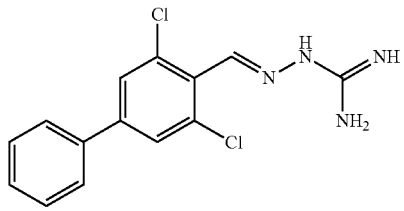 [SMILES: N=C(N)N/N=C/c1c(Cl)cc(-c2ccccc2)cc1Cl]

The mixture of compound (E)-4-((2-carbamimidoylhydrazono)methyl)-3,5-dichlorophenyl trifluoromethanesulfonate (150 mg, 0.40 mmol), phenyl boronic acid (622 mg, 0.51 mmol), Pd(PPh$_3$)$_4$ (23 mg, 0.02 mmol), and K$_2$CO$_3$ (136 mg, 0.99 mmol) in dimethoxyethane/H$_2$O (4:1) was irradiated at 150° C. for 30 min under microwave conditions. The black residue formed was filtered through Celite and the solvent was concentrated in vacuo. The residue was purified by silica gel chromatography using 80% ethyl acetate in hexanes to yield white powder (8%). $^1$H NMR (cd$_3$od, 400 MHz) δ 8.42 (s, 1H), 7.78 (s, 2H), 7.67 (d, 2H, J=7.6 Hz), 7.50 (t, 2H, J=7.6 Hz), 7.47 (t, 1H, J=7.0 Hz). $^{13}$C NMR (100 MHz, cd$_3$od) δ 144.32, 143.04, 137.20, 135.16, 128.94, 128.79, 127.63, 127.07, 126.65, 118.80. ESI-HRMS Calc m/z for C$_{14}$H$_{13}$Cl$_2$N$_4$ 307.0512 (M+H)$^+$, found 307.0507. HPLC 97.88% purity t$_R$=11.87 min.

Example 76. (E)-2-(2-chloro-6-ethylbenzylidene)hydrazine-1-carboximidamide acetate (JM3-81-2)

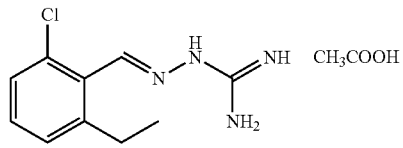

Light yellow color solid. $^1$H NMR (cd$_3$od, 400 MHz) δ 8.37 (s, 1H), 7.22 (d, 2H, J=5.1 Hz), 7.18 (t, 1H, J=5.1 Hz), 2.83 (q, 2H, J=7.5 Hz), 1.82 (s, 3H), 1.13 (t, 3H, J=7.3 Hz). $^{13}$C NMR (100 MHz, cd$_3$od) δ 178.27, 156.67, 145.88, 145.56, 134.43, 130.32, 129.67, 128.08, 127.09, 26.61, 22.19, 14.39. ESI-HRMS Calc m/z for C$_{10}$H$_{14}$ClN$_4$ 225.0902 (M+H)$^+$, found 225.0909. HPLC 97.44% purity t$_R$=8.97 min.

Example 77. (E)-2-(2-chloro-6-isopropylbenzylidene)hydrazine-1-carboximidamide acetate (JM3-89-2)

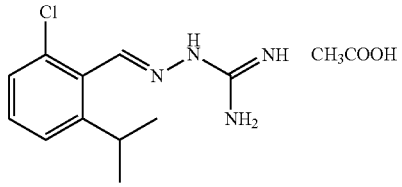

Light yellow solid. $^1$H NMR (cd$_3$od, 400 MHz) δ 8.26 (s, 1H), 7.23 (d, 1H, J=7.0 Hz), 7.16 (t, 2H, J=7.6 Hz), 3.54 (sep, 1H, J=6.4 Hz), 1.80 (s, 3H), 1.14 (d, 6H, J=6.4 Hz). $^{13}$C NMR (100 MHz, cd$_3$od) δ 178.63, 161.00, 150.28, 145.29, 133.38, 130.13, 128.22, 126.70, 124.35, 29.23, 22.68, 22.52. ESI-HRMS Calc m/z for C$_{11}$H$_{16}$ClN$_4$ 239.1058 (M+H)$^+$, found 239.1068. HPLC 99.63% purity t$_R$=9.90 min.

Example 78. (E)-2-(2,6-diisopropylbenzylidene)hydrazine-1-carboximidamide (JM3-99-2)

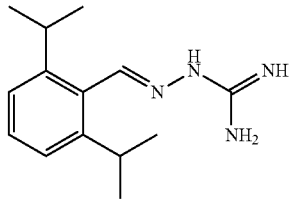 [SMILES: CC(C)c1cccc(C(C)C)c1/C=N/NC(=N)N]

Light yellow solid. $^1$H NMR (dmso-d$_6$, 400 MHz) δ 8.33 (s, 1H), 7.24 (t, 1H, J=7.8 Hz), 7.15 (d, 2H, J=7.58 Hz), 5.61 (br s, 2H), 5.41 (br s, 2H), 3.29-3.20 (m, 2H), 1.15 (d, 12H, J=6.8 Hz), $^{13}$C NMR (100 MHz, dmso-d$_6$) δ 150.28, 145.29, 133.83, 130.13, 126.70, 124.35, 29.63, 22.68. ESI-HRMS Calc m/z for C$_{14}$H$_{23}$N$_4$ 247.1917 (M+H)$^+$, found 247.1918. HPLC 96.12% purity t$_R$=11.42 min.

Example 79. 2-(2,6-dichlorobenzyl)-1H-imidazole (JM3-131-2)

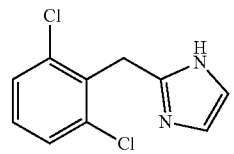 [SMILES: Clc1cccc(Cl)c1Cc1ncc[nH]1]

To a solution of dimethyl sulfoxide (127 mg, 1.63 mmol) in 7 ml dichloromethane cooled to −78° C. was then added a solution of oxalyl chloride (592 mg, 1.63 mmol) in 7 ml dichloromethane. The mixture was stirred for 50 minutes at −78° C. and then a solution of 2-(2,6-dichlorobenzyl)-4,5-dihydro-1H-imidazole (80 mg, 0.35 mmol) in 8 ml dichloromethane was added and stirring continued at −78° C. for 90 minutes. Then was added trimethylamine (338 mg, 3.34 mmol) and the reaction mixture was warmed to ambient temperature and stirring continued for 2 hours. To this solution was added concentrated aqueous ammonia and the reaction mixture extracted with ethyl acetate extracted and washed with brine, dried over Na$_2$SO$_4$, and concentrated in vacuo. The crude was purified on silica column using methanol in dichloromethane as eluent. The final product was obtained as white solid (82%). $^1$H NMR (dmso-d$_6$, 400 MHz) δ 11.75 (br s, 1H), 7.47 (d, 2H, J=8.0 Hz), 7.33 (t, 1H, J=7.8 Hz), 6.97 (s, 1H), 6.70 (s, 1H), 4.25 (s, 2H). $^{13}$C NMR (100 MHz, dmso-d$_6$) δ 143.80, 135.81, 134.39, 129.64, 128.84, 127.83, 116.26, 30.68. ESI-HRMS Calc m/z for C$_{10}$H$_9$Cl$_2$N$_2$ 227.0137 (M+H)$^+$, found 227.0143. HPLC 97.15% purity t$_R$=6.34 min.

Example 80. (E)-2-(2,6-bis(trifluoromethyl)benzylidene)hydrazine-1-carboximidamide acetate (JM3-141-2)

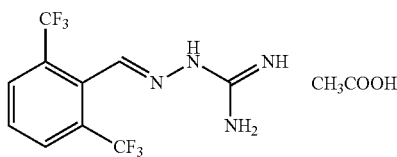

White solid. $^1$H NMR (dmso-d$_6$, 400 MHz) δ 8.25 (s, 1H), 8.07 (d, 2H, J=8.2 Hz), 7.70 (t, 1H, J=8.2 Hz), 6.00 (br s, 2H), 5.84 (br s, 2H), 1.87 (s, 3H). $^{13}$C NMR (100 MHz, dmso-d$_6$) δ 172.81, 161.92, 136.03, 131.02, 129.26, 128.96, 125.55, 122.83, 21.78. ESI-HRMS Calc m/z for C$_{10}$H$_9$F$_6$N$_4$ 299.0726 (M+H)$^+$, found 299.0733. HPLC 98.16% purity t$_R$=8.87 min.

Example 81. (E)-2-(2-(2,3-dichlorobenzylidene)hydrazinyl)-4,5-dihydro-1H-imidazole hydrochloride (JM3-149-2)

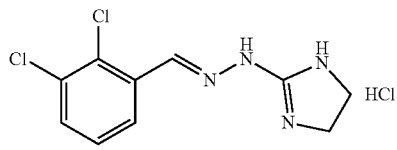 [SMILES: Clc1cccc(/C=N/NC2=NCCN2)c1Cl ; Cl]

Off-white solid. $^1$H NMR (dmso-d$_6$, 400 MHz) δ 12.58 (br s, 1H), 8.40 (s, 1H), 8.14 (d, 1H, J=7.6 Hz), 7.85 (br s, 2H), 7.60 (d, 1H, J=7.6 Hz), 7.37 (t, 1H, J=7.6 Hz), 3.57 (s, 4H). $^{13}$C NMR (150 MHz, dmso-d$_6$) δ 141.89, 141.03, 135.24, 132.61, 130.95, 130.61, 128.45, 126.06, 55.39, 42.83. ESI-HRMS Calc m/z for C$_{10}$H$_{11}$Cl$_2$N$_4$ 257.0355 (M+H)$^+$, found 257.0365. HPLC 99.20% purity t$_R$=9.09 min.

Example 82. (E)-2-(2-(2,3,6-trichlorobenzylidene)hydrazinyl)-4,5-dihydro-1H-imidazole hydrochloride (JM3-151-2)

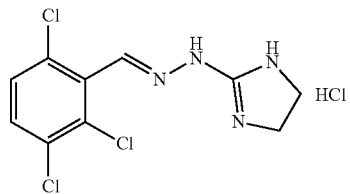 [SMILES: Clc1ccc(Cl)c(/C=N/NC2=NCCN2)c1Cl ; Cl]

Light yellow solid. $^1$H NMR (dmso-d$_6$, 400 MHz) δ 12.61 (br s, 1H), 8.63 (s, 2H), 8.38 (s, 1H), 7.77 (d, 1H, J=8.5 Hz), 7.65 (d, 1H, J=8.5 Hz), 7.60 (d, 1H, J=7.6 Hz), 3.72 (s, 4H). $^{13}$C NMR (100 MHz, dmso-d$_6$) δ 159.25, 144.01, 133.02, 132.71, 132.66, 132.08, 131.92, 130.24, 54.40, 43.26. ESI-HRMS Calc m/z for C$_{10}$H$_{10}$Cl$_3$N$_4$ 290.9966 (M+H)$^+$, found 290.9963. HPLC 98.06% purity t$_R$=9.20 min.

Example 83. (E)-2-(2-(2,3-dichlorobenzylidene)hydrazinyl)-1,4,5,6-tetrahydropyrimidine hydrochloride (JM3-153-2)

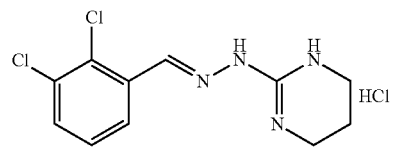 [SMILES: Clc1cccc(/C=N/NC2=NCCCN2)c1Cl ; Cl]

Light yellow solid (40%). $^1$H NMR (dmso-d$_6$, 400 MHz) δ 12.44 (s, 1H), 8.59 (s, 3H), 8.29 (d, 1H, J=7.9 Hz), 7.73 (d, 1H, J=7.9 Hz), 7.45 (t, 1H, J=7.9 Hz), 3.38 (t, 4H, J=5.1 Hz), 1.92 (m, 2H). $^{13}$C NMR (100 MHz, dmso-d$_6$) δ 155.41, 141.78, 133.81, 132.77, 132.22, 131.42, 128.69, 126.57, 38.49, 19.91. ESI-HRMS Calc m/z for C$_{11}$H$_{13}$Cl$_2$N$_4$ 271.0512 (M+H)$^+$, found 271.0509. HPLC 98.21% purity t$_R$=9.65 min.

Example 84. (E)-2-(2-(2,3,6-trichlorobenzylidene)hydrazinyl)-1,4,5,6-tetrahydropyrimidine hydrochloride (JM3-155-2)

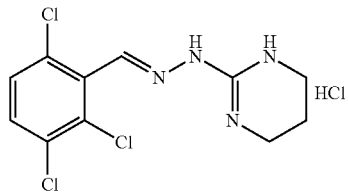 [SMILES: Clc1ccc(Cl)c(/C=N/NC2=NCCCN2)c1Cl ; Cl]

White solid (40%). $^1$H NMR (dmso-d$_6$, 400 MHz) δ 12.38 (s, 1H), 8.41 (s, 1H), 8.40 (br s, 2H), 7.82 (d, 1H, J=8.8 Hz), 7.69 (d, 1H, J=8.8 Hz), 3.40 (m, 4H), 1.95 (m, 2H). $^{13}$C NMR (100 MHz, dmso-d$_6$) δ 151.47, 141.88, 133.08, 132.87, 132.73, 132.14, 131.88, 130.17, 38.60, 19.82. ESI-HRMS Calc m/z for C$_{11}$H$_{12}$Cl$_3$N$_4$ 305.0122 (M+H)$^+$, found 305.0132. HPLC 98.10% purity t$_R$=9.77 min.

Example 85. (E)-N-butyl-2-(2,6-dichlorobenzylidene)hydrazine-1-carboximidamide hydroiodide (JM3-161-2)

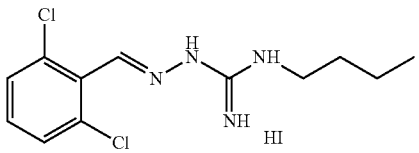

To a solution of methyl-2-(2,6-dichlorobenzylidene)hydrazine-1-carbimidothioate hydroiodide (150 mg, 0.38 mmol) in EtOH (4 mL) was added n-butyl amine (56.2 mg, 0.77 mmol). The reaction mixture was stirred at reflux for overnight. The EtOH was evaporated and triturated with ether to yield crude product as precipitate. The crude was purified by silica gel chromatography using 0-10% methanol in dichloromethane to yield final compound as white solid (50 mg, 32%). $^1$H NMR (dmso-d$_6$, 400 MHz) δ 11.71 (s, 1H), 8.41 (s, 1H), 7.93 (br s, 1H), 7.86 (br s, 2H), 7.60 (d, 2H, J=7.8 Hz), 7.48 (t, 1H, J=7.3 Hz), 3.26 (q, 2H, J=6.8 Hz), 1.57-1.47 (m, 2H), 1.38-1.28 (m, 2H), 0.91 (t, 3H, J=7.3 Hz). $^{13}$C NMR (100 MHz, dmso-d$_6$) δ 154.35, 140.93, 134.52, 132.12, 130.37, 129.57, 41.24, 30.94, 19.69, 14.03. ESI-HRMS Calc m/z for $C_{12}H_{17}C_{12}N_4$ 287.0825 (M+H)$^+$, found 287.0820. HPLC 97.03% purity $t_R$=10.52 min.

Example 86. 2-(2,3-dichlorobenzyl)-4,5-dihydro-1H-imidazole (JM3-179-2)

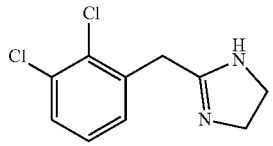 [SMILES: Clc1cccc(CC2=NCCN2)c1Cl]

Light yellow solid. $^1$H NMR (dmso-d$_6$, 400 MHz) δ 7.51 (d, 1H, J=7.5 Hz), 7.36 (d, 1H, J=7.0 Hz), 7.30 (t, 1H, J=7.8 Hz), 5.91 (br s, 1H), 3.61 (s, 2H), 3.10 (s, 4H). $^{13}$C NMR (100 MHz, dmso-d$_6$) δ 164.71, 138.25, 131.98, 130.44, 129.19, 128.29, 52.16, 34.14. ESI-HRMS Calc m/z for $C_{10}H_{11}Cl_2N_2$ 229.0294 (M+H)$^+$, found 229.0289 HPLC 96.02% purity $t_R$=7.14 min.

Example 87. 2-(2,3-dichlorobenzyl)-1,4,5,6-tetrahydropyrimidine (JM3-181-2)

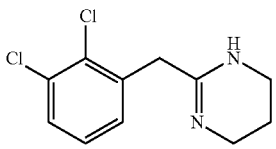 [SMILES: Clc1cccc(CC2=NCCCN2)c1Cl]

Brown solid. $^1$H NMR (dmso-d$_6$, 400 MHz) δ 7.53 (d, 1H, J=7.5 Hz), 7.36 (d, 1H, J=7.5 Hz), 7.31 (t, 1H, J=7.5 Hz), 3.57 (s, 2H), 3.19 (t, 4H, J=5.6 Hz), 1.7-1.63 (m, 2H). $^{13}$C NMR (100 MHz, dmso-d$_6$) δ 156.24, 137.71, 132.02, 130.39, 129.34, 128.40, 55.39, 40.83, 20.10. ESI-HRMS Calc m/z for $C_{11}H_{13}C_{12}N_2$ 243.0450 (M+H)$^+$, found 243.0460 HPLC 96.12% purity $t_R$=7.54 min.

Example 88. (E)-2-(2-iodobenzylidene)hydrazine-1-carboximidamide acetate (JM3-183-2)

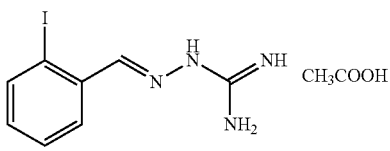

White powder. $^1$H NMR (dmso-d$_6$, 400 MHz) δ 8.20 (s, 1H), 8.10 (d, 1H, J=8.0 Hz), 7.86 (d, 1H, J=7.0 Hz), 7.38 (t, 1H, J=7.3 Hz), 7.08 (t, 1H, J=7.0 Hz), 6.85 (br s, 4H), 1.86 (s, 3H). $^{13}$C NMR (100 MHz, dmso-d$_6$) δ 174.03, 159.67, 147.15, 139.86, 137.28, 130.89, 128.64, 127.70, 99.67, 22.69. ESI-HRMS Calc m/z for $C_8H_{10}N_4$ 288.9945 (M+H)$^+$, found 288.9951. HPLC 97.03% purity $t_R$=8.62 min.

Examples 89-100 were prepare using the following general procedure.

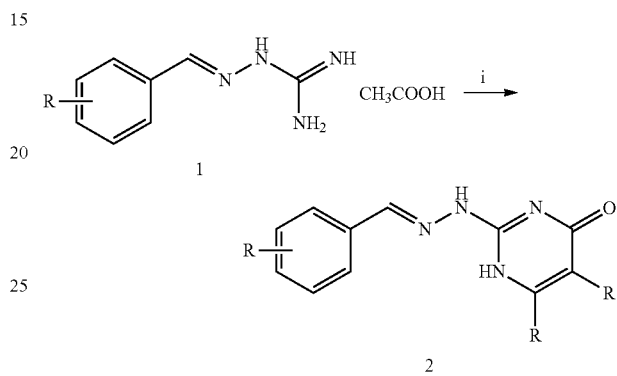

Reagents and conditions: (i) ethyl acetoacetate or ethyl 2-methylacetoacetate (1.2 eq), toluene, reflux, overnight, 30-75%.

A solution of compound 1 as an acetic acid salt (1 eq) and ethyl acetoacetate or ethyl 2-methylacetoacetate (1.2 eq) in toluene was refluxed for overnight. The solvent was evaporated and purified on silica with 0-15% methanol in dichloromethane to yield final compound 2 as solid.

Example 89. (E)-2-(2-(2,6-dichlorobenzylidene)hydrazinyl)-5,6-dimethylpyrimidin-4(1H)-one (JM3-191-2)

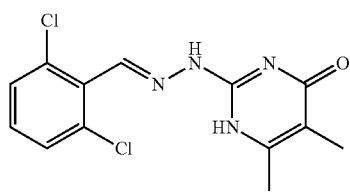 [SMILES: Cc1[nH]c(N/N=C/c2c(Cl)cccc2Cl)nc(=O)c1C]

White powder (38%). $^1$H NMR (dmso-d$_6$, 400 MHz) δ 11.59 (br s, 2H), 8.26 (s, 1H), 7.54 (d, 2H, J=8.2 Hz), 7.39 (t, 1H, J=8.2 Hz), 2.11 (s, 3H), 1.81 (s, 3H). $^{13}$C NMR (100 MHz, dmso-d$_6$) δ 161.90, 161.20, 153.02, 141.23, 133.60, 130.25, 129.90, 127.68, 102.37, 21.02, 11.30. ESI-HRMS Calc m/z for $C_{13}H_{13}C_{12}N_4o$ 311.0461 (M+H)$^+$, found 311.0469. HPLC 97.1% purity $t_R$=10.35 min.

Example 90. (E)-2-(2-(2,3-dichlorobenzylidene)hydrazinyl)-5,6-dimethylpyrimidin-4(1H)-one (JM3-195-2)

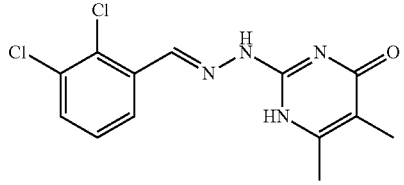 [SMILES: Cc1[nH]c(N/N=C/c2cccc(Cl)c2Cl)nc(=O)c1C]

White solid (43%). $^1$H NMR (dmso-d$_6$, 400 MHz) δ 11.53 (br s, 2H), 8.62 (d, 1H, J=7.5 Hz), 8.42 (s, 1H), 7.63 (d, 1H, J=7.5 Hz), 7.38 (t, 1H, J=7.8 Hz), 2.13 (s, 3H), 1.85 (s, 3H). $^{13}$C NMR (100 MHz, dmso-d$_6$) δ 163.26, 159.06, 152.25, 133.89, 133.56, 129.95, 129.57, 124.58, 119.26, 118.20, 102.67, 20.25, 11.05. ESI-HRMS Calc m/z for C$_{13}$H$_{13}$C$_{12}$N$_4$o 311.0461 (M+H)$^+$, found 311.0467. HPLC 96.58% purity t$_R$=11.03 min.

Example 91. (E)-2-(2-(2,6-dichlorobenzylidene)hydrazinyl)-6-methylpyrimidin-4(1H)-one (JM3-197-2)

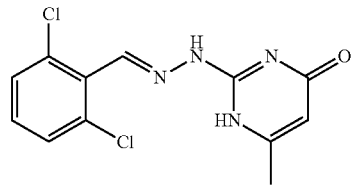 [SMILES: Cc1cc(=O)nc(N/N=C/c2c(Cl)cccc2Cl)[nH]1]

White solid (40%). $^1$H NMR (dmso-d$_6$, 400 MHz) δ 11.68 (br s, 2H), 8.32 (s, 1H), 7.58 (d, 2H, J=8.0 Hz), 7.43 (t, 1H, J=7.8 Hz), 5.56 (s, 1H), 2.10 (s, 3H). $^{13}$C NMR (100 MHz, dmso-d$_6$) δ 161.92, 161.26, 152.95, 141.02, 133.45, 130.05, 129.75, 126.59, 102.65, 21.02. ESI-HRMS Calc m/z for C$_{12}$H$_{11}$Cl$_2$N$_4$o 297.0304 (M+H)$^+$, found 297.0296. HPLC 96.28% purity t$_R$=10.34 min.

Example 92. (E)-2-(2-(2,3-dichlorobenzylidene)hydrazinyl)-6-methylpyrimidin-4(1H)-one (JM3-199-2)

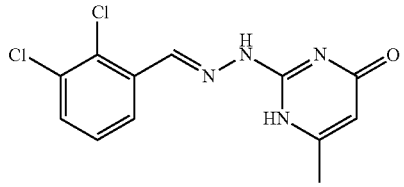 [SMILES: Cc1cc(=O)nc(N/N=C/c2cccc(Cl)c2Cl)[nH]1]

Off-White solid (46%). $^1$H NMR (dmso-d$_6$, 400 MHz) δ 11.52 (br s, 2H), 8.67 (d, 1H, J=7.8 Hz), 8.52 (s, 1H), 7.71 (d, 1H, J=7.8 Hz), 7.44 (t, 1H, J=8.0 Hz), 5.62 (s, 1H), 2.15 (s, 3H). $^{13}$C NMR (100 MHz, dmso-d$_6$) δ 162.93, 159.65, 152.05, 133.75, 133.25, 131.05, 129.98, 125.70, 119.78, 118.93, 103.05, 20.58. ESI-HRMS Calc m/z for C$_{12}$H$_{11}$C$_{12}$N$_4$o 297.0304 (M+H)$^+$, found 297.0315. HPLC 97.68% purity t$_R$=10.22 min.

Example 93. (E)-6-methyl-2-(2-(2,3,6-trichlorobenzylidene)hydrazinyl)pyrimidin-4(1H)-one (JM3-201-2)

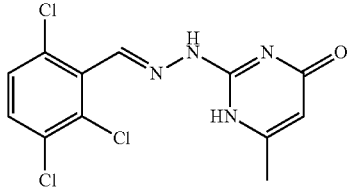 [SMILES: Cc1cc(=O)nc(N/N=C/c2c(Cl)ccc(Cl)c2Cl)[nH]1]

White solid (75%). $^1$H NMR (dmso-d$_6$, 400 MHz) δ 11.30 (br s, 2H), 8.27 (s, 1H), 7.69 (d, 1H, J=8.5 Hz), 7.60 (d, 1H, J=8.5 Hz), 5.55 (s, 1H), 1.81 (s, 3H). $^{13}$C NMR (100 MHz, dmso-d$_6$) δ 162.07, 153.05, 134.48, 133.16, 132.99, 132.84, 132.59, 132.01, 131.44, 130.36, 102.75, 19.09. ESI-HRMS Calc m/z for C$_{12}$H$_{10}$C$_{13}$N$_4$o 330.9915 (M+H)$^+$, found 330.9912. HPLC 98.51% purity t$_R$=11.48 min.

Example 94. (E)-2-(2-(2-chloro-6-fluorobenzylidene)hydrazinyl)-6-methylpyrimidin-4(1H)-one (JM3-203-2)

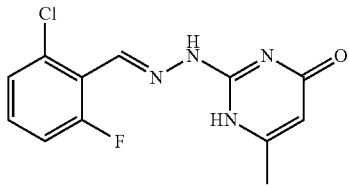

White solid (33%). $^1$H NMR (dmso-d$_6$, 400 MHz) δ 11.62 (br s, 2H), 8.32 (s, 1H), 7.50-7.30 (m, 3H), 5.57 (s, 1H), 2.11 (s, 3H). $^{13}$C NMR (100 MHz, dmso-d$_6$) δ 163.07, 156.89, 152.06, 138.50, 136.54, 130.28, 129.03, 128.90, 117.25, 115.35, 103.20, 20.28. ESI-HRMS Calc m/z for C$_{12}$H$_{11}$ClFN$_4$o 281.0600 (M+H)$^+$, found 281.0595. HPLC 98.06% purity t$_R$=9.34 min.

Example 95. (E)-5,6-dimethyl-2-(2-(2,3,6-trichlorobenzylidene)hydrazinyl)pyrimidin-4(1H)-one (JM3-205-7)

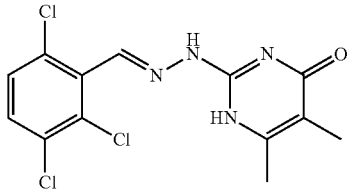 [SMILES: Cc1[nH]c(N/N=C/c2c(Cl)ccc(Cl)c2Cl)nc(=O)c1C]

Light yellow solid (75%). $^1$H NMR (dmso-d$_6$, 400 MHz) δ 11.48 (br s, 2H), 8.23 (s, 1H), 7.69 (d, 1H, J=8.5 Hz), 7.59 (d, 1H, J=8.5 Hz), 2.14 (s, 3H), 1.83 (s, 3H). $^{13}$C NMR (100 MHz, dmso-d$_6$) δ 162.26, 153.92, 138.96, 134.02, 132.92, 132.06, 132.02, 131.35, 129.05, 128.95, 102.75, 19.09, 11.06. ESI-HRMS Calc m/z for C$_{13}$H$_{12}$C$_{13}$N$_4$o 340.0071 (M+H)$^+$, found 340.0066. HPLC 96.57% purity t$_R$=11.05 min.

Example 96. (E)-2-(2-(2-chloro-6-fluorobenzylidene)hydrazinyl)-5,6-dimethylpyrimidin-4(1H)-one (JM3-207-2)

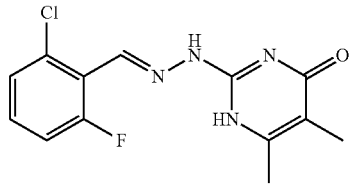 [SMILES: Cc1[nH]c(N/N=C/c2c(F)cccc2Cl)nc(=O)c1C]

White solid (31%). $^1$H NMR (dmso-$d_6$, 400 MHz) δ 11.61 (br s, 2H), 8.28 (s, 1H), 7.53-7.30 (m, 3H), 2.14 (s, 3H), 1.84 (s, 3H). $^{13}$C NMR (100 MHz, dmso-$d_6$) δ 162.98, 156.06, 151.96, 138.05, 136.03, 129.97, 128.95, 128.02, 118.03, 115.59, 105. 26, 20.25, 11.36. ESI-HRMS Calc m/z for $C_{13}H_{13}ClFN_4O$ 295.0756 (M+H)$^+$, found 295.0764. HPLC 97.57% purity $t_R$=9.58 min.

Example 97. (E)-2-(2-(3,4-dichlorobenzylidene)hydrazinyl)-5,6-dimethylpyrimidin-4(1H)-one (JM3-209-2)

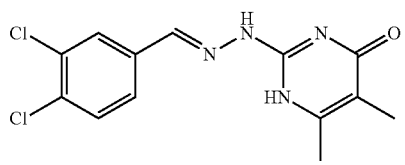 [SMILES: Cc1[nH]c(N/N=C/c2ccc(Cl)c(Cl)c2)nc(=O)c1C]

White solid (37%). $^1$H NMR (dmso-$d_6$, 400 MHz) δ 11.49 (br s, 2H), 8.42 (s, 1H), 7.98 (s, 1H), 7.81 (d, 1H, J=8.3 Hz), 7.65 (d, 1H, J=8.5 Hz), 2.11 (s, 3H), 1.84 (s, 3H). $^{13}$C NMR (100 MHz, dmso-$d_6$) δ 173.96, 159.67, 147.25, 139.65, 138.03, 130.26, 128.98, 127.62, 102.67, 22.03, 10.59. ESI-HRMS Calc m/z for $C_{13}H_{13}Cl_2N_4O$ 311.0461 (M+H)$^+$, found 311.0465. HPLC 98.20% purity $t_R$=11.33 min.

Example 98. (E)-2-(2-(3,4-dichlorobenzylidene)hydrazinyl)-6-methylpyrimidin-4(1H)-one (JM3-211-2)

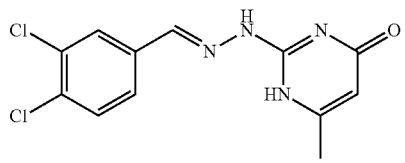 [SMILES: Cc1cc(=O)nc(N/N=C/c2ccc(Cl)c(Cl)c2)[nH]1]

White solid (62%). $^1$H NMR (dmso-$d_6$, 400 MHz) δ 11.42 (br s, 2H), 8.43 (s, 1H), 8.02 (s, 1H), 7.83 (d, 1H, J=8.5 Hz), 7.64 (d, 1H, J=8.5 Hz), 5.52 (s, 1H), 2.08 (s, 3H). $^{13}$C NMR (100 MHz, dmso-$d_6$) δ 174.03, 159.67, 147.15, 139.82, 137.28, 130.89, 128.64, 127.70, 99.67, 22.69. ESI-HRMS Calc m/z for $C_{12}H_{11}Cl_2N_4O$ 297.0304 (M+H)$^+$, found 297.0306. HPLC 98.75% purity $t_R$=11.02 min.

Example 99. (E)-2-(2-(2-chlorobenzylidene)hydrazinyl)-5,6-dimethylpyrimidin-4(1H)-one (JM3-213-2)

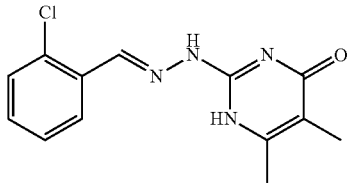 [SMILES: Cc1[nH]c(N/N=C/c2ccccc2Cl)nc(=O)c1C]

White solid (31%). $^1$H NMR (dmso-$d_6$, 400 MHz) δ 11.60 (br s, 2H), 8.59 (d, 1H, J=7.3 Hz), 8.40 (s, 1H), 7.45 (d, 1H, J=7.3 Hz), 7.42-7.34 (m, 2H), 2.11 (s, 3H), 1.85 (s, 3H). $^{13}$C NMR (100 MHz, dmso-$d_6$) δ 172.09, 162.85, 152.78, 140.23, 133.52, 131.85, 131.00, 129.906, 128.29, 127.68, 104.39, 21.68, 11.03. ESI-HRMS Calc m/z for $C_{13}H_{14}ClN_4O$ 277.0851 (M+H)$^+$, found 277.0852. HPLC 98.53% purity $t_R$=9.72 min.

Example 100. (E)-2-(2-(2-chlorobenzylidene)hydrazinyl)-6-methylpyrimidin-4(1H)-one (JM3-215-2)

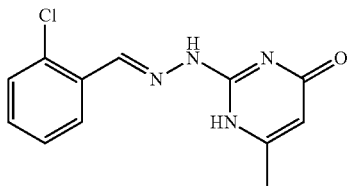 [SMILES: Cc1cc(=O)nc(N/N=C/c2ccccc2Cl)[nH]1]

Off-white solid (33%). $^1$H NMR (dmso-$d_6$, 400 MHz) δ 11.63 (br s, 2H), 8.61 (d, 1H, J=7.3 Hz), 8.44 (s, 1H), 7.47 (d, 1H, J=7.3 Hz), 7.43-7.35 (m, 2H), 5.56 (s, 1H), 2.09 (s, 3H). $^{13}$C NMR (100 MHz, dmso-$d_6$) δ 172.47, 162.91, 152.95, 140.60, 133.00, 132.07, 131.38, 129.99, 128.72, 127.64, 102.38, 21.53. ESI-HRMS Calc m/z for $C_{12}H_{12}ClN_4O$ 263.0644 (M+H)$^+$, found 263.0702. HPLC 99.10% purity $t_R$=9.34 min.

Example 101. (E)-2-(2-bromobenzylidene)hydrazine-1-carboxamide hydrochloride (JM3-219-2)

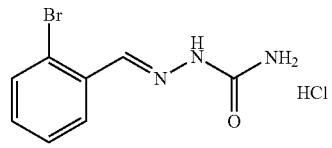 [SMILES: NC(=O)N/N=C/c1ccccc1Br ; Cl]

White crystals (88%). $^1$H NMR (dmso-$d_6$, 400 MHz) δ 10.51 (s, 1H), 8.20 (s, 1H), 8.17 (d, 1H, J=8.0 Hz), 7.61 (d, 1H, J=7.6 Hz), 7.38 (t, 1H, J=7.3 Hz), 7.28 (t, 1H, J=8.0 Hz), 6.57 (br s, 2H). $^{13}$C NMR (100 MHz, dmso-$d_6$) δ 156.99, 137.93, 133.89, 133.35, 131.12, 128.25, 127.83, 123.12. ESI-HRMS Calc m/z for $C_8H_9BrN_3O$ 241.9924 (M+H)$^+$, found 241.9930. HPLC 99.23% purity $t_R$=9.40 min.

Example 102. (E)-2-(2-fluorobenzylidene)hydrazine-1-carboxamide hydrochloride (JM3-221-2)

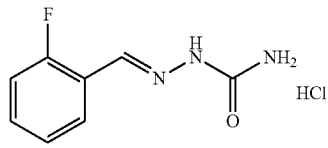 [SMILES: NC(=O)N/N=C/c1ccccc1F ; Cl]

White crystals (87%). $^1$H NMR (dmso-d$_6$, 400 MHz) δ 10.42 (s, 1H), 8.12 (t, 1H, J=7.5 Hz), 8.06 (s, 1H), 7.44-7.35 (m, 1H), 7.27-7.18 (m, 2H), 6.56 (br s, 2H). $^{13}$C NMR (100 MHz, dmso-d$_6$) δ 161.96, 159.50, 157.05, 132.11, 131.18, 126.86, 125.06, 122.82, 116.26. ESI-HRMS Calc m/z for C$_8$H$_9$FN$_3$O 182.0724 (M+H)$^+$, found 182.0729. HPLC 99.51% purity t$_R$=8.97 min.

Example 103. (E)-2-(2-chlorobenzylidene)hydrazine-1-carboxamide hydrochloride (JM3-223-2)

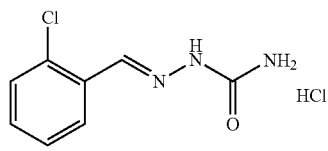 [SMILES: NC(=O)N/N=C/c1ccccc1Cl ; Cl]

White crystals (78%). $^1$H NMR (dmso-d$_6$, 400 MHz) δ 10.49 (s, 1H), 8.24 (s, 1H), 8.22-8.18 (m, 1H), 7.49-7.43 (m, 1H), 7.40-7.32 (m, 2H), 6.56 (br s, 2H). $^{13}$C NMR (100 MHz, dmso-d$_6$) δ 157.00, 135.52, 132.70, 132.40, 130.83, 130.11, 127.75, 127.43. ESI-HRMS Calc m/z for C$_8$H$_9$ClN$_3$O 198.0423 (M+H)$^+$, found 198.0435. HPLC 99.26% purity t$_R$=10.00 min.

Example 104. (E)-2-(2-iodobenzylidene)hydrazine-1-carboxamide hydrochloride (JM3-225-2)

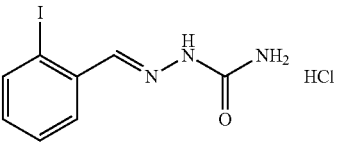 [SMILES: NC(=O)N/N=C/c1ccccc1I ; Cl]

White crystals (71%). $^1$H NMR (dmso-d$_6$, 400 MHz) δ 10.51 (s, 1H), 8.10-8.06 (m, 2H), 7.87 (d, 1H, J=7.8 Hz), 7.39 (t, 1H, J=7.8 Hz), 7.10 (t, 1H, J=7.8 Hz), 6.54 (br s, 2H). $^{13}$C NMR (100 MHz, dmso-d$_6$) δ 157.00, 142.57, 139.91, 136.67, 131.22, 128.76, 127.61, 99.49. ESI-HRMS Calc m/z for C$_8$H$_9$IN$_3$O 289.9785 (M+H)$^+$, found 289.9786. HPLC 99.01% purity t$_R$=10.82 min.

Example 105. 2-(2,6-dichlorobenzyl)hydrazine-1-carboximidamide (JM3-227-2)

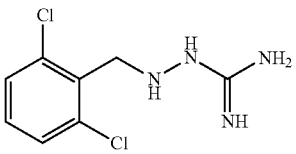 [SMILES: N=C(N)NNCc1c(Cl)cccc1Cl]

A solution of 1,3-dichloro-2-(chloromethyl)benzene (100 mg, 0.51 mmol) and aminoguanidine bicarbonate (69 mg, 0.51 mmol) was refluxed overnight in EtOH (5 mL). The solvent was evaporated and purified on silica with 0-10% methanol in dichloromethane to yield final compound as white solid (60%). $^1$H NMR (cd3od, 600 MHz) δ 7.53 (d, 2H, J=7.58 Hz), 7.32 (t, 1H, J=7.09 Hz), 5.04 (s, 2H). $^{13}$C NMR (150 MHz, dmso-d$_6$) δ 158.74, 136.89, 131.10, 128.89, 128.48, 48.90. ESI-HRMS Calc m/z for C$_8$H$_{11}$Cl$_2$N$_4$ 233.0355 (M+H)$^+$, found 233.0350. HPLC 96.78% purity t$_R$=6.52 min.

Example 106. (E)-2-(2-(2,6-dichlorophenyl)ethylidene)hydrazine-1-carboximidamide acetate (JM3-239-2)

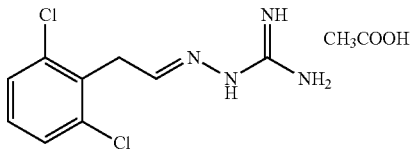

White solid (53%). $^1$H NMR (dmso-d$_6$, 400 MHz) δ 7.49 (d, 2H, J=8.1 Hz), 7.38-7.30 (m, 2H), 6.64 (br s, 4H), 3.85 (d, 2H, J=4.9 Hz), 1.79 (s, 3H). $^{13}$C NMR (100 MHz, dmso-d$_6$) δ 174.75, 158.28, 143.42, 135.39, 129.88, 128.99, 34.38, 23.25. ESI-HRMS Calc m/z for C$_9$H$_{11}$Cl$_2$N$_4$ 245.0355 (M+H)$^+$, found 245.0350. HPLC 98.05% purity t$_R$=6.58 min.

Example 107. (E)-1-((2,6-dichlorobenzylidene)amino)tetrahydropyrimidin-2(1H)-imine hydrobromide (JM3-255-2)

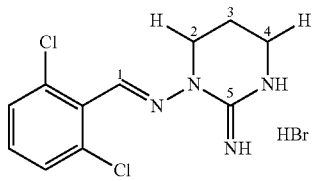

A solution of (E)-2-(2,6-dichlorobenzylidene)hydrazine-1-carboximidamide (150 mg, 0.65 mmol) and 1,3-dibromopropane (261 mg, 1.24 mmol) in EtOH (5 mL) was refluxed for overnight. The solvent was evaporated to yield a white compound. The resulted crude was purified on silica with 0-5% methanol in dichloromethane to yield final compound as white solid (63%). $^1$H NMR (dmso-d$_6$, 400 MHz) δ 8.23 (s, 1H), 7.62 (d, 2H, J=7.8 Hz), 7.50 (t, 1H, J=7.5 Hz), 3.83 (t, 2H, J=6.1 Hz), 3.35 (t, 2H, J=5.6 Hz), 2.17 (p, 2H, J=6.1 Hz). $^{13}$C NMR (100 MHz, dmso-d$_6$) δ 155.34, 139.47, 134.54, 132.18, 130.54, 129.63, 42.78, 37.48, 20.32. ESI-HRMS Calc m/z for C$_{11}$H$_{13}$Cl$_2$N$_4$ 271.0512 (M+H)$^+$, found 271.0510. HPLC 98.65% purity t$_R$=8.94 min. $^1$H NMR (CDCl$_3$, 400 MHz) δ 9.73 (br s, 1H), 8.73 (br s, 1H), 8.11 (s, 1H), 7.44 (d, 2H, J=7.8 Hz), 7.32 (t, 1H, J=7.3 Hz), 6.71 (br s, 1H), 3.82 (t, 2H, J=6.1 Hz), 3.53 (t, 2H, J=5.8 Hz), 2.34 (p, 2H, J=6.1 Hz). $^{13}$C NMR (100 MHz, CDCl$_3$) δ 154.06, 137.93, 135.10, 131.26, 129.55, 128.34, 41.70, 37.25, 20.19. (Reported structure was confirmed by HMBC. Correlations were observed for H$_2$/C$_1$, H$_2$/C$_5$ and H$_4$/C$_5$).

Example 108. (E)-2-(2,6-dichlorobenzylidene)-1-methylhydrazine-1-carboximidamide hydroiodide (JM3-257-2)

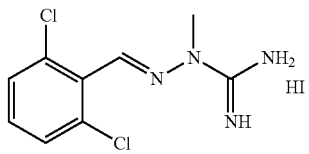

A solution of (E)-2-(2,6-dichlorobenzylidene)hydrazine-1-carboximidamide (200 mg, 0.86 mmol) and excess amount of methyl iodide in EtOH (3 mL) was refluxed for overnight. The solvent was evaporated and washed with dichloromethane followed by ether to yield final compound as off-white solid (62%). $^1$H NMR (dmso-d$_6$, 400 MHz) δ 8.19 (s, 1H), 7.91 (br s, 4H), 7.62 (d, 2H, J=8.1 Hz), 7.50 (t, 1H, J=7.5 Hz), 3.47 (s, 3H). $^{13}$C NMR (100 MHz, dmso-d$_6$) δ 156.70, 140.33, 134.53, 132.19, 130.47, 129.64, 32.08. ESI-HRMS Calc m/z for C$_9$H$_{11}$Cl$_2$N$_4$ 245.0355 (M+H)$^+$, found 245.0349. HPLC 99.25% purity t$_R$=8.41 min.

Example 109. (E)-2-(2,6-dimethylbenzylidene)hydrazine-1-carboximidamide (JM2-233-2)

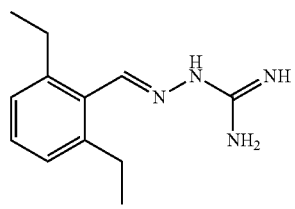 [SMILES: CCc1cccc(CC)c1/C=N/NC(=N)N]

Yellow solid (49%). $^1$H NMR (dmso-d$_6$, 600 MHz) δ 8.29 (s, 1H), 7.09 (t, 1H, J=7.0 Hz), 7.01 (d, 2H, J=7.6 Hz), 5.58 (br s, 2H), 5.38 (br s, 2H), 2.70 (q, 4H, J=7.0 Hz), 1.09 (t, 6H, J=7.6 Hz). $^{13}$C NMR (150 MHz, dmso-d$_6$) δ 159.25, 144.46, 143.22, 132.35, 128.40, 127.14, 27.02, 16.15. ESI-HRMS Calc m/z for C$_{12}$H$_{19}$N$_4$ 219.1604 (M+H)$^+$, found 219.1615. HPLC 96.24% purity t$_R$=7.95 min.

Example 110. Methyl (E)-2-(2,6-dichlorobenzylidene)hydrazine-1-carbimidothioate hydroiodide (JM2-169-2)

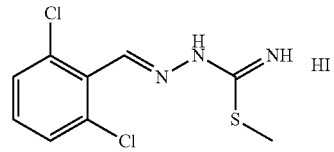

To a solution of 2-(2,6-dichlorobenzylidene)hydrazine-1-carbothioamide (400 mg, 1.61 mmol) in DMF (3 mL) was added iodomethane (454 mg, 3.22 mmol). The reaction mixture was stirred at 50° C. for 20 h. The DMF was evaporated under vacuum and the crude was triturated with ether to have a brown precipitate which was filtered and washed with ether to get the desired compound as yellow powder (99%). $^1$H NMR (dmso-d$_6$, 600 MHz) δ 13.22 (s, 1H), 9.34 (br s, 2H), 8.53 (s, 1H), 7.58 (d, 1H, J=7.0 Hz), 7.48 (t, 1H, J=6.4 Hz), 2.68 (s, 3H). $^{13}$C NMR (150 MHz, dmso-d$_6$) δ 167.65, 148.48, 134.59, 132.73, 139.98, 129.53, 13.92. ESI-MS (M+H)$^+$ 262.01.

Example 111. (E)-2-(2,6-dichlorobenzylidene)-N-methylhydrazine-1-carboximidamide hydroiodide (JM2-171-2)

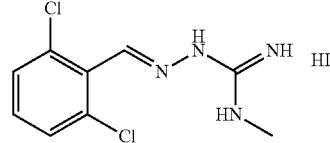

To a solution of methyl-2-(2,6-dichlorobenzylidene)hydrazine-1-carbimidothioate hydroiodide (200 mg, 0.51 mmol) in EtOH (4 mL) was added methylamine (24 mg, 0.79 mmol). The reaction mixture was stirred at reflux for overnight. The EtOH was evaporated and triturated with ether to yield crude product as precipitate. The crude was purified by silica gel chromatography using 10% methanol in dichloromethane to yield final compound as yellow solid (50 mg, 63%). $^1$H NMR (dmso-d$_6$, 600 MHz) δ 11.79 (s, 1H), 8.38 (s, 1H), 7.90 (br s, 1H), 7.84 (br s, 2H), 7.57 (d, 2H, J=8.2 Hz), 7.46 (t, 1H, J=8.2 Hz), 2.84 (d, 3H, J=4.1 Hz). $^{13}$C NMR (150 MHz, dmso-d$_6$) δ 155.51, 134.45, 133.47, 131.95, 130.51, 129.48, 28.62. ESI-HRMS Calc m/z for C$_9$H$_{11}$Cl$_2$N$_4$ 245.0355 (M+H)$^+$, found 245.0537. HPLC 99.30% purity t$_R$=7.14 min.

Example 112. (E)-2-(naphthalen-2-ylmethylene)hydrazine-1-carboximidamide acetate (JM1-111-2)

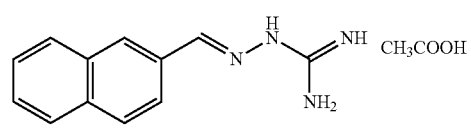

White powder. $^1$H NMR (dmso-d$_6$, 600 MHz) δ 8.15 (s, 1H), 8.06 (d, 1H, J=8.8 Hz), 7.98 (s, 1H), 7.98-7.81 (m, 3H), 7.51-7.43 (m, 2H), 6.51 (br s, 4H), 1.81 (s, 3H). $^{13}$C NMR (150 MHz, cd$_3$od) δ 179.52, 156.27, 147.36, 134.46, 133.13, 131.30, 129.13, 128.17, 128.09, 127.43, 126.92, 126.80, 122.37, 22.88. ESI-HRMS Calc m/z for C$_{12}$H$_{13}$N$_4$ 213.1135 (M+H)$^+$, found 231.1145. HPLC 99.56% purity $t_R$=6.21 min.

Example 113. (E)-2-(2-chloro-6-fluorobenzylidene)hydrazine-1-carbothioamide (JM1-113-2)

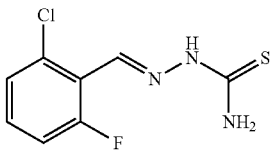 [SMILES: NC(=S)N/N=C/c1c(F)cccc1Cl]

White powder. $^1$H NMR (cd$_3$od, 600 MHz) δ 8.26 (s, 1H), 7.43 (d, 2H, J=6.4 Hz), 7.32 (t, 1H, J=9.4 Hz). $^{13}$C NMR (150 MHz, dmso-d$_6$) δ 178.79, 161.61, 159.91, 135.90, 134.02, 131.91, 126.63, 120.80, 115.83. ESI-HRMS Calc m/z for C$_8$H$_8$ClFN$_3$S 232.1016 (M+H)$^+$, found 232.0111. HPLC 99.74% purity $t_R$=6.21 min.

Example 114. (E)-2-(2,6-dichlorobenzylidene)hydrazine-1-carbothioamide (JM1-115-2)

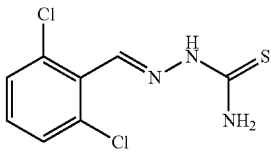 [SMILES: NC(=S)N/N=C/c1c(Cl)cccc1Cl]

White powder. $^1$H NMR (cd$_3$od, 600 MHz) δ 8.27 (s, 1H), 7.36 (q, 1H, J=8.2 Hz), 7.30 (d, 1H, J=8.2 Hz), 7.13 (t, J=7.6 Hz), 7.05 (d, 2H, 7.04 Hz). $^{13}$C NMR (150 MHz, dmso-d$_6$) δ 178.92, 138.07, 134.42, 131.46, 130.24, 129.67. ESI-HRMS Calc m/z for C$_8$H$_8$Cl$_2$N$_4$S 247.9810 (M+H)$^+$, found 247.9812. HPLC 98.01% purity $t_R$=10.74 min.

Example 115. (E)-2-(2,6-dimethylbenzylidene)hydrazine-1-carbothioamide (JM1-121-2)

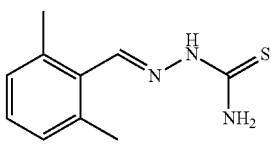

White powder. $^1$H NMR (dmso-d$_6$, 600 MHz) δ 11.31 (s, 1H), 8.43 (s, 1H), 8.17 (s, 1H), 7.37 (s, 1H), 7.43 (d, 2H, J=6.4 Hz), 7.32 (t, 1H, J=9.4 Hz), 2.36 (s, 6H). $^{13}$C NMR (150 MHz, dmso-d$_6$) δ 178.26, 143.63, 137.77, 131.13, 129.16, 129.03, 21.48. ESI-HRMS Calc m/z for C$_{10}$H$_{14}$N$_3$S 208.0903 (M+H)$^+$, found 208.0907. HPLC 96.79% purity $t_R$=10.66 min.

Example 116. (E)-2-(2-chloro-6-nitrobenzylidene)hydrazine-1-carbothioamide (JM1-125-2)

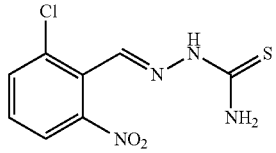 [SMILES: NC(=S)N/N=C/c1c(Cl)cccc1[N+](=O)[O-]]

Yellow powder. $^1$H NMR (cd3od, 600 MHz) δ 8.26 (s, 1H), 7.73 (d, 1H, J=8.2 Hz), 7.70 (d, 1H, J=7.6 Hz), 7.78 (t, 1H, J=7.6 Hz). $^{13}$C NMR (150 MHz, cd3od) δ 179.42, 170.36, 149.53, 135.24, 132.87, 130.87, 124.81, 122.13. ESI-HRMS Calc m/z for C$_8$H$_8$ClN$_4$O$_2$S 259.0051 (M+H)$^+$, found 259.0045. HPLC 98.40% purity $t_R$=9.90 min.

Example 117. (E)-2-(2,6-dibromobenzylidene)hydrazine-1-carbothioamide (JM1-127-2)

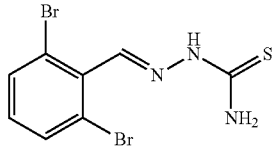 [SMILES: NC(=S)N/N=C/c1c(Br)cccc1Br]

White powder. $^1$H NMR (cd$_3$od, 600 MHz) δ 8.23 (s, 1H), 7.70 (d, 2H, J=7.6 Hz), 7.24 (t, 1H, J=8.2 Hz). $^{13}$C NMR (150 MHz, dmso-d$_6$) δ 178.92, 141.17, 133.38, 133.28, 132.16, 123.88. ESI-HRMS Calc m/z for C$_8$H$_8$Br$_2$N$_3$S 335.8800 (M+H)$^+$, found 335.8809. HPLC 99.44% purity $t_R$=11.07 min.

Example 118. (E)-2-(naphthalen-2-ylmethylene)hydrazine-1-carbothioamide (JM1-129-2)

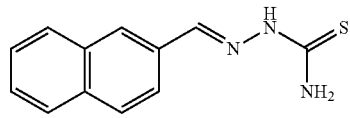 [SMILES: NC(=S)N/N=C/c1ccc2ccccc2c1]

White powder. $^1$H NMR (dmso-d$_6$, 600 MHz) δ 11.49 (s, 1H), 8.20 (d, 2H, J=18.2 Hz), 8.15 (d, 1H, J=8.8 Hz), 8.07 (d, 2H, J=16.4 Hz), 7.94-7.91 (m, 1H), 7.90-7.86 (m, 2H), 7.53-7.49 (m, 2H). $^{13}$C NMR (150 MHz, dmso-d$_6$) δ 178.43, 142.46, 134.06, 133.28, 132.45, 129.26, 128.64, 127.40, 127.06, 123.54. ESI-HRMS Calc m/z for C$_{12}$H$_{12}$N$_3$S 230.0746 (M+H)$^+$, found 230.0752. HPLC 97.13% purity $t_R$=10.94 min.

Example 119. (E)-2-(2-fluorobenzylidene)hydrazine-1-carbothioamide (JM1-135-2)

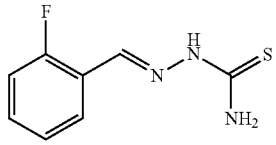 [SMILES: NC(=S)N/N=C/c1ccccc1F]

White powder. ¹H NMR (cd3od, 600 MHz) δ 8.22 (s, 1H), 8.05 (t, 1H, J=9.4 Hz), 7.41 (q, 1H, J=7.0 Hz), 7.20 (t, 1H, J=7.6 Hz), 7.13 (t, 1H, J=8.2 Hz). ¹³C NMR (150 MHz, dmso-d$_6$) δ 178.59, 162.07, 160.40, 135.22, 135.03, 132.17, 131.95, 127.35, 127.14, 125.25, 124.90, 122.77, 115.94. ESI-HRMS Calc m/z for $C_8H_9FN_3S$ 198.0496 (M+H)⁺, found 198.0500. HPLC 99.85% purity $t_R$=9.34 min.

Example 120. (E)-2-(2,6-dichlorobenzylidene)hydrazine-1-carboximidamide 2,2,2-trifluoroacetate (JM1-141-2)

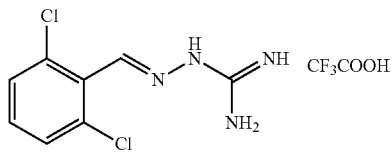 [SMILES: N=C(N)N/N=C/c1c(Cl)cccc1Cl ; "CF3COOH"]

White powder. ¹H NMR (cd₃od, 600 MHz) δ 8.25 (s, 1H), 7.48 (d, 2H, J=7.6 Hz), 7.38 (t, 1H, J=8.8 Hz). ¹³C NMR (150 MHz, cd₃od) δ 155.97, 146.09, 132.74, 132.53, 131.58, 123.39. ESI-HRMS Calc m/z for $C_8H_9Cl_2N_4$ 231.0199 (M+H)⁺, found 231.0201. HPLC 98.90% purity $t_R$=6.66 min.

Example 121. (E)-2-(2,6-dibromobenzylidene)hydrazine-1-carboximidamide 2,2,2-trifluoroacetate (JM1-143-2)

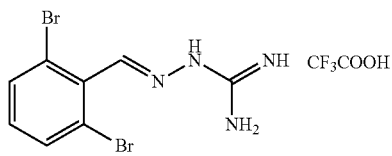 [SMILES: N=C(N)N/N=C/c1c(Br)cccc1Br ; "CF3COOH"]

White powder. ¹H NMR (cd₃od, 600 MHz) δ 8.75 (s, 1H), 8.21 (d, 2H, J=7.6 Hz), 7.74 (t, 1H, J=7.0 Hz). ¹³C NMR (150 MHz, cd₃od) δ 155.95, 143.00, 134.72, 131.00, 129.38, 128.80. ESI-HRMS Calc m/z for $C_8H_9Br_2N_4$ 318.9188 (M+H)⁺, 318.9183. HPLC 98.95% purity $t_R$=5.29 min.

Example 122. (E)-2-(2-bromo-6-nitrobenzylidene)hydrazine-1-carboximidamide acetate (JM1-175-2)

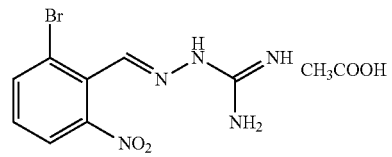

Yellow powder. ¹H NMR (cd3od, 600 MHz) δ 8.27 (s, 1H), 7.89 (d, 1H, J=8.2 Hz), 7.71 (d, 1H, J=8.2 Hz), 7.43 (t, 1H, J=7.6 Hz), 1.92 (s, 3H). ¹³C NMR (150 MHz, cd3od) δ 178.62, 157.98, 149.76, 141.22, 136.28, 130.64, 127.34, 124.06, 122.81, 22.27. ESI-HRMS Calc m/z for $C_8H_9BrN_5O_2$ 285.9934 (M+H)⁺, found 285.9936. HPLC 98.86% purity $t_R$=5.53 min.

Example 123. 1-((2,6-dichlorobenzyl)thio)guanidine (JM1-177-2)

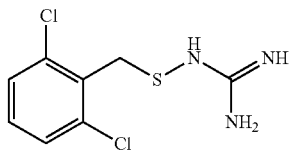 [SMILES: N=C(N)NSCc1c(Cl)cccc1Cl]

1,3-dichloro-2-(chloromethyl)benzene (500 mg, 2.5 mmol) and thiourea (194.6 mg, 2.5 mmol) was dissolved in EtOH (4 mL), added few drops of AcOH. The reaction mixture was refluxed for 2 h, then cooled to room temperature. The precipitated compound was filtered and recrystallized from EtOH to yield final compound as white color powder. The compound was obtained as HCl salt (580 mg, 84%). ¹H NMR (dmso-d$_6$, 600 MHz) δ 9.42 (s, 4H), 7.53 (d, 2H, J=7.6 Hz), 7.42 (d, 1H, J=8.2 Hz), 4.65 (s, 2H). ¹³C NMR (150 MHz, cd₃od) δ 178.652, 157.98, 149.76, 141.22, 136.28, 130.64, 130.64, 127.34, 124.06, 122.81, 22.27. ESI-HRMS Calc m/z for $C_8H_9Cl_2N_2S$ 234.9858 (M+H)⁺, found 234.9864. HPLC 98.17% purity $t_R$=14.74 min.

Example 124. (E)-2-(2-fluoro-6-nitrobenzylidene)hydrazine-1-carboximidamide acetate (JM1-179-2)

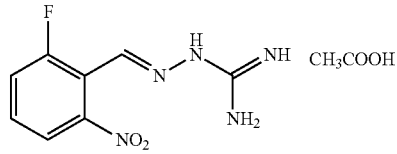

Yellow powder. ¹H NMR (cd3od, 600 MHz) δ 8.14 (s, 1H), 7.60 (d, 1H, J=8.2 Hz), 7.11 (q, 1H, J=7.6 Hz), 7.42 (t, 1H, J=9.3 Hz), 1.84 (s, 3H). ¹³C NMR (150 MHz, cd₃od) δ 178.75, 161.23, 159.54, 157.22, 148.78, 136.77, 131.20, 119.69, 118.64, 22.27. ESI-HRMS Calc m/z for $C_8H_9FN_5O_2$ 226.0735 (M+H)⁺, found 226.0738. HPLC 98.25% purity $t_R$=4.71 min.

Example 125. (E)-2-(2-chloro-5-fluorobenzylidene)hydrazine-1-carboximidamide acetate (JM1-185-2)

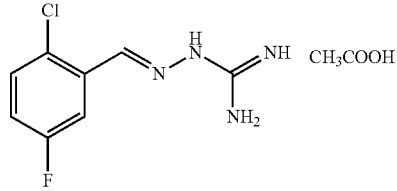

White powder. ¹H NMR (cd₃od, 600 MHz) δ 8.14 (s, 1H), 7.96 (d, 1H, J=9.3 Hz), 7.47-7.43 (m, 1H), 7.16 (t, 1H, J=8.8 Hz), 1.91 (s, 3H). ¹³C NMR (150 MHz, cd₃od) δ 179.10, 162.28, 160.66, 156.75, 142.04, 133.03, 132.97, 131.25, 131.20, 128.94, 118.27, 118.12, 113.33, 113.17, 22.52. ESI-HRMS Calc m/z for $C_8H_9ClFN_4$ 215.0494 (M+H)⁺, found 0498. HPLC 98.50% purity $t_R$=5.10 min.

Example 126. (E)-2-(2,6-difluorobenzylidene)hydrazine-1-carboximidamide acetate (JM1-191-2)

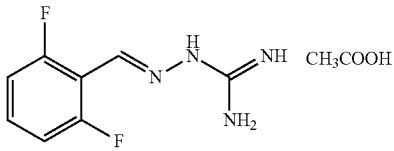

White powder. $^1$H NMR (cd3od, 600 MHz) δ 8.26 (s, 1H), 7.48-7.41 (m, 1H), 7.05 (t, 2H, J=8.0 Hz), 1.93 (s, 3H). $^{13}$C NMR (150 MHz, cd3od) δ 179.29, 181.86, 160.16, 156.58, 137.17, 131.68, 111.74, 111.60, 111.03, 22.59. ESI-HRMS Calc m/z for $C_8H_9F_2N_4$ 199.0790 (M+H)$^+$, found 199.0793. HPLC 99.5% purity $t_R$=4.63 min.

Example 127. (E)-2-(2-fluoro-6-methylbenzylidene)hydrazine-1-carboximidamide acetate (JM1-195-2)

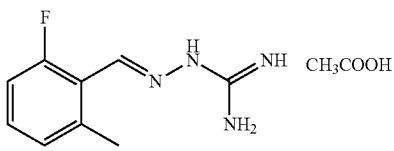

White powder. $^1$H NMR (cd3od, 600 MHz) δ 8.42 (s, 1H), 7.28 (q, 1H, J=7.6 Hz), 7.05 (d, 1H, J=7.6 Hz), 6.98 (t, 1H, J=9.9 Hz), 2.54 (s, 3H), 1.92 (s, 3H). $^{13}$C NMR (150 MHz, cd$_3$od) δ 179.21, 162.80, 161.14, 156.32, 142.21, 139.91, 130.77, 126.73, 119.61, 112.85, 112.85, 22.62, 20.53. ESI-HRMS Calc m/z for $C_9H_{12}FN_4$ 195.1041 (M+H)$^+$, found 195.1045. HPLC 98.8% purity $t_R$=5.50 min.

Example 128. 1-(2,6-dichlorophenyl)-1H-pyrazol-5-amine (JM1-217-2)

(2,6-dichlorophenyl)hydrazine hydrochloride (600 mg, 2.81 mmol) and 3,3-dimethoxypropanenitrile (400 mg, 2.79 mmol) were dissolved in 20 mL ethanol and refluxed for 18 h. The solvent was evaporated and residue was purified by silica gel chromatography using DCM/MeOH, to obtain final compound as off-white compound (430 mg, 68%). $^1$H NMR (dmso-d$_6$, 600 MHz) δ 7.77 (br s, 1H), 7.69 (d, 2H, J=8.2 Hz), 7.61 (t, 1H, J=8.2 Hz), 5.60 (s, 1H). $^{13}$C NMR (150 MHz, dmso-d$_6$) δ 151.30, 141.51, 139.01, 135.47, 134.02, 129.80, 89.77. ESI-HRMS Calc m/z for $C_9H_9Cl_2N_3$ 228.0090 (M+H)$^+$, found 228.0095.

Example 129. (E)-2-(2,6-dimethylbenzylidene)hydrazine-1-carboximidamide (JM2-233-2)

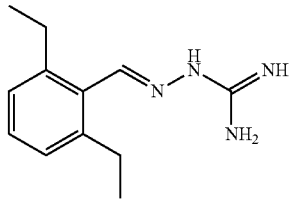 [SMILES: CCc1cccc(CC)c1/C=N/NC(=N)N]

Yellow solid (49%). $^1$H NMR (dmso-d$_6$, 600 MHz) δ 8.29 (s, 1H), 7.09 (t, 1H, J=7.0 Hz), 7.01 (d, 2H, J=7.6 Hz), 5.58 (br s, 2H), 5.38 (br s, 2H), 2.70 (q, 4H, J=7.0 Hz), 1.09 (t, 6H, J=7.6 Hz). $^{13}$C NMR (150 MHz, dmso-d$_6$) δ 159.25, 144.46, 143.22, 132.35, 128.40, 127.14, 27.02, 16.15. ESI-HRMS Calc m/z for $C_{12}H_{19}N_4$ 219.1604 (M+H)$^+$, found 219.1615. HPLC 96.24% purity $t_R$=7.95 min.

Example 130. 1-(1-(2,6-dichlorophenyl)-1H-pyrazol-5-yl)guanidine (JM1-285-2)

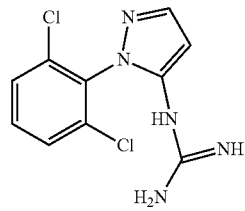

KO$^t$Bu (74 mg, 0.66 mmol) was added to a solution of 1-(2,6-dichlorophenyl)-1H-pyrazol-5-amine (100 mg, 0.44 mmol) in THF (5 mL) and stirred for 30 min at rt. To this mixture was added methyl carbamimidothioate sulfate (122 mg, 0.44 mmol) and refluxed for overnight. The compound was extracted with ether and evaporated to yield final compound as brown solid (Yield; 42%). $^1$H NMR (cd3od, 600 MHz) δ 9.02 (s, 1H), 7.71 (d, 1H, J=8.2 Hz), 7.61 (t, 1H, J=8.2 Hz), 7.42 (s, 1H), 5.46 (s, 1H). $^{13}$C NMR (150 MHz, cd3od) δ 156.75, 150.34., 140.95, 139.57, 135.75, 134.25, 128.90, 89.23. ESI-HRMS Calc m/z for $C_{10}H_{10}Cl_2N_5$ 270.0308 (M+H)$^+$, found 270.0316. HPLC 96.05% purity $t_R$=4.86 min.

Example 131. (E)-2-(2,6-dichlorobenzylidene)-N-phenylhydrazine-1-carboximidamide hydroiodide (JM2-175-2)

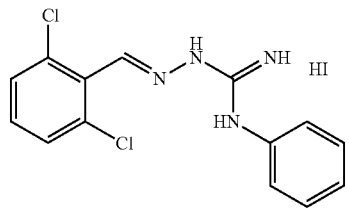

To a solution of methyl-2-(2,6-dichlorobenzylidene)hydrazine-1-carbimidothioate hydroiodide (100 mg, 0.25 mmol) in EtOH (4 mL) was added aniline (47 mg, 0.50 mmol). The mixture was stirred at reflux for overnight. The EtOH was evaporated and the triturated with ether to yield crude product as precipitate. The precipitate was filtered and washed with ether to get the final compound as light yellow solid (64%). $^1$H NMR (cd$_3$od, 600 MHz) δ 11.90 (s, 1H), 10.15 (br s, 1H), 8.50 (s, 1H), 8.10 (br s, 2H), 7.55 (d, 2H, J=7.8 Hz), 7.40 (t, 1H, J=7.8 Hz), 7.30-7.25 (m, 3H). $^{13}$C NMR (150 MHz, cd$_3$od) δ 153.0, 143.0, 134.2, 131.2, 128.9, 128.1, 127.8, 126.6, 124.0. ESI-HRMS Calc m/z for C$_{14}$H$_{13}$Cl$_4$N$_4$ 307.0512 (M+H)$^+$, found 307.0506. HPLC 97.80% purity $t_R$=7.90 min.

Example 132. (E)-2-(2,6-dichlorobenzylidene)hydrazine-1-carboximidamide bicarbonate (JM2-185-2)

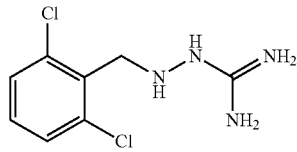 [SMILES: N=C(N)NNCc1c(Cl)cccc1Cl]

A solution of 1,3-dichloro-2-(chloromethyl)benzene (100 mg, 0.51 mmol) and aminoguanidine bicarbonate (69 mg, 0.51 mmol) was refluxed overnight in EtOH (5 mL). The solvent was evaporated and purified on silica with 0-10% methanol in dichloromethane to yield final compound as white solid (58%). $^1$H NMR (cd3od, 600 MHz) δ 7.53 (d, 2H, J=7.58 Hz), 7.32 (t, 1H, J=7.09 Hz), 5.04 (s, 2H). $^{13}$C NMR (150 MHz, dmso-d$_6$) δ 158.74, 136.89, 131.10, 128.89, 128.48, 48.90. ESI-HRMS Calc m/z for C$_8$H$_{11}$Cl$_2$N$_4$ 233.0355 (M+H)$^+$, found 233.0350. HPLC 96.78% purity $t_R$=6.52 min.

Example 133. (E)-2-(4-(benzyloxy)-2,6-dichlorobenzylidene)hydrazine-1-carboximidamide acetate (JM2-195-2)

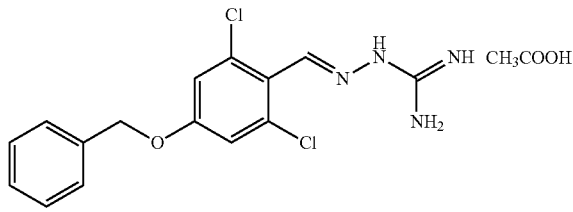

$^1$H NMR (dmso-d$_6$, 600 MHz) δ 8.09 (s, 1H), 7.41 (d, 2H, J=7.0 Hz), 7.37 (t, 2H, d, J=7.0 Hz), 7.31 (t, 1H, J=7.0 Hz), 7.15 (s, 2H), 5.71 (s, 2H), 5.61 (s, 2H), 5.15 (s, 2H), 1.86 (s, 3H). $^{13}$C NMR (150 MHz, dmso-d$_6$) δ 161.50, 157.59, 138.21, 136.65, 134.24, 128.89, 128.05, 128.51, 124.98, 116.02, 70.19, 22.18. ESI-HRMS Calc m/z for C$_{15}$H$_{15}$Cl$_2$N$_4$O 337.0617 (M+H)$^+$, found 337.0612. HPLC 99.64% purity $t_R$=8.02 min.

Example 134. Biological Activity Evaluation

Analgesic Potency Evaluation by Hot Plate and Tail Flick Assay

Mice 4-6 week old were purchased and allowed a one week acclimation period with free access to food and water. Animals are brought to the testing room 60 minutes prior to the beginning of testing for acclimation to the room.

A regulated hot plate was set at 55 degrees C. and monitored continuously. For treatment, animals were treated with test compound or vehicle using the determined route and dose. Treatment times were staggered to achieve standard testing times. Testing was begun 15 minutes post injection. A single animal was placed on the hotplate and the time lapse between the mouse being placed on the hot plate and the time it first shows a nociceptive response, by licking its back paws or jumping off, was recorded. The cutoff time for all animals was 30 seconds. Any animal that did not show a response before to the cut off time was returned to their cage and their time was recorded as 30 seconds.

For the tail flick test, mice were gently restrained in a cloth; the tail flick beam was centered on the dorsal surface of the tail (about 2-3 cm from the base). The heat source was activated, and the latency for withdrawal of the tail was recorded. The intensity of the tail flick beam was adjusted so that the average withdrawal time of the baseline measurement was 2 to 4 sec. For each animal, a baseline response latency was determined in two consecutive responses measured at 5 min intervals. Animals were tested at 15, 30, 45 and 60 min after drug administration (Table 1). To protect against tissue injury, the test was terminated after 10 sec if the animal did not withdraw its tail. Results for representative compounds are shown in the following Table 1.

In some experiments combination of two drugs (morphine+GA and/or its analogs or acetaminophen+GA and/or its analogs) were tested around their determined ED50 values. Experimental protocols listed in the following article were adapted.

Stone L S, German J P, Kitto K F, Fairbanks C A, Wilcox G L. Morphine and clonidine combination therapy improves therapeutic window in mice: synergy in antinociceptive but not in sedative or cardiovascular effects. PLoS One. 2014; 9(10):e109903. doi: 10.1371/journal.pone.0109903. Blood pressure and body temperature measurements were also conducted as listed in this article.

TABLE 1

Tail flick latencies induced by representative compounds. (dose 2 mg/kg by subcutaneous route unless stated otherwise)

| | | Mean | SEM | | | Mean | SEM |
|---|---|---|---|---|---|---|---|
| | JM1-191-2 | | | | JM1-195-2 | | |
| % MPE | 15 min | 5.5 | 4.5 | % MPE | 15 min | 5.0 | 1.6 |
| | 30 min | 7.8 | 3.0 | | 30 min | 14.9 | 5.0 |
| | 45 min | 8.1 | 3.9 | | 45 min | 16.8 | 9.0 |
| | 60 min | 2.5 | 4.1 | | 60 min | 17.6 | 7.3 |
| | JM2-171-2 | | | | JM2-185-2 | | |
| % MPE | 15 min | 34.8 | 9.1 | % MPE | 15 min | 13.0 | 2.6 |
| | 30 min | 72.1 | 19.7 | | 30 min | 7.1 | 1.2 |
| | 45 min | 79.7 | 16.7 | | 45 min | −4.3 | 1.5 |
| | 60 min | 94.8 | 5.2 | | 60 min | 5.0 | 2.0 |

TABLE 1-continued

Tail flick latencies induced by representative compounds. (dose 2 mg/kg by subcutaneous route unless stated otherwise)

| | | Mean | SEM | | | Mean | SEM |
|---|---|---|---|---|---|---|---|
| | JM2-195-2 | | | | JM2-175-2 | | |
| % MPE | 15 min | 15.9 | 6.4 | % MPE | 15 min | 3.2 | 3.4 |
| | 30 min | 6.3 | 4.7 | | 30 min | 11.1 | 5.5 |
| | 45 min | 6.2 | 5.0 | | 45 min | 4.7 | 3.0 |
| | 60 min | 6.2 | 1.7 | | 60 min | 5.7 | 5.5 |
| | JM2-233-2 | | | | JM2-253-2 | | |
| % MPE | 15 min | 6.9 | 2.3 | % MPE | 15 min | 10.8 | 4.7 |
| | 30 min | 0.4 | 2.5 | | 30 min | 2.1 | 3.0 |
| | 45 min | 7.3 | 4.5 | | 45 min | 3.3 | 4.1 |
| | 60 min | 3.4 | 4.7 | | 60 min | −0.9 | 3.9 |
| | JM2-269-2 | | | | JM2-257-2 | | |
| % MPE | 15 min | 6.3 | 1.5 | % MPE | 15 min | 14.0 | 5.4 |
| | 30 min | 15.5 | 1.9 | | 30 min | 2.9 | 3.5 |
| | 45 min | 12.7 | 2.5 | | 45 min | 8.1 | 5.8 |
| | 60 min | 11.2 | 0.3 | | 60 min | 9.8 | 2.1 |
| | JM2-255-2 | | | | JM2-287-2 | | |
| % MPE | 15 min | 9.4 | 2.7 | % MPE | 15 min | 4.8 | 5.0 |
| | 30 min | 17.3 | 5.3 | | 30 min | 11.2 | 1.8 |
| | 45 min | 15.1 | 4.1 | | 45 min | 22.9 | 7.3 |
| | 60 min | 11.7 | 2.3 | | 60 min | 41.0 | 8.3 |
| | JM2-83-2 | | | | JM1-175-2 | | |
| % MPE | 15 min | 15.1 | 6.3 | % MPE | 15 min | 26.7 | 10.7 |
| | 30 min | 13.5 | 4.2 | | 30 min | 45.0 | 14.0 |
| | 45 min | 16.6 | 4.7 | | 45 min | 55.1 | 16.0 |
| | 60 min | 32.5 | 11.9 | | 60 min | 58.1 | 15.8 |
| | 75 min | 37.8 | 12.9 | | 75 min | 39.9 | 13.2 |
| | 90 min | 37.2 | 11.9 | | 90 min | 30.8 | 7.5 |
| | 105 min | 27.9 | 10.7 | | | | |
| | 120 min | 49.8 | 12.4 | | | | |
| | 135 min | 45.8 | 16.0 | | | | |
| | 150 min | 47.7 | 14.5 | | | | |
| | JM2-109-2 | | | | JM2-275-2 | | |
| % MPE | 15 min | 23.5 | 11.7 | % MPE | 15 min | 4.9 | 2.0 |
| | 30 min | 14.1 | 13.8 | | 30 min | 2.8 | 6.6 |
| | 45 min | 12.4 | 3.4 | | 45 min | 4.9 | 3.1 |
| | 60 min | 14.1 | 7.5 | | 60 min | 5.0 | 3.3 |
| | BC1-272-1 | | | | BC1-45-1 | | |
| % MPE | 15 min | 76.7 | 23.1 | % MPE | 15 min | 52.6 | 33.7 |
| | 30 min | 85.6 | 20.3 | | 30 min | 55.8 | 31.5 |
| | 45 min | 96.2 | 10.0 | | 45 min | 92.7 | 14.7 |
| | 60 min | 97.4 | 6.9 | | 60 min | 90.5 | 19.0 |
| | BC2-5-1 | | | | BC2-35-1 | | |
| % MPE | 15 min | 16.8 | 20.2 | % MPE | 15 min | 89.5 | 29.8 |
| | 30 min | 4.8 | 10.0 | | 30 min | 91.7 | 23.5 |
| | 45 min | 9.1 | 6.4 | | 45 min | 92.3 | 17.9 |
| | 60 min | 4.4 | 11.1 | | 60 min | 91.5 | 24.0 |
| | BC2-45-1 | | | | BC2-27-1 | | |
| % MPE | 15 min | 57.6 | 48.9 | % MPE | 15 min | 34.8 | 38.6 |
| | 30 min | 100.0 | 0.0 | | 30 min | 63.3 | 43.0 |
| | 45 min | 100.0 | 0.0 | | 45 min | 83.3 | 38.9 |
| | 60 min | 100.0 | 0.0 | | 60 min | 82.3 | 33.1 |
| | BC2-47-1 | | | | BC2-57-1 | | |
| % MPE | 15 min | 80.1 | 28.5 | % MPE | 15 min | 82.8 | 35.9 |
| | 30 min | 92.5 | 21.1 | | 30 min | 80.2 | 29.8 |
| | 45 min | 100.0 | 0.0 | | 45 min | 94.5 | 10.8 |
| | 60 min | 100.0 | 0.0 | | 60 min | 85.2 | 28.3 |
| | JM2-87-2 | | | | JM2-109-2 | | |
| % MPE | 15 min | 24.2 | 3.0 | % MPE | 15 min | 7.2 | 4.5 |
| | 30 min | 64.2 | 11.3 | | 30 min | 14.8 | 1.1 |
| | 45 min | 60.7 | 12.2 | | 45 min | 12.1 | 3.6 |
| | 60 min | 67.8 | 9.3 | | 60 min | 9.3 | 3.1 |
| % MPE | 15 min | 7.9 | 2.1 | % MPE | 15 min | 7.6 | 2.8 |
| | 30 min | 10.6 | 4.0 | | 30 min | 2.9 | 2.5 |
| | 45 min | 8.4 | 6.0 | | 45 min | 4.7 | 3.5 |
| | 60 min | 5.3 | 6.9 | | 60 min | 4.6 | 1.6 |
| | JM3-141-2 | | | | JM3-141-2 | | |
| % MPE | 15 min | 6.0 | 5.2 | % MPE | 15 min | 34.0 | 16.0 |
| | 30 min | 27.0 | 14.1 | | 30 min | 45.5 | 13.5 |
| | 45 min | 17.5 | 10.6 | | 45 min | 54.9 | 15.8 |
| | 60 min | 26.3 | 16.8 | | 60 min | 41.0 | 10.0 |
| | JM3-239-2 | | | | JM3-257-2 | | |
| % MPE | 15 min | 16.6 | 4.8 | % MPE | 15 min | 3.3 | 0.9 |
| | 30 min | 7.4 | 3.9 | | 30 min | 12.5 | 1.3 |
| | 45 min | 2.0 | 4.0 | | 45 min | 14.6 | 2.3 |
| | 60 min | 2.2 | 2.7 | | 60 min | 10.8 | 4.5 |
| | JM3-257-2 (10 mg/kg) | | | | Lofexidine HCl | | |
| % MPE | 15 min | 18.9 | 7.1 | % MPE | 15 min | 92.7 | 7.3 |
| | 30 min | 31.3 | 1.9 | | 30 min | 100.0 | 0.0 |
| | 45 min | 65.5 | 20.1 | | 45 min | 100.0 | 0.0 |
| | 60 min | 60.2 | 12.5 | | 60 min | 89.0 | 7.3 |
| | 75 min | 65.3 | 20.0 | | 75 min | 92.8 | 4.2 |
| | 90 min | 33.7 | 7.7 | | 90 min | 91.9 | 8.1 |
| | JM2-111-2 | | | | JM2-101-2 | | |
| % MPE | 15 min | 6.8 | 3.8 | % MPE | 15 min | 6.6 | 3.7 |
| | 30 min | 11.5 | 1.9 | | 30 min | 11.2 | 2.0 |
| | 45 min | 6.7 | 1.5 | | 45 min | 6.0 | 3.8 |
| | 60 min | 1.2 | 1.4 | | 60 min | 6.2 | 2.4 |
| | JM2-97-2 | | | | E-Guanabenz | | |
| % MPE | 15 min | 87.1 | 12.9 | % MPE | 15 min | 77.3 | 6.4 |
| | 30 min | 100.0 | 0.0 | | 30 min | 96.3 | 3.7 |
| | 45 min | 100.0 | 0.0 | | 45 min | 99.9 | 0.1 |
| | 60 min | 100.0 | 0.0 | | 60 min | 100.0 | 0.0 |
| | JM2-271-2 | | | | JM3-81-2 | | |
| % MPE | 15 min | 5.4 | 1.6 | % MPE | 15 min | 3.6 | 2.9 |
| | 30 min | 8.4 | 4.1 | | 30 min | 17.4 | 5.7 |
| | 45 min | 15.6 | 8.3 | | 45 min | 9.4 | 5.2 |
| | 60 min | 2.9 | 3.6 | | 60 min | 5.1 | 7.0 |
| | JM3-11-2 | | | | JM3-17-2 | | |
| % MPE | 15 min | 7.0 | 2.4 | % MPE | 15 min | 14.6 | 4.0 |
| | 30 min | 10.5 | 5.0 | | 30 min | 6.9 | 5.8 |
| | 45 min | 5.5 | 1.6 | | 45 min | −1.2 | 3.5 |
| | 60 min | 5.2 | 3.7 | | 60 min | 1.0 | 3.0 |
| | JM3-57-2 | | | | JM3-81-2 (10 mg/kg) | | |
| % MPE | 15 min | 7.7 | 3.6 | % MPE | 15 min | 55.9 | 18.0 |
| | 30 min | 5.6 | 3.2 | | 30 min | 59.3 | 18.9 |
| | 45 min | 9.0 | 5.3 | | 45 min | 68.0 | 19.1 |
| | 60 min | 3.2 | 4.7 | | 60 min | 76.2 | 16.7 |
| | JM3-89-2 | | | | JM3-131-2 | | |
| % MPE | 15 min | 7.9 | 2.1 | % MPE | 15 min | 7.6 | 2.8 |
| | 30 min | 10.6 | 4.0 | | 30 min | 2.9 | 2.5 |
| | 45 min | 8.4 | 6.0 | | 45 min | 4.7 | 3.5 |
| | 60 min | 5.3 | 6.9 | | 60 min | 4.6 | 1.6 |
| | JM3-141-2 | | | | JM3-141-2 | | |
| % MPE | 15 min | 6.0 | 5.2 | % MPE | 15 min | 34.0 | 16.0 |
| | 30 min | 27.0 | 14.1 | | 30 min | 45.5 | 13.5 |
| | 45 min | 17.5 | 10.6 | | 45 min | 54.9 | 15.8 |
| | 60 min | 26.3 | 16.8 | | 60 min | 41.0 | 10.0 |

TABLE 1-continued

Tail flick latencies induced by representative compounds. (dose 2 mg/kg by subcutaneous route unless stated otherwise)

|  |  | Mean | SEM |  |  | Mean | SEM |
|---|---|---|---|---|---|---|---|
|  | JM3-239-2 |  |  |  | JM3-257-2 |  |  |
| % MPE | 15 min | 16.6 | 4.8 | % MPE | 15 min | 3.3 | 0.9 |
|  | 30 min | 7.4 | 3.9 |  | 30 min | 12.5 | 1.3 |
|  | 45 min | 2.0 | 4.0 |  | 45 min | 14.6 | 2.3 |
|  | 60 min | 2.2 | 2.7 |  | 60 min | 10.8 | 4.5 |
|  | JM3-257-2 (10 mg/kg) |  |  |  | Lofexidine HCl |  |  |
| % MPE | 15 min | 18.9 | 7.1 | % MPE | 15 min | 92.7 | 7.3 |
|  | 30 min | 31.3 | 1.9 |  | 30 min | 100.0 | 0.0 |
|  | 45 min | 65.5 | 20.1 |  | 45 min | 100.0 | 0.0 |
|  | 60 min | 60.2 | 12.5 |  | 60 min | 89.0 | 7.3 |
|  | 75 min | 65.3 | 20.0 |  | 75 min | 92.8 | 4.2 |
|  | 90 min | 33.7 | 7.7 |  | 90 min | 91.9 | 8.1 |

Evaluation in the Cellular ER Stress Model

Hela Cells were seeded in 96 well plates at a density of 2,000 cells per well 24 hours prior to treatment. ER stress was elicited by addition of fresh media containing 1 pig/ml tunicamycin (Sigma-Aldrich). E-guanabenz (EGA) and the test compounds were dissolved in dimethyl sulfoxide (DMSO) and added as indicated. DMSO was used as a mock treatment. Cell viability was assessed by measuring the reduction of WST-8 [2-(2-methoxy-4-nitrophenyl)-3-(4-nitrophenyl)-5-(2,4-disulfophenyl)-2H-tetrazolium] into formazan using Cell viability Counting Kit-8 (Dojindo) according to the supplier's recommendation, 48 hours after tunicamycin treatment. The optical density (OD) was read with a microplate reader (SpectraMax M5e, Molecular Devices). Concentration response graphs were generated for each drug using GraphPad Prism software (GraphPad Software, Ins., La Jolla, CA). Data for representative compounds is provided in the following Table.

TABLE

Summary of Anti-ERS activity.

| Compounds | % Cell Survival | | | Compounds | |
|---|---|---|---|---|---|
|  | Cmpd(2.5 µM) + Tuni | EGA(2.5 µM) + Tuni | Tuni | ERS (vs Tn) | EGA ERS (vs Tn) |
| JM2-83-2 | 53.75% | 75.93% | 43.02% | 1.25 | 1.76 |
| JM2-85-2 | 62.29% | 75.93% | 43.02% | 1.45 | 1.76 |
| JM2-97-2 | 63.14% | 75.93% | 43.02% | 1.47 | 1.76 |
| JM2-87-2 | 54.33% | 67.87% | 43.81% | 1.24 | 1.55 |
| JM2-89-2 | 56.88% | 67.87% | 43.81% | 1.30 | 1.55 |
| JM2-91-2 | 54.54% | 67.87% | 43.81% | 1.24 | 1.55 |
| JM2-95-2 | 52.99% | 67.87% | 43.81% | 1.21 | 1.55 |
| JM2-101-2 | 49.54% | 68.84% | 46.34% | 1.07 | 1.49 |
| JM2-103-2 | 48.66% | 68.84% | 46.34% | 1.05 | 1.49 |
| JM2-109-2 | 50.17% | 68.84% | 46.34% | 1.08 | 1.49 |
| BC1-267-2 | 42.28% | 76.73% | 41.63% | 1.02 | 1.84 |
| JM1-217-2 | 40.59% | 76.73% | 41.63% | 0.97 | 1.84 |
| JM1-285-2 | 41.94% | 76.73% | 41.63% | 1.01 | 1.84 |
| BC2-59-2 | 38.95% | 76.73% | 41.63% | 0.94 | 1.84 |
| BC2-7-1 | 66.66% | 76.73% | 41.63% | 1.60 | 1.84 |
| BC1-282-1 | 71.59% | 76.73% | 41.63% | 1.72 | 1.84 |
| JM1-113-2 | 27.64% | 69.09% | 36.76% | 0.40 | 1.88 |
| JM1-121-2 | 23.38% | 69.09% | 36.76% | 0.34 | 1.88 |
| JM1-129-2 | 24.07% | 69.09% | 36.76% | 0.35 | 1.88 |
| JM1-175-2 | 44.91% | 69.09% | 36.76% | 0.65 | 1.88 |
| JM1-185-2 | 54.37% | 69.09% | 36.76% | 0.79 | 1.88 |
| JM1-191-2 | 45.66% | 69.09% | 36.76% | 0.66 | 1.88 |
| JM1-221-2 | 38.58% | 69.09% | 36.76% | 0.56 | 1.88 |
| JM1-223-2 | 37.52% | 69.09% | 36.76% | 0.54 | 1.88 |
| JM1-225-2 | 35.89% | 69.09% | 36.76% | 0.52 | 1.88 |
| JM1-257-2 | 34.65% | 69.09% | 36.76% | 0.50 | 1.88 |
| JM2-59-2 | 46.19% | 69.09% | 36.76% | 0.67 | 1.88 |
| JM2-63-2 | 44.64% | 69.09% | 36.76% | 0.65 | 1.88 |
| JM2-111-1 | 34.62% | 59.09% | 31.64% | 1.09 | 1.87 |
| JM2-113-2 | 35.18% | 59.09% | 31.64% | 1.11 | 1.87 |
| JM2-115-2 | 35.58% | 59.09% | 31.64% | 1.12 | 1.87 |
| JM2-131-2 | 62.57% | 59.09% | 31.64% | 1.98 | 1.87 |
| JM2-133-2 | 57.15% | 59.09% | 31.64% | 1.81 | 1.87 |
| JM2-171-2 | 67.04% | 59.09% | 31.64% | 2.12 | 1.87 |
| JM2-175-2 | 34.31% | 59.09% | 31.64% | 1.08 | 1.87 |
| JM2-185-2 | 31.72% | 59.09% | 31.64% | 1.00 | 1.87 |
| JM2-191-2 | 39.48% | 59.09% | 31.64% | 1.25 | 1.87 |
| JM2-195-2 | 24.11% | 59.09% | 31.64% | 0.76 | 1.87 |
| JM2-253-2 | 39.58% | 59.09% | 31.64% | 1.25 | 1.87 |
| JM2-255-2 | 63.75% | 59.09% | 31.64% | 2.01 | 1.87 |
| JM2-275-2 | 29.84% | 41.31% | 29.61% | 1.01 | 1.39 |
| JM2-287-2 | 33.01% | 41.31% | 29.61% | 1.11 | 1.39 |
| JM2-233-2 | 31.75% | 38.45% | 26.34% | 1.21 | 1.46 |
| JM2-265-2 | 47.21% | 38.45% | 26.34% | 1.79 | 1.46 |
| JM2-271-2 | 32.32% | 38.45% | 26.34% | 1.23 | 1.46 |
| JM2-279-2 | 32.09% | 38.45% | 26.34% | 1.22 | 1.46 |
| JM2-289-2 | 33.75% | 38.45% | 26.34% | 1.28 | 1.46 |
| JM3-11-2 | 40.22% | 38.45% | 26.34% | 1.53 | 1.46 |

TABLE-continued

Summary of Anti-ERS activity.

| Compounds | % Cell Survival | | | Compounds | |
| --- | --- | --- | --- | --- | --- |
| | Cmpd(2.5 μM) + Tuni | EGA(2.5 μM) + Tuni | Tuni | ERS (vs Tn) | EGA ERS (vs Tn) |
| JM3-13-2 | 27.41% | 38.45% | 26.34% | 1.04 | 1.46 |
| JM3-17-2 | 28.67% | 38.45% | 26.34% | 1.09 | 1.46 |
| JM3-27-2 | 28.65% | 38.45% | 26.34% | 1.09 | 1.46 |
| JM3-29-2 | 32.20% | 38.45% | 26.34% | 1.22 | 1.46 |
| JM3-57-2 | 28.07% | 38.45% | 26.34% | 1.07 | 1.46 |
| JM3-63-2 | 15.88% | 38.45% | 26.34% | 0.60 | 1.46 |
| Z-guanabenz | 22.10% | 40.02% | 22.92% | 0.96 | 1.75 |
| JM3-67-2 | 23.33% | 34.60% | 22.94% | 1.02 | 1.51 |
| JM3-81-2 | 29.90% | 34.60% | 22.94% | 1.30 | 1.51 |
| JM3-89-2 | 22.02% | 34.60% | 22.94% | 0.96 | 1.51 |
| JM3-99-2 | 20.91% | 34.60% | 22.94% | 0.91 | 1.51 |
| JM3-131-2 | 22.83% | 34.60% | 22.94% | 1.00 | 1.51 |
| JM3-141-2 | 19.63% | 34.60% | 22.94% | 0.86 | 1.51 |
| JM3-149-2 | 29.08% | 33.28% | 23.22% | 1.25 | 1.43 |
| JM3-151-2 | 24.19% | 33.28% | 23.22% | 1.04 | 1.43 |
| JM3-153-2 | 35.95% | 33.28% | 23.22% | 1.55 | 1.43 |
| JM3-155-2 | 31.25% | 33.28% | 23.22% | 1.35 | 1.43 |
| JM3-161-2 | 14.65% | 33.28% | 23.22% | 0.63 | 1.43 |
| JM3-177-2 | 23.82% | 33.28% | 23.22% | 1.03 | 1.43 |
| JM3-179-2 | 20.40% | 33.28% | 23.22% | 0.88 | 1.43 |
| JM3-183-2 | 24.20% | 33.28% | 23.22% | 1.04 | 1.43 |
| JM3-191-2 | 40.62% | 33.28% | 23.22% | 1.75 | 1.43 |
| JM3-195-2 | 29.68% | 33.28% | 23.22% | 1.28 | 1.43 |
| JM3-181-2 | 19.60% | 26.00% | 19.17% | 1.02 | 1.36 |
| JM3-197-2 | 20.40% | 26.00% | 19.17% | 1.06 | 1.36 |
| JM3-199-2 | 22.92% | 26.00% | 19.17% | 1.20 | 1.36 |
| JM3-201-2 | 20.02% | 26.00% | 19.17% | 1.04 | 1.36 |
| JM2-203-2 | 19.74% | 26.00% | 19.17% | 1.03 | 1.36 |
| JM3-205-2 | 20.74% | 26.00% | 19.17% | 1.08 | 1.36 |
| JM3-207-2 | 23.08% | 26.00% | 19.17% | 1.20 | 1.36 |
| JM3-209-2 | 21.58% | 26.00% | 19.17% | 1.13 | 1.36 |
| JM3-211-2 | 20.22% | 26.00% | 19.17% | 1.05 | 1.36 |
| JM3-213-2 | 22.80% | 26.00% | 19.17% | 1.19 | 1.36 |
| JM3-215-3 | 21.01% | 26.00% | 19.17% | 1.10 | 1.36 |
| JM3-219-4 | 20.00% | 26.00% | 19.17% | 1.04 | 1.36 |
| JM3-221-2 | 28.94% | 35.13% | 23.66% | 1.22 | 1.49 |
| JM3-223-2 | 28.03% | 35.13% | 23.66% | 1.18 | 1.49 |
| JM3-225-2 | 22.76% | 35.13% | 23.66% | 0.96 | 1.49 |
| JM3-227-2 | 27.92% | 35.13% | 23.66% | 1.18 | 1.49 |
| JM3-239-2 | 28.08% | 35.13% | 23.66% | 1.19 | 1.49 |
| JM3-255-2 | 24.52% | 35.13% | 23.66% | 1.04 | 1.49 |
| JM3-257-2 | 31.25% | 35.13% | 23.66% | 1.32 | 1.49 |
| Salubrinal(25 μM) | 38.46% | 49.76% | 33.22% | 1.16 | 1.50 |
| Lofexidine Hcl | 35.43% | 49.76% | 33.22% | 1.07 | 1.50 |
| Sal003 | 33.17% | 40.42% | 32.23% | 1.03 | 1.25 |

Calculations: ERS activity vs Tuni = % cell survival (compound)/% cell survival (tunicamycin)

Figure 1B:
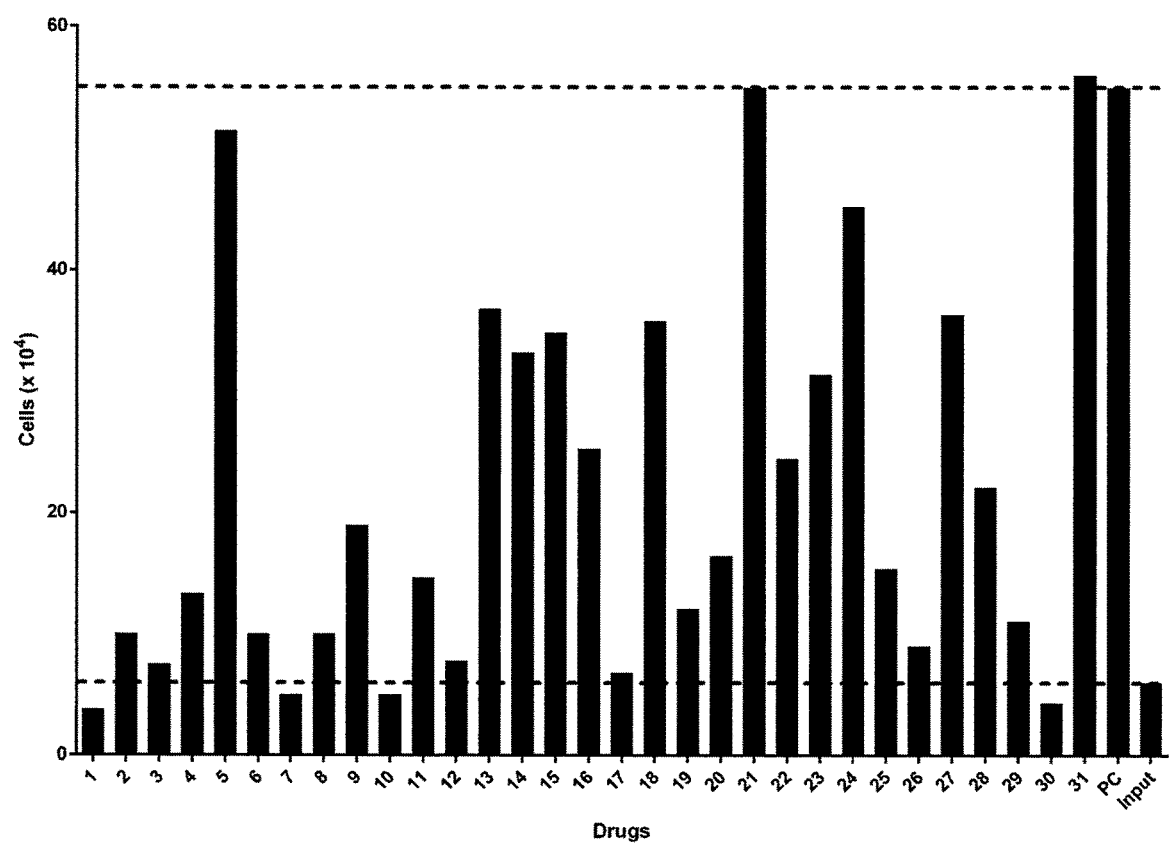

The Enzyme-Linked Immunospot (Elispot) Cell Infection Assay for Anti-Prion Activity The Elispot cell infection assay was adapted from previous studies (Mahal, S. P. et al. Proc Natl Acad Sci USA 104, 20908-20913; and Li, J. et al. Science 327, 869-872) with minor modifications (Table 2). Briefly, 200 μL of PMCA products at round 6 were collected and centrifuged at 100,000×g, 4° C. for 1 hour and the pellets were washed twice, followed by centrifugation at 100,000×g, 4° C. for 1 hour after each wash. After the final wash, the pellets were resuspended in 200 μL of CAD5 growth media (OPTI-MEM, 5% BGS and 1% penicillin and streptomycin) and sonicated for 30 seconds with 50% output (Misonic Sonicator XL2020). Each sample was serially diluted 10, 100, and 1,000 times and 60 μL of undiluted and diluted samples were used to infect CAD5 cells. After two 1:10 splits, 20,000 CAD5 cells/well were transferred to the Millipore 96-well Elispot plates (MSIPN4W) and subjected to the Elispot assay (Mahal, S. P. et al. Proc Natl Acad Sci USA 104, 20908-20913; and Li, J. et al. Science 327, 869-872). The images were taken by S6 Micro Analyzer (CTL Analyzers, LLC) and processed by the ImmunoSpot software (CTL Analyzers, LLC). The graph was generated using GraphPad Prism (GraphPad Software, Inc.) (FIGS. 1A and 1B).

TABLE 2

Anti-ERStress activity and anti-prion activity of representative compounds.

| Compound | EliSpot (Spots/10000 Cells) | AntiERStress (% Cell Survival) | AntiPrion (Number of Cells × $10^4$) | ERS (vs Tn) | Elispot (vs PC) | 1/Elispot |
|---|---|---|---|---|---|---|
| BC1-167-1 | 1500 | 45.93192 | 9 | 0.95 | 1.15 | 0.87 |
| BC1-171-1 | 1300 | 52.53729 | 16 | 1.08 | 1.00 | 1.00 |
| BC1-242-2 | 700 | 57.56368 | 50 | 1.19 | 0.54 | 1.86 |
| BC1-252-2 | 1800 | 49.48715 | 8 | 1.02 | 1.38 | 0.72 |
| BC1-256-2 | 900 | 54.76512 | 32 | 1.13 | 0.69 | 1.44 |
| BC1-259-2 | 800 | 62.86899 | 26 | 1.30 | 0.62 | 1.63 |
| BC1-262-1 | 700 | 64.70308 | 53 | 1.34 | 0.54 | 1.86 |
| BC1-267-2 | 1300 | 64.26003 | 18 | 1.33 | 1.00 | 1.00 |
| BC1-272-2 | 1300 | 95.09492 | 15 | 1.96 | 1.00 | 1.00 |
| BC1-282-1 | 1700 | 101.2576 | 10 | 2.09 | 1.31 | 0.76 |
| Z-Guanabenz | 2200 | 64.32858 | 3 | 1.33 | 1.69 | 0.59 |
| BC1-295-1 | 600 | 60.58403 | 37 | 1.25 | 0.46 | 2.17 |
| BC1-297-1 | 1400 | 90.49042 | 8 | 1.87 | 1.08 | 0.93 |
| BC2-3-1 | 700 | 82.07256 | 28 | 1.69 | 0.54 | 1.86 |
| BC2-5-1 | 800 | 104.9813 | 34 | 2.17 | 0.62 | 1.63 |
| BC2-7-1 | 1300 | 100.0136 | 3 | 2.06 | 1.00 | 1.00 |
| BC2-9-1 | 900 | 93.31728 | 33 | 1.93 | 0.69 | 1.44 |
| BC2-11-1 | 800 | 52.43021 | 38 | 1.08 | 0.62 | 1.63 |
| BC2-13-1 | 1800 | 68.97337 | 9 | 1.42 | 1.38 | 0.72 |
| BC2-17-1 | 1300 | 104.8795 | 16 | 2.16 | 1.00 | 1.00 |
| Sephin-1 | 800 | 87.19458 | 32 | 1.80 | 0.62 | 1.63 |
| BC2-19-1 | 1800 | 64.14785 | 5 | 1.32 | 1.38 | 0.72 |
| BC2-25-1 | 1200 | 51.70278 | 20 | 1.07 | 0.92 | 1.08 |
| BC2-45-1 | 2100 | 99.19487 | 10 | 2.05 | 1.62 | 0.62 |
| E-Guanabenz | 800 | 94.70235 | 56 | 1.95 | 0.62 | 1.63 |
| BC2-55-2 | 1300 | 70.68508 | 4 | 1.46 | 1.00 | 1.00 |
| BC2-61-1 | 1400 | 86.55959 | 10 | 1.79 | 1.08 | 0.93 |
| BC2-61-2 | 800 | 58.21462 | 50 | 1.20 | 0.62 | 1.63 |
| BC2-59-1 | 1400 | 104.6895 | 15 | 2.16 | 1.08 | 0.93 |
| Compound 7 | 1100 | 94.95489 | 15 | 1.96 | 0.85 | 1.18 |
| Positive Control | 1300 | — | 55 | | 1.00 | 1.00 |
| Input | — | — | 2 | | | |
| Vehicle | | 100 | — | | | |
| tunicamycin | — | 48.46011 | — | | | |

Calculations:
ERS activity vs Tn = % cell survival (compound)/% cell survival (tunicamycin)
Elispot (vs positive control) = Elispot (spots/10000 cells) for (Compound)/Elispot (spots/10000 cells) for (Positive control)
1/Elispot = 1/[Elispot (vs positive control)]
Higher (ERS activity vs Tn) or (1/Elispot) indicates better neuroprotective activity.

Protection Against Inflammation During Experimental Autoimmune Encephalomyelitis (EAE)

Figure 2:
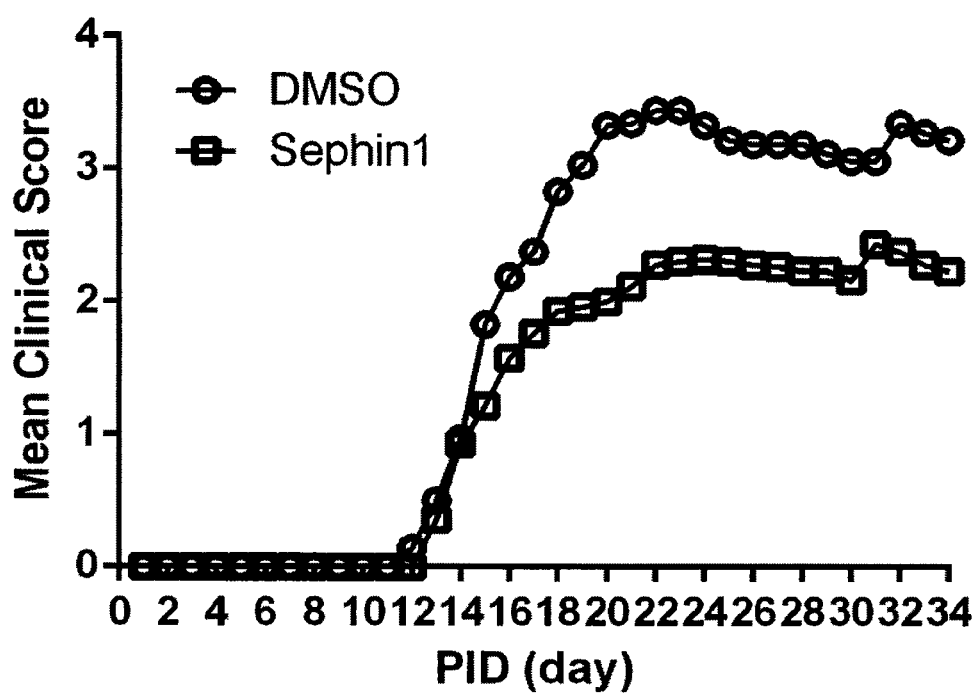
FIG. 2 shows sephin 1 treatment attends the EAE disease severity. N=7 mice.
Figure 3A:
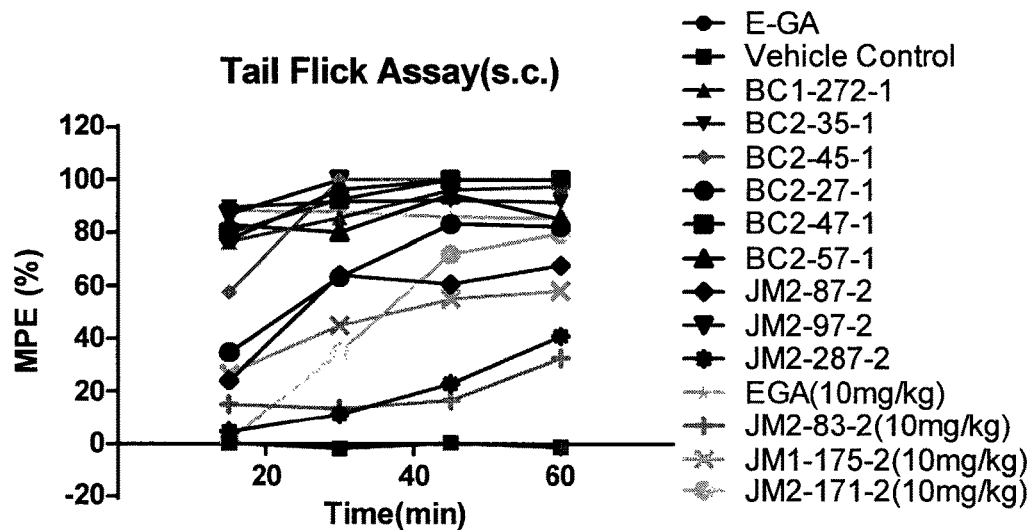
FIG. 3A shows data for representative compounds in the tail-flick assay of Example 134.
Figure 3B:
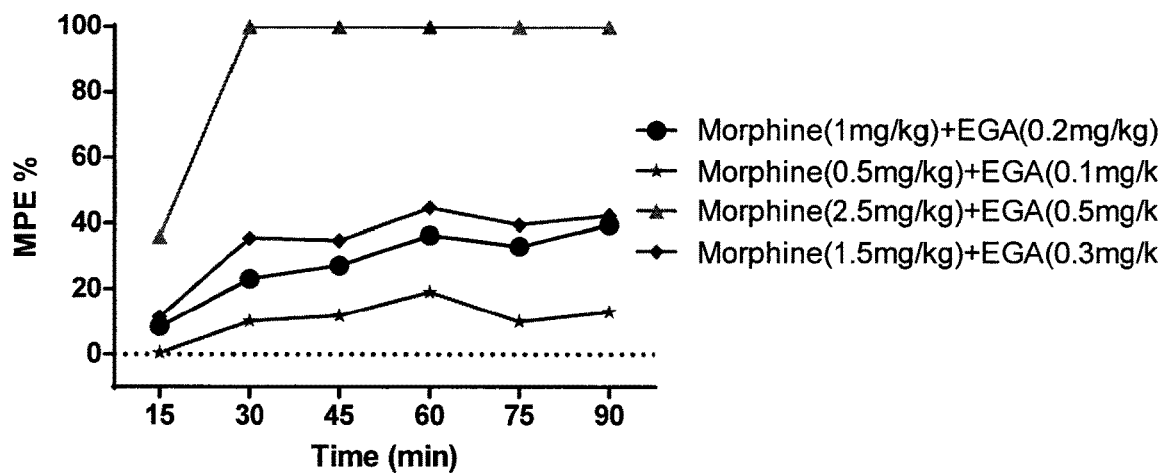
Figure 4A:
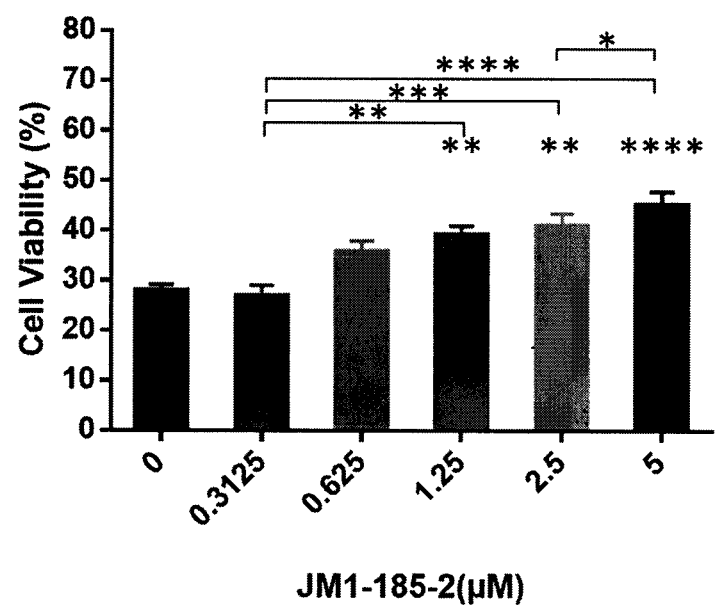
FIGS. 4A-4W show data for representative compounds and control compounds in the cell viability assay of Example 134. Viability of HeLa cells was assessed by the ability to reduce WST-8 into formazan, following treatments with tunicamycin for 48 hours, with or without the indicated concentrations of E-guanabenz or the test compound. Data are means±SEM (n=3). *P<0.05.
Figure 4B:
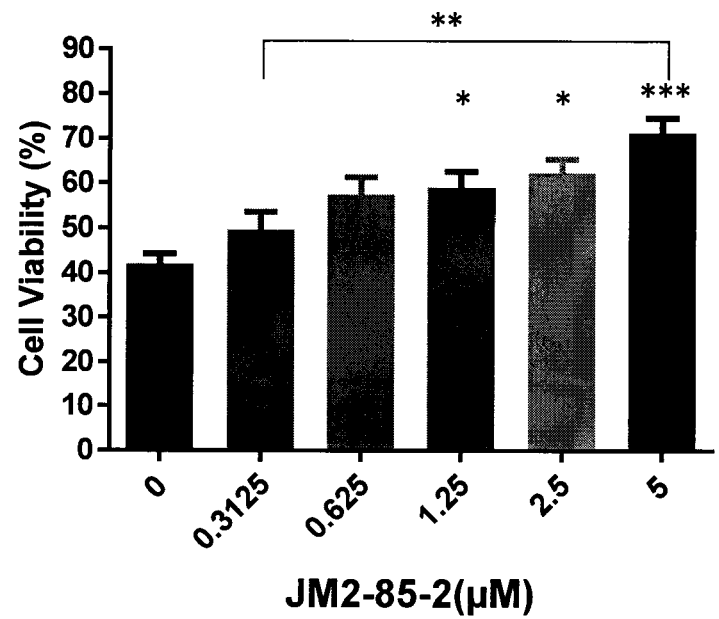
Figure 4C:
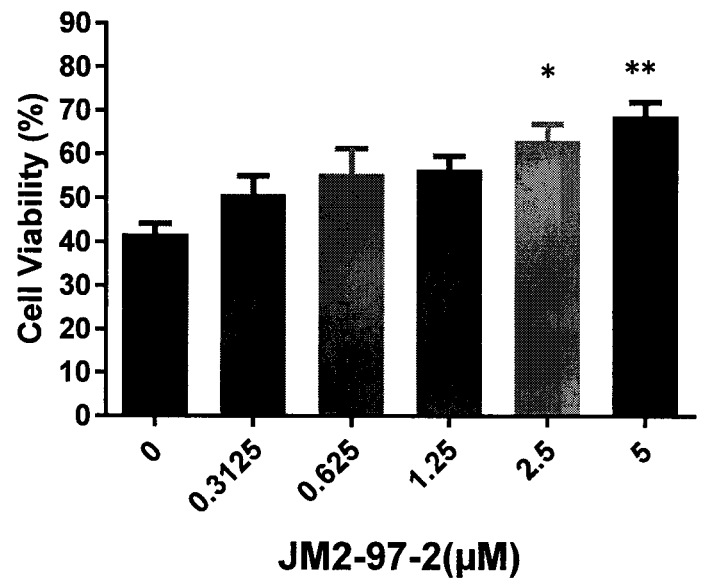
Figure 4D:
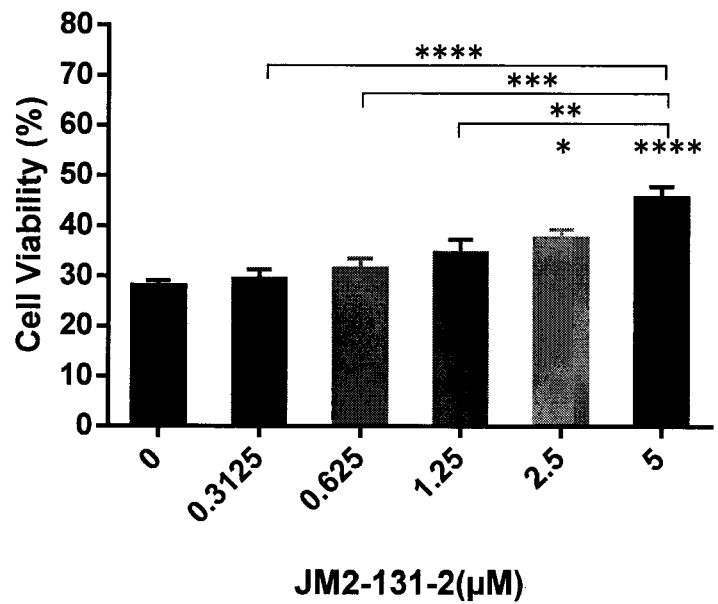
Figure 4E:
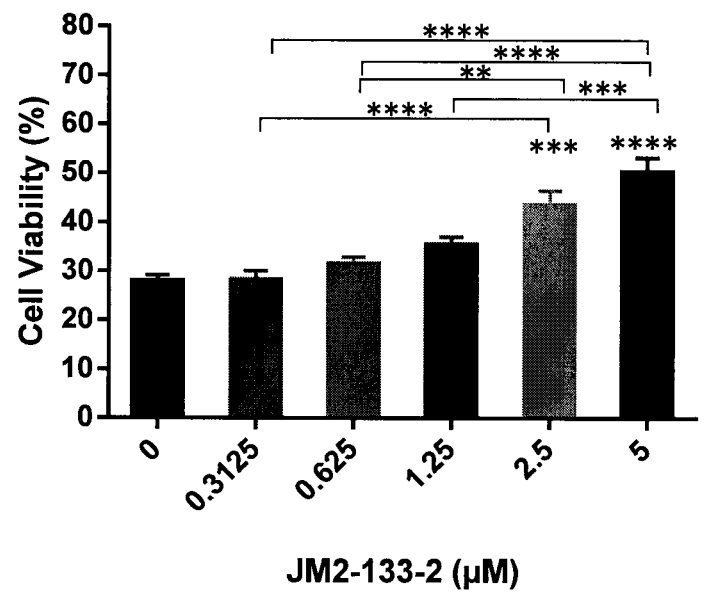
Figure 4F:
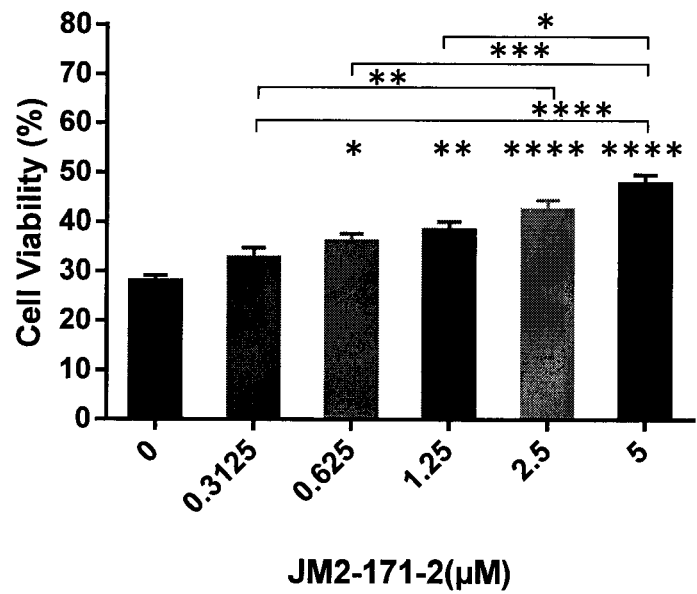
Figure 4G:
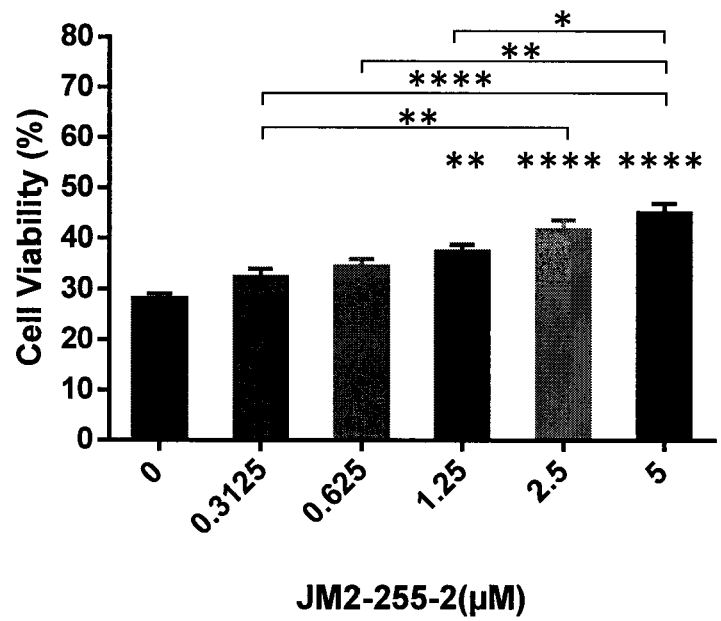
Figure 4H:
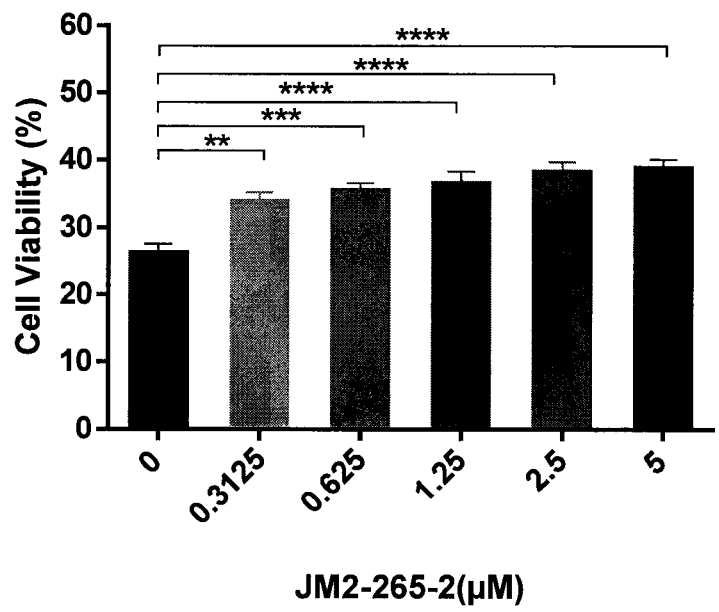
Figure 4I:
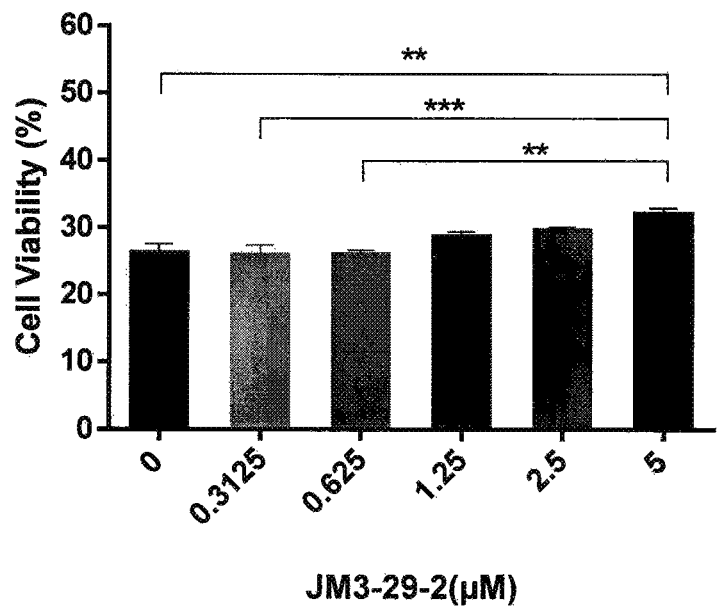
Figure 4J:
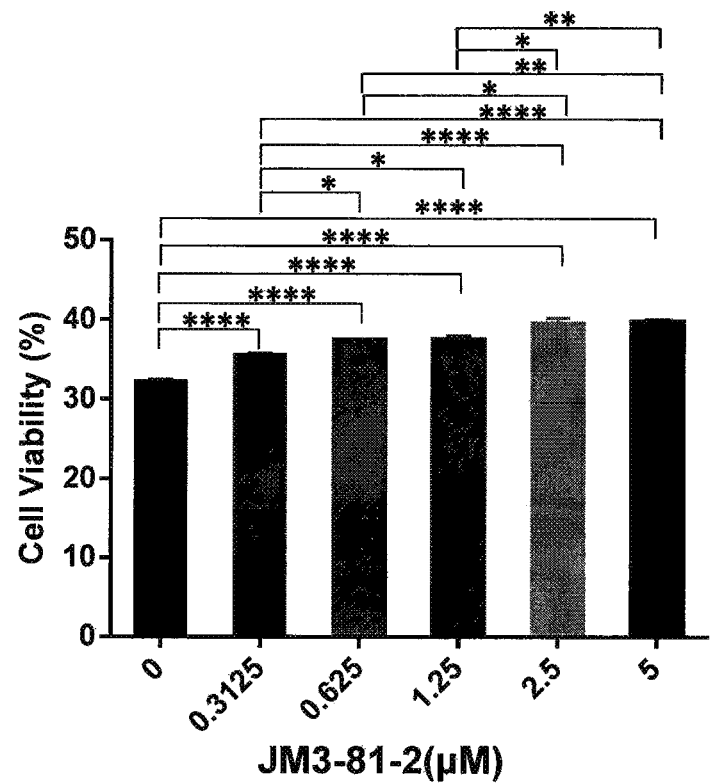
Figure 4K:
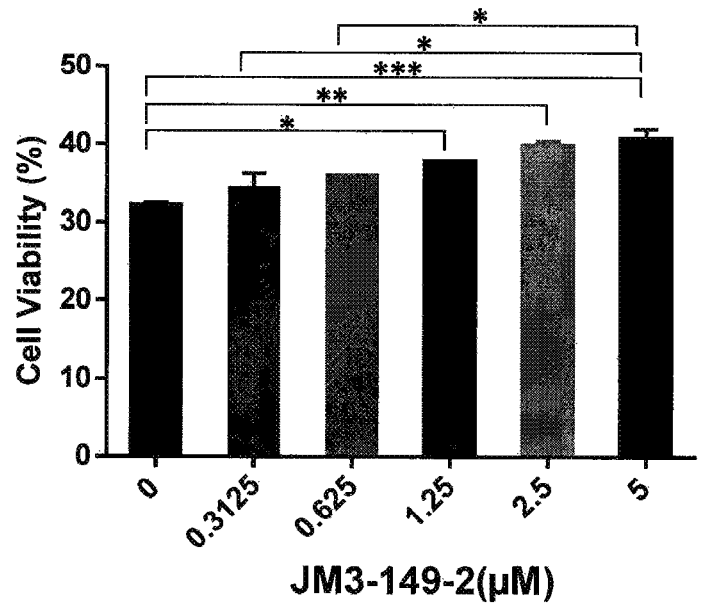
Figure 4L:
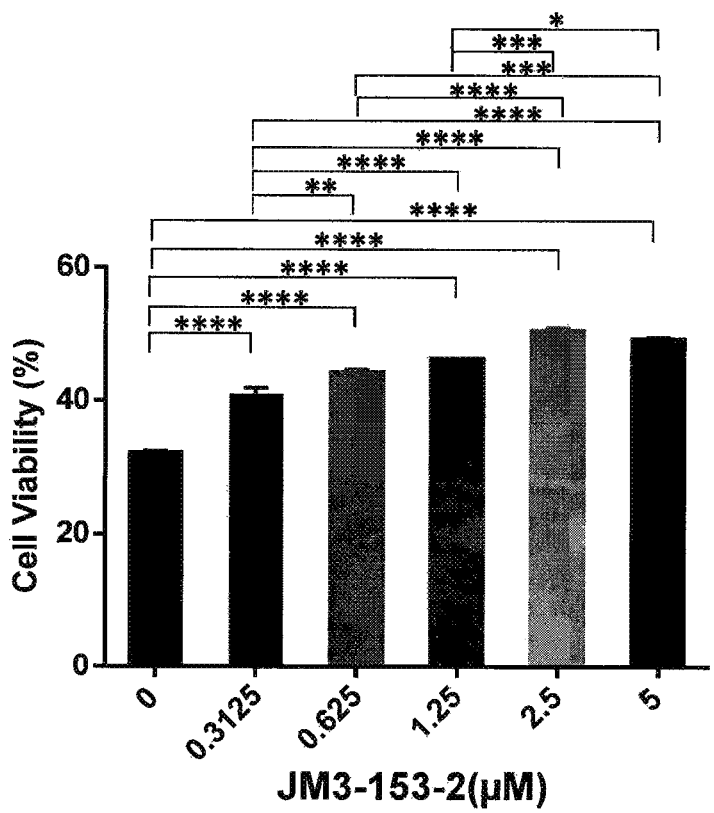
Figure 4M:
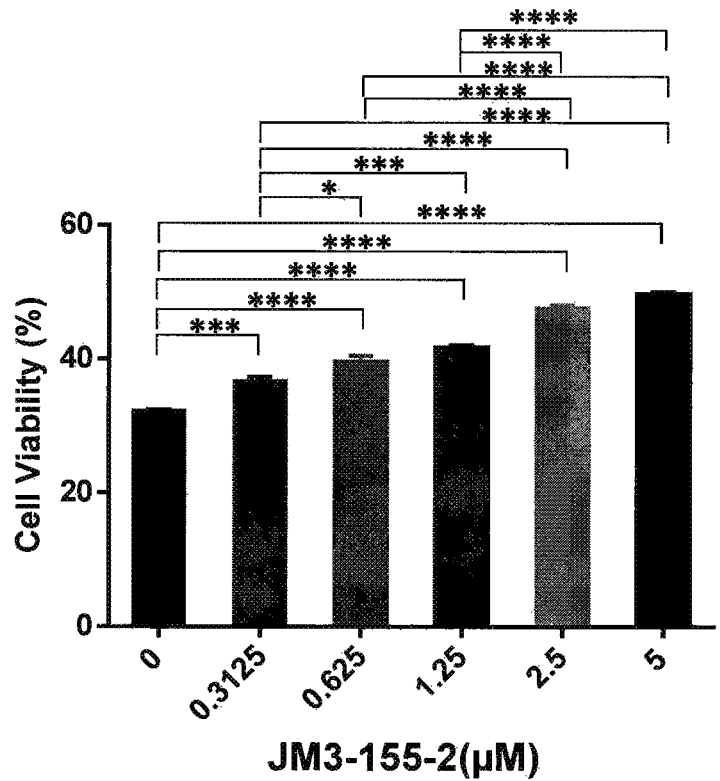
Figure 4N:
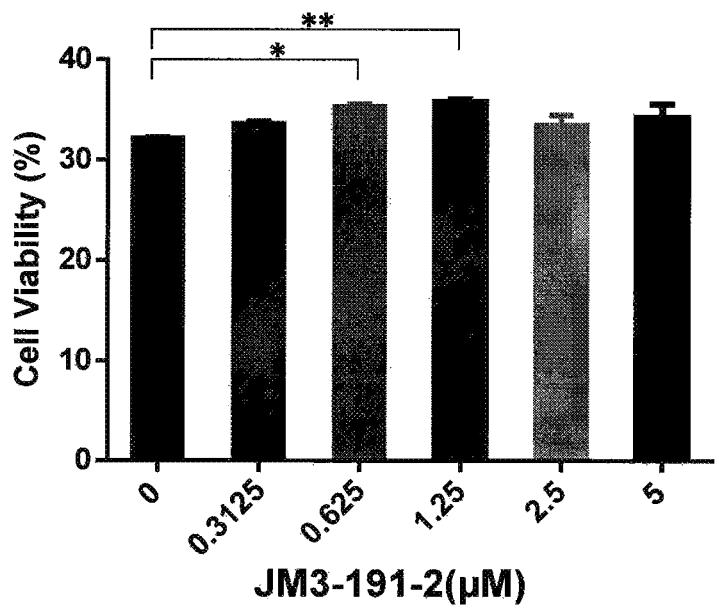
Figure 4O:
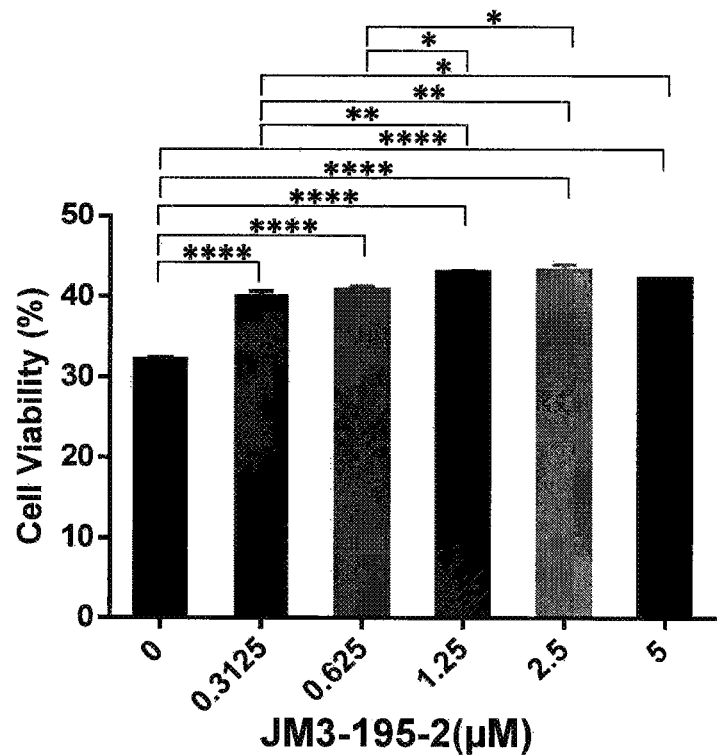
Figure 4P:
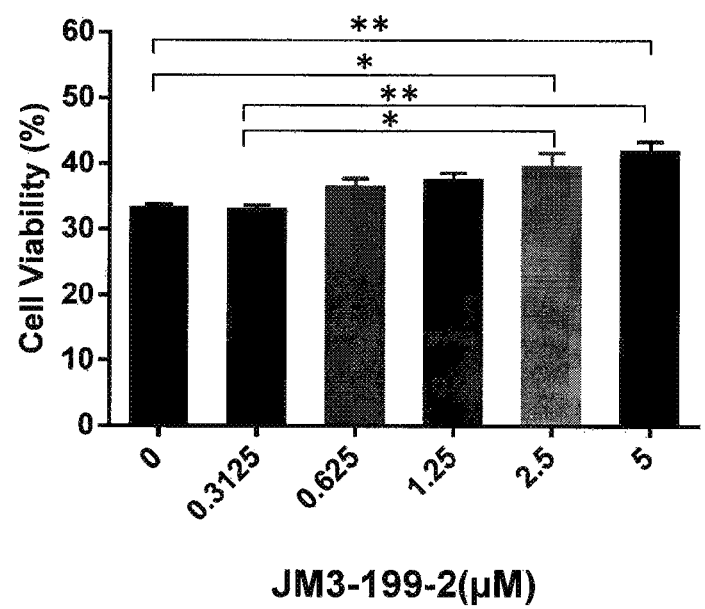
Figure 4Q:
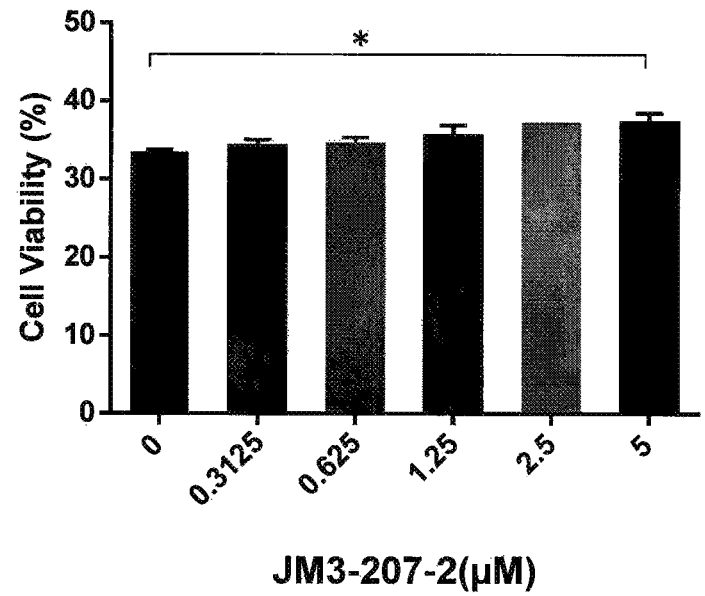
Figure 4R:
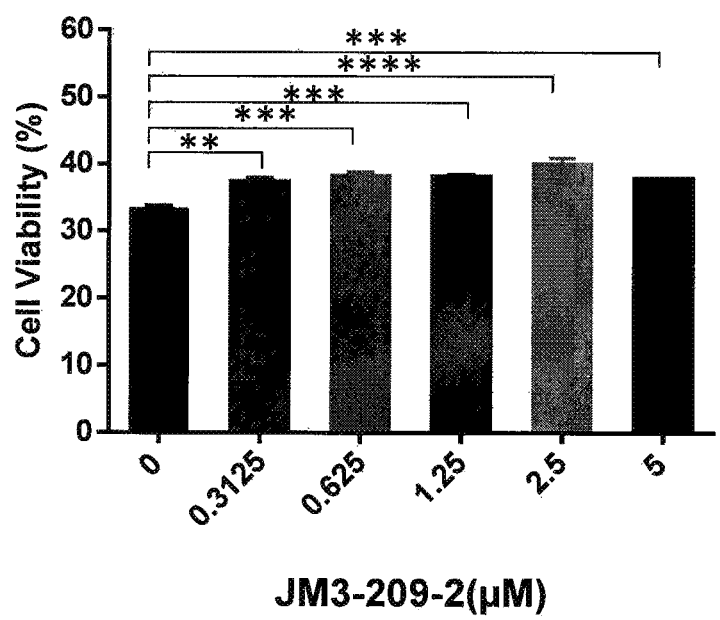
Figure 4S:
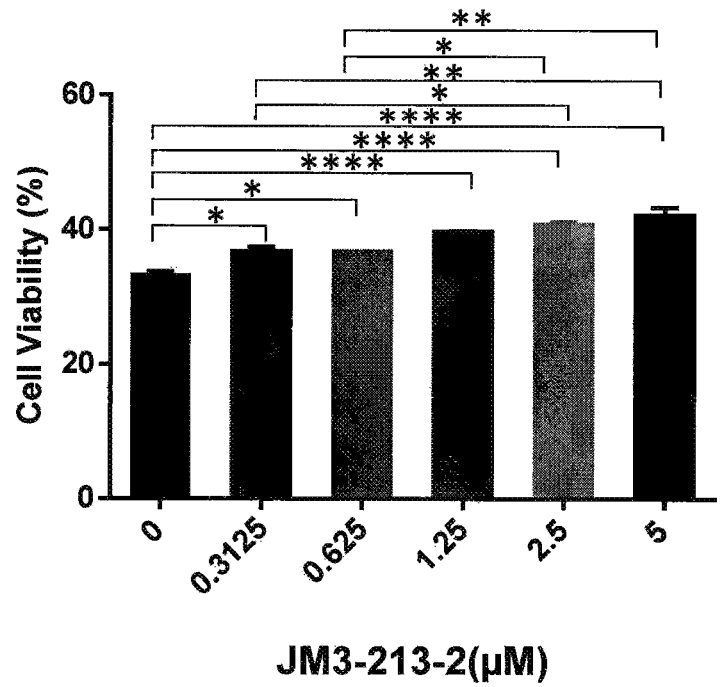
Figure 4T:
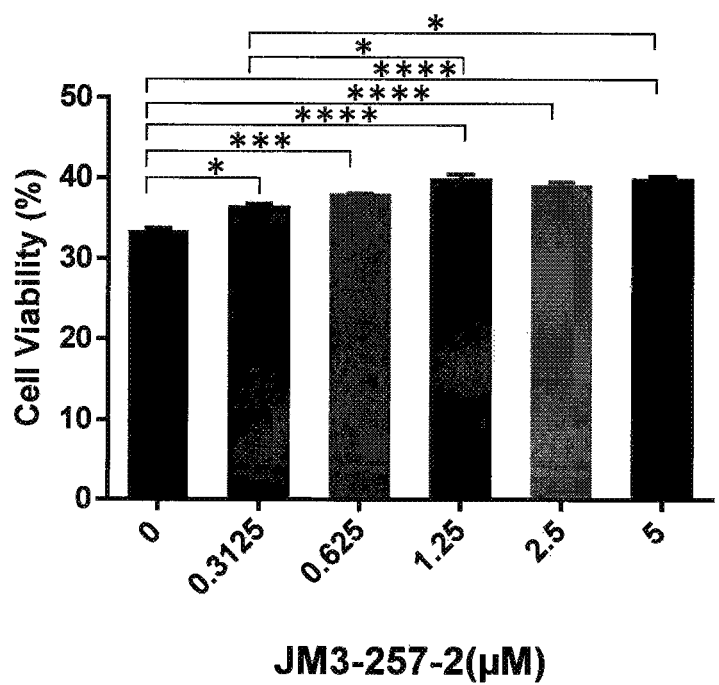
Figure 4U:
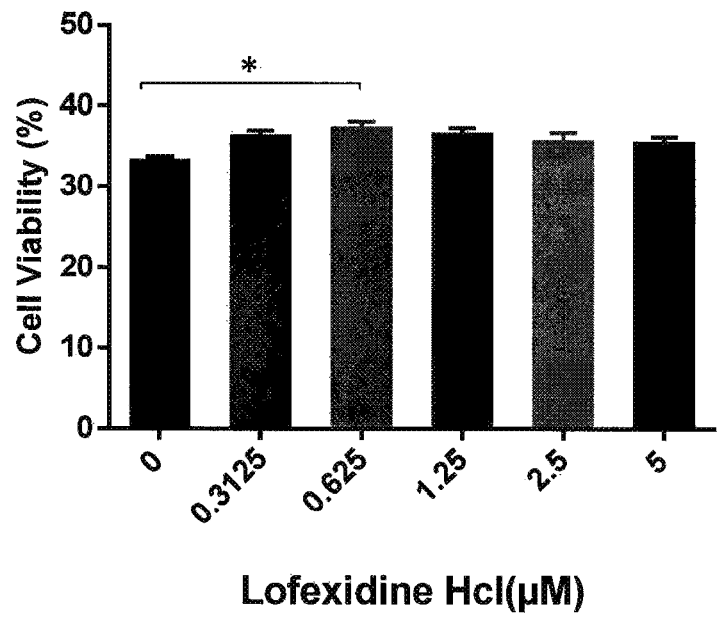
Figure 4V:
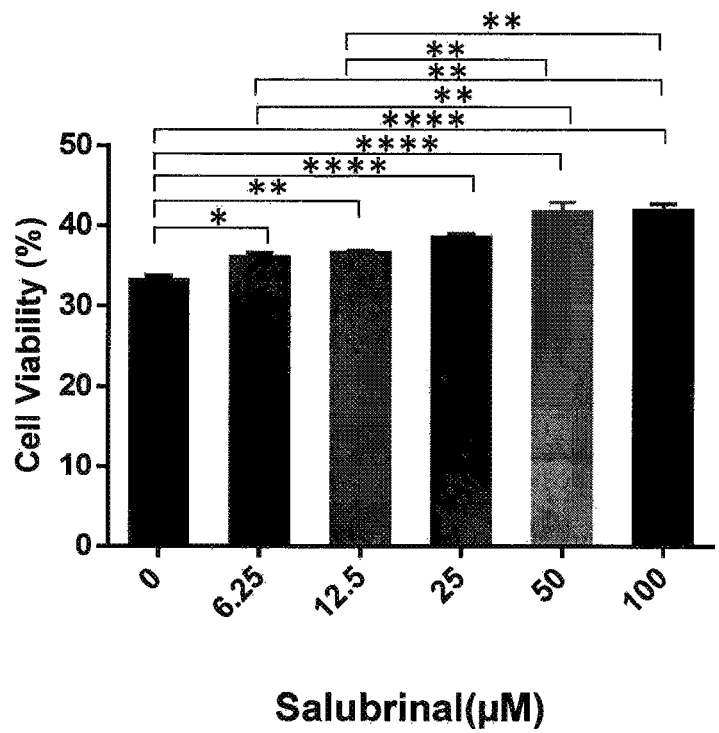
Figure 4W:
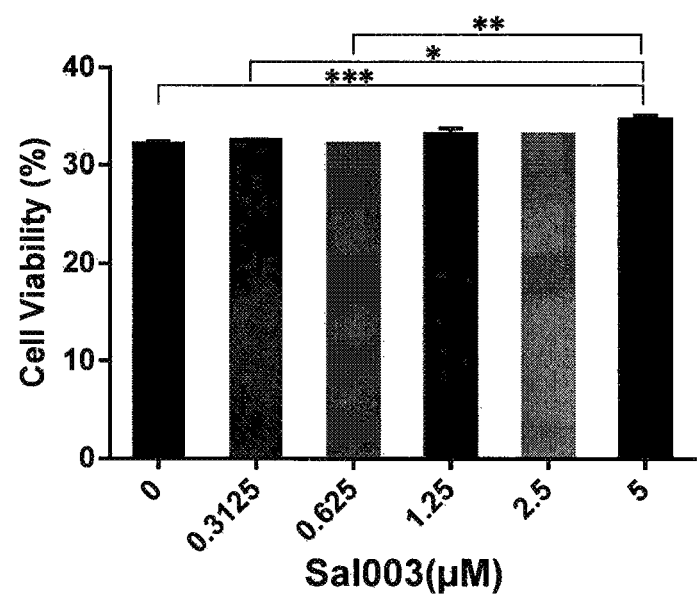

The MOG-induced EAE consists of the acute phase (the demyelination phase) and the chronic phase (the remyelination phase) (Lin W, et al. J Neurosci. 2013, 33:5980-5991; and Lin Y, et al. Am J Pathol. 2014, 184:507-519). Effect of treatment with the test compound was evaluated during the acute phase of EAE in terms of attenuation of mature oligodendrocyte apoptosis and demyelination. Eight-week-old female C57BL/6J mice were immunized with MOG35-55 peptide to induce EAE. Briefly, the mice received subcutaneous injections of 200 μg MOG35-55 peptide emulsified in complete Freund's adjuvant supplemented with 600 μg of *Mycobacterium tuberculosis* in the flank and tail base. Two intraperitoneal injections of 400 ng of pertussis toxin were given 24 h and 72 h later. Mice were treated with the test compound or vehicle daily starting on post immunization day (PID) 10. Clinical severity scores was recorded daily using a 0-5 point scale (0=healthy, 1=flaccid tail, 2=ataxia and/or paresis of hind limbs, 3=paralysis of hind limbs, 4=tetra paralysis, and 5=moribund or dead) up to PID 35. Preliminary results showed that treatment with Sephin 1 markedly attended the EAE disease severity (FIG. 2).

Example 135. Biological Evaluation of Acetaminophen Toxicity

Compound BC1-45-1 (guanabenz) and representative compounds of formulae Ia', Ib', Ic' and Id' are capable of reducing serum ALT levels and liver necrosis in mice overdosed with acetaminophen. The hepatoprotection provided by compound BC1-45-1 is superior to the currently used clinical antidote N-acetyl cysteine. Accordingly, a combination of acetaminophen with compound BC1-45-1 or a compound of formulae Ia', Ib', Ic' and Id' could improve the therapeutic window, thus reducing the risk of liver toxicity.

The effects of compounds BC1-45-1 and BC1-55-1, as well as representative compounds of formulae Ia', Ib', Ic' and Id', on the hepatotoxicity of acetaminophen were evaluated in the following assay(s).

Representative compounds were tested using protocols similar to those described by More S S, Nugent J, Vartak A P, Nye S M, and Vince R. Chem Res Toxicol. 2017; 30(3): 777-784. doi: 10.1021/acs.chemrestox.6b00291.

Results

Figure 5A:
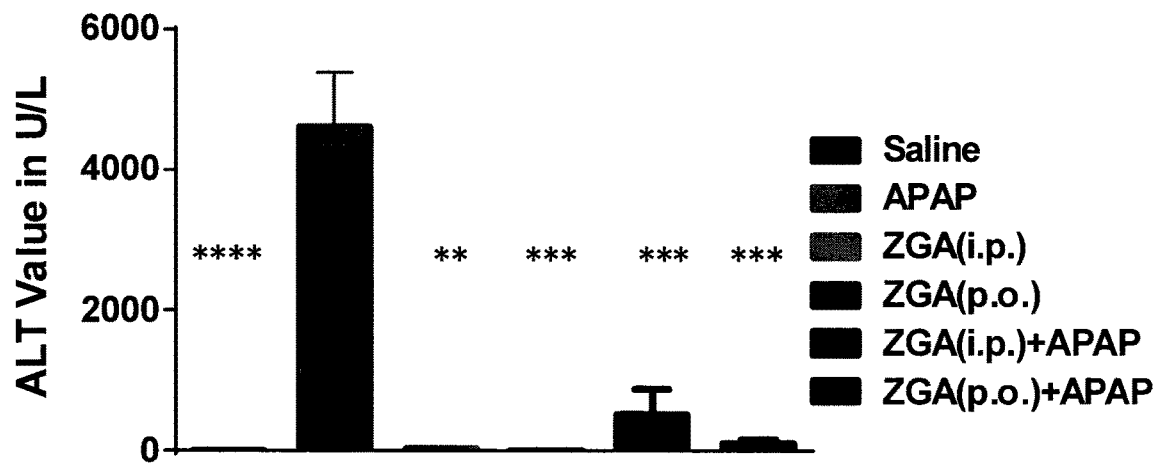
FIG. 5A provides data from the assay of Example 135 for compound BC1-55-1 showing that pretreatment (30 min) with compound BC1-55-1 can limit the hepatotoxicity of acetaminophen.
Figure 5B:
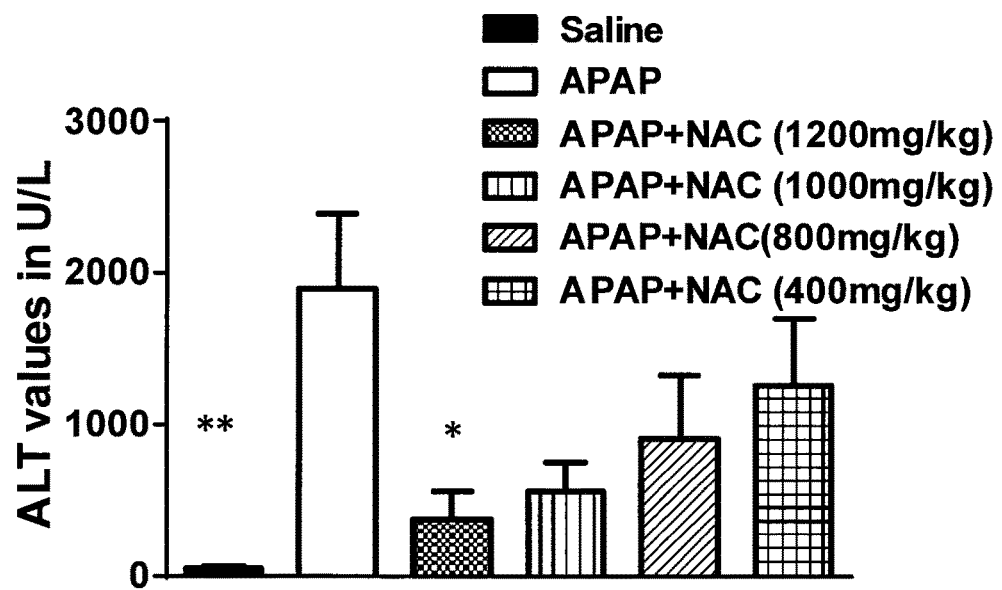
FIG. 5B provides comparative data from the assay of Example 135 for treatment with N-acetyl cysteine.

FIG. 5A demonstrates that pretreatment with compound BC1-55-1 limited the hepatotoxicity of acetaminophen (APAP). The survival rate was 100% for the pretreated animals. FIG. 5B demonstrates that pretreatment with N-acetyl cysteine was less effective in limiting the hepatotoxicity of acetaminophen. Twenty-five percent of the animals treated with N-acetyl cysteine died before completion of the study.

Figure 6A:
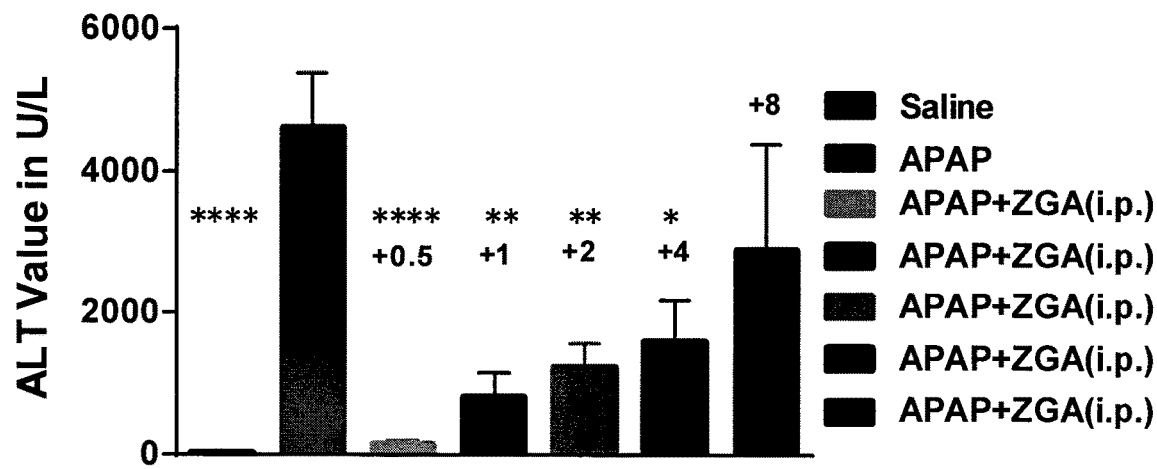
FIG. 6A provides data from the assay of Example 135 for compound BC1-55-1 showing that delayed administration of compound BC1-55-1 reduces elevated levels of ALT following acetaminophen overdose.
Figure 6B:
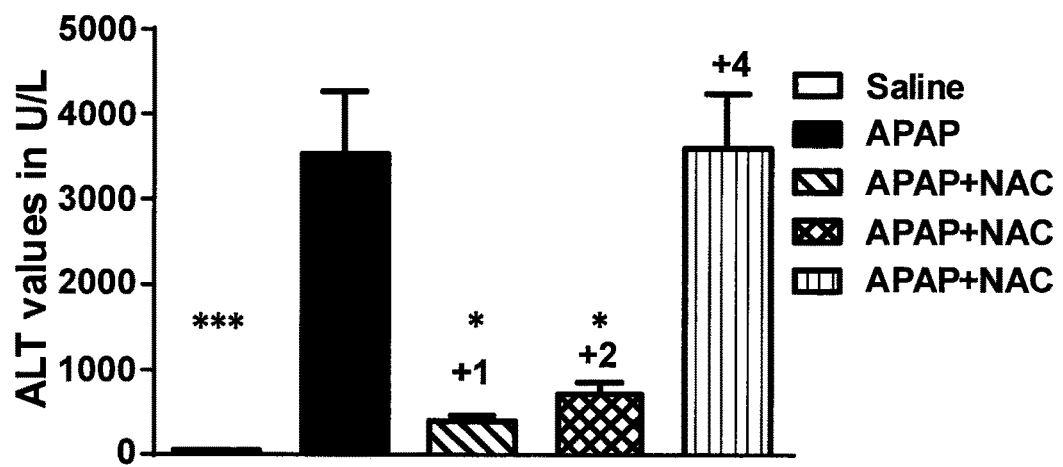
FIG. 6B provides comparative data from the assay of Example 135 for delayed treatment with N-acetyl cysteine.

FIG. 6A demonstrates that delayed administration of compound BC1-55-1 (0.5, 1, 2, 4 and 8 h post APAP administration) reduces elevated ALT levels after acetaminophen overdose. The survival rate was 100% for the animals treated with compound BC1-55-1. FIG. 6B demonstrates that delayed treatment with N-acetyl cysteine (1, 2 and 4 h) was less effective in limiting elevated ALT levels after acetaminophen overdose. Eighty-eight percent of the animals treated with N-acetyl cysteine four hours after acetaminophen overdose died before completion of the study.

Figure 7:
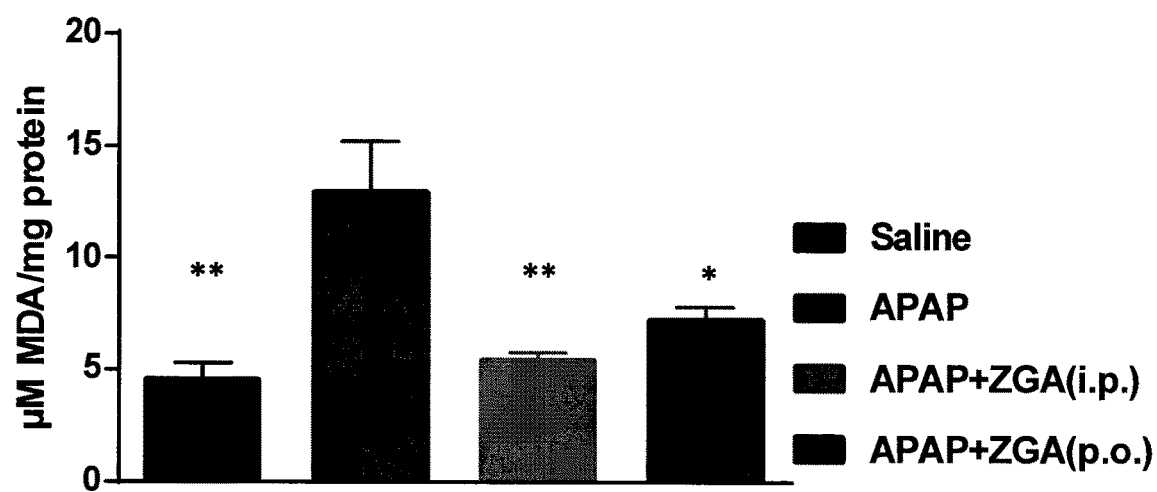
FIG. 7 provides data from the assay of Example 135 for compound BC1-55-1 showing that treatment with compound BC1-55-1 can reduce the lipid peroxidation products (measured by TBARS assay) elevated by acetaminophen overdose.

The TBARS data in FIG. 7 demonstrates that pretreatment with compound BC1-55-1 limited the elevated lipid peroxidation byproducts as measured by the TBARS assay after acetaminophen overdose (2.8 fold increase over the vehicle control group).

Figure 8A:
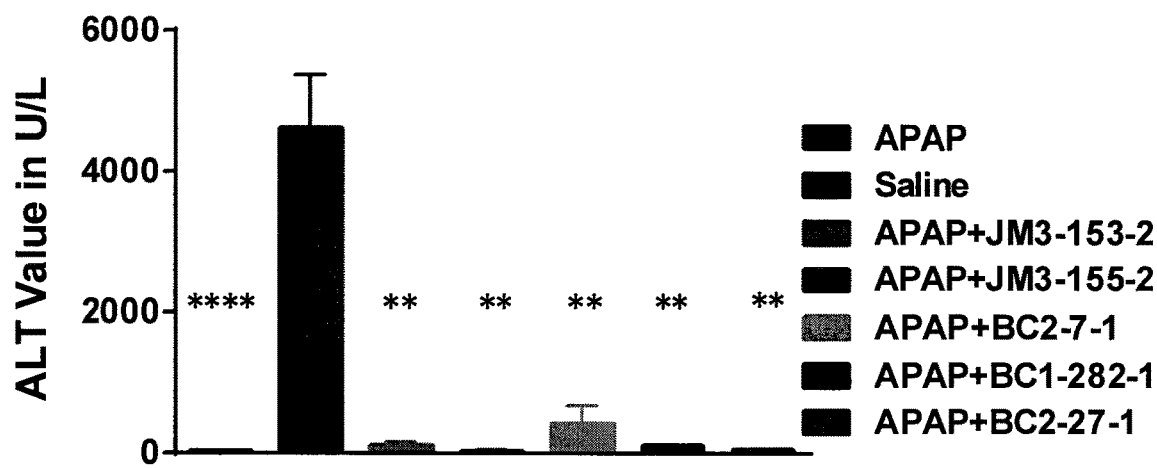
FIG. 8A provides data from the assay of Example 135 for representative compounds of formulae Ia', Ib', Ic', and Id' showing that the compounds reduce elevated levels of ALT following acetaminophen overdose.
Figure 8B:
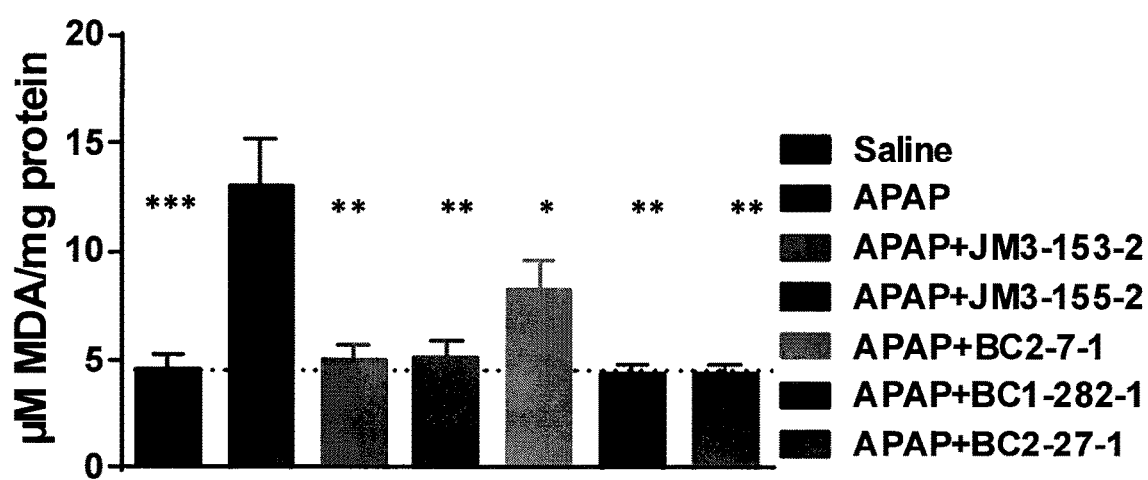
FIG. 8B provides TBARS data from the assay of Example 135 for acetaminophen overdose and effect of representative compounds of formulae Ia', Ib', Ic', and Id' on elevated TBARS (lipid peroxidation products).

FIGS. 8A and 8B demonstrate that representative compounds of formulae Ia', Ib', Ic' and Id' function as antidotes for acetaminophen induced hepatotoxicity.

Figure 9A:
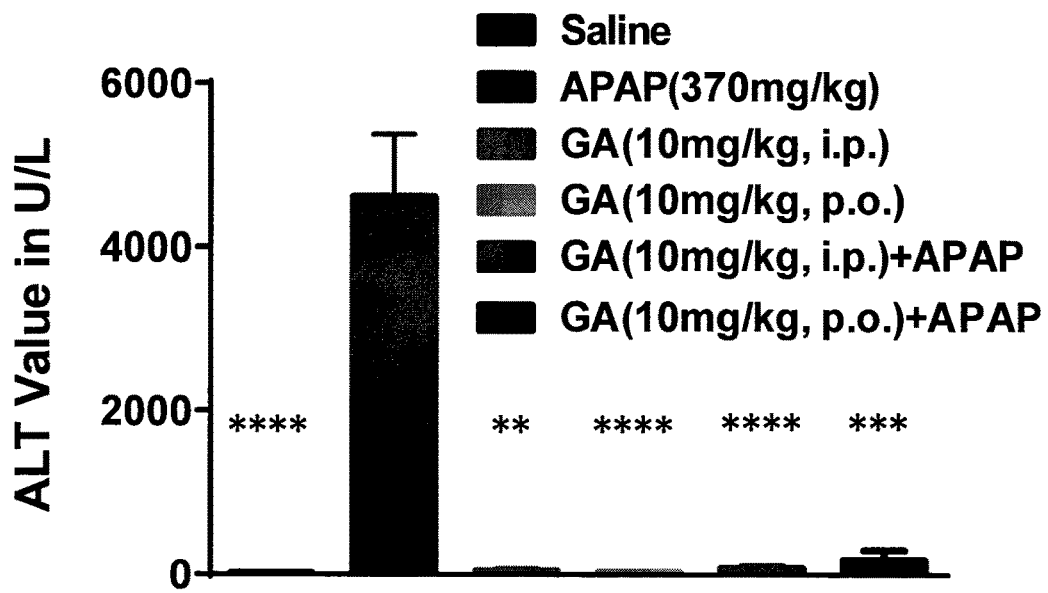
FIG. 9A provides data from the assay of Example 135 for compound BC1-45-1 (GA) showing that pretreatment (30 min) with compound BC1-45-1 can limit the hepatotoxicity of acetaminophen as measured by ALT levels.
Figure 9B:
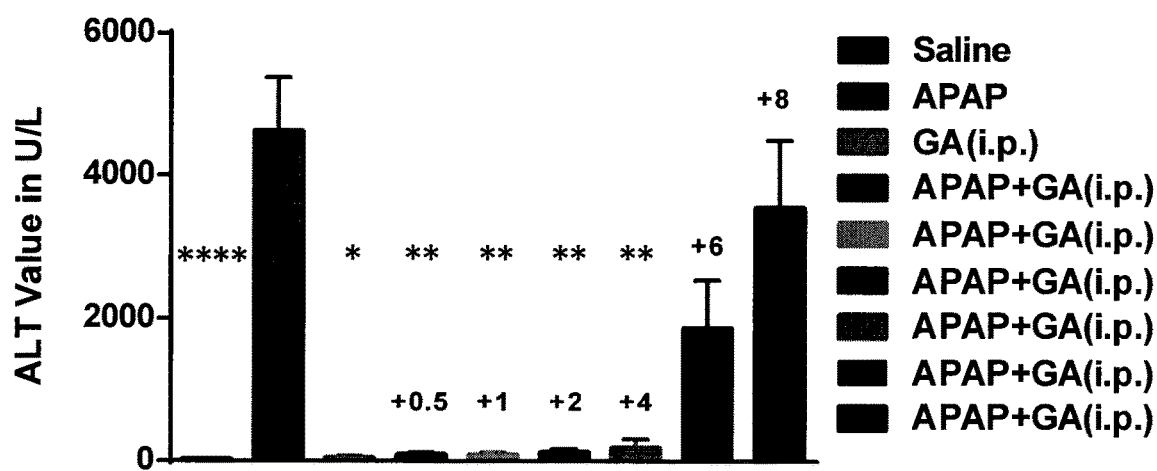
FIG. 9B provides data from the assay of Example 135 for compound BC1-45-1 showing that delayed administration of compound BC1-45-1 reduces elevated levels of ALT following acetaminophen overdose.

FIGS. 9A and B demonstrate that pretreatment and delayed treatment (0.5, 1, 2, 4, 6 and 8 h post acetaminophen administration) with compound BC1-45-1 (guanabenz) limited the hepatotoxicity of acetaminophen. The survival rate in all the BC1-45-1 treatments group was 100%.

Figure 10A:
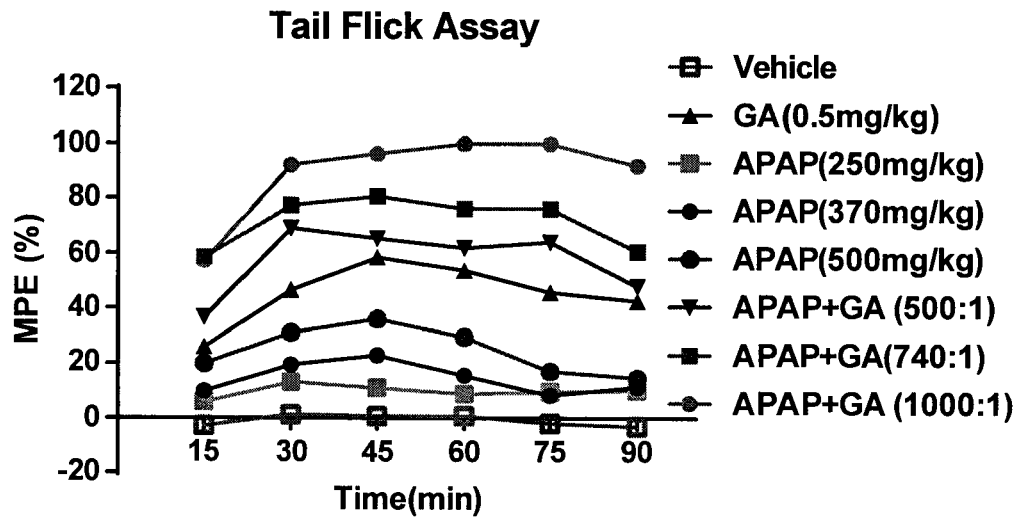
FIG. 10A provides data from the assay of example 135 for compound BC1-45-1 (GA) showing that combination of acetaminophen with low dose BC1-45-1 (GA) exhibited synergy in the analgesic activity as measured by the tail flick assay.
Figure 10B:
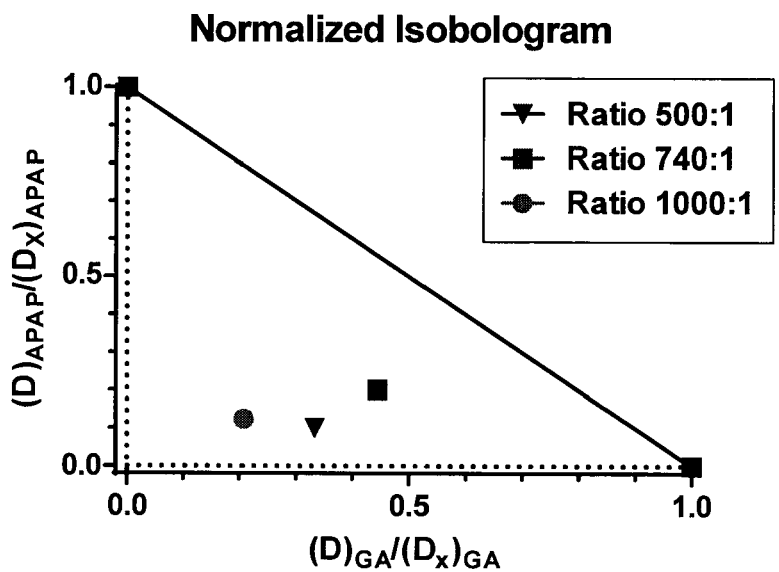
FIG. 10B provides isobologram analysis of the data presented in FIG. 10A.
Figure 10C:
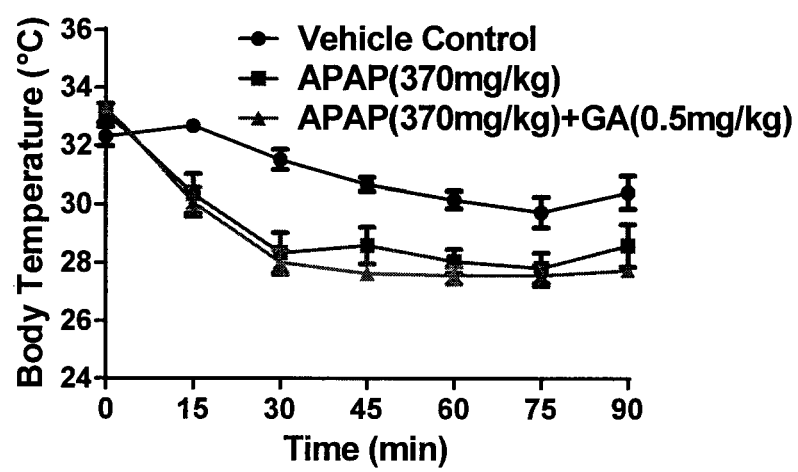
FIG. 10C provides data from the assay of Example 135 for compound BC1-45-1 (GA) showing that combination of low dose BC1-45-1 with acetaminophen does not have any effect on the hypothermic effect of acetaminophen.

FIG. 10A demonstrates analgesic synergy between acetaminophen and BC1-45-1 (guanabenz). Combination of these two compounds in various ratios ranging from 500:1 to 1000:1 for (acetaminophen: BC1-45-1) provided synergy at all the time points tested in the tail flick assay. Body temperature measurement (FIG. 10C) for this combination did not exhibit synergy in the hypothermic action of acetaminophen. BC1-45-1 did not have any effect on the hypothermic action of acetaminophen.

Example 136. Biological Evaluation of Antiviral Activity Against HSV

The antiviral activity of the following representative compounds was evaluated in a plaque reduction assay.

| Number | SW Number |
|---|---|
| BC1-45-1 (E-GA) | SW1 |
| BC1-55-1 (Z-GA) | SW2 |
| BC1-272-1 | SW3 |
| BC1-282-1 | SW4 |
| BC1-283-1 | SW5 |
| BC1-297-1 | SW6 |
| BC2-5-1 | SW7 |
| BC2-7-1 | SW8 |
| BC2-9-1 | SW9 |
| BC2-13-1 | SW10 |
| BC2-17-1 | SW11 |
| BC2-45-1 | SW12 |
| BC2-59-2 | SW13 |
| JM1-185-2 | SW14 |
| JM2-85-2 | SW15 |
| JM2-97-2 | SW16 |
| JM2-131-2 | SW17 |
| JM2-133-2 | SW18 |
| JM2-171-2 | SW19 |
| JM2-233-2 | SW20 |
| JM2-255-2 | SW21 |
| JM2-265-2 | SW22 |
| JM2-271-2 | SW23 |
| JM2-279-2 | SW24 |
| JM2-289-2 | SW25 |
| JM3-11-2 | SW26 |
| JM3-29-2 | SW27 |
| JM2-53-2 (Sal 003) | SW28 |
| JM3-177-2 (Sal) | SW29 |
| JM3-191-2 | SW30 |
| JM3-195-2 | SW31 |
| BC1-299-1 | SW32 |

Approach:

Test compounds for their ability to prevent HSV infection and spread in cell culture.

Method:

Plaque Reduction Assay. (1) Plate Vero cells into 24-well dish ($1 \times 10^5$ per well). (2) Next day, add test compounds or control inhibitor, ganciclovir (GCV), to cells. (3) The next day, remove medium and add 300 μL of HSV-1 KOS strain (200 plaque forming units per well) to 2 wells per compound. After two hours, test compound was added in 2% methylcellulose-containing medium. This medium is to promote plaque formation. (4) Three days later, medium is removed and cells are fixed/stained with MeOH and giemsa. Plaques are counted microscopically.

Reagents:

(1) SM compounds screened at 2.5 μM final concentration. (2) GCV used at 1 μM final concentration. (3) HSV-1 (KOS) is a lab strain and the stock virus concentration is about $6.7 \times 10^9$ plaque forming units per mL.

Figure 11A:
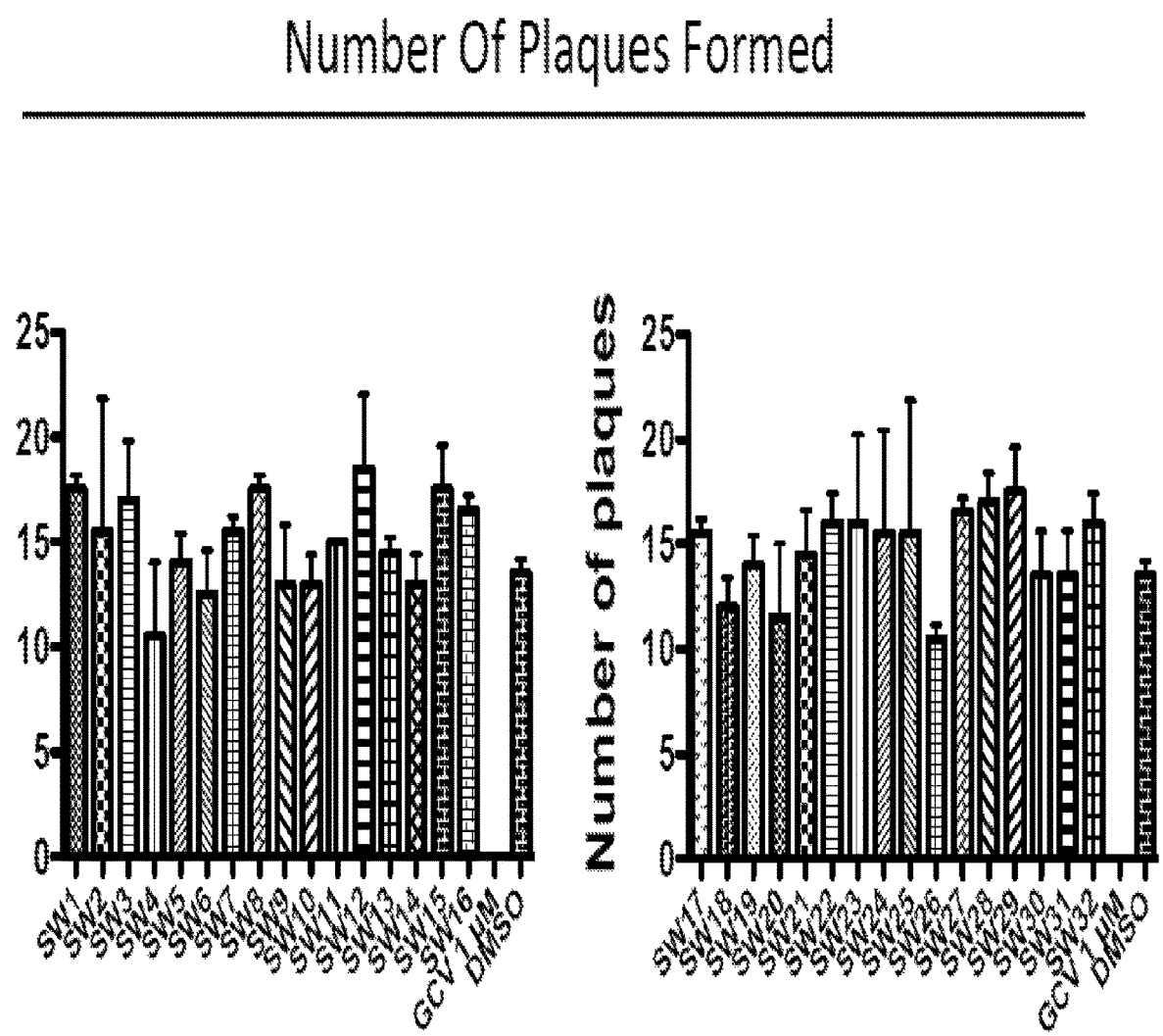
FIG. 11A provides data from the assay of example 136 for compounds SW1-SW32 showing the number of plaques formed.
Figure 11B:
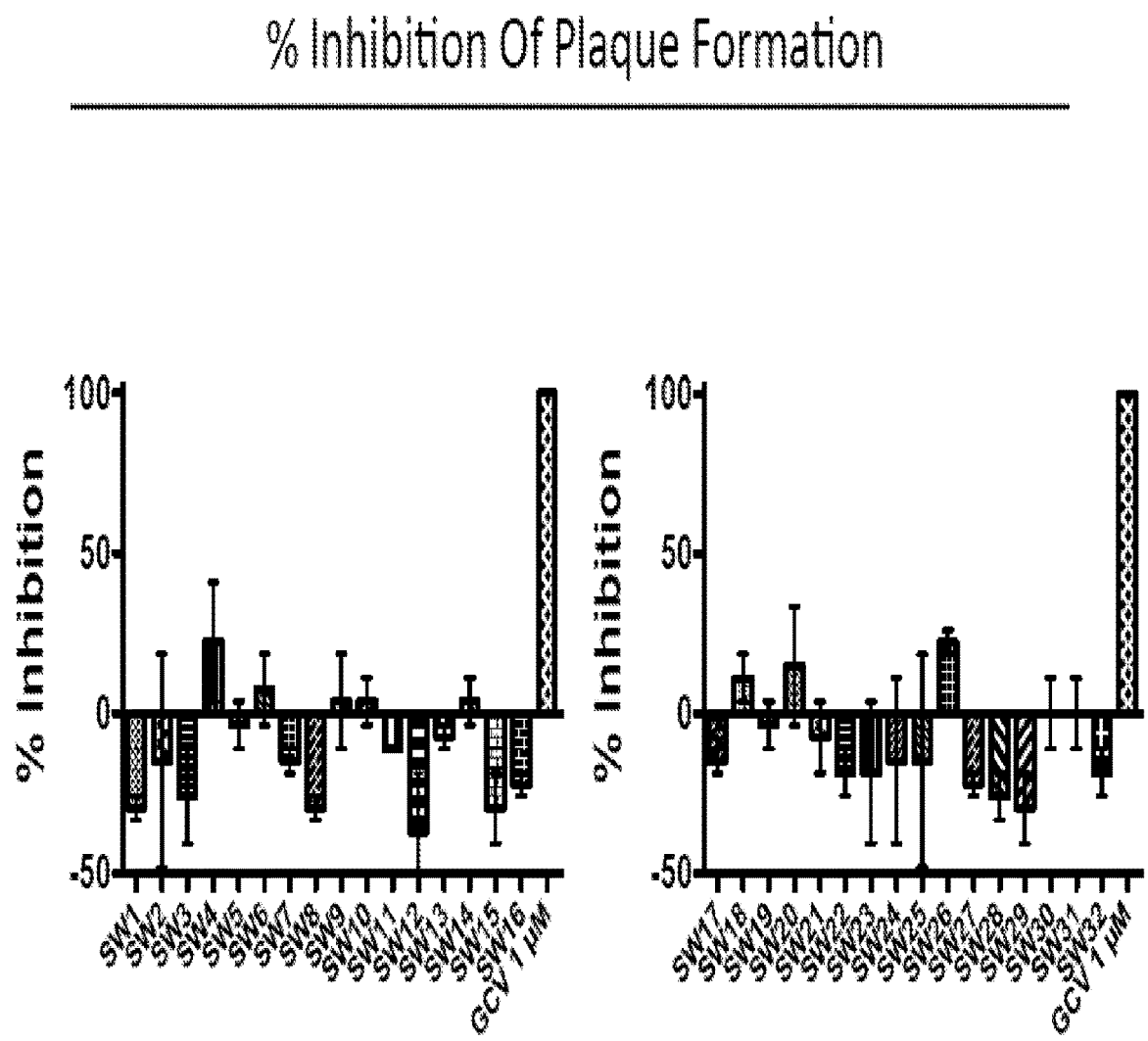
FIG. 11B provides data from the assay of example 136 for compounds SW1-SW32 showing the percent inhibition of plaque formation.
Figure 11C:
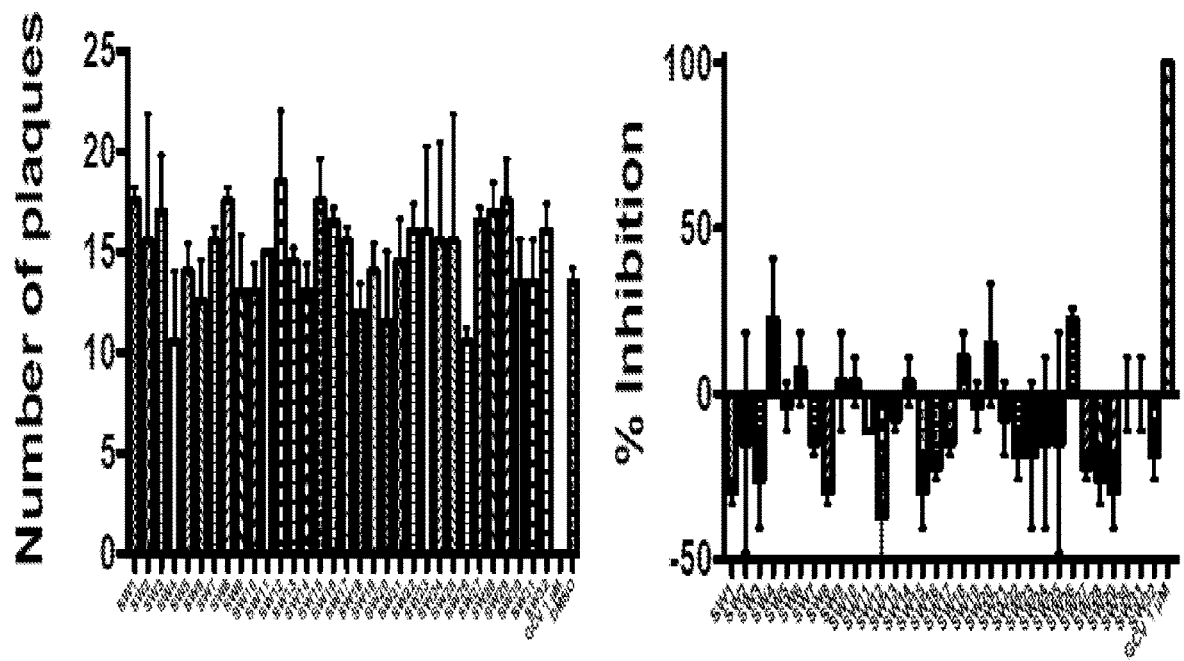
FIG. 11c provides data from the assay of example 136 for compounds SW1-SW32 showing graphs of all compounds together.

Data:

Antiviral data for the compounds identified above is provided in FIGS. 11A, 11B, and 11C.

Example 137

The following illustrate representative pharmaceutical dosage forms, containing a compound of formula Ia', Ib', Ic' or Id' (compound X), for therapeutic or prophylactic use in humans.

| (i) Tablet 1 | ms/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |

| (iii) Capsule | mg/capsule |
|---|---|
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for producing analgesia in an animal comprising administering to the animal a compound, wherein the compound is selected from the group consisting of:

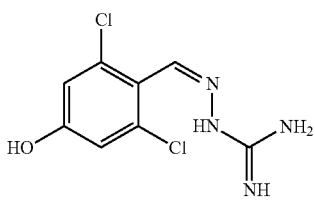

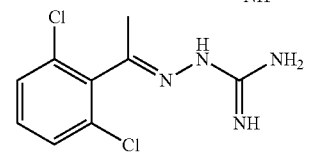

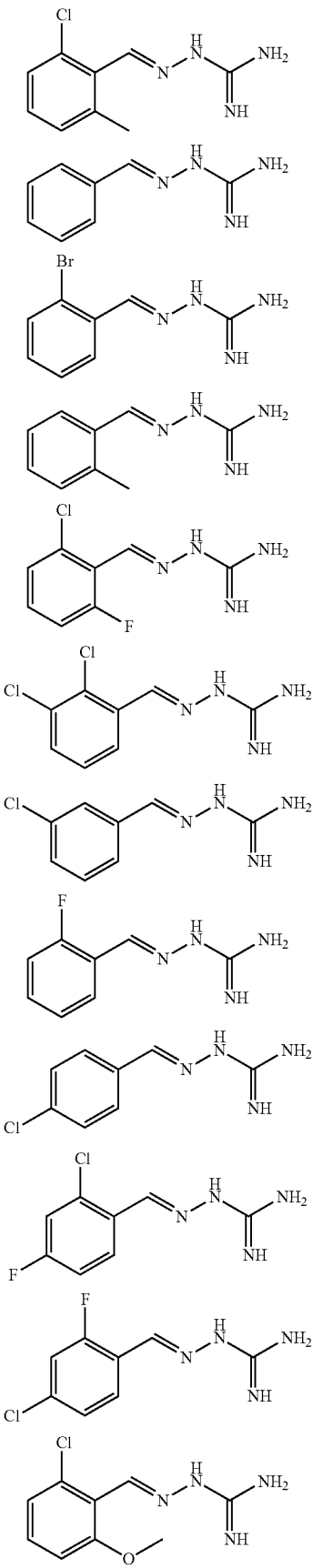

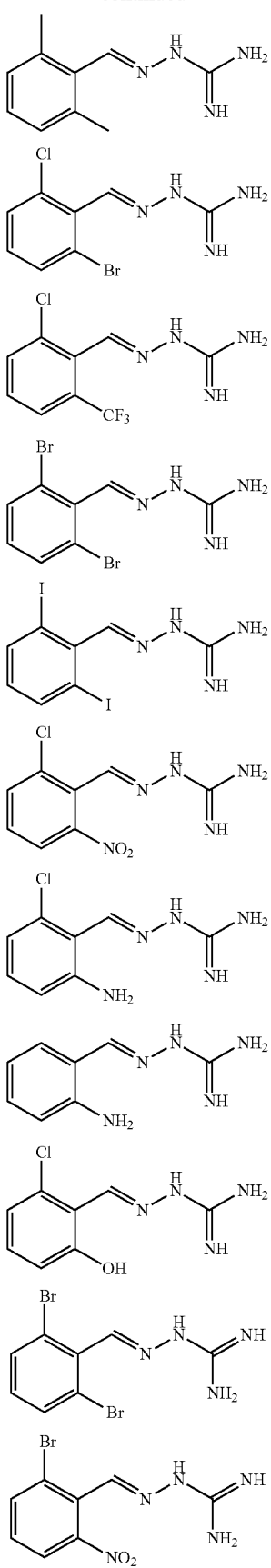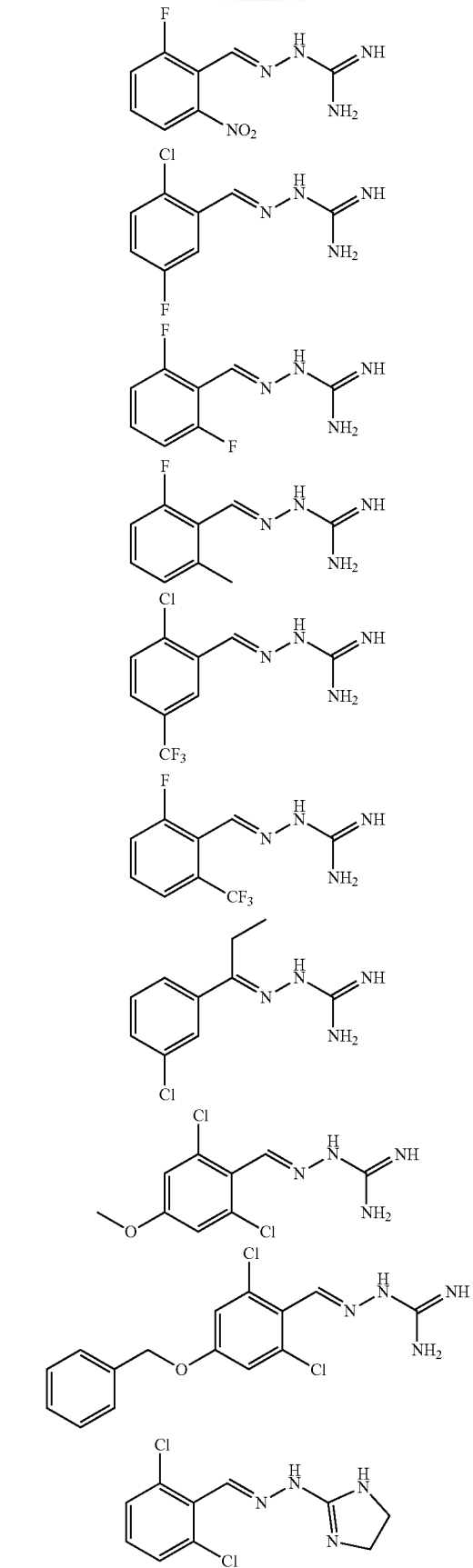

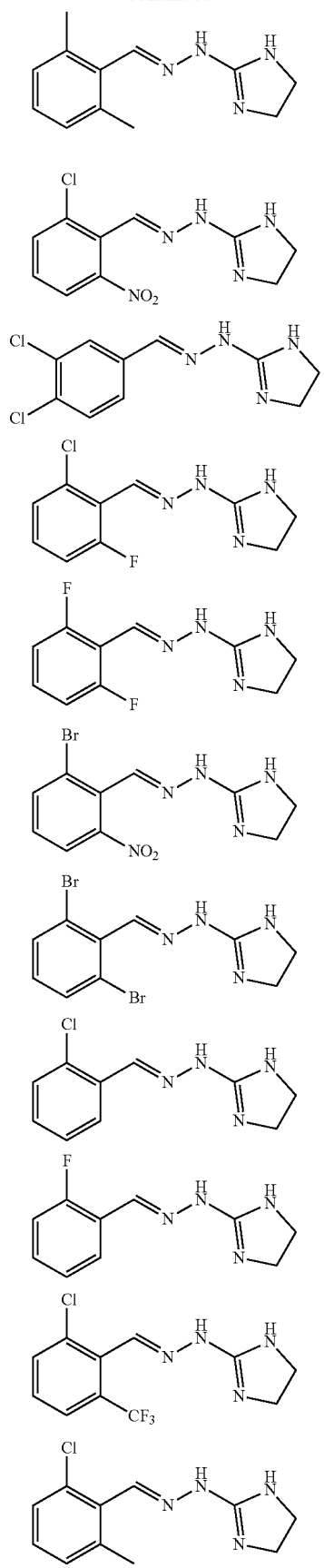
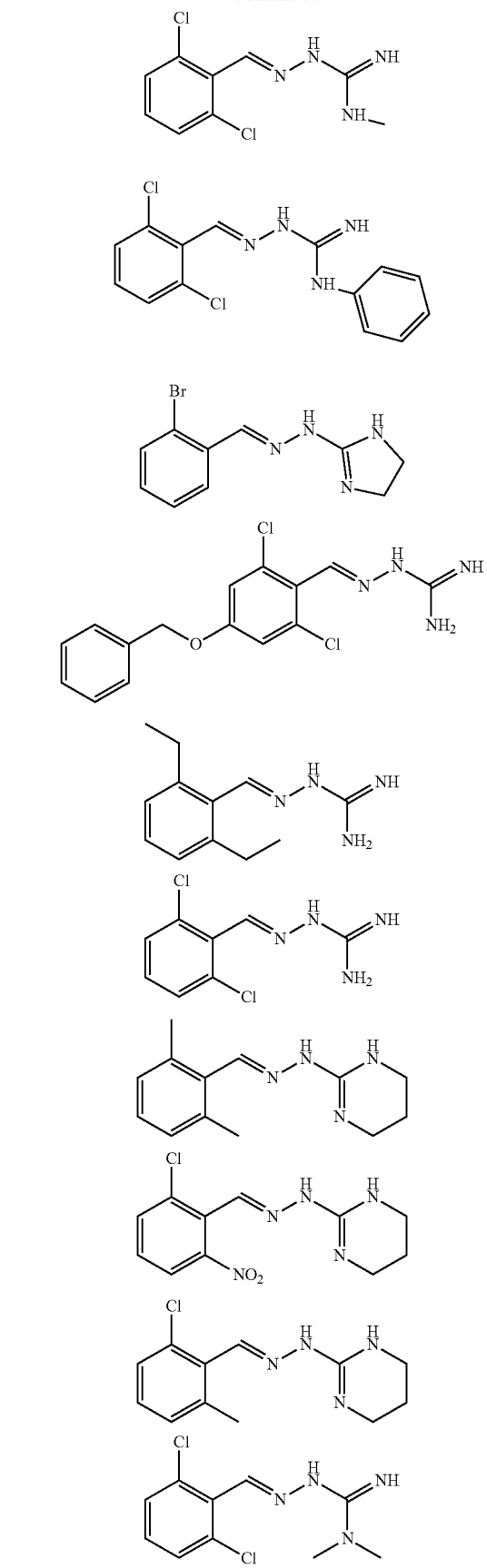

-continued
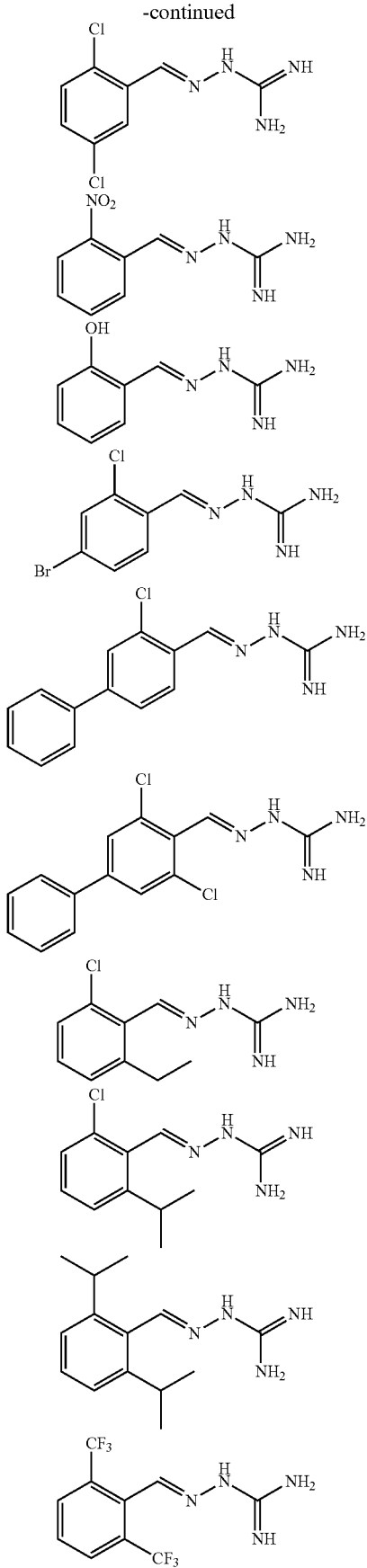
-continued
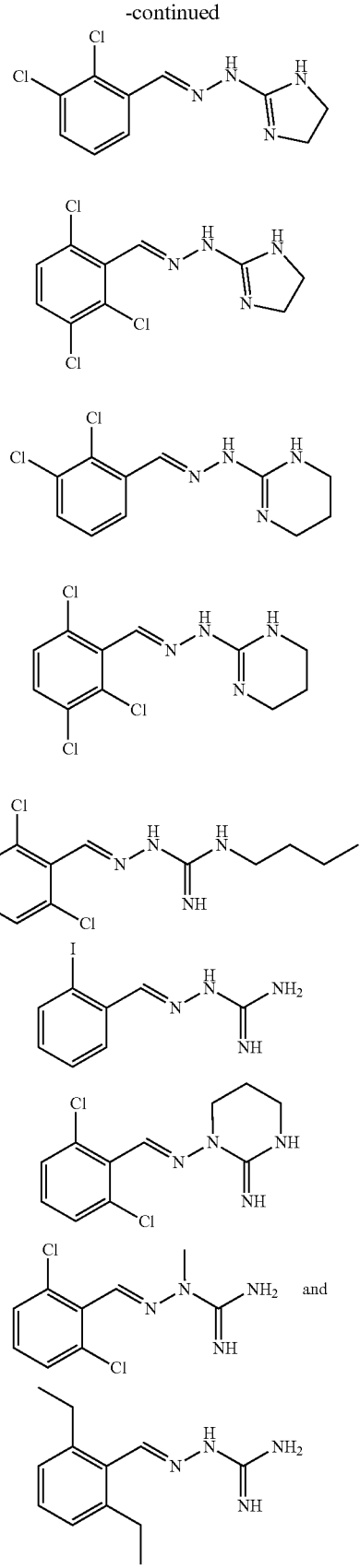
or a pharmaceutically acceptable salt thereof.

2. The method of claim 1, wherein the compound is

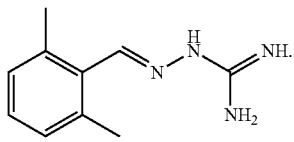

3. The method of claim 1, further comprising administering morphine to the animal.

4. The method of claim 1, wherein the analgesia is produced for synergy in antinociception with reduced sedation or cardiovascular effects.

5. The method of claim 1, further comprising administering acetaminophen to the animal.

6. A method for producing analgesia in an animal comprising administering to the animal a compound of formula Ia':

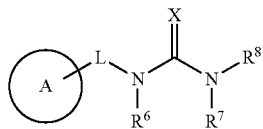

or a pharmaceutically acceptable salt thereof and further comprising administering acetaminophen to the animal;

i) wherein the compound of formula Ia':
ring A is phenyl, wherein the phenyl, is optionally substituted with one or more groups independently selected from the group consisting of $C_{1-4}$ alkyl, $C_{1-4}$ haloalkyl, $C_{3-8}$ cycloalkyl, —F, —Cl, —Br, —I, —OR$^a$, —SR$^a$, —N(R$^a$)$_2$, —NO$_2$ and —CN;
L is selected from the group consisting of:

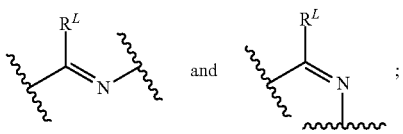

$R^L$ is hydrogen, $C_{1-4}$ alkyl, $C_{1-4}$ haloalkyl or $C_{3-8}$ cycloalkyl;

$R^6$ is hydrogen, or $C_{1-6}$ alkyl that is optionally substituted with one or more groups selected from —F, —Cl, —Br, —I, —OR$^f$, —SR$^f$, —N(R$^f$)$_2$, oxo, —NO$_2$ or —CN; or $R^6$ and $R^8$ taken together with the atoms to which they are attached form a heterocycle that is optionally substituted with one or more groups selected from —F, —Cl, —Br, —I, —OR$^i$, —SR$^i$, —N(R$^i$)$_2$, —NO$_2$ or —CN;

$R^7$ is hydrogen, or $C_{1-6}$ alkyl that is optionally substituted with one or more groups selected from —F, —Cl, —Br, —I, —OR$^g$, —SR$^g$, —N(R$^g$)$_2$, oxo, —NO$_2$ or —CN;

$R^8$ is hydrogen, or $C_{1-6}$ alkyl that is optionally substituted with one or more groups selected from —F, —Cl, —Br, —I, —OR$^h$, —SR$^h$, —N(R$^h$)$_2$, oxo, —NO$_2$ or —CN; or $R^6$ and $R^8$ taken together with the atoms to which they are attached form a heterocycle that is optionally substituted with one or more groups selected from —F, —Cl, —Br, —I, —OR$^i$, —SR$^i$, —N(R$^i$)$_2$, —NO$_2$ or —CN;

X is =O, =S or =N—R$^x$; wherein R$^x$ is hydrogen, or $C_{1-6}$ alkyl that is optionally substituted with one or more groups selected from —F, —Cl, —Br, —I, —OR$^i$, —SR$^i$, —N(R$^i$)$_2$, —NO$_2$ or —CN; or R$^x$ and R$^8$ taken together with the nitrogen atoms to which they are attached form a heteroaryl or an unsaturated heterocycle; wherein the heteroaryl and hetrocycle are optionally substituted with one or more groups selected from —F, —Cl, —Br, —I, —OR$^i$, —SR$^i$, —N(R$^i$)$_2$, —NO$_2$ or —CN;

each R$^a$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two R$^a$ groups taken together with the nitrogen to which they are attached form pyrrolidinyl, piperidinyl, piperazinyl or morpholinyl;

each R$^f$ is independently hydrogen, $C_{1-4}$ alkyl or $C_{1-4}$ haloalkyl; or two R$^f$ groups taken together with the nitrogen to which they are attached form pyrrolidinyl, piperidinyl, piperazinyl or morpholinyl;

each R$^g$ is independently hydrogen, $C_{1-4}$ alkyl or $C_{1-4}$ haloalkyl; or two R$^g$ groups taken together with the nitrogen to which they are attached form pyrrolidinyl, piperidinyl, piperazinyl or morpholinyl;

each R$^h$ is independently hydrogen, $C_{1-4}$ alkyl or $C_{1-4}$ haloalkyl; or two R$^h$ groups taken together with the nitrogen to which they are attached form pyrrolidinyl, piperidinyl, piperazinyl or morpholinyl; and each R$^i$ is independently hydrogen, $C_{1-4}$ alkyl or $C_{1-4}$ haloalkyl; or two R$^i$ groups taken together with the nitrogen to which they are attached form pyrrolidinyl, piperidinyl, piperazinyl or morpholinyl;

wherein the analgesia is produced for synergy in antinociception with reduced sedation or cardiovascular effects.

7. The method of claim 6, wherein the compound is selected from the group consisting of:

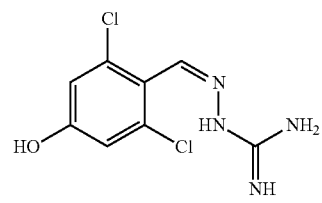

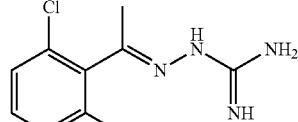

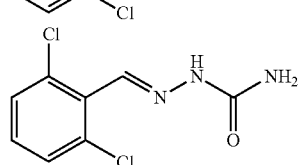

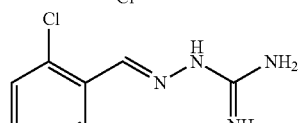

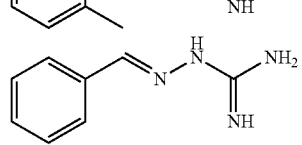

-continued
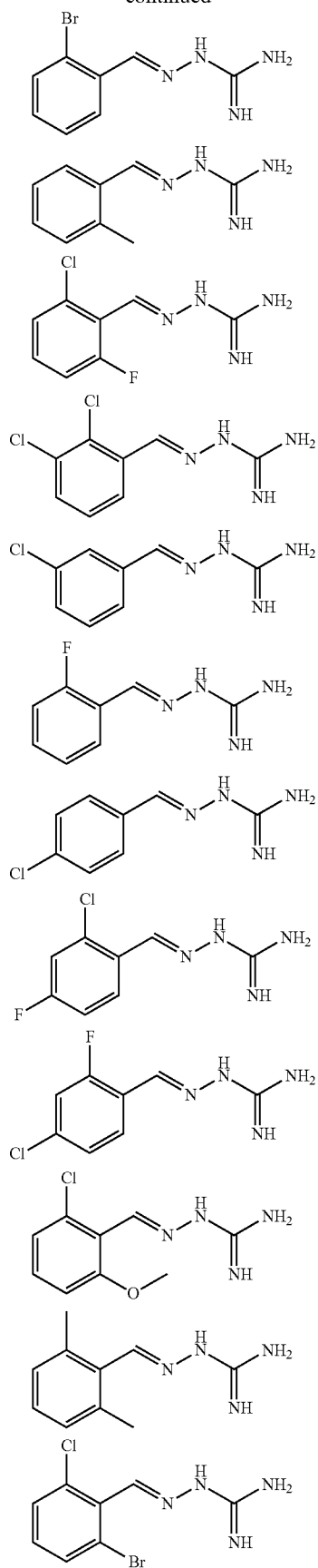
-continued
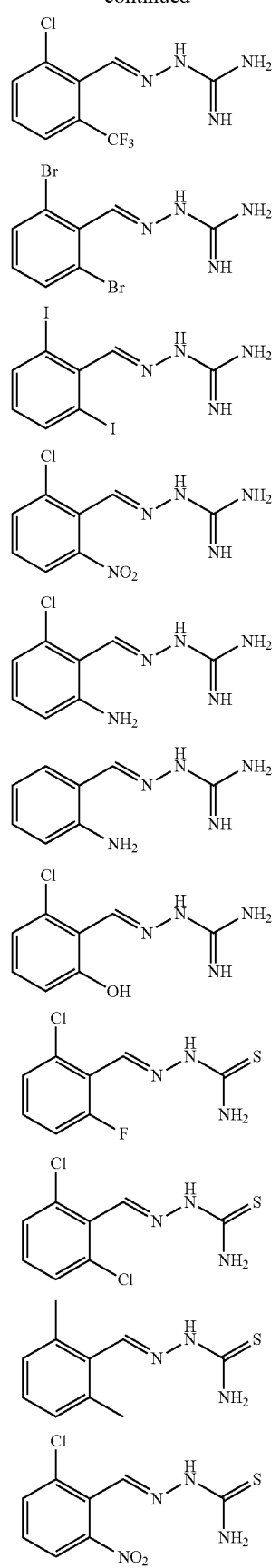

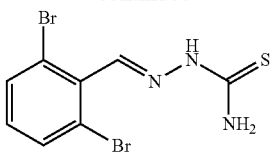
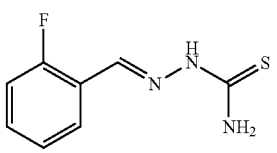
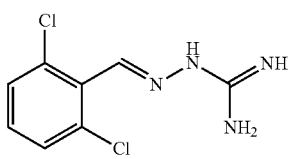
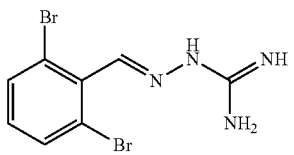
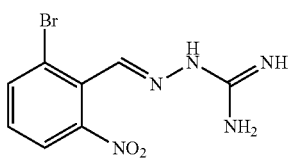
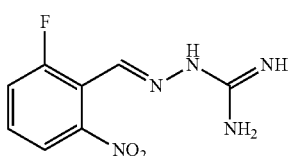
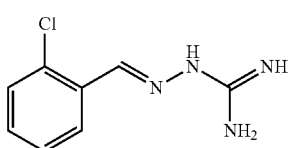
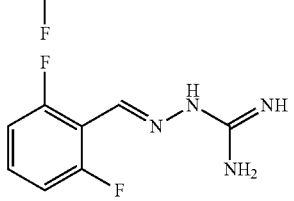
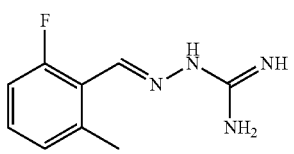
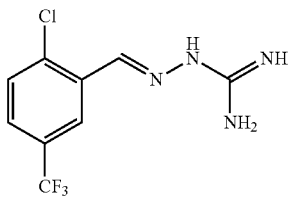
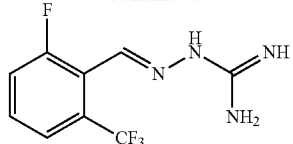
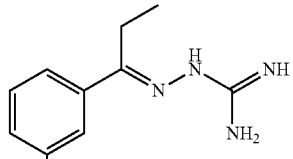
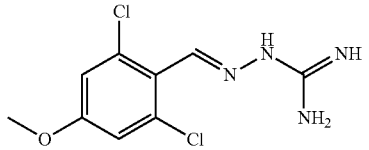
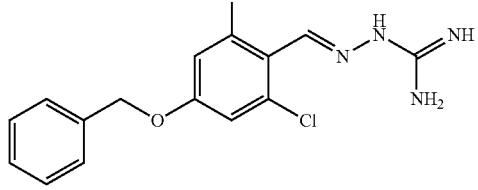
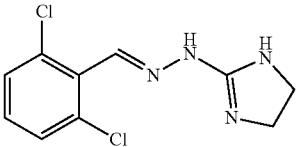
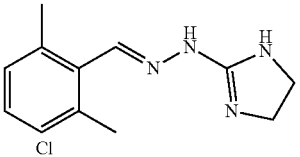
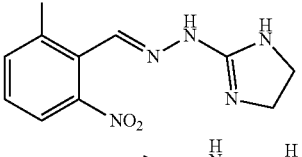
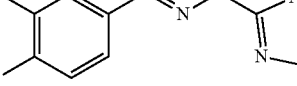
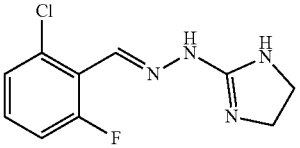
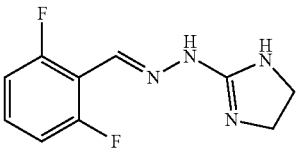
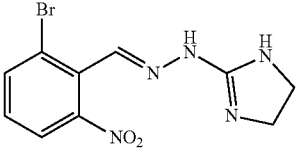

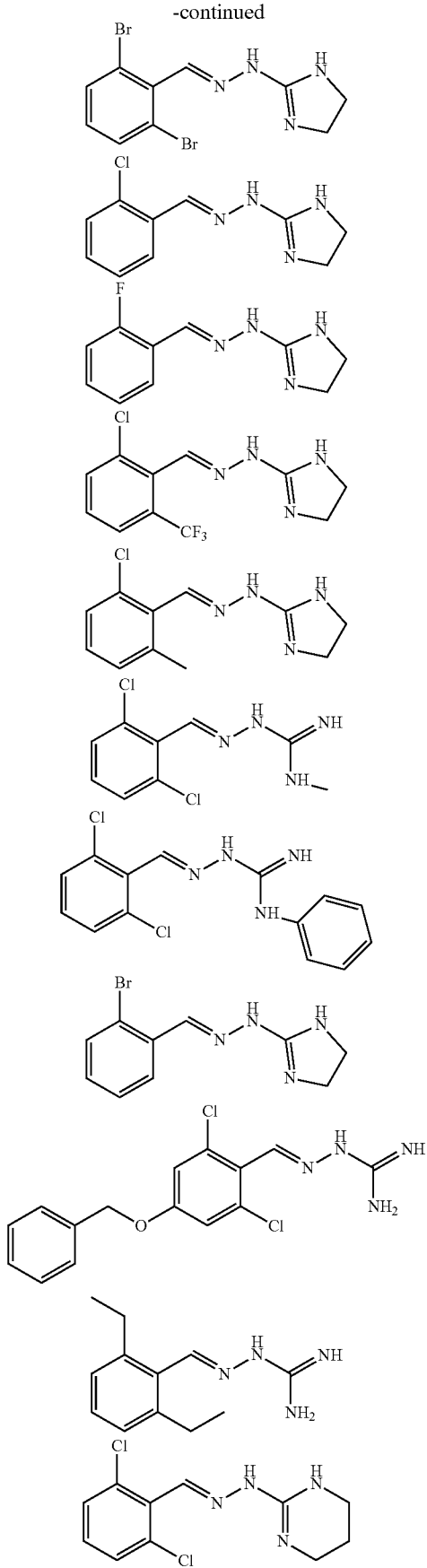
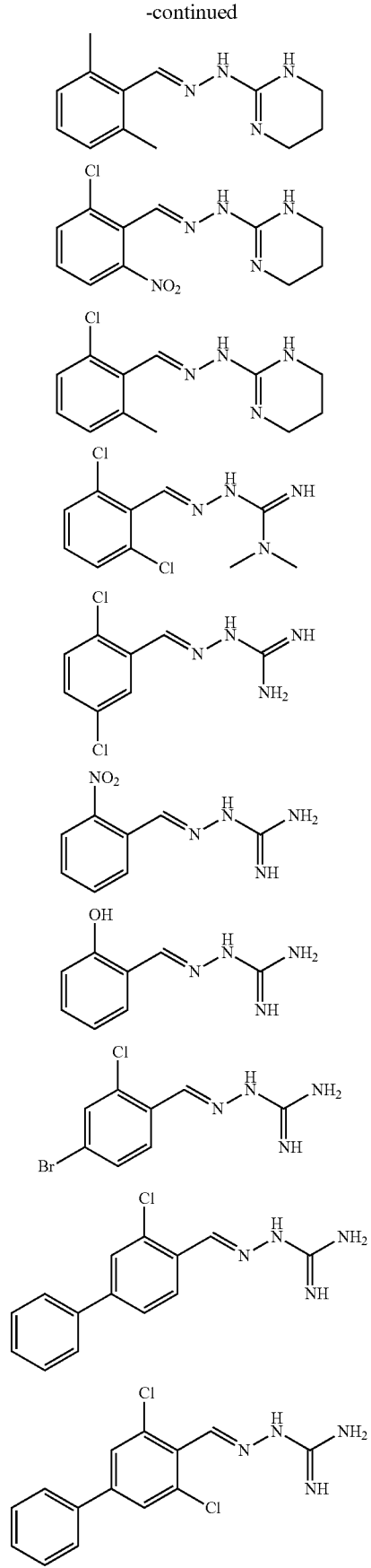

-continued
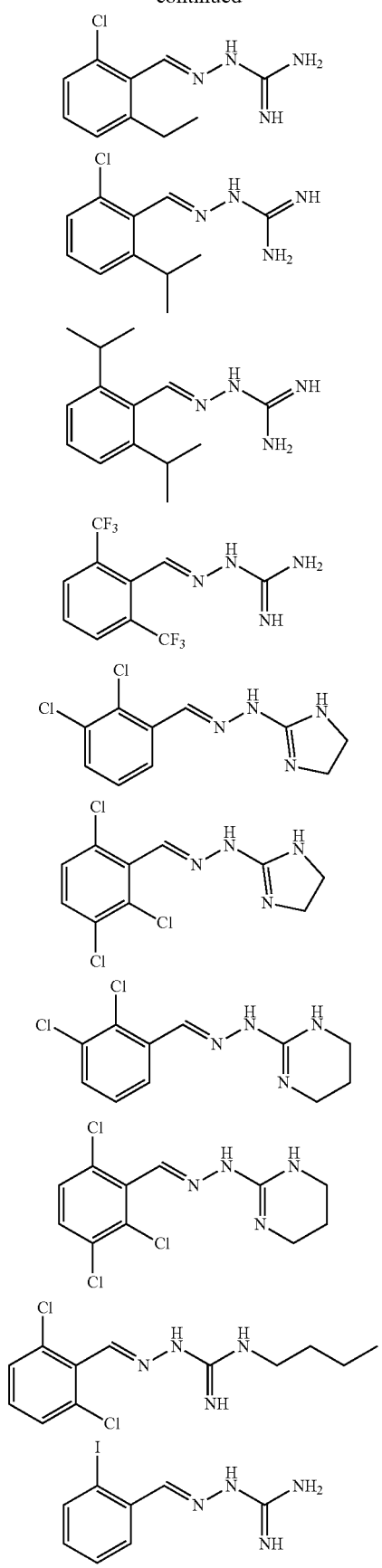
-continued
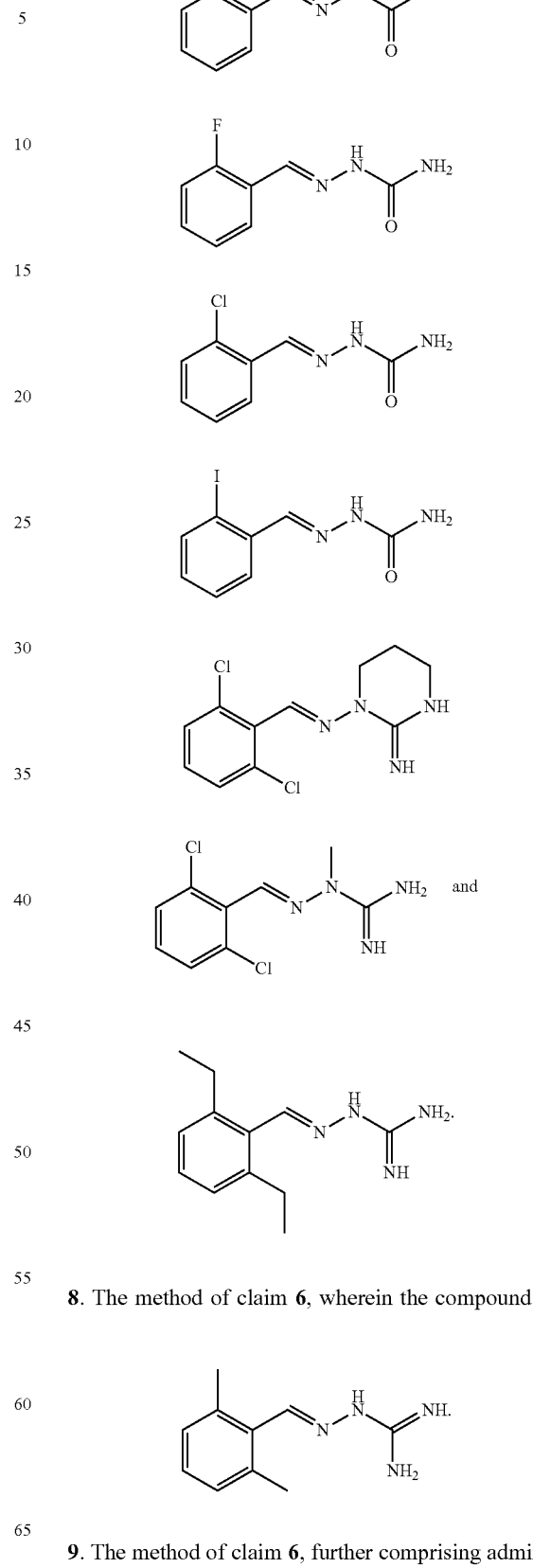
8. The method of claim 6, wherein the compound is
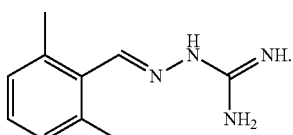
9. The method of claim 6, further comprising administering morphine to the animal.

10. The method of claim 6, wherein the compound is a compound of formula Ia:

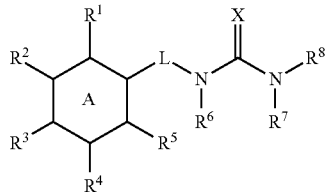

or a pharmaceutically acceptable salt thereof, wherein:
ring A is phenyl;
$R^1$ is $C_{1-4}$ alkyl, $C_{1-4}$ haloalkyl, $C_{3-8}$ cycloalkyl, —F, —Cl, —Br, —I, —$OR^a$, —$SR^a$, —$N(R^a)_2$, —$NO_2$ or —CN;
$R^2$ is hydrogen, $C_{1-4}$ alkyl, $C_{1-4}$ haloalkyl, $C_{3-8}$ cycloalkyl, —F, —Cl, —Br, —I, —$OR^b$, —$SR^b$, —$N(R^b)_2$, —$NO_2$ or —CN;
$R^3$ is hydrogen, $C_{1-4}$ alkyl, $C_{1-4}$ haloalkyl, $C_{3-8}$ cycloalkyl, —F, —Cl, —Br, —I, —$OR^c$, —$SR^c$, —$N(R^c)_2$, —$NO_2$ or —CN;
$R_4$ is hydrogen, $C_{1-4}$ alkyl, $C_{1-4}$ haloalkyl, $C_{3-8}$ cycloalkyl, —F, —Cl, —Br, —I, —$OR^d$, —$SR^d$, $N(R^d)_2$, —$NO_2$ or —CN;
$R^5$ is $C_{1-4}$ alkyl, $C_{1-4}$ haloalkyl, $C_{3-8}$ cycloalkyl, —F, —Cl, —Br, —I, —$OR^e$, —$SR^e$, —$N(R^e)_2$, —$NO_2$ or —CN;
the group

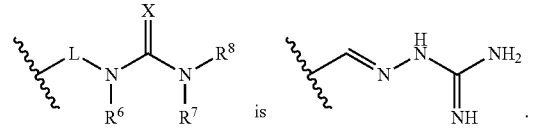

$R^b$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^b$ groups taken together with the nitrogen to which they are attached form pyrrolidinyl, piperidinyl, piperazinyl or morpholinyl;
$R^c$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^c$ groups taken together with the nitrogen to which they are attached form pyrrolidinyl, piperidinyl, piperazinyl or morpholinyl;
$R^d$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^d$ groups taken together with the nitrogen to which they are attached form pyrrolidinyl, piperidinyl, piperazinyl or morpholinyl; and
$R^e$ is independently hydrogen, $C_{1-4}$ alkyl or $C_{1-4}$ haloalkyl, wherein the $C_{1-4}$ alkyl and $C_{1-4}$ haloalkyl are optionally substituted with aryl or heteroaryl; or two $R^e$ groups taken together with the nitrogen to which they are attached form pyrrolidinyl, piperidinyl, piperazinyl or morpholinyl.

11. The method of claim 6, wherein the compound of formula Ia' or a pharmaceutically acceptable salt thereof is E-guanabenz or Z-guanabenz, or a pharmaceutically acceptable salt thereof.

12. The method of claim 1, wherein the compound comprises

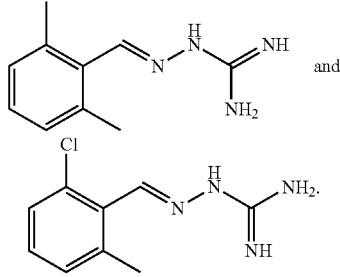

* * * * *